(12) United States Patent
Swayze et al.

(10) Patent No.: US 6,316,626 B1
(45) Date of Patent: Nov. 13, 2001

(54) AMINE COMPOUNDS AND COMBINATORIAL LIBRARIES COMPRISING SAME

(75) Inventors: Eric Edward Swayze, Carlsbad; Kelly G. Sprankle, Vista, both of CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/148,732

(22) Filed: Sep. 4, 1998

Related U.S. Application Data

(63) Continuation-in-part of application No. 08/924,851, filed on Sep. 5, 1997.

(51) Int. Cl.$^7$ .................................................. C07D 29/44

(52) U.S. Cl. .................... 546/207; 546/208; 546/244; 546/246

(58) Field of Search .................... 546/207, 208, 546/244, 246

(56) References Cited

U.S. PATENT DOCUMENTS

| | | |
|---|---|---|
| 3,819,561 | 6/1974 | Bruenner .......................... 260/362 A |
| 5,288,514 | 2/1994 | Ellman ..................................... 427/2 |
| 5,324,483 | 6/1994 | Cody et al. .......................... 422/131 |

FOREIGN PATENT DOCUMENTS

| | | |
|---|---|---|
| 0 528 678 A1 | 2/1993 | (EP) . |
| 0 544 307 A1 | 6/1993 | (EP) . |
| 02-028151 | 7/1988 | (JP) . |
| WO 91/19735 | 12/1991 | (WO) . |
| WO 93/23404 | 11/1993 | (WO) . |
| WO 94/08051 | 4/1994 | (WO) . |
| WO 94/24314 | 10/1994 | (WO) . |
| WO 94/26775 | 11/1994 | (WO) . |
| WO 94/27719 | 12/1994 | (WO) . |
| WO 94/28028 | 12/1994 | (WO) . |
| WO 94/28424 | 12/1994 | (WO) . |
| WO 96/39531 | 12/1996 | (WO) . |

OTHER PUBLICATIONS

Achari et al., "Facing up to Membranes", *Cold Spring Harbor Symp. Quant. Biol.*, 1987, 52, 441–452.
Atherton and R.C. Sheppard in *The Peptides*, Chapter 1, "The Fluorenylmethoxycarbonyl Amino Protecting Group", S. Udenfriend, J. Meienhofer, (Eds.), Academic Press, Orlando, 1987, vol. 9, pp. 1–38.
Bartlett et al., Book of Abstracts, 213th American Chemical Society National Meeting, San Francisco, 1997, *Am. Chem. Soc.*, Washington, D.C.
Beaucage et al., "Advances in the Synthesis of Oligonucleotides by the Phosphoramidite Approach", *Tetrahedron*, 1992, 48, 2223–2311.

Bodanszky, "Principles of Peptide Synthesis", Second Edition, John Wiley & Sons Publishers, Springer–Verlag, Berlin–New York, 1984, Chapters 1–8.
Bodanszky, Principles of Peptide Synthesis, 2nd Edition, 1983, Springer–Verlag, Berlin.
Bomalaski et al., "Human Extracellular Recombinant Phospholipase $A_2$ Induces an Inflammatory Response in Rabbit Joints", *J. Immunol.*, 1991, 146, 3904–3910.
Bunin and Ellman, "A General and Expedient Method for the Solid–Phase Synthesis of 1,4–Benzodiazepine Derivatives", *J. Am. Chem. Soc.*, 1992, 114, 10997–10998.
Burack et al., "Role of Lateral Phase Separation in the Modulation of Phospholipase $A_2$ Activity", *Biochemistry*, 1993, 32, 583–589.
Campbell et al., "Inhibition of Phospholipase $A_2$; a Molecular Recognition Study", *J. Chem. Soc., Chem. Commun.*, 1988, 1560–1562.
Carell et al., "A Novel Procedure for the Synthesis of Libraries Containing Small Organic Molecules", *Angew. Chem. Int. Ed. Engl.*, 1994, 33, 2059–2061.
Carell et al., "A Solution–Phase Screening Procedure for the Isolation of Active Compounds from a Library of Molecules", *Angew. Chem. Int. Ed. Engl.*, 1994, 33, 2061–2064.
Chen et al., "Inhibition of Ricin by an RNA Stem–Loop Containing a Ribo–Oxocarbenium Mimic", *J. Am. Chem. Soc.*, 1996, 118, 3067–3068.
Cho et al., "The Chemical Bases for Interfacial Activation of Monomeric Phospholipases $A_2$", *J. Biol. Chem.*, 1988, 263, 11237–11241.
Davidson et al., "1–Steary1,2–Stearoyiaminodeoxy Phoshatidylcholine, a Potent Reversible Inhibitor of Phospholipase $A_2$", *Biochem. Biophys. Res. Commun.*, 1986, 137, 587–592.
Davidson et al., "Inhibition of Phospholipase $A_2$ by "Lipocortins" and Calpactins", *Biol. Chem.*, 1987, 262; 1698–1705.
Dennis, E.A., The Enzymes, vol. 16, pp. 307–353, Boyer, P.D. (Ed.), Academic Press, New York, 1983.
DeWitt et al., "Diversomers" :An approach to nonpeptide, nonoligomeric chemical diversity, *Proc. Natl. Acad. Sci. USA*, 1993, 90, 6909–6913.

(List continued on next page.)

Primary Examiner—Bennett Celsa
(74) *Attorney, Agent, or Firm*—Woodcock Washburn Kurtz Mackiewicz & Norris LLP

(57) ABSTRACT

The present invention provides monocyclic, bicyclic and oligomeric amine compounds with at least two sites of diversity. These compounds are formed from monocyclic scaffolds which can be cyclized to form bicyclic amine scaffolds. These can then be reacted with building blocks to form the amine compounds of the invention. This invention further provides libraries or monocyclic, bicyclic and oligomeric amine compounds. Also provided are methods for preparing monocyclic, bicyclic and oligomeric amine compounds and libraries thereof. The present invention also provides pharmaceutical compositions of the monocyclic, bicyclic and oligomeric amine compounds.

2 Claims, 5 Drawing Sheets

OTHER PUBLICATIONS

Ecker et al., "Rational screening of oligonucleotide combinatorial libraries for drug discovery", *Nucleic Acids Res.,* 1993, 21, 1853–1856.

Ettinger et al., "Intrathecal Methotrexate Overdose Without Neurotoxicity", *Cancer,* 1978, 41, 1270–1273.

Ewel et al., "Polyinosinic–Polycytidylic Acid Complexed with Poly–L–lysine and Carboxymethylcellulose in Combination with Interleukin 2 in Patients with Cancer: Clinical and Immunological Effects[1]", *Cancer Research,* 1992, 52, 3005–3010.

Franson et al., "Phospholipid metabolism by phagocytic cells, Phospholipases $A_2$ associated with rabbit polymorphonuclear leukocyte granules", *J. Lipid Res.,* 1974, 15, 380–388.

Geysen et al., "Strategies for epitope analysis using peptide synthesis", *J. Immun. Meth.,* 1987, 102,259–274.

Glaser et al., "Phospholipase $A_2$ enzymes: regulation and inhibition", *TIPS Reviews,* 1992, 14, 92–98.

Grainger et al., "An enzyme caught in action: direct imaging of hydrolytic function and domain formation of phosphilipase $A_2$ in phosphatidycholine monolayers", *FEBS Lett.,* 1989, 252, 73–82.

Greene and Wuts, "Protective Groups in Organic Synthesis", 2nd Edition, John Wiley & Sons, 1991, pp. 10–143.

Griffart–Brunet, D. et al., "A Concise Diasteroselective Synthesis of the Natural (2R,3S)–2 Hydroxymethyl–3–Hydroxy Pyrrolidine", *Tetrahedron Letters,* 1994, 35, 119–122.

Hamper et al., "Solid–Phase Synthesis of Proline Analogs via a Three compent 1,3–Dipolar Cycloaddition", *Tetrahedron Lett.,* 1996, 37, 3671–3674.

Horenstein et al., "A New Class of C–Nucleoside Analogues. 1–(S)–aryl–1,4–dideoxy–1,4–imino–D– ribitols, Transition State Analogue Inhibitors of Nucleoside Hydrolase", *Tetrahedron Letters,* 1993, 34, 7213–7216.

Houghton et al., "Generation and use of synthetic peptide combinatorial libraries for basic research and drug discovery", *Nature,* 1991, 354, 84–86.

Johnson, C.R. et al., "Chemoenzymatic Synthesis of 1,3–Dideoxynojirimycin", *Tetrahedron Letters,* 1994, 35, 1833–1834.

Jung, M.E. et al. "Organic Chemistry of L–Tyrosine. 1. General Synthesis of Chiral Piperazines from Amino Acids", *J. Org. Chem.,* 1985, 50, 4909–4913.

Kemeny et al., "A Pilot Studyt of Hepatic Artery Floxuridine Combined with Systemic 5–Fuorouracil and Leucovorin", *Cancer,* 1993, 71, 1964–1971.

Lombardo and Dennis, "Cobra Venom Phospholipase $A_2$ Inhibition by Manoalide", *J. Biol. Chem.,* 1985, 260, 7234–7240.

Look et al., "Trimethylorthoformate: A Mild and Efffective Dehydrating Reagent for Solution and Solid Phase Imine Formation", *Tetrahedron Lett.,* 1995, 36, 2937–2940.

Luer and Haton, "Vanomycin Administration into the Cerebrospinal Fluid: A Review", *The Annual of Pharmacoterapy,* 1993, 27, 912–921.

Marki et al., "Differential inhibition of human secretory and cytosolic phospholipase $A_2$", *Agents Actions,* 1993, 38, 202–211.

Marzi, M. et al., "Asymmetric Synthesis of Trans–(2R, 5R)–Bis(Benzyloxymethyl)Pyrrolidine", *Tetrahedron Letters,* 1989, 30, 6075–6076.

Miyake et al., "The Novel Natual Product YM–26567–1 [(+)–trans– 4(3– dodecanoyl– 2, 4, 6–trihydroxyphenyl)–7–hydroxy–2–(4–hydroxyphenyl)chroman]: A Competitve Inhibitor of Group II Phospholipase $A_2$", *J. Pharmacol. Exp. Ther.,* 1992, 263, 1302–1307.

Morishita et al., "Single intraluminal delivery of antisense cdc2 kinase and proliferating–cell nuclear antigen oligonucleotides results in chronic inhibition of neointimal hyperplasma", *Proc. Natl. Acad. Sci. USA,* 1993, 90, 8474–8478.

Nefzi et al., "Solid Phase Synthesis of Heterocylic Compounds from Linear Peptides: Cyclic Ureas and Thioureas", *Tetrahedron Lett.,* 1997, 38, 931–934.

Noel et al., "Phospholipase $A_2$ Engineering. 3. Replacement of Lysine–56 by Neutral Residues Improves Catalytic Potency Significantly, Alters Substrate Specificity, and Clarifies the Mechanism of Interfacial Recogition", *J. Am. Chem. Soc.,* 1990, 112, 3704–3706.

Ohlmeyer et al., "Complex synthetic chemical libraries indexed with molecular tags", *Proc. Natl. Acad. Sci. USA,* 1993, 90, 10922–10926.

Oinuma et al., "Synthesis and Biological Evaluation of Substituted Benzenesulfonamidees as Novel Potent Membrane–Bound Phospholipase $A_2$ Inhibitors", *J. Med. Chem.,* 1991, 34, 2260–2267.

Overhand, M. et al. "A Concise Synthesis of the Antifungal Agent (+)–Preussin", *J. Org. Chem.,* 1994, 59, 4721–4722.

Owens et al., "the Rapid Indentification of HIV protease Inhibitor Through the Synthesis and Screening of Defined Peptide Mixture", *Biochem. Biophys. Res., Commun.,* 1991, 181, 402–408.

Pruzanski et al., "Enzymatic Activity and Immunoreactivity of Extracellular Phospholipase $A_2$ in Inflammatory Synovial Fluids", *Inflammation,* 1992, 16, 451–457.

Ritter, A.R. et al., "Asymmetric Syntheses of Novel Amino Acids and Peptides from AcyInitroso–Derived Cycloadducts", *Tetrahedron Lett.,* 1994, 35, 9379–9382.

Rubenstein et al., "Antisense Oligonucleotide Intralesional Therapy for Human PC–3 Prostate Tumors Carried in Athymic Nude Mice", *J. Surg. Oncol.,* 1996, 62, 194–200.

Sampson, B.A. et al., "Identification and Characterization of a New Gene of *Escherichia coil* K–12 Involved in Outer Membrane Permeability", *Genetics,* 1989, 122, 491–501.

Samukov et al., "2–(4–Nitrophenyl)sulfonylethoxycarbonyl (NEs) Group As a Base–Labile α–Amino Protection for Solid Phase Peptide Synthesis", *Tetrahedron Letters,* 1994, 35, 7821–7824.

Scott et al., "Interfacial Catalysis: The Mechanism of Phospholipase $A_2$", *Science,* 1990, 250, 1541–1546.

Sharer et al., "Specific Binding of the DNA Repair Enzyme AlkA to a Pyrrolidine–Based Inhibitor", *J. Am. Chem. Soc.,* 1995, 117, 6623–6624.

Simon et al., "Peptoids: A modular approach to drug discovery", *Proc. Natl. Acad. Sci. USA,* 1992, 89, 9367–9371.

Soro et al., "Total Synthesis of 2,4–Diamino–2,4–Di-amino–2,4–dideoxy–L–arabinose and 2,4–Diamino–2, 4–dideoxy–L–ribose", *J. Org. Chem.,* 1996, 61, 5172–5174.

Tanaka et al., "A Novel Type of Phospholipase $A_2$ Inhibitor, Thielocin A1β, and Mechanism of Action", *J. Antibiotics,* 1992, 45, 1071–1078.

Verhart et al., "New base–labile amino–protective groups for peptide synthesis", *Rec. Trav. Chim. Pays–Bas,* 1987, 107, 621–626.

Vishwanath et al., "Edema–Inducing Activity of Phospholipase $A_2$ Purifed from Human Synovial Fluid and Inhibition by Aristolochic Acid", *Inflammation*, 1988, 12, 549–561.

Washburn and Dennis, "Suicide–inhibitory Bifunctionally Linked Substrates (SIBLINKS) as Phospholipase $A_2$ Inhibitors", *J. Biol. Chem.*, 1991, 266, 5042–5048.

Wery et al., "Structure of recombinant human rheumatoid arthritic synovial fluid phospholipase $A_2$ at 2.2A resolution", *Nature*, 1991, 352, 79–82.

Wyatt et al., "Combinatorially selected guanosine–quartet structure is a potent inhibitor of human immunodeficiency virus envelope–mediated cell fusion", *Proc. Natl. Acad. Sci. USA*, 1994, 91, 1356–1360.

Yaida et al., "Distribution of phosphodiester and phosphorothioate oligonucleotides in rat brain after intraventricular and intrahippocampal administration determined by in situ hydridization", *Regul. Pept.*, 1995, 59, 193–199.

Yang et al., "Studies on the status of lysine residues in phospholipase $A_2$ from *Naja naja atra* (Taiwan cobra) snake venom", *Biochem. J.*, 1989, 262, 855–860.

Yokoyama et al., "A Convenient Method for C–Azanucleosides Synthesis", *J. Org. Chem.*, 1996, 61, 6079–6082.

Yuan et al., "Synthesis and Evaluation of Phospholipid Analogues as Inhibitors of Cobra Venom Phospholipase $A_2$", *J. Am. Chem. Soc.*, 1987, 109, 8071–8081.

Zimm et al., "Cerebrospinal Fluid Pharmacokinetics of Intraventricular and Intravenous Aziridinylbenzoquinone", *Cancer Research*, 1984, 44, 1698–1701.

Shaw, L.H., "Treatment of Intractable Cancer Pain by Electronically Controlled Parenteral Infusion of Analgesic Drugs", *Cancer*, 1993, 72, 3416–3425.

Zuckermann et al., "Efficient–Method for the Preparation of peptoids [Oligo(N–substituted glycines)] by Submonomer Solid–Phase Synthesis", *J. Am. Chem. Soc.*, 1992, 114, 10646–10647.

PCT International Search Report dated Jan. 22, 1999, 2 pages.

Bollinger, J.E. et al., "Lipophillic Hexadentate Aluminum, Gallium, Indium, and Iron Complexes of a New Phenolate–Derivatized Cyclohexanetriamine Ligand," *Inorganic Chem.*, 1994, 33(7), 1241–1242.

Rosen, T. et al., "A Convenient and Highly Chemoselective Method for the Reductive Acetylation of Azides," *J. Org. Chem.*, 1988, 53(7), 1580–1582.

I

IV

II

V

III

VI

VII

X

VIII

XI

IX

XII

XIII

XIV

XV

XVI

XVII

XVIII

Scaffold = a monocyclic or bicyclic amine scaffold

AMINE COMPOUNDS AND COMBINATORIAL LIBRARIES COMPRISING SAME

This Application is continuation-in-part of Ser. No. 08/924,851 Sep. 5, 1997.

FIELD OF THE INVENTION

This invention is directed to combinatorial libraries derived from monocyclic amine scaffolds which are derivatized, with building blocks, at various sites of diversity on the scaffold. Further, monocyclic scaffolds are converted into bicyclic scaffolds that are derivatized to afford additional combinatorial libraries of molecules. Also, the present invention is directed to the use of monocyclic and bicyclic amine scaffolds in the synthesis of molecules bearing more than one scaffold. These scaffolds are used to prepare diverse combinatorial libraries derived from the many building blocks used at multiple diversity sites.

BACKGROUND OF THE INVENTION

Traditional processes of drug discovery involve the screening of complex fermentation broths and plant extracts for a desired biological activity or the chemical synthesis of many new compounds for evaluation as potential drugs. The advantage of screening mixtures from biological sources is that a large number of compounds are screened simultaneously, in some cases leading to the discovery of novel and complex natural products with activity that could not have been predicted otherwise. The disadvantages are that many different samples must be screened and numerous purifications must be carried out to identify the active component, often present only in trace amounts. On the her hand, laboratory syntheses give unambiguous products, but the preparation of each new structure requires significant amounts of resources. Generally, the de novo design of active compounds based on the high resolution structures of enzymes has not been successful.

It is thus now widely appreciated that combinatorial libraries are useful per se and that such libraries and compounds comprising them have great commercial importance. Indeed, a branch of chemistry has developed to exploit the many commercial aspects of combinatorial libraries.

In order to maximize the advantages of each classical combinatorial approach, new strategies for combinatorial deconvolution have been developed independently by several groups. Selection techniques have been used with libraries of peptides (Geysen et al., *J. Immun. Meth.,* 1987, 102, 259; Houghten et al., *Nature,* 1991, 354, 84; Owens et al., *Biochem. Biophys. Res. Commun.,* 1991, 181, 402; Doyle, PCT WO 94/28424; Brennan, PCT WO 94/27719); nucleic acids (Wyatt et al., *Proc. Natl. Acad. Sci. U.S.A.,* 1994, 91, 1356; Ecker et al., *Nucleic Acids Res.,* 1993, 21, 1853); nonpeptides and small molecules (Simon et al., *Proc. Natl. Acad. Sci. U.S.A.,* 1992, 89, 9367; Zuckermann et al., *J. Am. Chem. Soc.,* 1992, 114, 10646; Bartlett et al., WO 91/19735; Ohlmeyer et al., *Proc. Natl. Acad. Sci. U.S.A.,* 1993, 90, 10922; DeWitt et al., *Proc. Natl. Acad. Sci. U.S.A.,* 1993, 90, 6909; Cody et al., U.S. Pat. No. 5,324,483; Houghten et al., PCT WO 94/26775; Ellman, U.S. Pat. No. 5,288,514; Still et al., WO 94/08051; Kauffman et al., PCT WO 94/24314; Carell et al., *Angew. Chem. Int. Ed. Engl.,* 1994, 33, 2059; Carell et al., *Angew. Chem. Int. Ed. Engel.,* 1994, 33, 2061; Lebl et al., WO 94/28028). A review of the above references reveals that the most advanced of these techniques are those for the selection of peptides and nucleic acids. Several groups are working on selection of heterocycles such as benzodiazepines.

The majority of the techniques reported to date involve iterative synthesis and screening of increasingly simplified subsets of oligomers such as peptides and oligonucleotides. Monomers or sub-monomers that have been utilized include amino acids, amino acid-like molecules, i.e. carbamate precursors, and nucleotides, both of which are bifunctional. Utilizing these techniques, libraries have been assayed for activity in either cell-based assays, or for binding and/or inhibition of purified protein targets.

However, the combinatorial chemical approach that has been more commonly utilized of late involves the use of a multifunctional scaffold bearing multiple diversity sites, and derivatizing these sites with varied building blocks to form libraries of diverse small molecule compounds. Libraries may be generated such that each individual compound may be synthesized and isolated separately, or synthesized and used as a mixture of several desirable compounds. A mixture of compounds may be obtained by using a mixture of scaffolds and/or building blocks. However, the synthesis of combinatorial libraries of discrete molecules (parallel synthesis) and of combinatorial pools of molecules (mixture synthesis or split-mix synthesis), and the screening of such libraries, have had significant limitations. These limitations include the need for selective protection and deprotection of desired reactive sites, limited experience with solid-phase chemical reactions, limited access to unique scaffolds for solid-phase synthesis, a small number of reactive functionalities on such scaffolds and often a small number of compound members of classes of building blocks that may be used for library generation. Acids, amines and amino acids are classes of building blocks that have been recognized to be of tremendous utility in combinatorial chemistry because of their reactivity with a variety of functional groups and the availability of large numbers of such compounds of diverse structures from commercial sources. Amino acids, for example, have been extensively used in the synthesis of small molecule combinatorial libraries. The use of amino acids as key building blocks in the construction of substituted heterocycle libraries has been practiced by several groups for exploring known pharmacophores, in cyclic ureas and in 'prospecting libraries' (Bunin and Ellman, *J. Am. Chem. Soc.,* 1992, 114, 10997; DeWitt et al., *Proc. Natl. Acad. Sci. USA,* 1993, 90, 6909; Nefzi, et al., *Tetrahedron Lett.,* 1997, 38, 931; Bartlett, et al., *Book of Abstracts,* 213th American Chemical Society National Meeting, San Francisco, 1997, American Chemical Society, Washington D.C., ORGN-273).

The diversity of a combinatorial library is represented by the inherent physical and chemical properties of each scaffold and building block used, the number of different building blocks used during each derivatization step, the physical and chemical properties of the bonds arising from the derivatization chemistry, and the interactions of the scaffold and building block chemistries. Taken together, these interactions provide a unique conformation for each individual compound in the combinatorial library.

In spite of advances in the synthesis of libraries of compounds, there still remains a need in the art for molecules which have fixed preorganized geometry which matches that of target biomolecules, including proteins and enzymes, nucleic acids, and lipids. It is also apparent that when targeting intervention of ligand-receptor interactions of large biomolecular targets that often have large binding sites, active sites, or binding epitopes, the inhibitors, agonists and antagonists desired will also need to be appropriately large. Thus, molecules larger than conventional small molecule drugs, such as oligomeric peptidomimetics, peptoids, and nucleotides, are considered candidates for screening for such activity. Oligomeric molecules derived from other, and often novel preorganized or rigid scaffolds may also be of value when targeting such ligand-receptor interactions. Combinatorially derived libraries should contain compounds which are rigid, yet still possess sufficient flexibility. It is preferable that this be achieved via automated synthesis on solid supports. It is also desirable to have use of scaffolds of some rigidity with multiple sites of diversity that may be selectively reacted via appropriate deprotection schemes during combinatorial library generation. Further, such scaffolds should offer diversity sites that may be reacted with a variety of building blocks, especially those classes of building blocks that comprise a large number of member compounds, such as acids, amines and amino acids.

SUMMARY OF THE INVENTION

In accordance with the present invention there are provided monocyclic amine compounds comprising a monocyclic amine scaffold bearing at least two sites of diversity, wherein at least one site of diversity is derived from a primary amino group that is exocyclic or is derived from a secondary amino group that is part of the cyclic structure of the scaffold. Also, the present invention provides libraries of monocyclic amine compounds. As used herein, 'library' means a collection of two or more compounds of the invention, as individual compounds or as mixtures. 'Library' also means a mixture of diastereomeric compounds.

Compounds of the present invention are of formula I, II, III, IV, V, or VI. It will be recognized by the art-skilled that the monocyclic amine compounds of the present invention bear chiral centers in their scaffolds. Thus, I, II, III, IV, V, and VI, all possess at least one or more chiral centers leading to enantiomeric, and often diastereomeric, molecules. The present invention includes all possible enantiomeric and diastereomeric structures of these monocyclic amine compounds. The monocyclic amine compounds and libraries of compounds of the present invention are of formula I, II, III, IV, V, or VI:

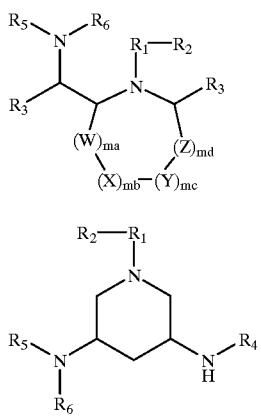

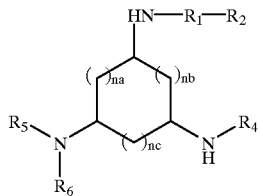

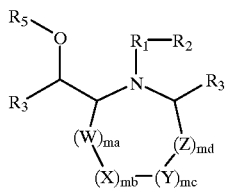

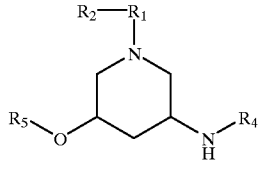

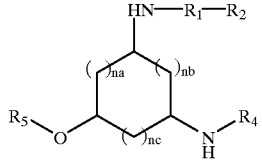

wherein:
$R_1$ and $R_{1'}$ are, individually $CH_2$, $CH(R_2)$, $C=O$, $C=S$, $S(=O)_2$, $C(=O)NH$, $C(=S)NH$ or $C(=O)O$;

$R_2$ is H, substituted or unsubstituted $C_1$–$C_{10}$ alkyl, substituted or unsubstituted $C_2$–$C_{10}$ alkenyl, substituted or unsubstituted $C_2$–$C_{20}$ alkynyl, substituted or unsubstituted $C_6$–$C_{14}$ aryl, substituted or unsubstituted $C_6$–$C_{14}$ aralkyl, substituted or unsubstituted $C_3$–$C_{14}$ cycloalkyl, substituted or unsubstituted $C_5$–$C_{14}$ fused cycloalkyl, substituted or unsubstituted $C_4$–$C_{14}$ heterocyclyl, substituted or unsubstituted $C_4$–$C_{14}$ heterocyclylalkyl, substituted or unsubstituted $C_4$–$C_{14}$ heteroaryl; substituted or unsubstituted $C_4$–$C_{14}$ heteroaralkyl, $CH(R_7)$—NH—$R_{7'}$ or $CH(R_7)$—NH—$R_{1'}$,—$R_3$; wherein the substituent groups are selected from the group consisting of acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy; or $R_1$ and $R_2$, together, are H, or an amino protecting group;

$R_3$ is H;
$R_4$ and $R_{4'}$ are, individually, H, $R_1$–$R_2$ or $R_{11}$–$R_{12}$;
$R_5$ is, H, substituted or unsubstituted $C_1$–$C_{10}$ alkyl, substituted or unsubstituted $C_2$–$C_{10}$ alkenyl, substituted or unsubstituted $C_2$–$C_{20}$ alkynyl, substituted or unsubstituted $C_6$–$C_{14}$ aryl, substituted or unsubstituted $C_6$–$C_{14}$ aralkyl, substituted or unsubstituted $C_3$–$C_{14}$ cycloalkyl, substituted or unsubstituted $C_5$–$C_{14}$ fused cycloalkyl, substituted or unsubstituted $C_4$–$C_{14}$ heterocyclyl, substituted or unsubstituted $C_4$–$C_{14}$ heterocyclylalkyl, substituted or unsubstituted $C_4$–$C_{14}$ heteroaryl; substituted or unsubstituted $C_4$–$C_{14}$ heteroaralkyl, —$R_1$–$R_2$, or $N(R_8)(R_9)$—$C(=O)$; wherein the substituent groups are selected from the group consisting of acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy;

$R_6$ is, H, substituted or unsubstituted $C_1$–$C_{10}$ alkyl, substituted or unsubstituted $C_2$–$C_{10}$ alkenyl, substituted or unsubstituted $C_2$–$C_{20}$ alkynyl, substituted or unsubstituted $C_6$–$C_{14}$ aryl, substituted or unsubstituted $C_6$–$C_{14}$ aralkyl, substituted or unsubstituted $C_3$–$C_{14}$ cycloalkyl, substituted or unsubstituted $C_5$–$C_{14}$ fused cycloalkyl, substituted or unsubstituted $C_4$–$C_{14}$ heterocyclyl, substituted or unsubstituted $C_4$–$C_{14}$ heterocyclylalkyl, substituted or unsubstituted $C_4$–$C_{14}$ heteroaryl; substituted or unsubstituted $C_4$–$C_{14}$ heteroaralkyl, —$R_1$-$R_2$, or —$C(=O)O$—$R_3$; wherein the substituent groups are selected from the group consisting of acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy; or $R_5$ and $R_6$, together, are $(CH_2)_{nd}$, $(CH_2)_{nd}$—O—$(CH_2)_{ne}$, $(CH_2)_{nd}$—N $(R_{10})$—$(CH_2)_{ne}$, or $(CH_2)_{nd}$—S—$(CH_2)_{ne}$, wherein $R_{10}$ is substituted or unsubstituted $C_1$–$C_{10}$ alkyl, substituted or unsubstituted $C_6$–$C_{14}$ aryl, or substituted or unsubstituted $C_6$–$C_{14}$ aralkyl, substituted or unsubstituted $C_4$–$C_{14}$ heteroaryl; substituted or unsubstituted $C_4$–$C_{14}$ heteroaralkyl;

$R_7$ is H, substituted or unsubstituted $C_1$–$C_{10}$ alkyl, substituted or unsubstituted $C_2$–$C_{10}$ alkenyl, substituted or unsubstituted $C_2$–$C_{20}$ alkynyl, substituted or unsubstituted $C_6$–$C_{14}$ aryl, substituted or unsubstituted $C_6$–$C_{14}$ aralkyl, substituted or unsubstituted $C_3$–$C_{14}$ cycloalkyl, substituted or unsubstituted $C_5$–$C_{14}$ fused cycloalkyl, substituted or unsubstituted $C_4$–$C_{14}$ heterocyclyl, substituted or unsubstituted $C_4$–$C_{14}$ heterocyclylalkyl, substituted or unsubstituted $C_6$–$C_{14}$ heteroaryl; substituted or unsubstituted $C_6$–$C_{14}$ heteroaralkyl, or groups such as those attached to the α-position of amino acids, wherein the substituent groups are selected from the group consisting of acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy;

$R_{7'}$ is H or an amino protecting group;

$R_8$ and $R_9$ are each, independently, H, substituted or unsubstituted $C_1$–$C_{10}$ alkyl, substituted or unsubstituted $C_2$–$C_{10}$ alkenyl, substituted or unsubstituted $C_2$–$C_{20}$ alkynyl, substituted or unsubstituted $C_6$–$C_{14}$ aryl, substituted or unsubstituted $C_6$–$C_{14}$ aralkyl, substituted or unsubstituted $C_3$–$C_{14}$ cycloalkyl, substituted or unsubstituted $C_5$–$C_{14}$ fused cycloalkyl, substituted or unsubstituted $C_4$–$C_{14}$ heterocyclyl, substituted or unsubstituted $C_4$–$C_{14}$ heterocyclylalkyl, substituted or unsubstituted $C_4$–$C_{14}$ heteroaryl; substituted or unsubstituted $C_4$–$C_{14}$ heteroaralkyl, wherein the substituent groups are selected from the group consisting of acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy; or $R_8$ and $R_9$, together, are $(CH_2)_{nd}$, $(CH_2)_{nd}$—O—$(CH_2)_{ne}$, $(CH_2)_{nd}$—N $(R_{10})$—$(CH_2)_{ne}$, or $(CH_2)_{nd}$—S—$(CH_2)_{ne}$, wherein $R_{10}$ is substituted or unsubstituted $C_1$–$C_{10}$ alkyl, substituted or unsubstituted $C_6$–$C_{14}$ aryl, or substituted or unsubstituted $C_6$–$C_{14}$ aralkyl, substituted or unsubstituted $C_4$–$C_{14}$ heteroaryl; substituted or unsubstituted $C_4$–$C_{14}$ heteroaralkyl;

$R_{11}$ is a linker moiety;

$R_{12}$ is a solid support;

W, X, Y, and Z are, independently, CH—$R_3$, O, S, CHN($R_4$) ($R_{4'}$), N—$R_1$-$R_2$ or CH—CH($R_3$)N($R_5$) ($R_6$);

ma, mb, mc and md are, independently, 0, 1, 2, or 3;

na, nb and nc are each, independently, 0 to 2, wherein the sum of na, nb and nc is from 0 to 5; and nd and ne are each, independently, 1 to 4; provided that said compound is not:

N-[1-[1,1'-biphenyl]-4-ylsulfonyl)-5-[[[4-[(2,4-dioxo-5-thiazolidinylidene)methyl]bezoy]amino]methyl]-3-pyrrolidinyl]-4-[(3-oxo-2(3H)-isothizolyl)methyl]-, [3S-[3.alpha.,5.alpha.(E)]]-benzamide; or N-[(4-amino-2-pyrrolidinyl) methyl]-3-methyl-L-valyl-L-1,2,3,4-tetrahydro-3-isoquinolinecarbonyl-, (2S-trans)-, tris (trifluoroacetate)-L-glutamine; or N-[[1-[(1,1-dimethylethoxy) carbonyl]-4-[[(1,1-dimethyletyhoxy) carbonyl]amino]-2-pyrrolidinyl]methyl]-3-methyl-L-1,2,3,4-tetrahydro-3-isoquinolinecarbonyl-, (2S-trans)-, tris (trifluoroacetate)- L-glutamine; or N-[(4-amino-2-pyrrolidinyl) methyl]-3-methyl-L-valyl-L-1,2,3,4-tetrahydro-3-isoquinolinecarbonyl-, (2S-trans)- trifluoroacetate L-glutamine; or N-[(4-amino-2-pyrrolidinyl) methyl]-3-methyl-L-valyl-L-1,2,3,4-tetrahydro-3-isoquinolinecarbonyl-, (2S-trans)-L-glutamine; or 3-[[[1-[(4-chlorophenyl) sulfonyl]-4-[[(4-chlorophenyl) sulfonyl]amino]-2-pyrrolidinyl]methyl]amino]-, (2S-trans)-benzoic acid; or 4-azido-2-(azidomethyl)-1-(p-tolylsulfonyl)-, (−)-pyrrolidine.

This invention also provides methods for preparing the monocyclic amine compounds of formula I, II, III, IV, V and VI. Further, in accordance with this invention, there are provided methods for preparing libraries of monocyclic amine compounds, comprising:

(a) selecting a monocyclic amine scaffold of formula VII, VIII, IX, X, XI or XII:

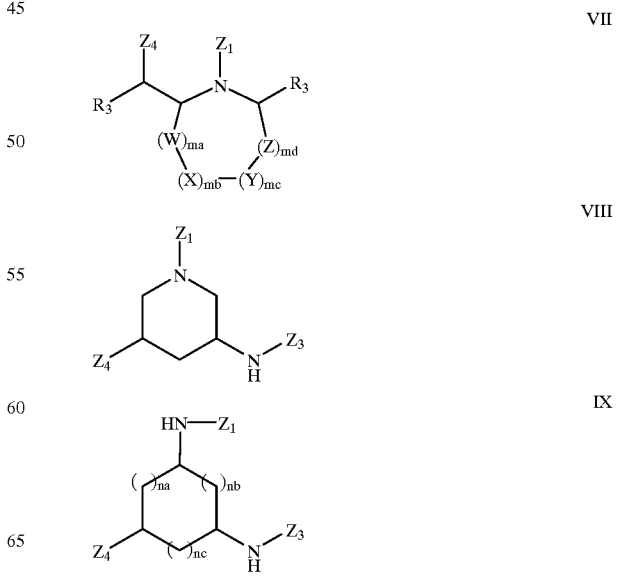

-continued

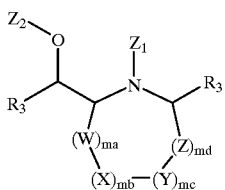

X

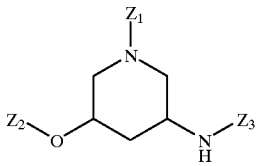

XI

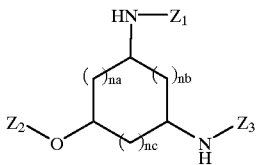

XII wherein:
Z$_1$ is an amino protecting group;
Z$_2$ is a hydroxyl protecting group;
Z$_3$ is H;
Z$_4$ is N$_3$, N—Pg or NH—Pg, wherein Pg is an amino protecting group;
R$_3$ is H, substituted or unsubstituted C$_1$–C$_{10}$ alkyl, substituted or unsubstituted C$_2$–C$_{10}$ alkenyl, substituted or unsubstituted C$_2$–C$_{20}$ alkynyl, substituted or unsubstituted C$_6$–C$_{14}$ aryl, substituted or unsubstituted C$_6$–C$_{14}$ aralkyl, substituted or unsubstituted C$_3$–C$_{14}$ cycloalkyl, substituted or unsubstituted C$_5$–C$_{14}$ fused cycloalkyl, substituted or unsubstituted C$_4$–C$_{14}$ heterocyclyl, substituted or unsubstituted C$_4$–C$_{14}$ heterocyclylalkyl, substituted or unsubstituted C$_4$–C$_{14}$ heteroaryl; substituted or unsubstituted C$_4$–C$_{14}$ heteroaralkyl, wherein the substituent groups are selected from the group consisting of acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy;
W, X, Y, and Z are, independently, CH—R$_3$, O, S, CH—NH—Z$_3$, N—Z$_1$, CH—O—Z$_2$ or CH—CH(R$_3$)Z$_4$; and
ma, mb, mc and md are, independently, 0, 1, 2, or 3;
(b) attaching said monocyclic amine scaffold to a solid support via a hydroxy or amino group to form a solid support-bound scaffold (i.e. Z$_3$ is a solid support or a linker moiety attached to a solid support);
(c) treating said amino protecting group with a deprotection reagent to form a free amino group (i.e. Z$_1$ is H);
(d) derivatizing the free amino group with a suitable building block;
(e) treating said hydroxyl protecting group, if present, with a deprotecting reagent to form a free hydroxyl group (i.e. Z$_2$ is H), or reduction of the azido group to form a free amino group;
(f) reacting the free hydroxyl or amino group with a building block or activating reagent;
(g) derivatizing the activated hydroxyl or amino group with another suitable building block; and
(h) cleaving the substituted monocyclic amine compound from the solid support.

It will be recognized by the art-skilled that all the classes of the monocyclic amine scaffolds of the present invention bear chiral centers. Thus scaffolds, VII, VIII, IX, X, XI and XII, all possess at least one or more chiral centers in their structure leading to enantiomeric, and often diastereomeric, compounds. The present invention includes all possible enantiomeric and diastereomeric structures of these monocyclic amine scaffolds.

The present invention also provides compounds comprising a bicyclic scaffold bearing at least two sites of diversity, wherein the bicyclic scaffold is readily generated from the aforementioned monocyclic amine scaffold via intramolecular cyclization. Of the many sites of diversity on the bicyclic amine scaffolds of the present invention, at least one site of diversity is derived from a primary amino group that is exocyclic or from a secondary amino group that is part of the cyclic structure of the scaffold. Also, the present invention provides libraries of bicyclic amine compounds derived from bicyclic scaffolds. Compounds of the libraries of the present invention are of formula XIII, XIV, or XV. It will be recognized by the art-skilled that the bicyclic amine compounds of the present invention bear chiral centers. Thus, compounds of formula XIII, XIV and XV, all possess at least one or more chiral centers in their scaffold structure leading to enantiomeric, and often diastereomeric, compounds. The present invention includes all possible enantiomeric and diastereomeric structures of these bicyclic amine compounds, except where the structure explicitly shows a specific stereochemistry. The bicyclic amine compounds and libraries of compounds of the present invention are of formula XIII, XIV, or XV:

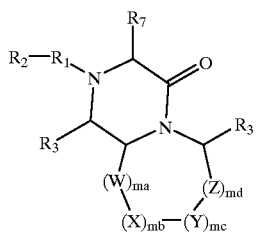

XIII

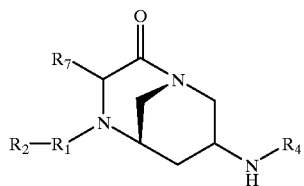

XIV

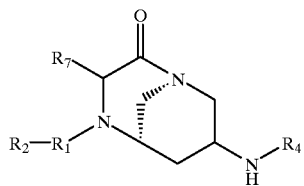

XV wherein:
R$_1$ and R$_{1'}$ are, individually CH$_2$, CH(R$_2$), C=O, C=S, S(=O)$_2$, C(=O)NH, C(=S)NH or C(=O)O;
R$_2$ is H, substituted or unsubstituted C$_1$–C$_{10}$ alkyl, substituted or unsubstituted C$_2$–C$_{10}$ alkenyl, substituted or unsubstituted C$_2$–C$_{20}$ alkynyl, substituted or unsubstituted C$_6$–C$_{14}$ aryl, substituted or unsubstituted C$_6$–C$_{14}$ aralkyl, substituted or unsubstituted C$_3$–C$_{14}$ cycloalkyl, substituted or unsubstituted $C_5$–$C_{14}$ fused cycloalkyl, substituted or unsubstituted $C_4$–$C_{14}$ heterocyclyl, substituted or unsubstituted $C_4$–$C_{14}$ heterocyclylalkyl, substituted or unsubstituted $C_4$–$C_{14}$ heteroaryl; substituted or unsubstituted $C_4$–$C_{14}$ heteroaralkyl, CH($R_7$)—NH—$R_7$, or CH($R_7$)—NH—$R_1'$—$R_3$; wherein the substituent groups are selected from the group consisting of acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy; or $R_1$ and $R_2$, together, are H, or an amino protecting group;

$R_3$ is H, substituted or unsubstituted $C_1$–$C_{10}$ alkyl, substituted or unsubstituted $C_2$–$C_{10}$ alkenyl, substituted or unsubstituted $C_2$–$C_{20}$ alkynyl, substituted or unsubstituted $C_6$–$C_{14}$ aryl, substituted or unsubstituted $C_6$–$C_{14}$ aralkyl, substituted or unsubstituted $C_3$–$C_{14}$ cycloalkyl, substituted or unsubstituted $C_5$–$C_{14}$ fused cycloalkyl, substituted or unsubstituted $C_4$–$C_{14}$ heterocyclyl, substituted or unsubstituted $C_4$–$C_{14}$ heterocyclylalkyl, substituted or unsubstituted $C_4$–$C_{14}$ heteroaryl; substituted or unsubstituted $C_4$–$C_{14}$ heteroaralkyl, wherein the substituent groups are selected from the group consisting of acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy;

$R_4$ and $R_{4'}$ are, individually, is H, N($R_8$)($R_9$)C(=O), $R_1$–$R_2$ or $R_{11}$–$R_{12}$;

$R_7$ is H, substituted or unsubstituted $C_1$–$C_{10}$ alkyl, substituted or unsubstituted $C_2$–$C_{10}$ alkenyl, substituted or unsubstituted $C_2$–$C_{20}$ alkynyl, substituted or unsubstituted $C_6$–$C_{14}$ aryl, substituted or unsubstituted $C_6$–$C_{14}$ aralkyl, substituted or unsubstituted $C_3$–$C_{14}$ cycloalkyl, substituted or unsubstituted $C_5$–$C_{14}$ fused cycloalkyl, substituted or unsubstituted $C_4$–$C_{14}$ heterocyclyl, substituted or unsubstituted $C_4$–$C_{14}$ heterocyclylalkyl, substituted or unsubstituted $C_6$–$C_{14}$ heteroaryl; substituted or unsubstituted $C_6$–$C_{14}$ heteroaralkyl, or groups such as those attached to the α-position of naturally-occurring or non-naturally occurring amino acids of D- or L-configuration, wherein the substituent groups are selected from the group consisting of acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy;

$R_{7'}$ is H or an amino protecting group;

$R_8$ and $R_9$ are each, independently, H, substituted or unsubstituted $C_1$–$C_{10}$ alkyl, substituted or unsubstituted $C_2$–$C_{10}$ alkenyl, substituted or unsubstituted $C_2$–$C_{20}$ alkynyl, substituted or unsubstituted $C_6$–$C_{14}$ aryl, substituted or unsubstituted $C_6$–$C_{14}$ aralkyl, substituted or unsubstituted $C_3$–$C_{14}$ cycloalkyl, substituted or unsubstituted $C_5$–$Cl_4$ fused cycloalkyl, substituted or unsubstituted $C_4$–$C_4$ heterocyclyl, substituted or unsubstituted $C_4$–$C_{14}$ heterocyclylalkyl, substituted or unsubstituted $C_4$–$C_{14}$ heteroaryl; substituted or unsubstituted $C_4$–$C_{14}$ heteroaralkyl, wherein the substituent groups are selected from the group consisting of acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy; or $R_8$ and $R_9$, together, are $(CH_2)_{nd}$, $(CH_2)_{nd}$—O—$(CH_2)_{ne}$, $(CH_2)_{nd}$—N($R_{10}$)—$(CH_2)_{ne}$, or $(CH_2)_{nd}$—S—$(CH_2)_{ne}$, wherein $R_{10}$ is substituted or unsubstituted $C_1$–$C_{10}$ alkyl, substituted or unsubstituted $C_6$–$C_{14}$ aryl, or substituted or unsubstituted $C_6$–$C_{14}$ aralkyl, substituted or unsubstituted $C_4$–$C_{14}$ heteroaryl; substituted or unsubstituted $C_4$–$C_{14}$ heteroaralkyl;

$R_{11}$ is a linker moiety; and $R_{12}$ is a solid support;

W, X, Y, and Z are, independently, CH—$R_3$, O, S, CHN($R_4$) ($R_{4'}$), N—$R_1$-$R_2$, CH—O—$R_4$ or CH—CH($R_3$) N($R_5$) ($R_6$); and ma, mb, mc and md are, independently, 0, 1, 2, or 3.

This invention also provides methods for preparing the bicyclic amine compounds of formula XIII, XIV, and XV. Further, in accordance with this invention, there are provided methods for preparing libraries of bicyclic amine compounds comprising:

(a) selecting a monocyclic amine scaffold of formula X, XI, or XII:

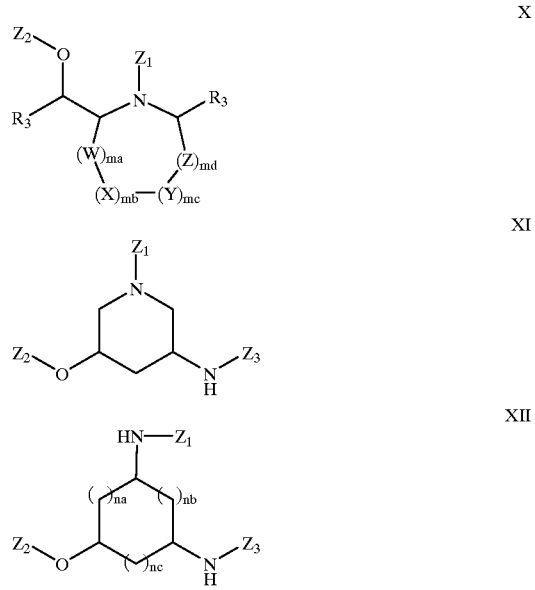

wherein:

$Z_1$ is an amino protecting group;

$Z_2$ is a hydroxyl protecting group;

$Z_3$ is H;

$Z_4$ is $N_3$, N—Pg or NH—Pg, wherein Pg is an amino protecting group;

$R_3$ is H, substituted or unsubstituted $C_1$–$C_{10}$ alkyl, substituted or unsubstituted $C_2$–$C_{10}$ alkenyl, substituted or unsubstituted $C_2$–$C_{20}$ alkynyl, substituted or unsubstituted $C_6$–$C_{14}$ aryl, substituted or unsubstituted $C_6$–$C_{14}$ aralkyl, substituted or unsubstituted $C_3$–$C_{14}$ cycloalkyl, substituted or unsubstituted $C_5$–$C_{14}$ fused cycloalkyl, substituted or unsubstituted $C_4$–$C_{14}$ heterocyclyl, substituted or unsubstituted $C_4$–$C_{14}$ heterocyclylalkyl, substituted or unsubstituted $C_4$–$C_{14}$ heteroaryl; substituted or unsubstituted $C_4$–$C_{14}$ heteroaralkyl, wherein the substituent groups are selected from the group consisting of acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy;

W, X, Y, and Z are, independently, CH—$R_3$, CH—NH—$Z_3$, N—$Z_1$, CH—O—$Z_2$ or CH—CH($R_3$)$Z_4$; and ma, mb, mc and md are, independently, 0, 1, 2, or 3;

(b) attaching said monocyclic amine scaffold to a solid support via a hydroxy or amino group to form a solid support bound scaffold (i.e. $Z_3$ is a solid support or a linker moiety attached to a solid support);

(c) reacting the amino group, if present, that attaches the scaffold to the solid support with a suitable building block;

(d) treating said amino protecting group of said scaffold with a deprotection reagent to form a free amino group (i.e. $Z_1$ is H);

(e) derivatizing the free amino group with an a-amino acid building block having an N-terminus protecting group;

(f) deprotecting the N-terminus protecting group with a deprotection reaction to form an unmasked amine;

(g) reacting the unmasked amine with an appropriate activating reagent to form an activated amino group;

(h) treating said hydroxyl protecting group of said scaffold with a deprotection reagent to form a free hydroxy group (i.e. $Z_2$ is H);

(i) subjecting the support bound intermediate of step (h) to cyclization conditions such that the free hydroxy group reacts with the activated amino group from step (g) to generate a bicyclic amine scaffold of formula XVI, XVII or XVIII:

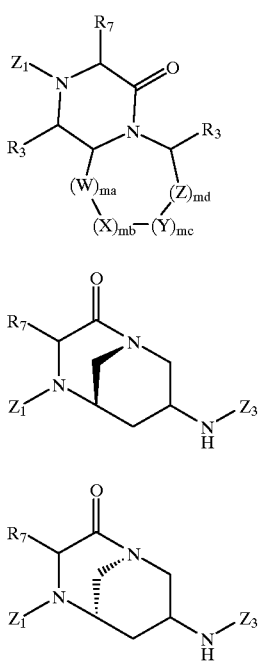

wherein:
$Z_1$ is an amino protecting group;
$Z_3$ is H;
$Z_4$ is $N_3$, N—Pg or NH—Pg, wherein Pg is an amino protecting group;
$R_3$ is H, substituted or unsubstituted $C_1$–$C_{10}$ alkyl, substituted or unsubstituted $C_2$–$C_{10}$ alkenyl, substituted or unsubstituted $C_2$–$C_{20}$ alkynyl, substituted or unsubstituted $C_6$–$C_{14}$ aryl, substituted or unsubstituted $C_6$–$C_{14}$ aralkyl, substituted or unsubstituted $C_3$–$Cl_4$ cycloalkyl, substituted or unsubstituted $C_5$–$C_{14}$ fused cycloalkyl, substituted or unsubstituted $C_4$–$C_{14}$ heterocyclyl, substituted or unsubstituted $C_4$–$C_{14}$ heterocyclylalkyl, substituted or unsubstituted $C_4$–$C_{14}$ heteroaryl; substituted or unsubstituted $C_4$–$C_{14}$ heteroaralkyl, wherein the substituent groups are selected from the group consisting of acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy;

$R_7$ is H, substituted or unsubstituted $C_1$–$C_{10}$ alkyl, substituted or unsubstituted $C_2$–$C_{10}$ alkenyl, substituted or unsubstituted $C_2$–$C_{20}$ alkynyl, substituted or unsubstituted $C_6$–$C_{14}$ aryl, substituted or unsubstituted $C_6$–$C_{14}$ aralkyl, substituted or unsubstituted $C_3$–$C_{14}$ cycloalkyl, substituted or unsubstituted $C_5$–$C_{14}$ fused cycloalkyl, substituted or unsubstituted $C_4$–$C_{14}$ heterocyclyl, substituted or unsubstituted $C_4$–$C_{14}$ heterocyclylalkyl, substituted or unsubstituted $C_6$–$C_{14}$ heteroaryl; substituted or unsubstituted $C_6$–$C_{14}$ heteroaralkyl, or groups such as those attached to the α-position of naturally-occurring or non-naturally occurring amino acids of D- or L-configuration, wherein the substituent groups are selected from the group consisting of acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy;

W, X, Y, and Z are, independently, CH—$R_3$, O, S, CH—NH—$Z_3$, N—$Z_1$, CH—O—$Z_2$ or CH—CH($R_3$)$Z_4$; and ma, mb, mc and md are, independently, 0, 1, 2, or 3;

(j) removing the activating group attached to the amino group of the bicyclic amine scaffold to form a free amino group;

(k) reacting the free amino group with a suitable building block; and (l) cleaving the substituted bicyclic amine compound from the solid support.

It will be recognized by the art-skilled that the bicyclic amine scaffolds and bicyclic amine compounds of the present invention bear chiral centers. Thus compounds of formula XIII, XIV and XV, possess at least one or more chiral centers in their structure leading to enantiomeric and often diastereomeric compounds. The present invention includes all possible enantiomeric and diastereomeric structures of the bicyclic amine molecules.

In an additional aspect, the present invention also provides oligomeric amine compounds comprising at least two or more monocyclic amine or bicyclic amine scaffolds, wherein the scaffolds are connected to each other via a variety of covalent inter-scaffold linkages including, but not limited to carbamate, alkylamine, urea, thiourea and amindine. These oligomeric amine compounds bear multiple sites of diversity that arise not only from the diversity sites offered by their component scaffolds, but also at sites that are created from the nature of the covalent inter-scaffold linkage. Also, the present invention provides libraries of such oligomeric compounds derived from multiple scaffolds. It will be recognized by the art-skilled that the oligomeric amine compounds of the present invention bear chiral centers. Thus oligomeric amine compounds of the present invention possess multiple chiral centers in their component scaffolds leading to enantiomeric, and often diastereomeric, compounds. The present invention includes all possible enantiomers and diastereomers of these compounds.

This invention also provides methods for preparing the oligomeric amine compounds. Further, in accordance with this invention, there are provided methods for preparing libraries of oligomeric amine compounds, comprising:

(a) selecting a monocyclic amine scaffold of formula VII, VIII, IX, X, XI, or XII:

VII
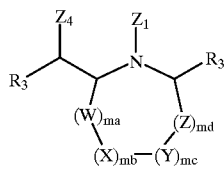

VIII
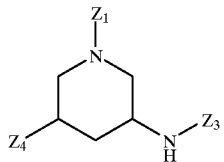

IX
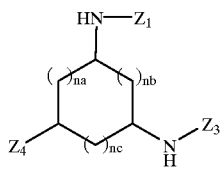

X
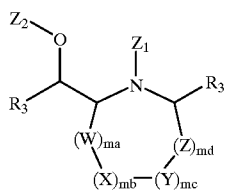

XI
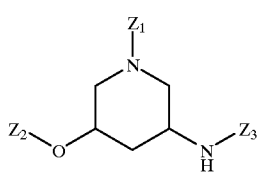

XII
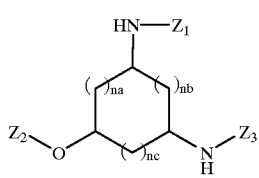

wherein:
$Z_1$ is an amino protecting group;
$Z_2$ is a hydroxyl protecting group;
$Z_3$ is H;
$Z_4$ is $N_3$, N—Pg or NH—Pg, wherein Pg is an amino protecting group;
$R_3$ is H, substituted or unsubstituted $C_1$–$C_{10}$ alkyl, substituted or unsubstituted $C_2$–$C_{10}$ alkenyl, substituted or unsubstituted $C_2$–$C_{20}$ alkynyl, substituted or unsubstituted $C_6$–$C_{14}$ aryl, substituted or unsubstituted $C_6$–$C_{14}$ aralkyl, substituted or unsubstituted $C_3$–$C_{14}$ cycloalkyl, substituted or unsubstituted $C_5$–$C_{14}$ fused cycloalkyl, substituted or unsubstituted $C_4$–$C_{14}$ heterocyclyl, substituted or unsubstituted $C_4$–$C_{14}$ heterocyclylalkyl, substituted or unsubstituted $C_4$–$C_{14}$ heteroaryl; substituted or unsubstituted $C_4$–$C_{14}$ heteroaralkyl, wherein the substituent groups are selected from the group consisting of acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy;

W, X, Y, and Z are, independently, CH—$R_3$, O, S, CH—NH—$Z_3$, N—$Z_1$, CH—O—$Z_2$ or CH—CH($R_3$)$Z_4$; and ma, mb, mc and md are, independently, 0, 1, 2, or 3;

(b) attaching said monocyclic amine scaffold to a solid support to form a solid support-bound scaffold;

(c) derivatizing said scaffold with a suitable building block to form a substituted scaffold, or effecting a cyclization reaction to form a bicyclic scaffold;

(d) removing the amino protecting group or hydroxy protecting group of said scaffold from step (c) with a deprotection reagent to form a free amino or hydroxy group;

(e) activating the amino or hydroxy group with an appropriate activating reagent;

(f) reacting the intermediate from step (e) with another monocyclic amine scaffold;

(g) repeating steps (c), (d), (e) and (f) in sequence, as many times as desired to form an oligomeric amine compound; and (h) cleaving said oligomeric amine compound from the solid support.

It will be recognized by the art-skilled that these oligomeric amine compounds of the present invention bear at least one or more chiral centers in their structure leading to enantiomeric, and often diastereomeric, compounds. The present invention includes all possible enantiomers and diastereomers of these oligomeric amine compounds.

DETAILED DESCRIPTION OF THE INVENTION

Figure 1:
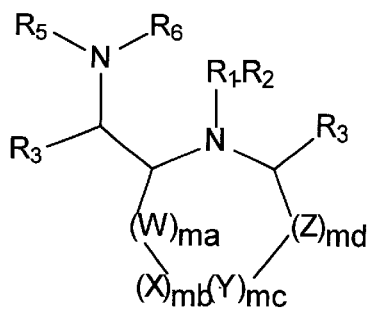
FIG. 1 is a schematic showing the formulae of monocyclic amine compounds.
Figure 1:
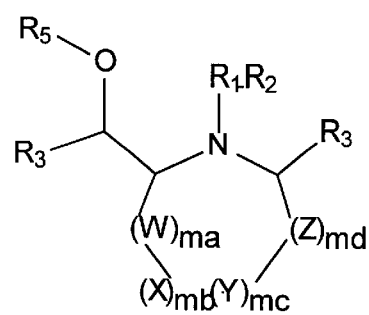
Figure 1:
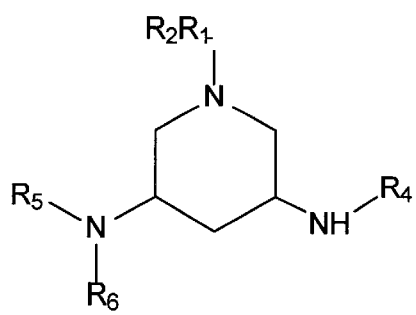
Figure 1:
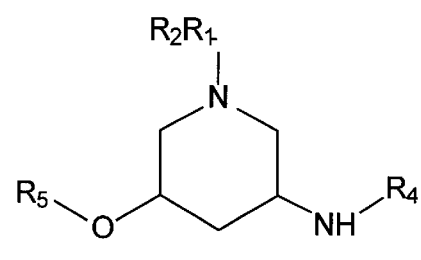
Figure 1:
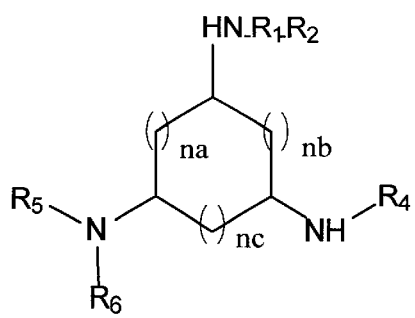
Figure 1:
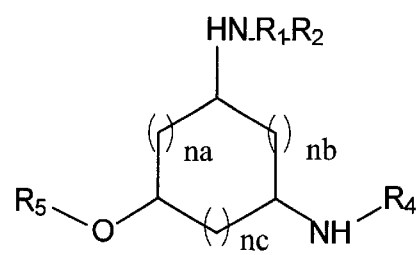
Figure 2:
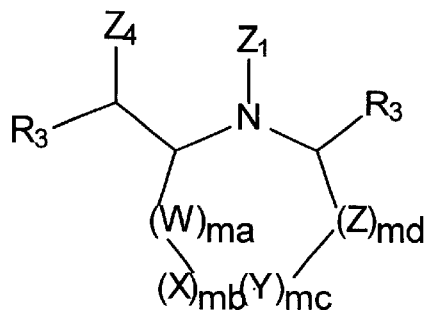
FIG. 2 is a schematic showing the formulae of monocyclic amine scaffolds used to synthesize libraries of monocyclic, bicyclic and oligomeric amine compounds.
Figure 2:
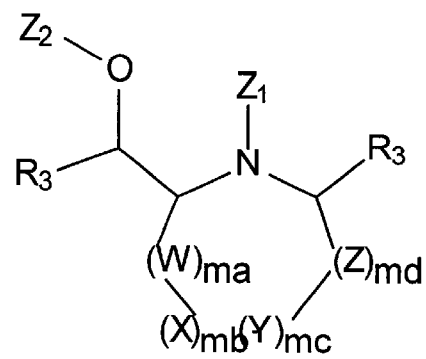
Figure 2:
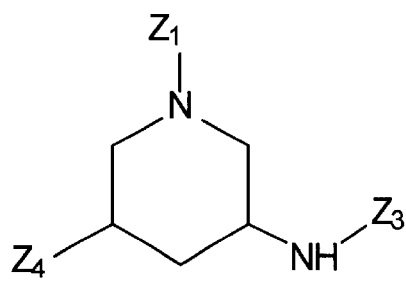
Figure 2:
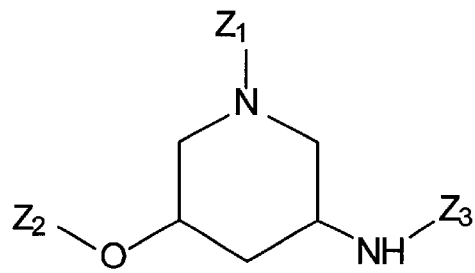
Figure 2:
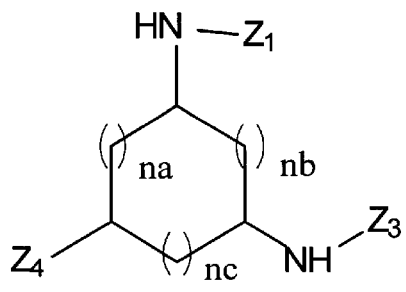
Figure 2:
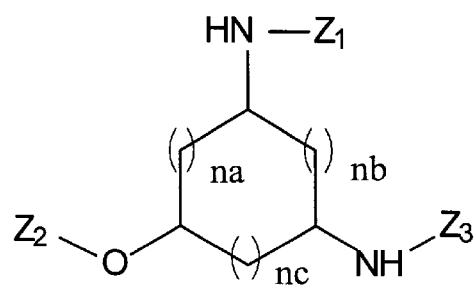
Figure 3:
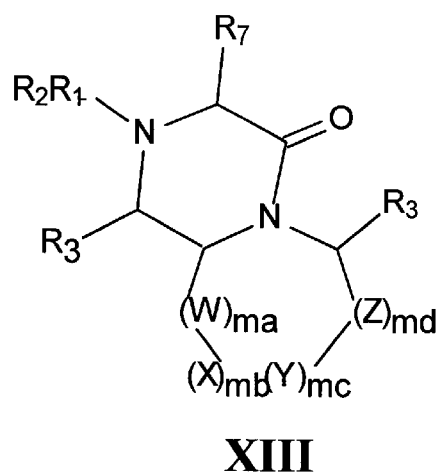
FIG. 3 is a schematic showing the formulae of bicyclic amine compounds.
Figure 3:
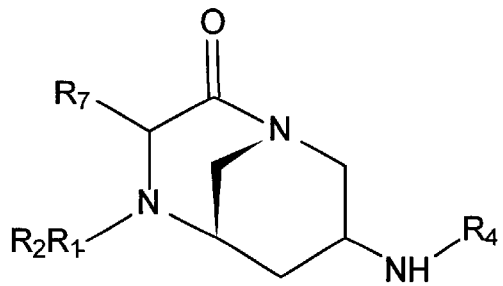
Figure 3:
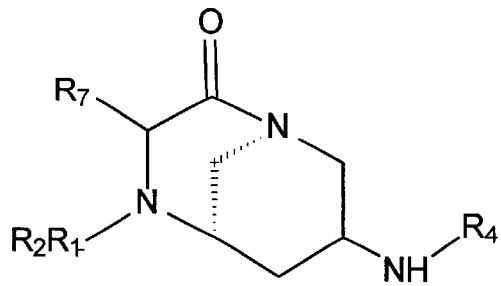
Figure 4:
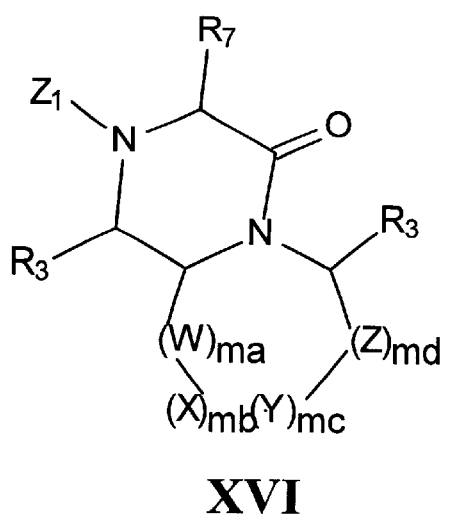
FIG. 4 is a schematic showing the formulae of bicyclic amine scaffolds.
Figure 4:
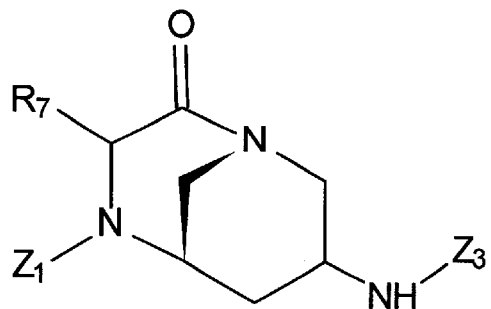
Figure 4:
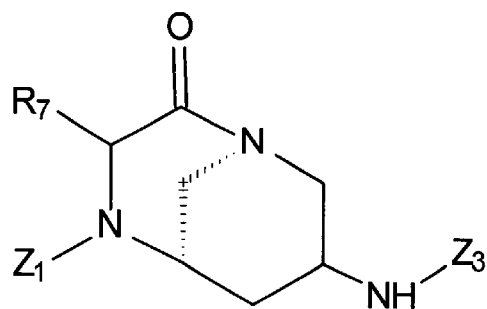
Figure 5:
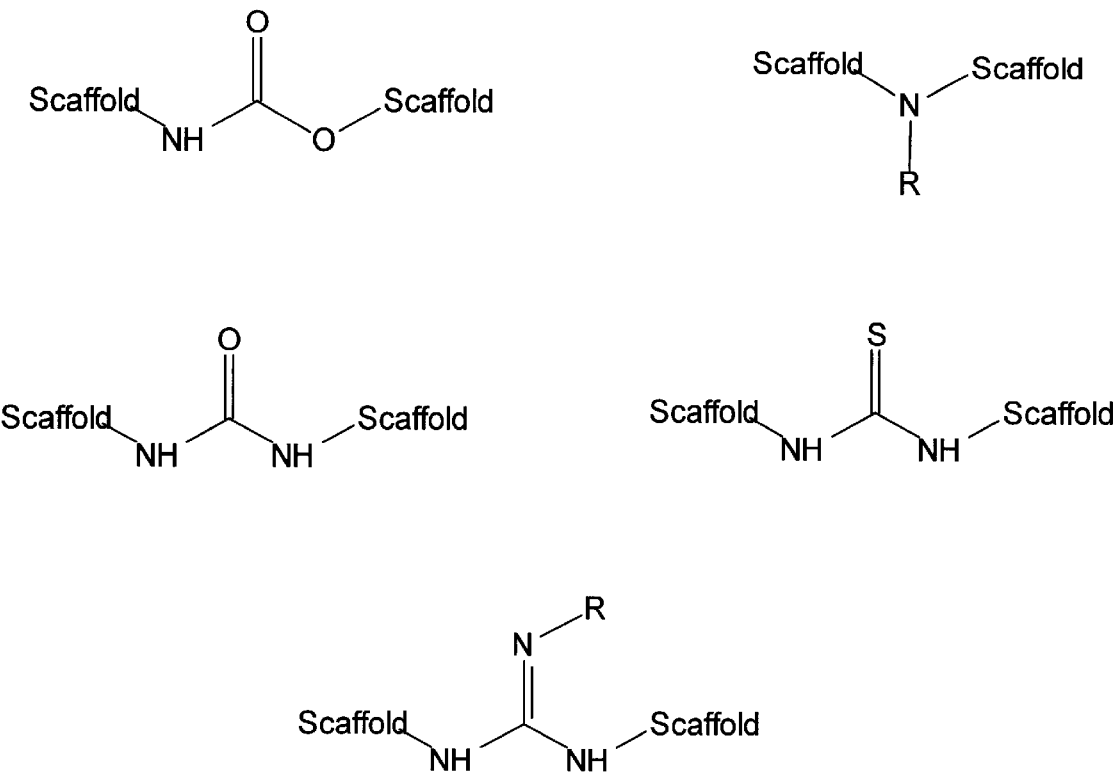
FIG. 5 is a schematic showing the general structure of oligomeric amine compounds.

The present invention is directed to monocyclic, and bicyclic amine compounds derived from monocyclic amine scaffolds, and combinatorial libraries thereof. The present invention also provides oligomeric amine compounds comprising two or more monocyclic or bicyclic amine scaffolds connected via covalent inter-scaffold linkages.

Monocyclic Amine Compounds and Libraries

As used in the context of the present invention, a monocyclic amine is a cyclic compound bearing at least one amino reactive center as part of the cyclic ring structure, or a cyclic compound that bears all reactive diversity sites as pendant groups from its cyclic scaffold. Typically, monocyclic amine scaffolds are cyclic compounds bearing three reactive centers, also known as diversity sites or combinatorial sites. At least one of these diversity sites is an amino group that may or may not be part of the cyclic structure of the scaffold and is protected by a protecting group ($Z_1$). The second diversity site may be an amino group or a hydroxy group. If the scaffold comprises another amino diversity site, it is differentially protected with another protecting group ($Z_2$), which may be cleaved from the scaffold under conditions that do not affect the first amino protecting group ($Z_1$). The third diversity site on the monocyclic amine scaffolds of the present invention, may either be a protected hydroxy group or a masked amino group, such as an azido group. All three diversity sites are protected or masked in such a fashion that the protection and deprotection schemes are orthogonal in nature, i.e. one may be deprotected selectively without affecting the integrity of any of the other masking groups.

The present invention provides a method for unmasking the amino protecting group and attaching the unmasked amino group, via a cleavable linker to a solid support. Further chemistry may be performed at this solid support bound amino group through the use of appropriate reactive building blocks. A second amino group may next be exposed via removal of its protecting group and the compound further combinatorialized via reaction with appropriate building blocks. Finally, the third combinatorial site is unmasked via cleavage of the hydroxyl protecting group or reduction of the azido group, to reveal reactive hydroxy and amino groups, respectively. These groups are reacted further with additional building blocks to yield further diversity in the library of monocyclic amine molecules so synthesized. Each site of diversity is exploited by the choice of a variety of appropriate building blocks of varied chemical structures which are reacted at the amino or hydroxyl combinatorial sites to afford the structurally diverse, substituted monocyclic amine compounds of the present invention.

Monocyclic amine compounds of formula I, II, III, IV, V, and VI of the present invention bear multiple chiral centers in their structure. This leads to the possibility of structurally distinct molecules that are enantiomers or diastereomers. The present invention includes all possible enantiomers and diastereomers of these monocyclic amine compounds. The monocyclic amine compounds and libraries of these monocyclic amine compounds of the present invention not only include individual, chirally pure, compounds, but also include mixtures of enantiomeric and diastereomeric compounds. Such stereochemical mixtures of chiral monocyclic amine-derived compounds of the present invention may be used for a variety of purposes, including screening for biological activity in a variety of biochemical and cellular assays.

Synthesis of some of the monocyclic amine scaffolds of the invention is accomplished via similar paths starting from the inexpensive trans-4-hydroxy-L-proline, which provides the desired chiral centers. Intentional racemization of the C-2 center of trans-4-hydroxy-L-proline affords both stereoisomers at C-2 thereby allowing simultaneous exploration of the biological effects of both stereoisomers.

To prepare the pyrrolidine scaffolds of formula VII, trans-4-hydroxy-L-proline was epimerized by treatment with 2M Ba(OH)$_2$ at 200° C. for 5 hours followed by acidification to pH 4 with 2M sulfuric acid, to provide a 1:1 mixture of diastereomers of 4-hydroxy-proline. The racemized 2-carboxylate was esterified with trimethylsilyl chloride (TMS-Cl) in methanol and then treated with TEOC-N-hydroxysuccinimide so as to protect the pyrrolidine nitrogen atom with a TEOC group and afford 1-TEOC-2-carbomethoxy-(4R)-hydroxy-pyrrolidine. The overall yield of these transformations was 95%. Subsequent mesylation of the 4-hydroxy group, followed by azide inversion at 80° C. in DMF and finally simultaneous reduction of the ester and azide using lithium borohydride in THF gave the 1-TEOC-2-hydroxymethyl-4-amino-pyrrolidine. Trifluoroacetylation of the 4-amino group, followed by sequential mesylation of the free hydroxy group and azide displacement afforded an excellent yield of a diastereomeric mixture of the pyrrolidine scaffold, wherein the stereochemistry at the 4-positions in both is S, while one is 2R and the other 2S. Alternatively, the 1-TEOC-2-carbomethoxy-(4R)-hydroxy-pyrrolidine intermediate, synthesized as described above, may be subjected to a double inversion sequence, using bromotriphenylphosphonium bromide to prepare the corresponding 4-bromo derivative of inverted configuration, followed by treatment with sodium azide to give the 4S-azido derivative. Finally reduction with lithium borohydride, followed sequentially by trifluoroacetylation of the 4-amino group, mesylation and displacement with azide affords a mixture of the two other diastereomers of the pyrrolidine scaffold, wherein the stereochemistry at the 4-position in both diastereomers is R, while one diastereomer is 2R and the other 2S.

The synthesis of the piperidine scaffolds of formula VII, follows a strategy similar to that described above. The epimerized 4-hydroxy-proline, as prepared above, is esterified, then protected at the proline nitrogen-atom using p-methoxy-benzyl chloride (PMB) at reflux in tetrahydrofuran (THF) and subsequently at the 4-hydroxy group using TBDMS Chloride in the presence of imidazole in DMF. Reduction of the carboxylate ester with lithium borohydride in THF at reflux, followed by trifluoroacetylation at −78° C. to room temperature in THF and then ring expansion using 3 equivalents of triethylamine afforded the 1-PMB-3R-O-TBDMS-piperidin-5-ol. The 5-position is a racemic mixture of both stereoisomers. Hydrogenation to remove the PMB group, followed by reaction with TEOC-N-hydroxysuccinimide afforded the 1-TEOC-3R-O-TBDMS-piperidin-5-ol. Mesylation of the free 5-hydroxy group followed by inversion of stereochemistry using sodium azide, reduction of the azide and trifluoroacetylation of the intermediate 5-amino group afforded the 1-TEOC-3R-O-TBDMS-5-trifluoroacetylamino-piperidine. From this compound selective desilylation followed by mesylation and azide inversion afforded a piperidine scaffold wherein the stereochemistry at the 3 position in both diastereomers is S, while one diastereomer is 5R and the other is 5S. Alternatively, desilylation, followed by a double inversion sequence that uses bromotriphenylphosphonium bromide, followed by sodium azide treatment, gave a piperidine scaffold of formula VII with 3R stereochemistry but both isomers at position 5.

Other scaffolds may be synthesized following similar synthetic strategies, starting with the appropriate cyclic amines.

The monocyclic amine scaffolds of the invention may be used in the synthesis of diverse monocyclic amine compounds, and libraries of such compounds, through selective deprotection or unmasking of the reactive amino or hydroxy groups and their reactions with appropriate building blocks. These chemical transformations may be performed either in solution or via solid-phase chemistry.

Typically, a monocyclic amine scaffold of formula VII, VIII, IX, X, XI or XII is first treated with a mild base to cleave the trifluoroacetyl group. The exposed, or unmasked, amino group is then reacted with a variety of building blocks, or is attached to a solid support with or without the assistance of a linker followed by reaction of the amino group with appropriate building blocks. A second protecting group (such as TEOC) is next cleaved selectively using either fluoride or trifluoroacetic acid, as desired, to unmask another amino group, which too may be further reacted with a variety of building blocks. Finally, the third combinatorial site on the monocyclic amine scaffolds is unmasked via reduction of an azide or via cleavage of an amine or a hydroxy protecting group. This third diversity site may be further combinatorialized using a variety of building blocks that react with an amine or hydroxy group. Cleavage of the substituted monocyclic amine products from the solid support, if necessary, then affords a library of monocyclic amine compounds.

Bicyclic Amine Compounds and Libraries

The present invention also provides combinatorial libraries of compounds derived from bicyclic amine scaffolds.

As used in the context of the present invention, a bicyclic amine is a bicyclic compound bearing at least one amino reactive center as part of the cyclic ring structure. Typically, bicyclic amine scaffolds are bicyclic compounds bearing at least three diversity sites. At least two of these diversity sites are amino groups that may or may not be part of the cyclic structure of the scaffold. The third diversity site on the bicyclic amine scaffolds of the present invention, is typically derived from substituents located at the α-position of amino acids.

The bicyclic compounds of the present invention of formula XIII, XIV, and XV bear multiple chiral centers in their structure. This leads to the possibility of structurally distinct molecules that are enantiomers or diastereomers. The present invention includes all possible enantiomers and diastereomers. The bicyclic amine compounds and libraries of these bicyclic amines of the present invention include not only individual, chirally pure, compounds, but mixtures of enantiomeric and diastereomeric compounds as well. Such stereochemical mixtures of chiral bicyclic amine compounds of the present invention may be used for a variety of purposes, including screening for biological activity in a variety of biochemical and cellular assays.

The bicyclic amine compounds of the present invention are also of interest from the standpoint of generating novel molecular structures which have unique spatial orientations of the pendant substituents. The novel structure and substitution pattern of the scaffold enables the probing of unique spatial relationships and pharmacophoric space with these molecules for biological activity and binding to biomolecular targets. Further, the bicyclic nature of these compounds add another dimension of rigidity to their structure which is otherwise inaccessible from their simpler monocyclic analogs. This altered structural rigidity may assist in improving interactions with biomolecular targets, biological activity or in providing improved understanding of such binding interactions.

The bicyclic amines of formula XIII are synthesized from the monocyclic amine scaffold of formula X, while bicyclic amines of formula XIV and XV are synthesized from the monocyclic amine scaffold of formula XI. Synthesis of bicyclic amines of formula XIII commences with DMT-protected 4-hydroxyprolinol. The 4-hydroxy group is first converted to a 4-amino group with inverted stereochemistry at the 4-position via initial protection of the pyrrolidine nitrogen atom as the 2-trimethylsilylethoxycarbonyl (TEOC) derivative. The use of the TEOC group is preferred over the Fmoc protecting group since the latter is base labile and may be cleaved by subsequent building blocks, such as amines, used for diversification of this class of bicyclic amine compounds. The N-TEOC-O-DMT-4-hydroxyprolinol was then mesylated using a mixture of methanesulfonyl chloride and pyridine in dichloromethane and subsequently reacted with sodium azide in DMF at 80° C. to afford the N-TEOC-O-DMT-4-azido-prolinol. Reduction with Sn(II)/thiophenol afforded the N-TEOC-O-DMT-4-amino-prolinol. This material was then loaded onto a solid support via a reductive amination protocol that uses borane-pyridine complex as the reducing agent and a solid support bearing a linker with a terminal aldehyde moiety. Also, the solid support bearing an aldehyde linker was generated via reaction of a solid support with hydroxy groups (e.g. Argogel-OH) with 4-hydroxybenzaldehyde in the presence of 5-triphenylphosphonium-1,1-dioxo-3,3-dimethyl-2,5-thiadiazolidine betaine. Preparation of this aldehdyic linker support was difficult when standard Mitsunobu reaction conditions, following reports in the literature, were used. The use of the sulfonamide betaine reagent gave complete conversion and clean aldehyde resin as determined by $C^{13}$-nmr.

Reductive alkylation of the appropriately protected aminoprolinol with the aldehyde resin afforded quantitative loading of the prolinol onto the resin. The generation of the bicyclic scaffold was next carried out on the solid support while simultaneously introducing diversity at the various sites of the molecule. The TEOC amino protecting group was removed by treatment with fluoride and the unmasked amino group reacted with an amino acid building block, such as N—Fmoc—Ala—OH, using standard coupling conditions like those used for amide and peptide synthesis (using HATU and diisopropylethylamine in methylene chloride). The Fmoc protecting group on the amino acid derived substituent, now attached to the solid support bound scaffold, was then removed under basic conditions. This amino group was then reacted with 2-nitrobenzene sulfonyl chloride in the presence of diisopropylethylamine to generate the 2-nitrobenzene sulfonamide at this position. The DMT group protecting the hydroxy moiety on the scaffold was next removed under acidic conditions and the free hydroxy group subjected to Mitsunobu conditions using an excess of 5-triphenylphosphonium-1,1-dioxo-3,3-dimethyl-2,5-thiadiazolidine betaine in a 5% DMF in dichloromethane solution. This afforded good cyclization of the substituted hydroxy scaffold, with subsequent removal of the 2-nitrobenzenesulfonyl group with a nucleophilic thiolate anion, to afford the bicyclic amine scaffold attached to the support. This support-bound bicyclic scaffold now bears a free, cyclic amine moiety which is further reacted with additional building blocks. Finally, the substituted bicyclic amine compound was cleaved from the solid support using a mixture of trifluoroacetic acid and triethylsilane, as scavenger.

The bicyclic amine compounds and libraries thereof are typically prepared via solid-phase chemistry. Typically, the generation of bicyclic amines and libraries of bicyclic amines, may be performed via automated, solid phase synthesis by commencing synthesis with the loading of a cyclic amine scaffold of formula X, onto a solid support, with or without the assistance of a linker, followed by reaction of this attached amino group with appropriate building blocks. The second protecting group (such as TEOC) is next cleaved selectively to unmask another amino group, which too may be further reacted with a variety of building blocks, preferably N-Fmoc-a-amino acids. This Fmoc group is then removed under basic conditions, such as piperidine in DMF, and the generated amino group reacted with 2-nitrobenzene sulfonyl chloride in the presence of a tertiary amine to generate a pendant sulfonamide. The DMT protected hydroxy group of the scaffold is next unmasked under acidic conditions and then subjected to Mitsunobu reaction, using 5-triphenyl-phosphonium-1,1-dioxo-3,3-dimethyl-2,5-thiadiazolidine betaine, to cyclize the amino group of the pendant sulfonamide onto the hydroxy group bearing carbon atom of the scaffold. This intra-molecular cyclization generates the solid support-bound bicyclic amine scaffold with a free cyclic amino group after the 2-nitrobenzene sulfonyl group is removed. This cyclic amino group is the third combinatorial site, and is combinatorialized using a variety of building blocks that react with an amine group. Finally, cleavage of the substituted bicyclic amine compounds from the solid support then affords a library of bicyclic amine compounds.

Oligomeric Amine Compounds and Libraries

The present invention also provides combinatorial libraries of compounds derived from a plurality of monocyclic and bicyclic amine scaffolds. The oligomeric amine compounds of the present invention comprise two or more monocyclic or bicyclic amine or bicyclic amine scaffolds connected to each other via covalent inter-scaffold linkages.

As used in the context of the present invention, an oligomeric compound is one that includes more than one of the abovementioned monocyclic amine scaffolds of formula VII, VIII, IX, X, XI, and XII, or bicyclic scaffolds of formula XVI, XVII and XVIII. The linkages between scaffolds present within the oligomeric amine compounds are covalent in nature and typically connect at one of the reactive sites on each scaffold. It is preferred that the oligomeric amine compounds contain up to 20 scaffold units that are connected at their amino and hydroxy moieties via urea, thiourea, guanidino, and amino linkages. Typically, the oligomeric amine compounds bear multiple diversity sites, present in their component scaffold units, that are not involved in the inter-scaffold linkage and are available for full exploitation as sites for the introduction of a wide variety of structurally diverse and functionally different building blocks. All the diversity sites are protected or masked in such a fashion that the protection and deprotection schemes are orthogonal in nature, i.e. one may be deprotected selectively without affecting the integrity of any of the other masking groups. This, allows for selective functionalization of individual diversity sites as the scaffolds are attached or constructed during synthesis of the oligomeric amine compounds. Alternatively, this also allows for the simultaneous reaction of multiple diversity sites, if so desired, with the same building blocks.

The present invention provides a method for preparing such oligomeric amine compounds by first removing an amino protecting group, if present, of a scaffold such as VII, VIII, IX, X, XI or XII and attaching the unmasked amino group, via a cleavable linker, to a solid support. Further chemistry may be performed at this solid support bound amino group through the use of appropriate reactive building blocks. Alternatively scaffolds may be attached to a solid support via a hydroxy group. A second amino group may next be exposed via removal of another amino protecting group and the molecule further combinatorialized via reaction with appropriate building blocks. Next, the third combinatorial site is unmasked via cleavage of the O-DMT group or reduction of the azido group. The free hydroxy group may then be subjected to cyclization under Mitsunobu conditions to afford a bicyclic scaffold attached to the solid support. The reactive amino group on the monocyclic amine, or a reactive amino group generated on the bicyclic scaffold, is next reacted with an activating group such as carbonyl diimidazole. Also, the hydroxy group on the scaffolds may be activated in a similar manner, or via oxidation to the aldehyde, which may be reacted via reductive alkylation. The activated amino or hydroxy group is next reacted with another scaffold such as VII, VIII, IX, X, XI or XII to generate molecules comprising two scaffolds that are attached to each other via a urea, carbamate, guanidino or amino linkage. The combinatorial sites on the second scaffold may next be sequentially unmasked and reacted with a variety of building blocks. Another reactive site may be subjected to the same set of reactions described above, in order to attach another scaffold to the growing oligomeric compound. Repeated rounds of scaffold attachment and combinatorialization on the newly attached scaffold leads to extension of the oligomeric compound. Upon generation of the desired oligomeric size and level of combinatorialization, the oligomeric amine compounds are cleaved from the solid support.

When scaffolds are linked via amine or thiourea linkages further combinatorialization is possible on the linkage via reaction of the linking amine with a variety of building blocks or via alkylation of the thiourea followed by displacement with an amine building block to form a guanidine.

The oligomeric amine compounds of the present invention bear multiple chiral centers in their structure. This leads to the possibility of structurally distinct molecules that are enantiomers or diastereomers. The oligmeric compounds of the present invention include all possible enantiomers and diastereomers of the constituent scaffolds VII, VIII, IX, X, XI, and XII, and of the bicyclic scaffolds of type XVI, XVII and XVIII. The oligomeric amine compounds of the present invention include individual, chirally pure, compounds, as well as mixtures of enantiomeric and diastereomeric compounds. Such stereochemical mixtures of oligomeric amine compounds derived from cyclic, bimonocyclic amine scaffolds of the present invention, may be used for a variety of purposes, including screening for biological activity in a variety of biochemical and cellular assays.

Synthesis of the oligomeric amine compounds of the present invention, and libraries thereof, is accomplished via a general strategy that begins with the attachment of the abovementioned monocyclic amine scaffolds to solid supports, selective deprotection or unmasking of reactive amino or hydroxy groups and their reactions with appropriate building blocks, the generation of bicyclic amine scaffolds as needed, and the connection of one scaffold unit to another via reactions on individual reactive sites on each scaffold. These chemical transformations may be performed either in solution or via solid-phase chemistry.

Amine Scaffolds

The present invention provides combinatorial libraries of monocyclic amines derived from a variety of such scaffolds. These scaffolds provide a framework bearing a number of reactive groups, such as amino and hydroxy, all of which can be functionalized and derivatized using a wide variety of building blocks via several different chemical reactions. This invention relates specifically to monocyclic amine scaffolds of formula VII, VIII, IX, X, XI, and XII, and bicyclic amine scaffolds of formula XVI, XVII, and XVIII.

A wide variety of cyclic and bicyclic amine scaffolds are represented by formulae VII, X and XVI.

Preferred structures of cyclic and bicyclic amine scaffolds of these formulae are shown below:

SCAFFOLDS OF FORMULA VII

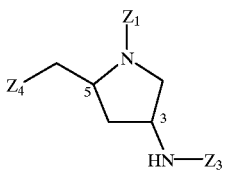
VIIa

SCAFFOLDS OF FORMULA X

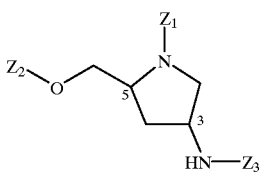
Xa

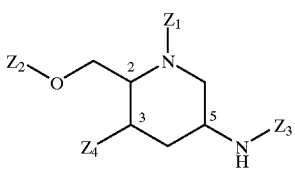
Xb

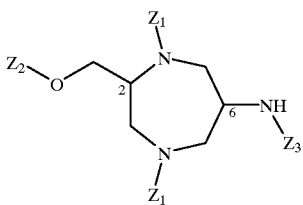
Xc

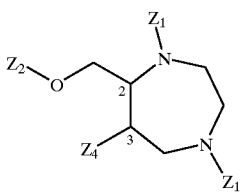
Xd

SCAFFOLDS OF FORMULA XVI

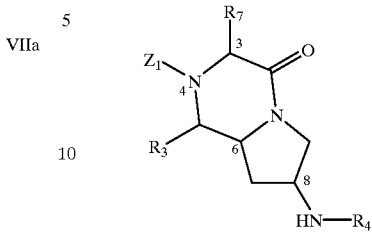
XVIa

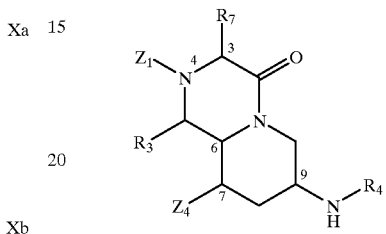
XVIb

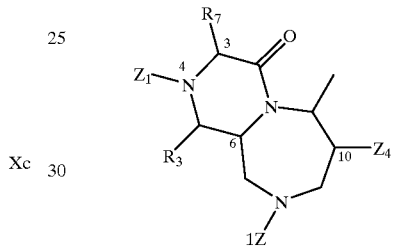
XVIc

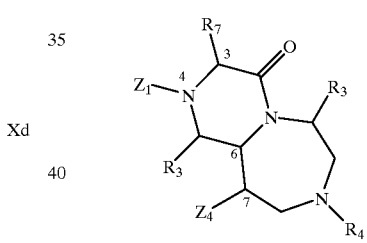
XVId

It is preferred that a scaffold of formula VII be a 3,5-disubstituted pyrrolidine VIIa, as numbered above and bearing additional substituents or protecting groups on the ring nitrogen atom.

It is preferred that a scaffold of formula X be a 3,5-disubstituted pyrrolidine Xa, a 3,5-disubstituted piperidine Xb, a 2,6-disubstituted-1,4-diazepine Xc or a 3,7-disubstituted-1,4-diazepine Xd, as numbered above and bearing additional substituents or protecting groups on the ring nitrogen atoms.

It is also preferred that a scaffold of formula XVI be a 3,8-disubstituted-1,4-diazabicyclo[4.3.0]nonan-2-one XVIa, 3,7,9-trisubstituted-1,4-diazabicyclo[4.4.0]decan-2-one XVIb, 3,10-disubstituted-1,4,8-triazabicyclo[4.5.0]undecan-2-one XVIc, or 3,7-disubstituted-1,4,9-triazabicyclo[4.5.0]undecan-2-one XVId, as numbered below and bearing additional substituents or protecting groups on the ring nitrogen atoms.

Bicyclic amine compounds of the present invention are preferably generated from the monocyclic amine scaffolds of the present invention via intramolecular Mitsunobu reaction. Likewise, oligomeric amine compounds of the present invention are also generated from the monocyclic amine scaffolds by covalent linkage of one scaffold to another scaffold using solid-phase chemistry. The amino groups of the scaffolds are either primary or secondary. These may be protected with a variety of amino protecting groups which are later unmasked during library synthesis via appropriate deprotection reactions. The protecting groups include, but are not limited to, carbamate protecting groups, such as 9-fluorenylmethyloxycarbonyl (Fmoc), 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), and benzyloxycarbonyl (Cbz); amide protecting groups, such as formyl, acetyl, trihaloacetyl, benzoyl, and nitrophenylacetyl; sulfonamide protecting groups, such as 2-nitrobenzenesulfonyl; and imine and cyclic imide protecting groups, such as phthalimido and dithiasuccinoyl. Following deprotection, the free amine may subsequently be reacted with a wide variety of building blocks.

The reactive hydroxyl groups may be either primary or secondary, and are typically exocyclic or acyclic substituents. These too may be selectively protected and deprotected to allow selective functionalization of each hydroxy group with appropriate building blocks. The protecting groups include, but are not limited to, ethers, such as substituted alkyl ethers, aryl ethers and silyl ethers; esters; and sulfonates. Preferred hydroxy protecting groups include trityl, monomethoxy trityl (MMT), dimethoxy trityl (DMT), t-butyl ethers, t-butyldimethylsilyl ethers, and t-butyldiphenylsilyl ethers. Following deprotection, the free hydroxyl group may subsequently be reacted with a wide variety of building blocks.

It will be recognized by the art-skilled that the monocyclic and bicyclic amine scaffolds of the present invention bear chiral centers. The present invention includes all possible enantiomeric and diastereomeric structures of these monocyclic amine scaffolds. As a result the present invention encompasses all enantiomers and diastereomers of the monocyclic amine, bicyclic amine and oligomeric amine compounds.

Diversity Sites

The amine scaffolds of the present invention may be derivatized at any of their reactive sites, also referred to as diversity sites or combinatorial sites. These sites may be combinatorialized with diverse building blocks. Sites that are available for combinatorializing include the reactive amino and hydroxy groups. Derivatization of scaffolds at diversity sites is achieved using a variety of building blocks that include, but are not limited to, carboxylic acids, acid halides, anhydrides, sulfonic acids, sulfonyl halides, isocyanates, isothiocyanates, ketones, aldehydes, amines, and amino acids.

The present invention provides for the addition of functional groups onto a monocyclic and bicyclic amine scaffold which is attached to a solid support. The preparation of the combinatorial libraries begins with a monocyclic amine scaffold attached to the solid support directly, or through a linker stable to the synthesis conditions, but cleavable to release the compound into solution at the end of the synthesis. Preferred linkers include esters, particularly those derived from succinic acid. Alternatively, the scaffolds can be coupled to a constant moiety attached to the support, such as DMT, ethylene glycol or a similar diol.

The scaffolds of the present invention are a structurally diverse set of monocyclic and bicyclic amines which give different relative orientations of the functional groups and the pendant, diverse substituents. The amine of the scaffold, also referred to as the reactive amino group, or amino combinatorial site, is typically protected with a base labile protecting group, such as Fmoc or Teoc, and the hydroxyl group is blocked with a protecting group, such as the dimethoxytrityl (DMT) ether, which is removable with a mild acid. Additional combinatorial sites may be present on the scaffolds in the form of protected hydroxy or amino groups or other masked functional groups which may be selectively reacted with building blocks when desired.

In addition to the combinatorial sites offered by the structure of the scaffolds used in the present invention, additional combinatorial sites may be available if the building blocks chosen for library generation bear additional functional groups that may be selectively protected and deprotected. Thus, for example, building blocks used at the amino combinatorial site may be selected to include Fmoc-protected amino acids such that the carboxyl group of the amino acid reacts with the free amino site of the scaffold. The resulting compounds would bear a pendant Fmoc protected amino group which could subsequently be deprotected under basic conditions, such as piperidine in dimethyl formamide, and then reacted further with other building blocks such as, for example, carboxylic acids, acid halides and sulfonyl halides. Thus, the monocyclic amine libraries of the present invention are not limited to merely two combinatorial sites. Three, and even more, diversity sites may be available for combinatorializing depending on the selective deprotection and reaction strategies used.

Bicyclic amines of the present invention are preferably generated from monocyclic amines via intramolecular Mitsunobu reaction. Likewise, oligomeric amine compounds of the present invention are also generated from the monocyclic scaffolds by covalent linkage of one monocyclic or bicyclic amine scaffold to another scaffold using solid-phase chemistry.

The scaffolds and building blocks used in the combinatorial library bear varied functional groups which, taken together, provide diverse properties ("diversity") to the resulting library members. These functional groups include hydrogen-bond donors and acceptors, ionic moieties, polar moieties, hydrophobic moieties, aromatic centers, and electron-donors and acceptors. Together, the properties of the individual scaffolds and building blocks contribute to the uniqueness of the individual compounds in which they are found. Thus, a library of such compounds would have a myriad of properties, i.e., "diversity." Collectively, the properties of the individual scaffold and building blocks, which together form an individual library compound, contribute to the uniqueness of the compound and impart certain characteristics thereto for interaction with cellular, enzymatic or nucleic acid target sites.

Amino Protection. Deprotection and Reactions

One feature of the present invention is the use of an amino protecting group to block the reactive amino site or amino combinatorial site on the scaffold. Once the scaffold is attached to the solid support, the amino protecting group can be removed under basic (non-hydrolytic) conditions. The amino group is then derivatized, or functionalized, with the diverse building block or functional group of choice. This building block can be attached to the amino combinatorial site via a variety of linkages including, but not limited to, alkyl, amide, sulfonamide, carbamate, urea, aminoalkane, thiocarbamate, and thiourea. This can be accomplished by choosing the appropriate electrophile to derivatize the amino group. For example, carboxylic acids can be activated using peptide coupling reagents such as EDC, BOP or HATU and reacted with the scaffold nitrogen atom to give amides. Other reagents which can be used include, among others, acid chlorides, acid fluorides, acid imidazolides, acid anhydrides, sulfonyl chlorides, chloroformates, isocyanates, aldehydes (under reductive alkylation conditions), alkyl halides, and isothiocyanates. Thus, each time a specific linkage is desired in a library, it is introduced onto the scaffold via the appropriate coupling conditions using suitable building blocks at the amino combinatorial site.

Another feature of the present invention is the introduction of additional sites of diversity onto the scaffolds of the present invention. This may be accomplished via the use of functionalized building blocks for reaction at the amino combinatorial sites. Such building blocks include, among others, Fmoc-amino acids where the amino group of the amino acid building block is selectively protected with a labile protecting group, such as Fmoc. The carboxylic group of the amino acid building block reacts with the amino combinatorial site on the scaffolds of this invention. The products so generated may be further combinatorialized via deprotection of the Fmoc group on the pendant amino group derived from the previously used amino acid building block and reaction of this amine with additional building blocks as described below. Monocyclic, bicyclic and oligomeric amine libraries of this invention may therefore bear two or more sites of diversity based on the selective protection and deprotection of functional groups including amines and alcohols on the scaffolds and based on the building blocks used.

In another aspect of the present invention, amino protecting groups, which are stable to acid treatment and are selectively removed with base treatment, are used to make reactive amino groups selectively available for substitution. Examples of such groups are the FMOC ( E. Atherton and R. C. Sheppard in *The Peptides,* S. Udenfriend, J. Meienhofer, Eds., Academic Press, Orlando, 1987, volume 9, p.1), and various substituted sulfonylethyl carbamates exemplified by the Nsc group (Samukov et al., *Tetrahedron Lett,* 1994, 35, 7821; Verhart and Tesser, *Rec. Trav. Chim. Pays-Bas,* 1987, 107, 621). Additional amino protecting groups include but are not limited to, carbamate protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide protecting groups, such as 2-nitrobenzenesulfonyl; and imine and cyclic imide protecting groups, such as phthalimido and dithiasuccinoyl.

Hydroxyl Protection, Deprotection and Reactions

A protecting group, such as a member of the trityl family, may be used as the acid labile hydroxyl-protecting group of the scaffold. The trityl family includes trityl, monomethoxytrityl, dimethoxytrityl and trimethoxytrityl. The dimethoxytrityl group is preferred a nd can be added by reacting the primary hydroxyl group with 4,4'-dimethoxytrityl chloride. Other hydroxyl protecting groups can also be used. Representative hydroxyl protecting groups are described in the literature (Beaucage et al., *Tetrahedron,* 1992, 48, 2223). Preferred hydroxyl protecting groups are acid-labile groups, such as trityl, monomethoxytrityl, dimethoxytrityl, trimethoxytrityl, 9-phenylxanthine-9-yl (Pixyl), and 9-(p-methoxyphenyl)-xanthine-9-yl (MOX).

In other aspects of the present invention, acid labile groups, such as BOC-type protecting groups, which are stable to trichloroacetic acid (TCA) treatment employed for DMT removal are used to protect additional hydroxy groups that may serve as additional combinatorial sites. These protecting groups a re stable to extended TCA treatment, but are removed by trifluoroacetic acid (e.g. 5% in $CH_2Cl_2$). Another class of protecting groups which is compatible with this methodology is the allyl class. These groups are cleaved using transition metal catalysts. These types of protecting group are particularly valuable in cases where the selective deprotection of a particular functional group is desired while the library member is still attached to the solid support, allowing a new reactive site to be uncovered.

In another aspect of the present invention, silyl protecting groups which may be selectively stable to acidic or basic conditions may also be used to protect selected hydroxy groups that may serve as combinatorial sites. These protecting groups are typically introduced via reaction of the hydroxy group with the appropriate chlorosilane. Cleavage is typically performed with fluoride reagents such as HF or tetrabutylammonium fluoride (TBAF), and in some instances under acidic conditions. Silyl protecting groups such as trimethylsilyl (TMS), triethylsiliyl (TES), triisopropylsilyl (TIPS), dimethylisopropylsilyl (IPDMS), diethylisopropylsilyl (DEIPS), mimethylthexylsilyl (TDS), t-butyldimethylsilyl (TBDMS), t-butyldiphenylsilyl (TBDPS), and triphenylsilyl (TPS) may be used. Their formation, use and cleavage have been reviewed (Greene and Wuts, *Protective Groups in Organic Chemistry,* 2d edition, John Wiley and Sons, 1991).

Additional protecting group tactics which are compatible with the methodology of the present invention include photolabile protecting groups.

Building Blocks

A number of different classes of compounds are suitable for use as building blocks for the synthesis of diversely substituted monocyclic, bicyclic, and oligomeric amine compounds of the present invention.

The building blocks and their functional groups can be selected based on chain length, i.e. short versus long, based on the use of a ring versus a linear group, use of an aromatic versus aliphatic group, use of a functionalized group versus a non-functionalized group, to mention only a few of the wide variety of chemical functional groups available. Indeed, simply varying functional moieties, e.g. acid, alcohol, aldehyde, amide, amine, amidine, azo, azoxy, double bond, ether, ethylene oxide, guanidine, halide, haloalkyl, hydrazine, hydroxylamine, ketone, mercaptan, nitrate, nitrile, nitro, nitroso, quaternary nitrogen, sulfide, sulfone, sulfoxide, triple bond, urea, etc., at a single amino combinatorial site, e.g. a simple alkyl building block, yields a vast array of diversity functions. When this is expanded to include placement of such varied functional moieties on a broad platform of backbones, e.g. a series of alkyl compounds, a series of aryl compounds, a series of alicyclic compounds, etc., the potential for a vast array of chemical functional groups is apparent. Other chemical functional groups include alkyl, alkenyl, alkynyl, alicyclic and substituted alkyl, alkenyl, alkynyl, alicyclic, aryl and substituted aryl, aralkyl, substituted aralkyl, heterocyclyl, nucleobases such as pyrimidines and purines, metal chelating groups and moieties as found in the α-position of amino acids.

Building blocks used for the synthesis of diverse monocyclic amine compounds of the present invention may be attached to the scaffolds, or may be present at different locations on the compounds of the present invention. Building blocks may be attached to the amino and hydroxy sites on the scaffolds of the present invention. Further, additional building blocks may also be attached to functional groups pendant from building blocks attached to the scaffolds. Such pendant building blocks may be incorporated into the cyclic, bicyclic, cycloalkyl and oligomeric amine compounds of the present invention via the choice of appropriate functional group protection and deprotection strategies.

The building blocks that are suitable for use in the libraries of this invention include, but are not limited to, carboxylic acids, acid halides, sulfonic acids, sulfonyl halides, anhydrides, isocyanates, isothiocyanates, amines, amino acids, aldehydes, ketones and alkyl halides.

Carboxylic acids suitable for use as building blocks include, but are not limited to, substituted and unsubstituted alkyl, alkenyl, alkynyl, cycloalkyl, aryl, aralkyl, heterocyclyl, and heteroaryl carboxylic acids. These may be chiral and can be used as individual enantiomers, diastereomers or as racemic mixtures. Carboxylic acid building blocks also include protected amino acids, including Fmoc amino acids and BOC amino acids. Carboxylic building blocks used in this invention may be commercially purchased, isolated from natural products, or chemically synthesized following commonly known chemical reactions.

Attachment of carboxylic acids onto the scaffolds of this invention may be performed at either the amino or hydroxy combinatorial diversity sites on the scaffold. Direct attachment of commercially available, isolated or synthesized carboxylic acids to amines or alcohols of the scaffold leads to amide or ester substituents, respectively, at these diversity sites. Carboxylic acid building blocks may also be attached to secondary combinatorial sites that are introduced via functional groups attached to other building blocks attached to the scaffolds. These secondary combinatorial sites may be functional groups such as, but not limited to, hydroxy, amino, and thiol. Attachment may be performed by chemical or biochemical means. Chemical means of attachment include, but are not limited to, acylation of the amine or alcohol by use of activating reagents such as carbodiimides, for example, dicylcohexyl carbodiimide, and diisopropyl carbodiimide; acid or sulfonyl chlorides, for example, trimethylacetyl chloride, methanesulfonyl chloride, triisopropylbenzensulfonyl chloride; N-hydroxyimides, for example N-hydroxysuccinimide; and carbonyl diimidazole; and uronium salts, for example, O-(7-azabenzotriazol-1-yl)-tetramethyluronium hexafluorophosphate (HATU). In general, the carboxylic acid is first activated to a more reactive species such as an anhydride via reaction with the activating reagent, followed by reaction with the nucleophilic amino or hydroxy group of the scaffold. Reactions typically may also include adjunct reagents such as a base to quench the by-products of the acylation reaction and an appropriate solvent.

Carboxylic acid building blocks may also be attached to the scaffolds of the present invention at available sites of diversity via biochemical means. Biochemical means for attachment of such acid building blocks include, but are not limited to, the use of purified enzymes, semipure enzymatic mixtures, cell or tissue extracts, catalytic antibodies and proteins or mixtures thereof as catalysts for the acylation of the reactive amino or hydroxy group of the scaffold. These biochemical catalysts may be for example lipases, ligases, proteases and esterases isolated or prepared from a variety of microbial, plant and animal sources.

Acid halides suitable for use as building blocks include, but are not limited to, fluoro, chloro, bromo, and iodo derivatives of substituted and unsubstituted alkyl, alkenyl, alkynyl, cycloalkyl, aryl, aralkyl, heterocyclyl, and heteroaryl carboxylic acids. The carboxylic acids from which the acid halides are derived may be chiral and these acid halides are usable either as individual enantiomers, diastereomers or as racemic mixtures. Acid halide building blocks used in this invention may be commercially purchased, isolated from natural products, or chemically synthesized following commonly known chemical reactions.

Attachment of acid halides onto the scaffolds of this invention may be performed at either the amino or hydroxy combinatorial diversity sites on the scaffold. Direct attachment of commercially available, isolated or synthesized acid halides to amines or alcohols of the scaffold leads to amide or ester substituents, respectively, at these diversity sites. Acid halide building blocks may also be attached to secondary combinatorial sites that are introduced via functional groups attached to other building blocks attached to the scaffolds. These secondary combinatorial sites may be functional groups such as, but not limited to, hydroxy, amino, and thiol. Attachment may be performed by chemical or biochemical means. Chemical means of attachment include, but are not limited to, acylation of the amine or alcohol by use of the acid halide in the presence of a base such as, for example, ammonia, primary, secondary or tertiary amines or heterocyclic amines, in an appropriate solvent. Preferred amines used to quench the byproducts of the acylation reaction include tertiary amines such as triethylamine and diisopropyl ethylamine, and heterocyclic amines such as pyridine.

Acid halide building blocks may also be attached to the scaffolds of the present invention at available sites of diversity via biochemical means. Biochemical means for attachment of such acid building blocks include, but are not limited to, the use of purified enzymes, semipure enzymatic mixtures, cell or tissue extracts, catalytic antibodies and proteins or mixtures thereof as catalysts for the acylation of the reactive amino or hydroxy group of the scaffold. These biochemical catalysts may be isolated or prepared from a variety of microbial, plant and animal sources.

Sulfonic acids suitable for use as building blocks include, but are not limited to, substituted and unsubstituted alkyl, alkenyl, alkynyl, cycloalkyl, aryl, aralkyl, heterocyclyl, and heteroaryl sulfonic acids. These may be chiral and can be used either as individual enantiomers, diastereomers or as racemic mixtures. Sulfonic acid building blocks used in this invention may be commercially purchased, isolated from natural products, or chemically synthesized following commonly known chemical reactions.

Attachment of sulfonic acids onto the scaffolds of this invention may be performed at either the amino or hydroxy combinatorial diversity sites on the scaffold. Direct attachment of commercially available, isolated or synthesized sulfonic acids to amines or alcohols of the scaffold leads to sulfonamide or sulfonate substituents, respectively, at these diversity sites. Sulfonic acid building blocks may also be attached to secondary combinatorial sites that are introduced via functional groups attached to other building blocks attached to the scaffolds. These secondary combinatorial sites may be functional groups such as, but not limited to, hydroxy, amino, and thiol. Attachment may be performed by chemical or biochemical means. Chemical means of attachment include, but are not limited to, sulfonylation of the amine or alcohol by use of activating reagents such as carbodiimides, for example, dicylcohexyl carbodiimide, and diisopropyl carbodiimide; acid or sulfonyl chlorides, for example, trimethylacetyl chloride, methanesulfonyl chloride, triisopropylbenzensulfonyl chloride; N-hydroxyimides, for example N-hydroxysuccinimide; and carbonyl diimidazole. In general, the sulfonic acid is activated first to a more reactive species such as a mixed anhydride via reaction with the activating reagent followed by reaction with the nucleophilic amino or hydroxy group of the scaffold. Reactions typically may also include adjunct reagents such as a base to quench the byproducts of the acylation reaction in an appropriate solvent.

Sulfonic acid building blocks may also be attached to the scaffolds of the present invention at available sites of diversity via biochemical means as described above for carboxylic acids.

Sulfonyl halides suitable for use as building blocks include, but are not limited to, fluoro, chloro, bromo, and iodo derivatives of substituted and unsubstituted alkyl, alkenyl, alkynyl, cycloalkyl, aryl, aralkyl, heterocyclyl, and heteroaryl sulfonic acids. The sulfonic acids from which the sulfonyl halides are derived may be chiral and these sulfonyl halides are usable either as individual enantiomers, diastereomers or as racemic mixtures. Sulfonyl halide building blocks used in this invention may be commercially purchased, isolated from natural products, or chemically synthesized following commonly known chemical reactions.

Attachment of sulfonyl halides onto the scaffolds of this invention may be performed at either the amino or hydroxy combinatorial diversity sites on the scaffold. Direct attachment of commercially available, isolated or synthesized sulfonyl halides to amines or alcohols of the scaffold leads to sulfonamide or sulfonate substituents, respectively, at these diversity sites. Sulfonyl halide building blocks may also be attached to secondary combinatorial sites that are introduced via functional groups attached to other building blocks attached to the scaffolds. These secondary combinatorial sites may be functional groups such as, but not limited to, hydroxy, amino, and thiol. Attachment may be performed by chemical or biochemical means. Chemical means of attachment include, but are not limited to, acylation of the amine or alcohol by use of the acid halide in the presence of a base such as, for example, ammonia, primary, secondary or tertiary amines or heterocyclic amines, in an appropriate solvent. Preferred amines used to quench the byproducts of the sulfonylation reaction include tertiary amines such as triethylamine and diisopropyl ethylamine, and heterocyclic amines such as pyridine.

Sulfonyl halide building blocks may also be attached to the scaffolds of the present invention at available sites of diversity via biochemical means as described above for acid halides.

Anhydrides suitable for use as building blocks include, but are not limited to, those derived from substituted and unsubstituted alkyl, alkenyl, alkynyl, cycloalkyl, aryl, aralkyl, heterocyclyl, and heteroaryl carboxylic acids or sulfonic acids. The carboxylic and sulfonic acids from which the anhydrides are derived may be chiral and these anhydrides are usable either as individual enantiomers, diastereomers or as racemic mixtures. Anhydride building blocks used in this invention may be commercially purchased, isolated from natural products or chemically synthesized following commonly known chemical reactions. The anhydrides used as building blocks may be symmetrical anhydrides derived from one acid, or mixed anhydrides derived from two different acids.

Attachment of anhydrides onto the scaffolds of this invention may be performed at either the amino or hydroxy combinatorial diversity sites on the scaffold. Direct attachment of commercially available, isolated or synthesized acid halides to amines or alcohols of the scaffold leads to amide or ester substituents, respectively, at these diversity sites. Anhydride building blocks may also be attached to secondary combinatorial sites that are introduced via functional groups attached to other building blocks attached to the scaffolds. These secondary combinatorial sites may be functional groups such as, but not limited to, hydroxy, amino, and thiol. Attachment may be performed by chemical or biochemical means. Chemical means of attachment include, but are not limited to, acylation of the amine or alcohol by use of the anhydride in the presence of an acid such as p-toluenesulfonic acid or a base such as, for example, sodium acetate or heterocyclic amines, in an appropriate solvent. Preferred amines used to assist in the acylation reaction include pyridine and dimethylaminopyridine.

Anhydride building blocks may also be attached to the scaffolds of the present invention at available sites of diversity via biochemical means as described above for acid halide building blocks.

Isocyanates suitable for use as building blocks include, but are not limited to, substituted and unsubstituted alkyl, alkenyl, alkynyl, cycloalkyl, aryl, aralkyl, heterocyclyl, and heteroaryl isocyanates. The isocyanate building blocks may be chiral and these are usable either as individual enantiomers, diastereomers or as racemic mixtures. Isocyanate building blocks used in this invention may be commercially purchased, isolated from natural products, or chemically synthesized following commonly known chemical reactions.

Attachment of isocyanates onto the scaffolds of this invention may be performed at either the amino or hydroxy combinatorial diversity sites on the scaffold. Direct attachment of commercially available, isolated or synthesized isocyanates to amines or alcohols of the scaffold leads to urea or carbamate substituents, respectively, at these diversity sites. Isocyanate building blocks may also be attached to secondary combinatorial sites that are introduced via functional groups attached to other building blocks attached to the scaffolds. These secondary combinatorial sites may be functional groups such as, but not limited to, hydroxy, amino, and thiol. Attachment may be performed by chemical or biochemical means. Chemical means of attachment include, but are not limited to, reaction of the amine or alcohol with the isocyanate in the presence of an appropriate solvent such as N-methylpyrrolidone.

Isocyanate building blocks may also be attached to the scaffolds of the present invention at available sites of diversity via biochemical means. Biochemical means for attachment of such isocyanate building blocks include, but are not limited to, the use of purified enzymes, semipure enzymatic mixtures, cell or tissue extracts, catalytic antibodies and proteins or mixtures thereof as catalysts. These biochemical catalysts may be isolated or prepared from a variety of microbial, plant and animal sources.

Isothiocyanates suitable for use as building blocks include, but are not limited to, substituted and unsubstituted alkyl, alkenyl, alkynyl, cycloalkyl, aryl, aralkyl, heterocyclyl, and heteroaryl isothiocyanates. The isothiocyanate building blocks may be chiral and these are usable either as individual enantiomers, diastereomers or as racemic mixtures. Isothiocyanate building blocks used in this invention may be commercially purchased, isolated from natural products or chemically synthesized following commonly known chemical reactions.

Attachment of isothiocyanates onto the scaffolds of this invention may be performed at either the amino or hydroxy combinatorial diversity sites on the scaffold. Direct attachment of commercially available, isolated or synthesized isothiocyanates to amines or alcohols of the scaffold leads to thiourea or thiocarbamate substituents, respectively, at these diversity sites. Isothiocyanate building blocks may also be attached to secondary combinatorial sites that are introduced via functional groups attached to other building blocks attached to the scaffolds. These secondary combinatorial sites may be functional groups such as, but not limited to, hydroxy, amino, and thiol. Attachment may be performed by chemical or biochemical means. Chemical means of attachment include, but are not limited to, reaction of the amine or alcohol with the isothiocyanate in the presence of an appropriate solvent such as N-methylpyrrolidone.

Isothiocyanate building blocks may also be attached to the scaffolds of the present invention at available sites of diversity via biochemical means as described for isocyanate building blocks.

Amines suitable for use as building blocks include, but are not limited to, substituted or unsubstituted alkyl, alkenyl, alkynyl, cycloalkyl, aryl, aralkyl, heterocyclyl, and heteroaryl amines. Amine building blocks include primary and secondary amines, and "masked amines" such as phthalimide. Amines of this invention are also meant to include amino acids and amino acid derivatives, polyalkylamino compounds and aminoalkylamines such as aminopropylamines and further heterocycloalkylamines, such as, for example, imidazol-1-, 2-, or 4-yl-propylamine. The amine building blocks may be chiral and these may be used either as individual enantiomers, diastereomers or as racemic mixtures. Amine building blocks used in this invention may be commercially purchased, isolated from natural products, or chemically synthesized following commonly known chemical reactions.

Amino groups amenable to the present invention have the formula $N(Y_1)Y_2$, wherein:

$Y_1$ is H, or $[T_1]_j$-$T_2$;

$Y_2$ is $[T_3]_k$-$T_1$, or $Y_1$, and $Y_2$ together form a nitrogen heterocycle;

$T_1$ and $T_3$ independently, are $C_2$–$C_{10}$ alkyl, $C_2$–$C_{10}$ alkenyl, $C_2$–$C_{10}$ alkynyl, $C_4$–$C_7$ carbocylo alkyl or alkenyl, a heterocycle, an ether having 2 to 10 carbon atoms and 1 to 4 oxygen or sulfur atoms, a polyalkyl glycol, or $C_7$–$C_{14}$ aralkyl;

j and k independently, are 0 or 1;

$T_2$ and $T_4$ independently are H, $C_1$–$C_2$ alkyl, $C_2$–$C_{20}$ alkenyl, $C_2$–$C_{20}$ alkynyl, $C_6$–$C_{14}$ aryl, $C_7$–$C_{15}$ aralkyl, halogen, CH=O, $OR_{12}$, $SR_{21}$, $NR_{12}R_{13}$, C(=NH)$NR_{12}R_{13}$, CH($NR_{12}R_{13}$), NHC(=NH) $NR_{12}R_{13}$, CH ($NH_2$)C(=O) OH, C(=O)$NR_{12}R_{13}$, C(=O) $OR_{12}$, a metal coordination group, a reporter group, a nitrogen-containing heterocycle, a purine, a pyrimidine, a phosphate group, a polyether group, or a polyethylene glycol group.

Attachment of amines onto the scaffolds of this invention may be performed at the hydroxy combinatorial diversity sites on the scaffold via a carbamate linkage. Thus amines are not reacted directly onto the hydroxy group of the scaffold. This indirect attachment of the amine building block to the scaffold's hydroxy group may be performed by chemical or biochemical means. Chemical means of attachment includes, but is not limited to, a first step of activation of the hydroxy group via reaction with an activating reagent such as carbonyl diimidazole so as to afford a imidazolyl carbonyl substituent on the scaffold's hydroxy group. Alkyl haloformates may also be used as activating reagents. The activated hydroxy group is subsequently reacted with the amine building block, in an appropriate solvent, to afford the carbamate substituent at this diversity site on the scaffold.

Amine building blocks may also be attached to the monocyclic and bicyclic scaffolds of this invention, via reductive amination reactions. This is typically accomplished via reaction with a carbonyl group on the scaffold, such as an aldehyde or ketone that is generated via oxidation of a hydroxy group on the scaffold. Reductive alkylation with a primary amine then affords a secondary amine that may be further functionalized via reaction with additional building blocks. Amine building blocks may also be attached to secondary combinatorial sites that are introduced via functional groups present on other building blocks attached to the scaffolds. These secondary combinatorial sites may be functional groups such as, but not limited to, aldehydes, ketones, carboxylic acids and sulfonic acids.

Amino acids suitable for use as building blocks may be naturally-occurring or non-naturally-occurring. Naturally-occurring amino acids include a-amino acids where the chiral center has a D-configuration. Such naturally-occurring amino-acids may be either essential or non-essential amino acids. Non-naturally-occurring amino acid building blocks include a-amino acids with chiral centers bearing an L-configuration. Non-naturally-occurring amino acids also include amino acids bearing unusual side chains that do not exist in nature and are prepared synthetically, such as halo- and cyano- substituted benzyl, tetrahydroisoquinolylmethyl, cyclohexylmethyl, and pyridylmethyl. Additional amino-acid building blocks include b-amino acids. Amino acid building blocks may be used with or without protecting groups on their C-terminus, N-terminus and on functional groups pendant from their side chains.

Attachment of amino acid building blocks to combinatorial sites on the scaffold or the secondary combinatorial sites on pendant building blocks may be performed by chemical or biochemical means. Attachment of amino acid building blocks onto scaffolds of the present invention and their incorporation into libraries may be achieved in several different ways. N-protected amino acids such as Fmoc- and BOC- amino acids may be attached via their carboxylic acid functionality onto the amino or hydroxyl combinatorial sites of the scaffolds or functional groups pendant from other building blocks used in generating the compounds of the present invention. Amino acids bearing protected carboxyl groups may also be used as building blocks via reaction of their amino groups with activated functionalities present on the scaffolds or pendant from other building blocks attached to the scaffolds, such as, for example, O-imidazolylcarbonyl, and N-chloroformate groups.

Amino acid building blocks may also be attached to secondary combinatorial sites that are introduced via functional groups attached to other building blocks attached to the scaffolds. These secondary combinatorial sites may be functional groups such as, but not limited to, hydroxy, amino, carboxy and thiol. Chemical means of attachment include, but are not limited to, conventional peptide chemistry.

Amino acid building blocks may also be attached to the scaffolds of the present invention at available sites of diversity via biochemical means. Biochemical means for attachment of such amino acid building blocks include, but are not limited to, the use of purified enzymes, semipure enzymatic mixtures, cell or tissue extracts, catalytic antibodies and proteins or mixtures thereof as catalysts. These biochemical catalysts may be for example lipases, ligases, proteases and esterases isolated or prepared from a variety of microbial, plant and animal sources.

Aldehydes suitable for use as building blocks include, but are not limited to, substituted and unsubstituted alkyl, alkenyl, alkynyl, cycloalkyl, aryl, aralkyl, heterocyclyl, and heteroaryl aldehydes. These may be chiral and are usable either as individual enantiomers, diastereomers or as racemic mixtures. Aldehyde building blocks used in this invention may be commercially purchased, isolated from natural products, or chemically synthesized following commonly known chemical reactions.

Ketones suitable for use as building blocks include, but are not limited to, substituted and unsubstituted alkyl, alkenyl, alkynyl, cycloalkyl, aryl, aralkyl, heterocyclyl, and heteroaryl ketones. These may be chiral and are usable either as individual enantiomers, diastereomers or as racemic mixtures. Ketone building blocks used in this invention may be commercially purchased, isolated from natural products, or chemically synthesized following commonly known chemical reactions. The two groups attached to the carbonyl center of the ketone building blocks of this invention may either be the same or different.

Attachment of aldehydes and ketones onto the scaffolds of this invention may be performed at the amino combinatorial diversity sites on the scaffold. Direct attachment of commercially available, isolated or synthesized carbonyl compound (aldehyde or ketone) to amines of the scaffold, under reductive conditions, leads to alkyl substituents, respectively, at these diversity sites. Carbonyl building blocks may also be attached to secondary combinatorial sites that are introduced via functional groups attached to other building blocks attached to the scaffolds. These secondary combinatorial sites may be functional groups such as, but not limited to, amines. Attachment may be performed by chemical or biochemical means. Chemical means of attachment of the carbonyl compound (aldehyde or ketone) include, but are not limited to, reductive alkylation of the amine of the scaffold by use of reducing agents such as, for example, sodium cyanoborohydride, sodium triacetoxyborohydride, and borane in pyridine. The reductive alkylation is typically performed by mixing the scaffold and carbonyl compound together with the reducing agent in an appropriate solvent at room temperature.

Alkylating reagents suitable for use as building blocks include, but are not limited to, substituted and unsubstituted alkyl, alkenyl, alkynyl, cycloalkyl, aryl, aralkyl, heterocyclyl, and heteroaryl halides, mesylates and tosylates. These may be chiral and are usable either as individual enantiomers, diastereomers or as racemic mixtures. Alkylating building blocks used in this invention may be commercially purchased, isolated from natural products, or chemically synthesized following commonly known chemical reactions.

Attachment of alkylating building blocks to the scaffolds of this invention may be performed at either the amino or hydroxyl combinatorial diversity sites on the scaffold. Direct attachment of commercially available, isolated, or synthesized alkylating building block to amines or alcohols of the scaffold leads to N-alkyl and O-alkyl substituents, respectively, at these diversity sites. Alkylating building blocks may also be attached to secondary combinatorial sites that are introduced via functional groups attached to other building blocks attached to the scaffolds. These secondary combinatorial sites may be functional groups such as, but not limited to, hydroxy, amino, and thiol. Attachment may be performed by chemical or biochemical means. Chemical means of attachment of the alkylating agent include, but are not limited to, reaction in the presence of a suitable base such as sodium or potassium carbonate, sodium hydride, or amines, in an appropriate solvent such as dimethylformamide, at ambient or elevated temperature.

Alkyl, alkenyl, and alkynyl groups according to the invention include, but are not limited to, substituted and unsubstituted straight chain, branched chain, and alicyclic hydrocarbons. Further, in the context of this invention, a straight chain compound means an open chain compound, such as an aliphatic compound, including alkyl, alkenyl, or alkynyl. A branched compound, as used herein, comprises a straight chain compound, such as an alkyl, alkenyl, alkynyl compound, which has further straight or branched chains attached to the carbon atoms of the straight chain. A cyclic compound, as used herein, refers to closed chain compounds, i.e. a ring of carbon atoms, such as an alicyclic or cycloalkyl compound. Cyclic compounds also include aromatic compounds where the closed chain is aromatic in nature. The straight, branched, or cyclic compounds may be internally interrupted, as in alkoxy or heterocyclic compounds. In the context of this invention, internally interrupted means that the carbon chains may be interrupted with heteroatoms such as O, N, or S. However, if desired, the carbon chain may have no heteroatoms.

Further, in the context of this invention, aryl groups include, but are not limited to, substituted and unsubstituted aromatic hydrocarbyl groups. Aralkyl groups include but are not limited to groups having both aryl and alkyl functionalities, such as benzyl and xylyl groups. Aryl and aralkyl groups include, but are not limited to, phenyl, benzyl, xylyl, naphthyl, tolyl, pyrenyl, anthracyl, azulyl, phenethyl, cinnamyl, benzhydryl, and mesityl. These can be substituted or unsubstituted.

Heterocycles present in building blocks may be rings where one of the ring atoms is a heteroatom and where the ring may be aromatic (heteroaryl) or may not be aromatic (heterocyclyl) in nature. Heterocycles include, but are not limited to, imidazole, pyrrole, pyrazole, indole, 1H-indazole, a-carboline, carbazole, phenothiazine, phenoxazine, tetrazole, thiazole, oxazole, isoxazole, oxadiazole, benzoxazole, benzimidazole, triazole, pyrrolidine, piperidine, pyridine, purine, pyrimidine, triazine, quinoline, isoquinoline, quinazoline, piperazine and morpholine groups.

The aliphatic and aromatic groups as noted above may be substituted or unsubstituted. In the context of this invention, substituted or unsubstituted means that the compounds may have any one or more of a variety of substituents, in replacement, for example, of one or more hydrogen atoms in the compound, or may have no substituents. Typical substituents that may be present include, but are not limited to acyl, alcohol, alkoxy, alkoxycarbonyl, alkylsulfonyl, alkyl, aryl, alkenyl, alkynyl, amino, amido, azido, carboxylic acid, cyano, guanidino, halo, haloalkyl, haloalkoxy, hydroxyl, hydrazino, nitro, sulfide, sulfone, sulfonate and sulfonamide, thiol, thioalkoxy, groups.

A number of building blocks may be introduced into the compounds of the present invention in a protected form and subsequently deprotected to form the final desired compound. In general, a protecting group renders a chemical functionality of a molecule inert to specific reaction conditions which can later be removed from such functionality in a molecule without substantially damaging the remainder of the molecule (Greene and Wuts, Protective Groups in Organic Synthesis, 2d edition, John Wiley & Sons, New York, 1991). For example, amino groups can be protected as phthalimido groups, as 9-fluorenylmethoxycarbonyl (FMOC) groups, and with triphenylmethylsulfenyl, t-BOC or CBZ groups. Hydroxyl groups can be protected as acetyl groups. Representative hydroxyl protecting groups are described by Beaucage et al., *Tetrahedron* 1992, 48, 2223. Preferred hydroxyl protecting groups are acid-labile, such as the trityl, monomethoxytrityl, dimethoxytrityl, trimethoxytrityl, 9-phenylxanthine-9-yl (Pixyl) and 9-(p-methoxyphenyl)xanthine)-9-yl (MOX). Chemical functional groups can also be "protected" by including them in a precursor form. Thus, an azido group may be used and considered to be a "protected" form of an amine since the azido group is easily converted to the amine.

$R_2$, $R_3$, $R_5$, $R_6$, $R_7$, $R_8$, $R_9$, in the libraries of the present invention include but are not limited to, H, alkyl or substituted alkyl, alkenyl or substituted alkenyl, alkynyl or substituted alkynyl, carbocyclic alkyl, alkenyl or alkynyl or substituted carbocyclic, or aryl or substituted aryl where the substituent groups are selected from hydroxyl, amino, alkoxy, alcohol, benzyl, phenyl, nitro, thiol, thioalkoxy, halogen, alkyl, aryl, alkenyl, or alkynyl groups; an gluether having 2 to 10 carbon atoms and 1 to 4 oxygen or sulfur atoms; a nitrogen, sulfur or oxygen containing heterocycle; a metal coordination group; a conjugate group; halogen; hydroxyl (OH); thiol (SH); keto (C=O); carboxyl (COOH); amide ($CONR_{12}$), amidine (C(=NH) $NR_{12}R_{13}$), guanidine ($NHC(=NH)NR_{12}R_{13}$), glutamyl ($R^1OOCCH(NR_{12}R_{13})$ $(CH_2)_2C(=O)$), nitrate ($ONO_2$), nitro ($NO_2$), nitrile (CN), trifluoromethyl ($CF_3$), trifluoromethoxy ($OCF_3$), O-alkyl, S-alkyl, NH-alkyl, N-dialkyl, O-aralkyl, S-aralkyl, NH-aralkyl, amino ($NH_2$), azido ($N_3$), hydrazino ($NHNH_2$), hydroxylamino ($ONH_2$), sulfoxide (SO), sulfone ($SO_2$), sulfide (S—), disulfide (S—S), silyl, a nucleosidic base, an amino acid side chain, a carbohydrate, a biopharmaceutically active moiety, or group capable of hydrogen bonding where the substituent groups are selected from hydroxyl, amino, alkoxy, alcohol, benzyl, phenyl, nitro, thiol, thioalkoxy, halogen, alkyl, aryl, alkenyl, and alkynyl groups.

As used herein, a "building block" is one which, when attached to a molecular scaffold, imparts to that molecule a particular and unique characteristic. It contributes diversity to the scaffold by rendering the scaffold molecule different in some way from what it was before attachment of the group. Several chemical building blocks can be attached to a particular scaffold, and when considered together, the sum total of their properties will impart global diversity characteristics to the scaffold. Each set of combinations of chemical building blocks attached to a particular scaffold will modify the scaffold such that the molecule having each particular combinations of groups will be different from the molecule having any of the other combinations of building blocks. When all of the combinations of the building blocks or groups on the scaffold are considered, a library of compounds will be formed that include all of the possible combinations of scaffolds and building blocks.

Solid Supports

Solid supports, also called resins, according to the invention include controlled pore glass (CPG), polystyrene and cross-linked polystyrene/divinylbenzene resins, polyethylene glycol grafted polymers such as polystyrene, tentagel (R), Argogel(R), or Poros (a copolymer of polystyrene/ divinylbenzene). These may be functionalized with a variety of groups including, but not limited to, hydroxy, carboxy, thio, amino, and aldehyde, for example: Wang resin, Merrifield resin, hydroxymethyl polystyrene resin, formyl polystyrene resin, aminomethyl (AM) resin, MBHA resin, Rink amide and acid resins, Seiber resin, oxime resin, trityl resin, and thiol 4-methoxytrityl resin.

Particularly useful are solid supports bearing aldehyde linkers that allow for loading of amine scaffolds of this invention via reductive amination reactions. A number of commercially available supports, such as ArgoGel-MB-CHO resin, bear pendant aldehyde linkers that may be used for this purpose. Alternatively, acid stable resins such as, but not limited to, ArgoGel-OH may be derivatized with linkers such as, but not limited to, hydroxybenzaldehydes via Mitsunobu reactions so as to generate a pendant phenoxybenzaldehyde that is subsequently used for reaction with the cyclic amine scaffolds of this invention.

Chemistry to Attach Scaffold to Solid Support

Scaffolds VII, VIII, IX, X, XI or XII may be attached to solid supports in a number of different ways, as is evident from the chemical literature. There is a choice of attachment site on the scaffold, attachment functionality on the solid support and the linker that attaches the scaffold to the support. Typically, the scaffolds of the present invention are attached to the solid support at one of their amino groups. The solid support may bear any one of several possible functional groups for attachment of the scaffold including, but not limited to hydroxy, amino, carboxyl, and aldehyde. Preferably, the scaffold's amino group is reacted with an aldehyde functionality of the solid support via reductive amination.

A variety of linkers are available to choose from depending on the conditions under which the scaffold is to be attached to and cleaved from the support. Commercially available linkers that may be used include, but are not limited to, succinate, alkyl, —$(CH_2CH_2O)_n$— where n is 1 to 50, 3-carboxypropane sulfonamide (safety catch linker), hydroxymethylbenzoic acid (HMBA), hydroxymethylphenoxyacetic acid (HMPA), 4-(4-hydroxymethyl-3-methoxyphenoxy)butyric acid (HMPB), trityl, 4-hydroxyalkyl-2-methoxy-5-nitro-phenoxy (photolabile linker), Rink acid and amide linkers.

Bicyclic amines, of the present invention, are preferably generated from support-bound monocyclic amines via intramolecular Mitsunobu reaction. However, preformed bicyclic amine scaffolds may also be used in this invention, via attachment onto solid supports using procedures similar to those used for the monocyclic amine scaffolds. Likewise, oligomeric amine compounds of the present invention, are also generated from support-bound monocyclic scaffolds by covalent linkage of one scaffold sub-unit to another via their reactive hydroxy or amino groups.

Aldehyde resins, such as ArgoGel-MB-CHO, may be used for the loading of amine scaffolds of this invention. Typically, the resin is treated with the appropriately protected amine scafold as a solution in a 4:1 mixture of methanol and trimethyl orthoformate and the mixture shaken at room temperature for several hours to effect imine formation. This mixture is then treated with 2 equivalents of borane-pyridine complex and 2 equivalents of acetic acid for several hours to effect reduction of the imine and the loading of the scaffold onto the resin via an amine linkage. This linkage is base stable and tolerant of mildly acidic conditions. When cleavage of the scaffold is desired, the resin is exposed to neat trifluoroacetic acid (TFA).

A hydroxy group of the scaffold may also be attached to the support via first conversion to its succinate derivative by reaction with succinic anhydride and subsequent reaction with hydroxy or amino derivatized resin. This affords the scaffold attached to the resin via a succinate linker. The esterification of scaffold or resin may be effected via the use of coupling or activating reagents. These coupling and activating reagents include, but are not limited to, carbodiimides, such as for example, dicylcohexyl carbodiimide, and diisopropyl carbodiimide; acid or sulfonyl chlorides, such as for example, trimethylacetyl chloride, methanesulfonyl chloride, triisopropylbenzensulfonyl chloride; N-hydroxyimides, for example N-hydroxysuccinimide; and carbonyl diimidazole. In general, the carboxylic acid is first activated to a more reactive species such as an anhydride via reaction with the activating reagent, followed by reaction with the nucleophilic hydroxy group of the scaffold. Reactions typically may also include adjunct reagents such as a base to quench the byproducts of the acylation reaction and an appropriate solvent.

Cleavage from Solid Support

Isolation of the compounds of the libraries of the present invention may be effected via exposure of the solid support bound products to appropriate conditions that cleave the bonds that attach the scaffold to the solid support. For example, when the scaffolds of the present invention are attached to the solid support via a succinate linker at one of the hydroxyl groups of the scaffold, cleavage of this ester linkage is facile under basic conditions. Treatment of the compound libraries with a mixture of triethylamine and water affords cleavage from the solid support and the compounds of the present invention. When the scaffolds of the present invention are attached to a carboxy derivatized solid support, for example, these ester linkages may also be cleaved under basic conditions such as an appropriate amine, such as triethylamine, in a polar medium such as water or an appropriate alcohol. If the compounds of the present invention are synthesized by attachment of the scaffolds to a trityl solid support then cleavage of the products may be effected via acidic cleavage using acids such as trichloroacetic acid or trifluoroacetic acid in an appropriate solvent such as dichloromethane.

Typically, the monocyclic, bicyclic and oligomeric amine compounds of the present invention are attached on solid supports via an benzylamine linkage pendant on an aldehdye resin, for example ArgoGel-MB-CHO. Cleavage of this linkage may be effected under strongly acidic conditions. This linkage is base stable and tolerant of mildly acidic conditions. When cleavage of the monocyclic, bicyclic or oligomeric amine is desired, the resin is exposed to neat trifluoroacetic acid (TFA) containing triethylsilane (2.5%) as scavenger for a period of several hours. This clevage procedure is repeated and the combined cleaved product solutions are concentrated to afford the monocyclic, bicyclic or oligomeric amines of the present invention.

Synthesizing a combinatorial library having a large degree of chemical diversity is an important aspect of the present invention. Chemical diversity can be generated at several levels in combinatorial libraries. Chemical diversity is introduced at one level by varying the structure of the monocyclic amine scaffold used. On another level, diversity is introduced via the choice and manipulation of stereochemical configurations at various, and often, multiple locations on the monocyclic, bicyclic and oligomeric amine structures. This stereochemical control may be exercised during the generation and use of the amine scaffolds of this invention, such that chirally pure scaffolds are synthesized and used or scaffolds bearing both possible configurations at a particular chiral center or specific centers are used. This allows for rapid generation and use of large libraries of monocyclic, bicyclic and oligomeric amine compounds that thoroughly explore all possible spatial orientations of their pendant functional or substituent groups. Exploration of chemical space via the controlled use of chiral centers is an important aspect of this invention. Typically for a particular scaffold, all possible diastereomers are generated, either as individual compounds or as sets of compounds. These are then used for library generation to afford monocyclic, bicyclic and oligomeric amine compounds of corresponding stereochemistry.

Additional diversity may be introduced into monocyclic, bicyclic and oligomeric amine libraries by reaction of the scaffold's amino group with a broad diversity of building blocks that react via many different functional groups. In the case of monocyclic, bicyclic and oligomeric amine libraries, a further level of diversity is possible by the choice of a number of structurally diverse building blocks that are used for reaction at the combinatorial sites present on the scaffold. Reactions of varied building blocks with these scaffolds afford further diversity in the compounds of the present invention.

Chemical diversity arises not only from the different structures of the scaffolds, the wide variety of building blocks available and used in the present invention, but also from the manner in which these building blocks can be attached to combinatorial sites, directly or via tethering groups to combinatorial sites, and the relative positioning of different building blocks attached to the scaffold. Stereochemical control on substituents, the generation of bicyclic amines from monocyclic scaffolds and the generation of oligomeric amines from monocyclic and bicyclic amine scaffolds add further dimensions of diversity to the cyclic amine libraries of this invention.

Compounds of the Present Invention

Monocyclic amine compounds of the present invention are of formula I, II, III, IV, V, or VI and bear multiple sites of diversity. It will be recognized by the art-skilled that the monocyclic amine compounds of the present invention bear chiral centers in their scaffolds. Thus, I, II, III, IV, V, and VI, all possess at least one or more chiral centers leading to enantiomeric, and often diastereomeric, molecules. The present invention includes all possible enantiomeric and diastereomeric structures of these monocyclic amine compounds.

Each monocyclic amine compound of the libraries of the present invention are of formula I, II, III, IV, V, or VI:

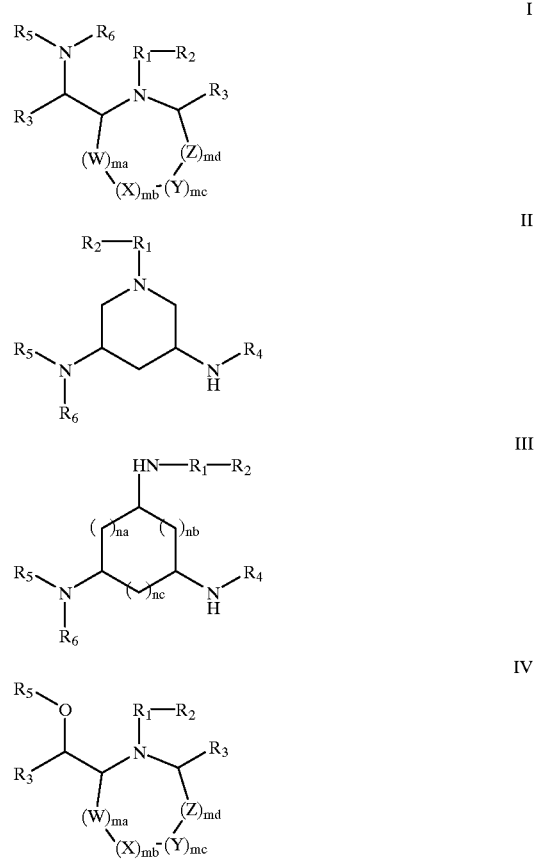

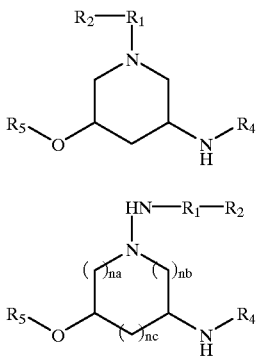

wherein:

$R_1$ and $R_{1'}$ are, individually $CH_2$, $CH(R_2)$, C=O, C=S, $S(=O)_2$, C(=O)NH, C(=S)NH or C(=O)O;

$R_2$ is H, substituted or unsubstituted $C_1$–$C_{10}$ alkyl, substituted or unsubstituted $C_2$–$C_{10}$ alkenyl, substituted or unsubstituted $C_2$–$C_{20}$ alkynyl, substituted or unsubstituted $C_6$–$C_{14}$ aryl, substituted or unsubstituted $C_6$–$C_{14}$ aralkyl, substituted or unsubstituted $C_3$–$C_{14}$ cycloalkyl, substituted or unsubstituted $C_5$–$C_{14}$ fused cycloalkyl, substituted or unsubstituted $C_4$–$C_{14}$ heterocyclyl, substituted or unsubstituted $C_4$–$C_{14}$ heterocyclylalkyl, substituted or unsubstituted $C_4$–$C_{14}$ heteroaryl; substituted or unsubstituted $C_4$–$C_{14}$ heteroaralkyl, CH($R_7$)—NH—$R_{7'}$ or CH($R_7$)—NH—$R_{1'}$—$R_3$; wherein the substituent groups are selected from the group consisting of acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy; or $R_1$ and $R_2$, together, are H, or an amino protecting group;

$R_3$ is H;

$R_4$ and $R_{4'}$ are, individually, H, $R_1$–$R_2$ or $R_{11}$–$R_{12}$;

$R_5$ is, H, substituted or unsubstituted $C_1$–$C_{10}$ alkyl, substituted or unsubstituted $C_2$–$C_{10}$ alkenyl, substituted or unsubstituted $C_2$–$C_{20}$ alkynyl, substituted or unsubstituted $C_6$–$C_{14}$ aryl, substituted or unsubstituted $C_6$–$C_{14}$ aralkyl, substituted or unsubstituted $C_3$–$C_{14}$ cycloalkyl, substituted or unsubstituted $C_5$–$C_1$ fused cycloalkyl, substituted or unsubstituted $C_4$–$C_{14}$ heterocyclyl, substituted or unsubstituted $C_4$–$C_{14}$ heterocyclylalkyl, substituted or unsubstituted $C_4$–$C_{14}$ heteroaryl; substituted or unsubstituted $C_4$–$C_{14}$ heteroaralkyl, —$R_1$-$R_2$, or N($R_8$)($R_9$)—C(=O); wherein the substituent groups are selected from the group consisting of acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy;

$R_6$ is, H, substituted or unsubstituted $C_1$–$C_{10}$ alkyl, substituted or unsubstituted $C_2$–$C_{10}$ alkenyl, substituted or unsubstituted $C_2$–$C_{20}$ alkynyl, substituted or unsubstituted $C_6$–$C_{14}$ aryl, substituted or unsubstituted $C_6$–$C_{14}$ aralkyl, substituted or unsubstituted $C_3$–$C_{14}$ cycloalkyl, substituted or unsubstituted $C_5$–$C_{14}$ fused cycloalkyl, substituted or unsubstituted $C_4$–$C_{14}$ heterocyclyl, substituted or unsubstituted $C_4$–$C_{14}$ heterocyclylalkyl, substituted or unsubstituted $C_4$–$C_{14}$ heteroaryl; substituted or unsubstituted $C_4$–$C_{14}$ heteroaralkyl, —$R_1$-$R_2$, or —C(=O)O—$R_3$; wherein the substituent groups are selected from the group consisting of acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy; or $R_5$ and $R_6$, together, are $(CH_2)_{nd}$, $(CH_2)_{nd}$—O—$(CH_2)_{ne}$, $(CH_2)_{nd}$—N($R_{10}$)—$(CH_2)_{ne}$, or $(CH_2)_{nd}$—S—$(CH_2)_{ne}$, wherein $R_{10}$ is substituted or unsubstituted $C_1$–$C_{10}$ alkyl, substituted or unsubstituted $C_6$–$C_{14}$ aryl, or substituted or unsubstituted $C_6$–$C_{14}$ aralkyl, substituted or unsubstituted $C_4$–$C_{14}$ heteroaryl; substituted or unsubstituted $C_4$–$C_{14}$ heteroaralkyl;

$R_7$ is H, substituted or unsubstituted $C_4$–$C_{10}$ alkyl, substituted or unsubstituted $C_2$–$C_{10}$ alkenyl, substituted or unsubstituted $C_2$–$C_{20}$ alkynyl, substituted or unsubstituted $C_6$–$C_{14}$ aryl, substituted or unsubstituted $C_6$–$C_{14}$ aralkyl, substituted or unsubstituted $C_3$–$C_{14}$ cycloalkyl, substituted or unsubstituted $C_5$–$C_{14}$ fused cycloalkyl, substituted or unsubstituted $C_4$–$C_{14}$ heterocyclyl, substituted or unsubstituted $C_4$–$C_{14}$ heterocyclylalkyl, substituted or unsubstituted $C_6$–$C_{14}$ heteroaryl; substituted or unsubstituted $C_6$–$C_{14}$ heteroaralkyl, or groups such as those attached to the α-position of amino acids, wherein the substituent groups are selected from the group consisting of acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy;

$R_{7'}$ is H or an amino protecting group;

$R_8$ and $R_9$ are each, independently, H, substituted or unsubstituted $C_1$–$C_{10}$ alkyl, substituted or unsubstituted $C_2$–$C_{10}$ alkenyl, substituted or unsubstituted $C_2$–$C_{20}$ alkynyl, substituted or unsubstituted $C_6$–$C_{14}$ aryl, substituted or unsubstituted $C_6$–$C_{14}$ aralkyl, substituted or unsubstituted $C_3$–$C_{14}$ cycloalkyl, substituted or unsubstituted $C_5$–$C_{14}$ fused cycloalkyl, substituted or unsubstituted $C_4$–$C_{14}$ heterocyclyl, substituted or unsubstituted $C_4$–$C_{14}$ heterocyclylalkyl, substituted or unsubstituted $C_4$–$C_{14}$ heteroaryl; substituted or unsubstituted $C_4$–$C_{14}$ heteroaralkyl, wherein the substituent groups are selected from the group consisting of acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy; or $R_8$ and $R_9$, together, are $(CH_2)_{nd}$, $(CH_2)_{nd}$—O—$(CH_2)_{ne}$, $(CH_2)_{nd}$—N($R_{10}$)—$(CH_2)_{ne}$, or $(CH_2)_{nd}$—S—$(CH_2)_{ne}$, wherein $R_{10}$ is substituted or unsubstituted $C_1$–$C_{10}$ alkyl, substituted or unsubstituted $C_6$–$C_{14}$ aryl, or substituted or unsubstituted $C_6$–$C_{14}$ aralkyl, substituted or unsubstituted $C_4$–$C_{14}$ heteroaryl; substituted or unsubstituted $C_4$–$C_{14}$ heteroaralkyl;

$R_{11}$ is a linker moiety;

$R_{12}$ is a solid support;

W, X, Y, and Z are, independently, CH—$R_3$, O, S, CHN($R_4$)($R_{4'}$), N—$R_1$-$R_2$ or CH—CH($R_3$)N($R_5$)($R_6$);

ma, mb, mc and md are, independently, 0, 1, 2, or 3;

na, nb and nc are each, independently, 0 to 2, wherein the sum of na, nb and nc is from 0 to 5; and nd and ne are each, independently, 1 to 4.

The present invention also provides amine compounds comprising a bicyclic scaffold bearing at least two sites of diversity, wherein the bicyclic scaffold is readily generated from the aforementioned monocyclic amine scaffold via intramolecular cyclization. Of the many sites of diversity on the bicyclic amine scaffolds of the present invention, at least one site of diversity is derived from a primary amino group that is exocyclic or from a secondary amino group that is part of the cyclic structure of the scaffold. Also, the present invention provides libraries of bicyclic amine compounds derived from bicyclic scaffolds. Compounds of the libraries of the present invention are of formula XIII, XIV, or XV. It will be recognized by the art-skilled that the bicyclic amine compounds of the present invention bear chiral centers. Thus, compounds of formula XIII, XIV and XV, all possess at least one or more chiral centers in their scaffold structure leading to enantiomeric, and often diastereomeric, compounds. The present invention includes all possible enantiomeric and diastereomeric structures of these bicyclic amine compounds, except where the structure explicitly shows a specific stereochemistry. The bicyclic amine compounds and libraries of compounds of the present invention are of formula XIII, XIV, or XV:

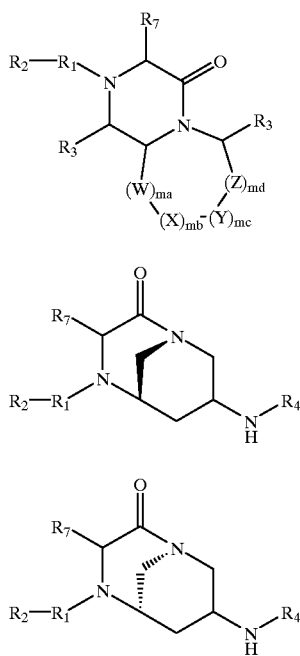

wherein:

$R_1$ and $R_{1'}$ are, individually CH$_2$, CH(R$_2$), C=O, C=S, S(=O)$_2$, C(=O)NH, C(=S)NH or C(=O)O;

$R_2$ is H, substituted or unsubstituted $C_1$–$C_{10}$ alkyl, substituted or unsubstituted $C_2$–$C_{10}$ alkenyl, substituted or unsubstituted $C_2$–$C_{20}$ alkynyl, substituted or unsubstituted $C_6$–$C_{14}$ aryl, substituted or unsubstituted $C_6$–$C_{14}$ aralkyl, substituted or unsubstituted $C_3$–$C_{14}$ cycloalkyl, substituted or unsubstituted $C_5$–$C_{14}$ fused cycloalkyl, substituted or unsubstituted $C_4$–$C_{14}$ heterocyclyl, substituted or unsubstituted $C_4$–$C_{14}$ heterocyclylalkyl, substituted or unsubstituted $C_4$–$C_{14}$ heteroaryl; substituted or unsubstituted $C_4$–$C_{14}$ heteroaralkyl, CH(R$_7$)—NH—R$_{7'}$ or CH(R$_7$)—NH—R$_{1'}$—R$_3$; wherein the substituent groups are selected from the group consisting of acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy; or $R_1$ and $R_2$, together, are H, or an amino protecting group;

$R_3$ is H, substituted or unsubstituted $C_1$–$C_{10}$ alkyl, substituted or unsubstituted $C_2$–$C_{10}$ alkenyl, substituted or unsubstituted $C_2$–$C_{20}$ alkynyl, substituted or unsubstituted $C_6$–$C_{14}$ aryl, substituted or unsubstituted $C_6$–$C_{14}$ aralkyl, substituted or unsubstituted $C_3$–$C_{14}$ cycloalkyl, substituted or unsubstituted $C_5$–$C_{14}$ fused cycloalkyl, substituted or unsubstituted $C_4$–$C_{14}$ heterocyclyl, substituted or unsubstituted $C_4$–$C_{14}$ heterocyclylalkyl, substituted or unsubstituted $C_4$–$C_{14}$ heteroaryl; substituted or unsubstituted $C_4$–$C_{14}$ heteroaralkyl, wherein the substituent groups are selected from the group consisting of acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy;

$R_4$ and $R_{4'}$ are, individually, is H, N(R$_8$) (R$_9$)C(=O), $R_1$–$R_2$ or $R_{11}$–$R_{12}$;

$R_7$ is H, substituted or unsubstituted $C_1$–$C_{10}$ alkyl, substituted or unsubstituted $C_2$–$C_{10}$ alkenyl, substituted or unsubstituted $C_2$–$C_{20}$ alkynyl, substituted or unsubstituted $C_6$–$C_{14}$ aryl, substituted or unsubstituted $C_6$–$C_{14}$ aralkyl, substituted or unsubstituted $C_3$–$C_{14}$ cycloalkyl, substituted or unsubstituted $C_5$–$C_{14}$ fused cycloalkyl, substituted or unsubstituted $C_4$–$C_{14}$ heterocyclyl, substituted or unsubstituted $C_4$–$C_{14}$ heterocyclylalkyl, substituted or unsubstituted $C_6$–$C_{14}$ heteroaryl; substituted or unsubstituted $C_6$–$C_{14}$ heteroaralkyl, or groups such as those attached to the α-position of naturally-occuring or non-naturally occuring amino acids of D- or L-configuration, wherein the substituent groups are selected from the group consisting of acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy;

$R_{7'}$ is H or an amino protecting group;

$R_8$ and $R_9$ are each, independently, H, substituted or unsubstituted $C_1$–$C_{10}$ alkyl, substituted or unsubstituted $C_2$–$C_{10}$ alkenyl, substituted or unsubstituted $C_2$–$C_{20}$ alkynyl, substituted or unsubstituted $C_6$–$C_{14}$ aryl, substituted or unsubstituted $C_6$–$C_{14}$ aralkyl, substituted or unsubstituted $C_3$–$C_{14}$ cycloalkyl, substituted or unsubstituted $C_5$–$C_{14}$ fused cycloalkyl, substituted or unsubstituted $C_4$–$C_{14}$ heterocyclyl, substituted or unsubstituted $C_4$–$C_{14}$ heterocyclylalkyl, substituted or unsubstituted $C_4$–$C_{14}$ heteroaryl; substituted or unsubstituted $C_4$–$C_{14}$ heteroaralkyl, wherein the substituent groups are selected from the group consisting of acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy; or $R_8$ and $R_9$, together, are (CH$_2$)$_{nd}$, (CH$_2$)$_{nd}$—O—(CH$_2$)$_{ne}$, (CH$_2$)$_{nd}$—N(R$_{10}$)—(CH$_2$)$_{ne}$, or (CH$_2$)$_{nd}$—S—(CH$_2$)$_{ne}$, wherein R$_{10}$ is substituted or unsubstituted $C_1$–$C_{10}$ alkyl, substituted or unsubstituted $C_6$–$C_{14}$ aryl, or substituted or unsubstituted $C_6$–$C_{14}$ aralkyl, substituted or unsubstituted $C_4$–$C_{14}$ heteroaryl; substituted or unsubstituted $C_4$–$C_{14}$ heteroaralkyl;

$R_{11}$ is a linker moiety; and $R_{12}$ is a solid support;

W, X, Y, and Z are, independently, CH—R$_3$, O, S, CHN(R$_4$) (R$_{4'}$), N—R$_1$–R$_2$, CH—O—R$_4$ or CH—CH(R$_3$) N(R$_5$) (R$_6$); and ma, mb, mc and md are, independently, 0, 1, 2, or 3.

In an additional aspect, the present invention provides oligomeric amine compounds comprising at least two or more monocyclic amine or bicyclic amine scaffolds, wherein the scaffolds are connected to each other via a variety of covalent inter-scaffold linkages including, but not limited to carbamate, alkylamine, urea, thiourea and amindine. These oligomeric amine compounds bear multiple sites of diversity that arise not only from the diversity sites offered by their component scaffolds, but also at sites that are created from the nature of the inter-scaffold linkage. Also, the present invention provides libraries of such oligomeric compounds derived from multiple scaffolds. It will be recognized by the art-skilled that the oligomeric amine compounds of the present invention bear chiral centers. Thus oligomeric amine compounds of the present invention, possess multiple chiral centers in their component scaffolds leading to enantiomeric, and often diastereomeric, compounds. The present invention includes all possible enantiomers and diastereomers of these oligomeric amine compounds.

The present invention provides combinatorial libraries of monocyclic amines derived from a variety of monocyclic scaffolds. This invention provides compounds obtained from monocyclic amine scaffolds of formula VII, VIII, IX, X, XI, and XII, and bicyclic amine scaffolds of formula XVI, XVII, and XVIII.

A wide variety of cyclic and bicyclic amine compounds are represented by formulae I, IV and XIII. Preferred structures of cyclic and bicyclic amine compounds of this invention, derived from these scaffolds, are of the formulae shown below:

COMPOUNDS OF FORMULA I

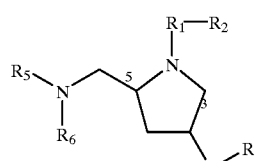

Ia

COMPOUNDS OF FORMULA IV

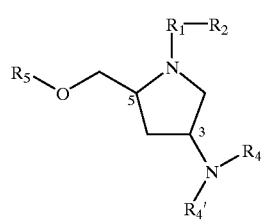

IVa

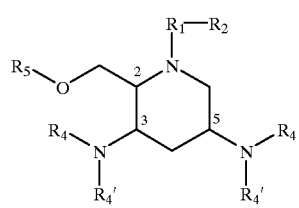

IVb

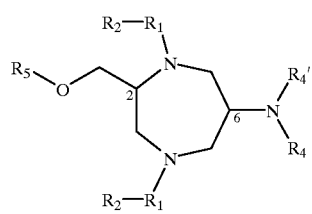

IVc

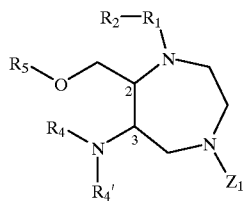

IVd

It is preferred that monocyclic amines of formula I of the present invention (derived form scaffolds of formula VII) be 3,5-disubstituted pyrrolidines Ia, and the ring system is numbered as shown.

It is preferred that monocyclic amines of the present invention derived from scaffolds of formula X be 3,5-disusbstituted pyrrolidines IVa, 3,5-disybstituted piperidines IVb, 2,6-disubstituted 1,4-diazepines IVc, or 3,7-disubstitited 1,4-diazepines IVd, and the ring systems are numbered as shown above.

It is also preferred that bicyclic amines of formula XIII of the present invention (derived from scaffolds of formula XVI) be 3,8-disubstituted 1,4-diazabicyclo[4.3.0]nonan-2-ones XIIIa, 3,7,9-trisubstituted 1,4-diazabicyclo[4.4.0]decan-2-ones XIIIb, 3,10-disubstituted 1,4,8-triazabicyclo[4.5.0]undecan-2-ones XIIIc, or 3,7-disubstituted 1,4,9-triazabicylo[4.5.0]undecan-2ones XIIId, and are numbered as shown below.

COMPOUNDS OF FORMULA XIII

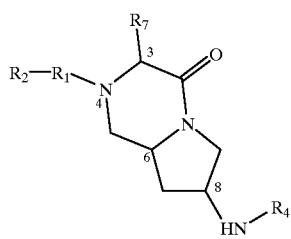

XIIIa

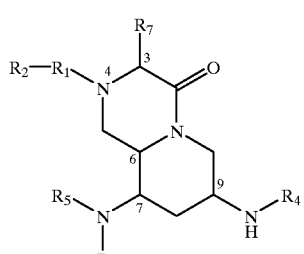

XIIIb

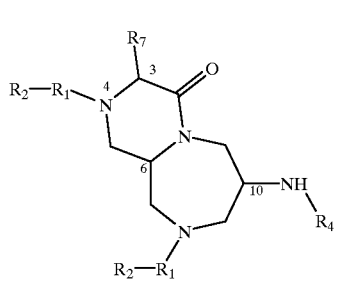

XIIIc

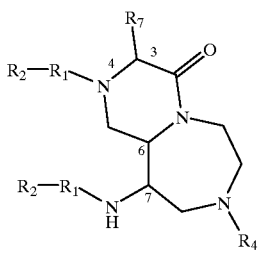

Process of Combinatorial Chemistry of the Present Invention

In one aspect of the invention, a combinatorial library of monocyclic, bicyclic or oligomeric amine compounds is synthesized by first attaching a plurality of monocyclic amine scaffolds to individual solid supports, each scaffold being one of formula VII, VIII, IX, X, XI or XII:

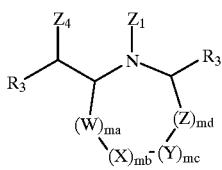

VII

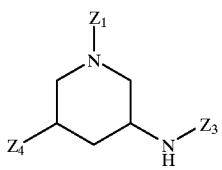

VIII

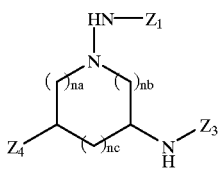

IX

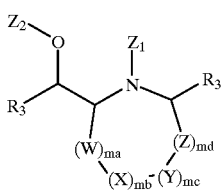

X

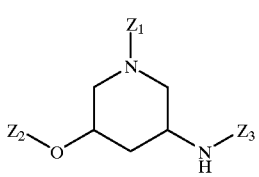

XI

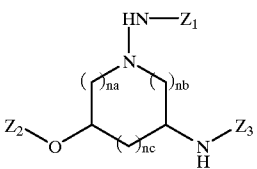

XII wherein:

$Z_1$ is an amino protecting group;

$Z_2$ is a hydroxyl protecting group;

$Z_3$ is H;

$Z_4$ is $N_3$, N—Pg or NH—Pg, wherein Pg is an amino protecting group;

$R_3$ is H, substituted or unsubstituted $C_1$–$C_{10}$ alkyl, substituted or unsubstituted $C_2$–$C_{10}$ alkenyl, substituted or unsubstituted $C_2$–$C_{20}$ alkynyl, substituted or unsubstituted $C_6$–$C_{14}$ aryl, substituted or unsubstituted $C_6$–$C_{14}$ aralkyl, substituted or unsubstituted $C_3$–$C_{14}$ cycloalkyl, substituted or unsubstituted $C_5$–$C_{14}$ fused cycloalkyl, substituted or unsubstituted $C_4$–$C_{14}$ heterocyclyl, substituted or unsubstituted $C_4$–$C_{14}$ heterocyclylalkyl, substituted or unsubstituted $C_4$–$C_{14}$ heteroaryl; substituted or unsubstituted $C_4$–$C_{14}$ heteroaralkyl, wherein the substituent groups are selected from the group consisting of acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy;

W, X, Y, and Z are, independently, CH—$R_3$, O, S, CH—NH—$Z_3$, N—$Z_1$, CH—O—$Z_2$ or CH—CH($R_3$)$Z_4$; and ma, mb, mc and md are, independently, 0, 1, 2, or 3.

In another aspect of the invention, a combinatorial library of monocyclic, bicyclic or oligomeric amine compounds is synthesized by first attaching a plurality of preformed bicyclic scaffolds to individual solid supports, or converting monocyclic scaffolds bound to solid supports via intramolecular Mitsunobu cyclization into bicyclic scaffolds, and each bicyclic scaffold being one of formula XVI, XVII or XVIII:

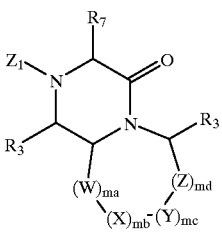

XVI

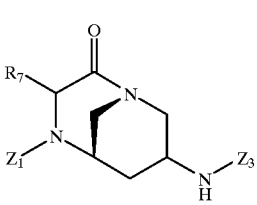

XVII

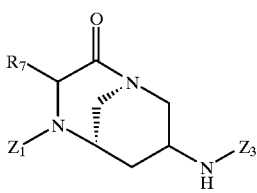

XVIII

Amine scaffolds are typically loaded onto solid supports, such as ArgoGel-MB-CHO, bearing pendant aldehyde groups via a reductive amination reaction. Reductive aminations in the solid phase may be performed with a variety of reducing agents, including, but not limited to, sodium cyanoborohydride, sodium triacetoxyborohydride and borane in pyridine. Alternatively, bifunctional groups may be attached to the solid support and used to link the amine scaffold to the solid support. Many such bifunctional compounds known in the art and are commercially available. Solid supports are also available with linking groups previously attached which are ready for use without a derivatization step. Alternatively, the scaffold's free amino or hydroxyl group is first attached to one end of a bifunctional linker and the linker bearing the scaffold at one end is subsequently attached to the solid support at its other end. For example, the scaffold may be reacted with succinic anhydride and converted to its succinate derivative. This succinate is then attached to the solid support via an acylation reaction that uses an activating or coupling reagent such as an appropriate carbodiimide. Following loading of the scaffold onto the solid support, the support is washed extensively with excess solvents to remove any unreacted starting material or reagents.

For scaffolds that have been loaded onto the solid support via reductive alkylation, the resulting secondary amine linkage is a potential combinatorial site to introduce diversity into the library of cyclic amines being synthesized. This amine may be reacted with a suitable building block that may be selected from a wide variety of possibilities including, but not limited to, carboxylic acids, acid chlorides, sulfonyl chlorides, isocyanates, isothiocyanates, aldehydes and ketones.

The protecting group on one of the combinatorial sites on the solid support bound scaffold is removed next, This combinatorial site, typically an amine, is reacted with a suitable building block such as a substituted carboxylic acid or another electrophilic reagent or building block (acid chloride, anhydride, sulfonyl chloride, etc.) using standard coupling methods (for examples, see Bodansky, *Principles of Peptide Synthesis,* 1984, Springer-Verlag, Berlin). Carbamates can be obtained by the treatment of the amine with an appropriate alkyl or aryl chloroformate, in the presence of a catalyst such as pyridine. A urea or thiourea can be formed by reacting the amino combinatorial site with an isocyanate or isothiocyanate, or by treatment with carbonyl diimidazole followed by a second amine, in the presence of base. Sulfonamides can be prepared from the amine by the reaction with a sulfonyl chloride in the presence of a base. The amine can be alkylated with alkyl halides or sulfonates. Additionally, amino compounds can be functionalized by reaction with an aldehyde or ketone forming a Schiff base. The Schiff base is then reduced in the presence of a reducing agent, such as sodium cyanoborohydride or borane in pyridine. Following both the amine deprotection and the building block coupling steps, the solid support is washed extensively with excess solvents to remove any unreacted starting materials or reagents from the reactions.

Pendant functional groups on building blocks, which require protection, are derivatized using acid labile protecting groups which are stable to TCA or with acid stable but base labile protecting groups such as Fmoc. If present, the acid labile trityl protecting group on the hydroxy group of the scaffold is removed by treating with an acid (3% TCA in dichloromethane). The resin is once again washed with excess solvent to remove any traces of acid and to prepare the resin for reaction or intramolecular cyclization at the hydroxy combinatorial site.

Alternatively, if an azide is present on the scaffold, this serves as a masked amino combinatorial site and unmasking is typically done under reducing conditions. Upon reduction of the azide, the resulting amine is now available for further combinatorialization. Reaction of the new combinatorial site, either a hydroxy or amino site, may now be performed with a variety of building blocks that may be selected from a wide variety of possibilities including, but not limited to, carboxylic acids, acid chlorides, sulfonyl chlorides, isocyanates, isothiocyanates, aldehydes and ketones. The hydroxy group may also be first activated to form an acylated intermediate followed by nucleophilic attack with amines so as to afford highly diverse substituted carbamates. In order to accomplish this, the free hydroxyl is first activated by reacting with carbonyl diimidazole. Reaction of this activated hydroxyl group with a primary or secondary amine provides facile access to carbamate derivatives of cyclic amines.

Following extensive washing of the solid support, the support bound compound is then cleaved using reagents and reaction conditions appropriate for the type of linker used in attaching the amine scaffold to the solid support. For example, cleavage conditions could involve the use of aqueous or organic bases, aqueous or organic acids, or even photolytic cleavage. In one mode of practice of the present invention, the solid support bound product is cleaved with trifluoroacetic acid containing 2.5% triethylsilane, for several hours. Filtration, to remove the cleaved support, and concentration of the product solution under reduced pressure or in a speed vac affords the cyclic amine products of the present invention. The products so isolated can be analyzed to determine purity and identity using methods such as mass spectrometry, HPLC and capillary electrophoresis.

In another aspect of the present invention, the hydroxy site revealed upon cleavage of the trityl protecting group allows for intramolecular Mitsunobu cyclization to afford bicyclic amines. Synthesis of bicyclic amines typically commences with loading and a first round of combinatorialization at the linking secondary amine. Deprotection of an amino site, as described above, is followed by reaction with a Fmoc-amino acid. The resulting derivative compound is treated with piperidine to cleave the Fmoc group and the exposed amino group reacted with 2-nitrobenzenesulfonyl chloride. This intermediate is next treated with DCA to cleave the dimethoxytrityl protecting group and the exposed hydroxy group subjected to Mitsunobu conditions. This leads to intramolecular cyclization between the hydroxy group and the nitrobenzenesulfonamide group so as to afford a solid support bound bicyclic amine scaffold. This may be subjected to further rounds of combinatorialization via sequential deprotection and reactions with diverse building blocks. Acidic cleavage of the derivatized bicyclic compound from the solid support, as described above, affords the bicyclic amines of the present invention.

At any one of the many points in the syntheses of the monocyclic and bicyclic amines of the present invention, the building block used for reaction with a diversity site on the solid support bound monocyclic or bicyclic scaffold, may also be another monocyclic or bicyclic scaffold molecule. In such instances a dimeric compound is synthesized comprising two cyclic amine scaffolds linked together via a covalent linkage. Repeated rounds of using scaffolds as building blocks leads to the generation of oligomeric compounds.

Such oligomeric amines of the present invention may bear inter-scaffold linkages that are carbamate, urea, amine, or guanindine in nature. Such linkages may be generated via reactions between amino and hydroxy groups of the scaffolds with or without activation.

Activation of a hydroxy combinatorial site on a solid support bound scaffold may be carried out via reaction with triphosgene. Reaction of this activated group with the amino group of an incoming cyclic amine scaffold leads to the generation of a carbamate inter-scaffold linkage. Similarly, activation of an amino combinatorial site on a solid support bound scaffold may be carried out via reaction with triphosgene or thiophosgene. Reaction of such activated groups with the amino group of an incoming amine scaffold leads to the generation of urea and thiourea inter-scaffold linkages, respectively.

Alternatively, an amino combinatorial site on a solid support bound scaffold may be reductively alkylated with a ketone scaffold such as a substituted pyrrolidin-3-one or piperidin-3-one to generate an amine inter-scaffold linkage. This linkage may be subjected to further combinatorialization using a variety of building blocks that react with amino groups. Yet another inter-scaffold linkage that is present in the oligomeric amines of the present invention is the guanidine linkage. This linkage is generated from the thiourea linkage via S-alkylation of the thiourea with iodoacetonitrile followed by displacement of the cyanomethyl sulfide with a suitable primary or secondary amine.

Repeated rounds of combinatorialization and inter-scaffold linkage formation lead to the generation of higher-order oligomers that comprise both monocyclic and bicyclic scaffolds that bear diverse substitutents on their combinatorial sites and are linked together via carbamate, urea, thiourea, amine or guanidine linkages. The oligomeric amines of the present invention also include compounds where several different scaffolds are present in the same compound. Also, oligomeric amines of the present invention, include compounds where different linkages are present at different locations within the same molecule.

The monocyclic, bicyclic and oligomeric amines of the present invention bear multiple chiral centers. These compounds may be prepared in a chirally pure form or as mixtures of diastereomers, as desired.

Diversity in the monocyclic, bicyclic and oligomeric amine libraries of the present invention may be controlled via proper selection of scaffolds, building blocks and the number and manner in which they are reacted during the course of combinatorial library generation. Combinatorial libraries of the present invention may be generated via parallel synthesis techniques to generate a collection of individual amine compounds bearing diverse building block arrayed around one of many different scaffolds. Alternatively, the libraries of the present invention may be generated via split-mix strategies that typically generate mixtures of compounds with many combinations of scaffolds and building blocks arrayed in the members of each population of amine compound mixtures synthesized.

Parallel synthesis of amine compound libraries may be performed via the preparation of solid supports bearing individual scaffolds. Each solid support bound scaffold is then separately subjected to multiple steps that deprotected the amino group, react it with one specific molecular member of the desired class of building block, then deprotected a second combinatorial site, react this with another building blocks and so on, until all sites of diversity have been derivatized as desired. All of these discrete amine compounds may be cleaved from the solid support to afford a library of discrete amine compounds that may be used for biological screening and evaluation.

Another approach to combinatorial libraries of the present invention involves a split-mix approach wherein a large batch of solid support may be derivatized with one scaffold. This solid support may then be divided into several portions, say ten portions, each of which is subjected to a first round of combinatorialization. The ten solid support bound products are then mixed together and the one mixture divided into ten pools such that each pool is expected to contain a nominally equal mixture of the ten first round products bound to the solid support. Each pool is then subjected to a second round of combinatorialization. This affords ten pools, each pool being a mixture of ten unique amine compounds, i.e. a library comprising a total of 100 compounds.

An additional approach to the synthesis of monocyclic, bicyclic and oligmeric amine libraries of the present invention, entails the derivatization of a solid support with a known mixture of scaffolds so as to synthesize mixtures of solid support bound scaffolds. Subsequent rounds of scaffold deprotection and reaction with individual building blocks, as above, will automatically generate mixtures of amine compounds. These mixtures will be characteristic in that the molecular members of a library generated in this manner will bear either one of the utilized scaffolds and all of the building blocks used during synthesis. A further approach to the generation of amine compound mixture libraries of the present invention, is to react the solid support with one scaffold and then during the subsequent rounds of combinatorialization, as above, use mixtures of building blocks instead of individual molecules for reaction at the diversity sites on the scaffold. This affords amine compound libraries where the scaffold is fixed while there is complete diversity at the building block sites. It should be obvious to the art-skilled that the libraries of the present invention may also be generated via the use of mixtures of scaffolds for attachment to the solid support followed by the use of mixtures of building blocks during each round of combinatoralization. Such an approach will afford amine compound libraries where all combinations of the scaffold and building block are represented in the population that comprises this mixture library.

Generation of monocyclic, bicyclic and oligomeric amine libraries of the present invention may be performed via conventional or manual synthetic manipulations or via automated synthesis. Thus each step of the process for the synthesis of combinatorial libraries of amine compounds, as described above, may be performed manually by a scientist to generate either discrete libraries or libraries of mixtures, as desired. Additionally, each step or some steps of the process for the synthesis of combinatorial libraries of amine compounds, as described above, may be performed by an automated instrument or robot instructed to perform the necessary steps of the process. Such an automated or semi-automated process can also generate either discrete libraries or libraries of mixtures, as desired.

Some examples of discrete members of the libraries of bicyclic amines are shown in the table below. The general structure of these compounds is shown below.

2,3,8-Trisubstituted 1,4-Diazabicyclo[4.3.0]nonan-2-ones

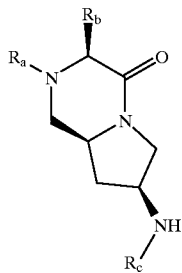

| Compd. | $R_c$ | $R_b$ | $R_a$ | HPLC purity | Mass Expected/ Found |
|---|---|---|---|---|---|
| 1 | tolylcarbamoyl | Me | H | 80 | 302 |
| 2 | isopropyl-carbamoyl | Me | H | 80 | 254 |
| 3 | benzyl-carbamoyl | Me | H | 85 | 302 |
| 4 | tolylcarbamoyl | Benzyl | H | 80 | 378 |
| 5 | isopropyl-carbamoyl | Benzyl | H | 85 | 330 |
| 6 | benzyl-carbamoyl | Benzyl | H | 75 | 378 |
| 7 | tolylcarbamoyl | Me | tolycarbamoyl | 95 | 451 |
| 8 | tolylcarbamoyl | Me | L-alanyl | 88 | 373 |

Some examples of bicyclic amine compounds synthesized as diastereomeric mixtures using the protocols described above are shown below. These compounds are synthesized as mixtures by starting with a scaffold that is a mixture of two diastereomers. The general structure of these 3,8-Disubstituted 1,4-diazabicyclo[4.3.0]nonan-2-ones and the substituents are shown below:

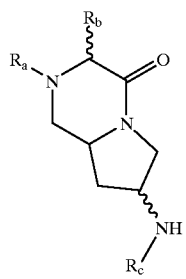

| Cpd. | $R_a$ | $R_b$ | $R_c$ | Mass Expected/ Found |
|---|---|---|---|---|
| 9 | m-toluoyl | H | 2-nitrobenzenesulfonyl | 458 |
| 10 | tolylcarbamoyl | H | 2-nitrobenzenesulfonyl | 473 |
| 11 | methoxybenzenesulfonyl | H | 2-nitrobenzenesulfonyl | 510 |
| 12 | tolylcarbamoyl | H | m-toluoyl | 406 |
| 13 | methoxybenzenesulfonyl | H | tolylcarbamoyl | 458 |
| 14 | m-toluoyl | H | methoxybenzenesulfonyl | 443 |
| 15 | thymidi-1-yl-acetyl | H | thymidi-1-yl-acetyl | 439 |
| 16 | thymidi-1-yl-acetyl | H | m-toluoyl | 487 |
| 17 | tolylcarbamoyl | H | thymidi-1-yl-acetyl | 454 |
| 18 | methoxybenzenesulfonyl | H | m-toluoyl | 443 |
| 20 | tolylcarbamoyl | H | m-toluoyl | 406 |
| 21 | methoxybenzenesulfonyl | H | thymidi-1-yl-acetyl | 491 |
| 22 | nicotinoyl | H | thymidi-1-yl-acetyl | 426 |

The building blocks and functional groups appended to the reactive amino groups of the monocyclic, bicyclic and oligomeric amine compounds of the present invention can be of various structures that impart particular interactive properties to the compounds. These chemical functional groups can effect interactions of at least the following types: hydrogen-bond donors and acceptors, ionic, polar, hydrophobic, aromatic, electron donors and acceptors, pi bond stacking and metal binding. As a result of such interactions, the monocyclic, bicyclic and oligomeric amine compounds of the present invention have unique properties affecting the overall global shape, the conformational space, electron density, dipole moment, ability of the compound to interact with enzyme pockets and other binding sites, and other similar properties.

In certain embodiments, representative compounds of the invention include but are not limited to:

23 N-((2R,6R,8aR)-6-(4-aminobutyl)-5-oxo-7-{N-[4-(trifluoromethyl)phenyl]carbamoyl}(1,2,3,6,7,8,8a-heptahydro-7-azaindolizin-2-yl))[(2,6-dibromo-4-fluorophenyl)amino]carboxamide;

24 N-{(2R,6R,8aR)-6-(4-aminobutyl)-7-[N-(3,4-dichlorophenyl)carbamoyl]-5-oxo(1,2,3,6,7,8,8a-heptahydro-7-azaindolizin-2-yl)}[(3,4-dichlorophenyl)amino]carboxamide;

25 N-((2R,6R,8aR)-6-(4-aminobutyl)-7-{N-[3,5-bis(trifluoromethyl)phenyl]carbamoyl}-5-oxo(1,2,3,6,7,8,8a-heptahydro-7-azaindolizin-2-yl))[(3,4-dichlorophenyl)amino]carboxamide;

26 N-((2R,6R,8aR)-6-(4-aminobutyl)-5-oxo-7-{N-[4-(trifluoromethyl)phenyl]carbamoyl}(1,2,3,6,7,8,8a-heptahydro-7-azaindolizin-2-yl))[(3,4-dichlorophenyl)amino]carboxamide;

27 N-{(2R,6R,8aR)-6-(4-aminobutyl)-7-[N-(3,4-dichlorophenyl)carbamoyl]-5-oxo(1,2,3,6,7,8,8a-heptahydro-7-azaindolizin-2-yl)}{[3,5-bis(trifluoromethyl)phenyl]amino}carboxamide;

28 N-((2R,6R,8aR)-6-(4-aminobutyl)-7-{N-[3,5-bis(trifluoromethyl)phenyl]carbamoyl}-5-oxo(1,2,3, 6,7, 8,8a-heptahydro-7-azaindolizin-2-yl)){[3,5-bis(trifluoromethyl)phenyl]amino}carboxamide;

29 N-((2R,6R,8aR)-6-(4-aminobutyl)-5-oxo-7-{N-[4-(trifluoromethyl)phenyl]carbamoyl}(1,2,3,6,7,8,8a-heptahydro-7-azaindolizin-2-yl)){[3,5-bis(trifluoromethyl)phenyl]amino}carboxamide;

30 N-{(2R,6R,8aR)-6-(4-aminobutyl)-7-[N-(3,4-dichlorophenyl)carbamoyl]-5-oxo(1,2,3,6,7,8,8a-heptahydro-7-azaindolizin-2-yl)}{[4-(trifluoromethyl)phenyl]amino}carboxamide;

31 N-((2R,6R,8aR)-6-(4-aminobutyl)-5-oxo-7-{N-[4-(trifluoromethyl)phenyl]carbamoyl}(1,2,3,6,7,8,8a-heptahydro-7-azaindolizin-2-yl)){[4-(trifluoromethyl)phenyl]amino}carboxamide;

32 N-{(8aS,2R,6R)-6-(4-aminobutyl)-7-[N-(3,4-dichlorophenyl)carbamoyl]-5-oxo(1,2,3,6,7,8,8a-heptahydro-7-azaindolizin-2-yl)}[(3,4-dichlorophenyl)amino]carboxamide;

33 N-((8aS,2R,6R)-6-(4-aminobutyl)-7-{N-[3,5-bis(trifluoromethyl)phenyl]carbamoyl}-5-oxo(1,2,3,6,7,8,8a-heptahydro-7-azaindolizin-2-yl))[(3,4-dichlorophenyl)amino]carboxamide;

34 N-((8aS,2R,6R)-6-(4-aminobutyl)-5-oxo-7-{N-[4-(trifluoromethyl)phenyl]carbamoyl}(1,2,3,6,7,8,8a-heptahydro-7-azaindolizin-2-yl))[(3,4-dichlorophenyl)amino]carboxamide;

35 N-{(8aS,2R,6R)-6-(4-aminobutyl)-7-[N-(3,4-dichlorophenyl)carbamoyl]-5-oxo(1,2,3,6,7,8,8a a-heptahydro-7-azaindolizin-2-yl)}{[3,5-bis(trifluoromethyl)phenyl]amino}carboxamide;

36 N-((8aS,2R,6R)-6-(4-aminobutyl)-7-{N-[3,5-bis(trifluoromethyl)phenyl]carbamoyl}-5-oxo(1,2,3,6,7,8,8a-heptahydro-7-azaindolizin-2-yl)){[3,5-bis(trifluoromethyl)phenyl]amino}carboxamide;

37 N-((8aS,2R,6R)-6-(4-aminobutyl)-5-oxo-7-{N-[4-(trifluoromethyl)phenyl]carbamoyl}(1,2,3,6,7,8,8a-heptahydro-7-azaindolizin-2-yl)){[3,5-bis(trifluoromethyl)phenyl]amino}carboxamide;

38 N-{(8aS,2R,6R)-6-(4-aminobutyl)-7-[N-(3,4-dichlorophenyl)carbamoyl]-5-oxo(1,2,3,6,7,8,8a-heptahydro-7-azaindolizin-2-yl)}{[4-(trifluoromethyl)phenyl]amino}carboxamide;

39 N-{(2S,6R,8aR)-6-(4-aminobutyl)-7-[N-(3,4-dichlorophenyl)carbamoyl]-5-oxo(1,2,3,6,7,8,8a-heptahydro-7-azaindolizin-2-yl)}[(3,4-dichlorophenyl)amino]carboxamide;

40 N-((2S,6R,8aR)-6-(4-aminobutyl)-7-{N-[3,5-bis(trifluoromethyl)phenyl]carbamoyl}-5-oxo(1,2,3,6,7,8,8a-heptahydro-7-azaindolizin-2-yl))[(3,4-dichlorophenyl)amino]carboxamide;

41 N-{(2S,6R,8aR)-6-(4-aminobutyl)-7-[N-(3,4-dichlorophenyl)carbamoyl]-5-oxo(1,2,3,6,7,8,8a-heptahydro-7-azaindolizin-2-yl)}{[3,5-bis(trifluoromethyl)phenyl]amino}carboxamide;

42 N-((2S,6R,8aR)-6-(4-aminobutyl)-7-{N-[3,5-bis(trifluoromethyl)phenyl]carbamoyl}-5-oxo(1,2,3,6,7,8,8a-heptahydro-7-azaindolizin-2-yl)){[3,5-bis(trifluoromethyl)phenyl]amino}carboxamide;

43 N-((2S,6R,8aR)-6-(4-aminobutyl)-5-oxo-7-{N-[4-(trifluoromethyl)phenyl]carbamoyl}(1,2,3,6,7,8,8a-heptahydro-7-azaindolizin-2-yl)){[3,5-bis(trifluoromethyl)phenyl]amino}carboxamide;

44 N-{(2S,8aS,6R)-6-(4-aminobutyl)-7-[N-(3,4-dichlorophenyl)carbamoyl]-5-oxo(1,2,3,6,7,8,8a-heptahydro-7-azaindolizin-2-yl)}[(3,4-dichlorophenyl)amino]carboxamide;

45 N-((2S,8aS,6R)-6-(4-aminobutyl)-7-{N-[3,5-bis(trifluoromethyl)phenyl]carbamoyl}-5-oxo(1,2,3,6,7,8,8a-heptahydro-7-azaindolizin-2-yl))[(3,4-dichlorophenyl)amino]carboxamide;

46 N-{(2S,8aS,6R)-6-(4-aminobutyl)-7-[N-(3,4-dichlorophenyl)carbamoyl]-5-oxo(1,2,3,6,7,8,8a-heptahydro-7-azaindolizin-2-yl)}{[3,5-bis(trifluoromethyl)phenyl]amino}carboxamide;

47 N-((2S,8aS,6R)-6-(4-aminobutyl)-7-{N-[3,5-bis(trifluoromethyl)phenyl]carbamoyl}-5-oxo(1,2,3,6,7,8,8a-heptahydro-7-azaindolizin-2-yl)){[3,5-bis(trifluoromethyl)phenyl]amino}carboxamide;

48 N-((2S,8aS,6R)-6-(4-aminobutyl)-5-oxo-7-{N-[4-(trifluoromethyl)phenyl]carbamoyl}(1,2,3,6,7,8,8a-heptahydro-7-azaindolizin-2-yl)){[3,5-bis(trifluoromethyl)phenyl]amino}carboxamide; and 49 N-((2S,8aS,6R)-6-(4-aminobutyl)-5-oxo-7-{N-[4-(trifluoromethyl)phenyl]carbamoyl}(1,2,3,6,7,8,8a-heptahydro-7-azaindolizin-2-yl)){[4-(trifluoromethyl)phenyl]amino}carboxamide.

In general, for therapeutic or prophylactic treatment, a patient suspected of requiring such therapy is administered an amine compound of the present invention, commonly in a pharmaceutically acceptable carrier, in amounts and for periods of time which will vary depending upon the nature of the particular disease, its severity and the patient's overall condition. The compounds of the present invention can be formulated in a pharmaceutical composition, which may include carriers, thickeners, diluents, buffers, preservatives, surface active agents and the like. Pharmaceutical compositions may also include one or more additional active ingredients such as antimicrobial agents, anti-inflammatory agents, anesthetics and the like.

The pharmaceutical composition may be administered in a number of ways depending upon whether local or systemic treatment is desired, and upon the area to be treated. Administration may be topical (including ophthalmic, vaginal, rectal, intranasal, transdermal), oral or parenteral, for example, by intravenous drip, subcutaneous, intraperitoneal or intramuscular injection or intrathecal or intraventricular administration.

Formulations for topical administration may include transdermal patches, ointments, lotions, creams, gels, drops, suppositories, sprays, liquids and powders. Conventional pharmaceutical carriers, nucleic acid carriers, aqueous, powder or oily bases, thickeners and the like may be necessary or desirable in certain circumstances. Coated condoms, gloves and the like may also be useful. Topical administration also includes delivery of the compounds of the invention into the epidermis of an animal by electroporation. Zewart et al., WO 96/39531, published Dec. 12, 1996.

Compositions for oral administration include powders or granules, suspensions or solutions in aqueous or non-aqueous media, capsules, sachets, or tablets. Thickeners, flavorings, diluents, emulsifiers, dispersing aids or binders may be desirable.

Intraluminal administration, for direct delivery of the compounds of the invention to an isolated portion of a tubular organ or tissue (e.g., artery, vein, ureter or urethra) may be desired for the treatment of patients with diseases or conditions afflicting the lumen of such organs or tissues. To effect this mode of administration, a catheter or cannula is surgically introduced by appropriate means. After isolation of the portion of the tubular organ or tissue for which treatment is sought, the compound of the invention is infused through the catheter or cannula. The infusion catheter or cannula is then removed, and flow within the tubular organ or tissue is restored by removal of the ligatures which effected the isolation of a segment thereof. Morishita et al., *Proc. Natl. Acad. Sci., U.S.A.,* 1993, 90, 8474.

Intraventricular administration, for direct delivery of compounds of the invention to the brain of a patient, may be desired for the treatment of patients with diseases or conditions afflicting the brain. To effect this mode of administration, a silicon catheter is surgically introduced into a ventricle of the brain, and is connected to a subcutaneous infusion pump (Medtronic, Inc., Minneapolis, Minn.) that has been surgically implanted in the abdominal region. Zimm et al., *Cancer Research,* 1984, 44, 1698; and Shaw, *Cancer,* 1993, 72(11 Suppl.), 3416. The pump is used to inject the compound, and allows precise dosage adjustments and variation in dosage schedules with the aid of an external programming device. The reservoir capacity of the pump is 18–20 mL, and infusion rates may range from 0.1 mL/hour to 1 mL/hour. Depending on the frequency of administration, ranging from daily to monthly, and the dose to be administered, ranging from 0.01 µg to 100 g per kg of body weight, the pump reservoir may be refilled at 3–10 week intervals. Refilling of the pump is accomplished by percutaneous puncture of the self-sealing septum of the pump. Compositions for intraventricular administration may include sterile aqueous solutions which may also contain buffers, diluents and other suitable additives.

Intrathecal administration, for the direct delivery of compounds of the invention into the spinal column of a patient, may be desired for the treatment of patients with diseases of the central nervous system. To effect this route of administration, a silicon catheter is surgically implanted into the L3–4 lumbar spinal interspace of the patient, and is connected to a subcutaneous infusion pump which has been surgically implanted in the upper abdominal region. Luer and Hatton, *The Annals of Pharmacotherapy*, 1993, 27, 912; Ettinger et al., *Cancer*, 1978, 41, 1270; and Yaida et al., *Regul. Pept.*, 1995, 59, 193. The pump is used to inject the compound, and allows precise dosage adjustments and variations in dose schedules with the aid of an external programming device. The reservoir capacity of the pump is 18–20 mL, and infusion rates may vary from 0.1 mL/hour to 1 mL/hour. Depending on the frequency of administration, ranging from daily to monthly, and dosage to be administered, ranging from 0.01 μg to 100 g per kg of body weight, the pump reservoir may be refilled at 3–10 week intervals. Refilling of the pump is accomplished by a single percutaneous puncture to the self-sealing septum of the pump. Compositions for intrathecal administration may include sterile aqueous solutions which may also contain buffers, diluents and other suitable additives.

To effect delivery to areas other than the brain or spinal column via this method, the silicon catheter may be configured to connect the subcutaneous infusion pump to, e.g., the hepatic artery, for delivery to the liver. Kemeny et al., *Cancer*, 1993, 71, 1964. Infusion pumps may also be used to effect systemic delivery. Ewel et al., *Cancer Research*, 1992, 52, 3005; and Rubenstein et al., *J. Surg. Oncol.*, 1996, 62, 194.

Compositions for parenteral, intrathecal or intraventricular administration, or liposomal systems, may include sterile aqueous solutions which may also contain buffers, diluents and other suitable additives. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of the amine compounds of the present invention, and can generally be estimated based on $EC_{50}$s found to be effective in in vitro and in vivo animal models. In general, dosage is from 0.01 μg to 100 g per kg of body weight, and may be given once or more daily, weekly, monthly or yearly, or even once every 2 to 20 years.

Amine compounds of the present invention with desired biological activity were determined by using the appropriate biological assay procedures described below.

The following examples and assay procedures illustrate the present invention, and are not intended to limit the same.

EXAMPLES

Example 1

Epimerization of Trans-hydroxyproline

Trans-4-hydroxyproline (150 g, 1.15 moles) and $Ba(OH)_2$ (0.599 mmoles) were placed in a stainless steel bomb and 300 mL of water was added. The bomb was sealed and placed in an oil bath at 200° C. for 14 hours. The bomb was cooled to room temperature and the contents transferred to a large (2 L) beaker and acidified to pH 4 with 3 M $H_2SO_4$. The precipitate of $BaSO_4$ was removed by vacuum filtration through a pad of celite. The filtrate was then concentrated to afford a brown solid which was dried overnight under vacuum to give 146.80 g of 4R-hydroxy-D,L-proline (98% yield). The epimeric ratio was checked via 400 MHz NMR by integrating the peaks at 3.1 and 3.3 ppm. The ratio of these protons and the D and L isomers is 1:1:

$^1H$ ($D_2O$) δ3.4 (s, 0.5H), 3.3 (s, 0.5H), 3.1 (t, 0.5H), 3.0 (dd, 0.5H), 2.2 (m, 1H), 2.1 (m, 1H), 1.2 (m, 1H), 1.0 (dd, 0.5H), 0.9 (m, 0.5H).

Example 2

N-Teoc-4R-hydroxy-D,L-proline Methyl Ester

An epimeric mixture of 4R-hydroxy-D,L-proline was suspended in 1.2 L of methanol. To this was slowly added chlorotrimethylsilane (290 mL, 250 g, 2.30 moles) over a period of 30 minutes. The reaction was stirred overnight. The clear solution was concentrated to one third the volume and added slowly to 3.5 L of ethyl ether, to afford a precipitate of the hydrochloride as a light brown solid. The precipitate was collected by vacuum filtration and dried under high vacuum to remove the remaining ether and silane. 181.20 g of 4-hydoxy-proline methyl ester hydrochloride was isolated as an ivory colored solid (90% yield):

$^1H$ ($CD_3OD$) δ4.6 (m, 2H), 3.9 (d, 3H); 3.4 (m, 2H) 2.4 (m, 2H); $^{13}C$ ($CD_3OD$) 38.36, 38.60, 54.03, 55.08, 59.56, 59.71, 70.15, 70.64, 170.55 ppm.

Teoc Protection

4-Hydoxyproline methyl ester hydrochloride (32.00 g, 189 mmoles) was dissolved in 500 mL of 1:1 water/dioxane. To this solution was added triethylamine (39.5 mL, 28.69 g, 283 mmoles) followed by TEOC-NHS (58.71 g, 226 mmoles) and the reaction stirred overnight at room temperature. The reaction was concentrated to approximately ½ volume and poured into 200 mL 1M HCl and extracted 3× with dichloromethane. The combined extracts were dried with $MgSO_4$ and concentrated to afford 52.0 g of the trimethylsilyl ethyl carbamate protected product as a pale yellow oil (95% yield):

$^1H$ NMR ($CDCl_3$, 200 MHz) δ4.4 (m, 2H), 4.1 (m, 2H), 3.6 (m, 6H), 2.1 (m, 2H), 0.9 (m, 2H), 0.0 (s, 9H); $^{13}C$ NMR ($CDCl_3$) 174.68, 173.20, 155.32, 154.96, 69.55, 68.83, 63.65, 57.65, 57.49, 55.12, 54.74, 54.30, 52.52, 52.01, 38.94, 38.18, 17.54, −1.65 ppm; HRMS (FAB$^+$) Expected M+H 290.1424 Observed 290.1429.

Example 3

N-Teoc-4R-O-methanesulfonyl-D,L-proline Methyl Ester

N-Teoc-4R-hydroxy-D,L-proline methyl ester (20.00 g, 69.1 mmoles) was dissolved in 500 mL of 1:1 $CH_2Cl_2$:pyridine and cooled to 0° C. To this solution was added methanesulfonyl chloride (6.5 mL, 9.50 g, 82.9 mmoles) and the reaction stirred at room temperature. TLC (3:7 ethyl acetate hexane) showed the reaction to be complete after 4 hours. The reaction mixture was concentrated to a viscous oil and poured into 0.1M citric acid and extracted three times with dichloromethane. The combined extracts were washed with brine and dried over $MgSO_4$, then concentrated to afford 24.14 g of the product as an oil (95% crude yield):

$^1H$ ($CDCl_3$) δ5.2 (m, 1H), 4.5 (m, 1H), 4.1 (m, 2H), 3.8 (m 5H), 3.0 (d, 3H), 2.5 (m, 1H), 2.2 (m, 1H), 1.0 (m, 2H), 0.0 (s, 9H) ppm.

Example 4

N-Teoc-4S-azido-D,L-proline Methyl Ester

N-Teoc-4R-O-methanesulfonyl-D,L-proline methyl ester was dissolved in 500 mL DMF, and $NaN_3$ (6.75 g, 104 mmoles) was added and the reaction heated to 80° C. for 3 hours. The reaction was concentrated to one third the volume and poured into 500 mL of saturated $NaHCO_3$ and extracted three times with ethyl acetate. The combined extracts are dried over $Na_2SO_4$, filtered and concentrated to an oil. Filtration through a silica gel pad with 3:7 ethyl acetate/hexane, followed by concentration, resulted in a pale yellow oil weighing 19.16 g. This material was used directly for reduction to the amine:

$^1$H (CDCL$_3$) δ4.4 (m, 1H), 4.2 (m, 3H), 3.7 (m, 4H), 3.5 (m 1H), 2.3 (m, 2H), 0.9 (m, 2H), 0.0 (s, 9H); $^{13}$C (CDCL$_3$) 172.39, 171.61, 154.62, 63.84, 59.10, 58.54, 58.20, 57.51, 52.19, 51.42, 51.10, 50.95, 36.21, 36.08, 35.18, 34.97, 17.68, 1.67 ppm; HRMS (FAB$^+$) Expected M+Na 337.1308 Observed 337.1319.

Example 5

N-TEOC-3S-N-trifluoroacetamido-5-hydroxymethyl Pyrrolidine

N-Teoc-4S-azido-D,L-proline methyl ester (6.00 g, 19.1 mmoles) was dissolved in 100 mL of dry THF and cooled to 0° C. A 2M solution of LiBH$_4$ in THF (12.0 mL, 24 mmoles, 5 eq of hydride) was added, followed by a 0.5 M solution of 9-BBN (3.48 mL, 1.92 mmoles, 0.10 eq). The cold bath was removed and the reaction stirred at room temperature for 4 hours. TLC (1:1 EtOAc/Hexane) showed the all of the starting material had been consumed. The reaction mixture was acidified with 3M H$_2$SO$_4$ to pH 4, neutralized with 1M NaOH to pH 8 and partitioned between ethyl acetate and saturated NaHCO$_3$. The aqueous phase was then extracted two more times with ethyl acetate and the combined organic extracts washed with brine, dried over MgSO$_4$, filtered, and concentrated to give a clear oil. The oil was dissolved in methanol and ethyl trifluoroacetate (4.2 mL, 5.0 g, 35 mmoles, 1.8 eq) was added followed by triethylamine (5.6 mL, 4.0 g, 40 mmoles, 2 eq) and the reaction stirred overnight. The solution was concentrated to an oil and chromatographed over silica gel with 20 % EtOAc/hexane and the product that elutes as the middle fraction was collected. Concentration of the product fraction afforded 4.60 g of N-TEOC-3S-N-trifluoroacetamido-5-hydroxymethyl pyrrolidine (66% yield):

$^1$H (CDCL$_3$) δ9.4 (d, 1H), 4.1 (m, 4H), 3.5 (m, 5H), 2.3 (m 1H), 1.8 (m, 1H), 1.0 (t, 2H), 0.0 (s, 9H) ; $^{13}$C (CDCL$_3$) 156.79, 155.73, 69.21, 65.49, 64.18, 63.71, 63.06, 59.09, 58.80, 58.25, 54.54, 52.17, 51.92, 47.58, 34.12, 33.86, 17.81, 14.10, −1.59 ppm; $^{19}$F (CDCL$_3$) −77.21 ppm (referenced to CFCl$_3$ at 0 ppm); HRMS (FAB+) expected (M+Na) 379.1277 observed (379.1288).

Example 6

N-TEOC-3S-trifluoroacetamido-5-azidomethyl-pyrrolidine

N-TEOC-3S-N-trifluoroacetamido-5-hydroxymethyl pyrrolidine(5.78 g, 16.2 mmoles) was dissolved in 75 mL of 1:1 dichloromethane:pyridine and cooled to 0° C. Methanesulfonyl chloride (1.50 mL, 2.23 g, 19.5 mmoles) was added and the reaction stirred for 2 hours while warming to room temperature. TLC (3/7 EtOAc/hexane) indicated consumption of starting material and the solution was concentrated to one third the original volume. The reaction mixture was partitioned between ethyl acetate and saturated NaHCO$_3$ and the aqueous layer extracted two additional times with ethyl acetate. The combined extracts were washed with brine, dried over MgSO$_4$, filtered, and concentrated to give an oil. The oil was dissolved in 75mL of DMF and sodium azide (1.55 g, 23.4 mmoles, 1.2 eq) and the reaction heated to a bath temperature of 85° C. for 4 hours. TLC (3/7 EtOAc/hexane) showed consumption of all the starting material. The solution was concentrated to an off white slurry and partitioned between ethyl acetate and saturated NaHCO$_3$. The aqueous layer was extracted two additional times with ethyl acetate and the extracts combined, washed with brine, dried over MgSO$_4$, filtered, and concentrated to an oil. Chromatography with 2/8 EtOAc/hexane yielded 2.90 g (47% yield) of N-TEOC-3S-trifluoroacetamido-5-azidomethyl-pyrrolidine as a clear oil:

$^1$H (CDCL$_3$) δ9.2 (d, 1H), 4.1 (m, 4H), 3.5 (m, 4H), 2.1 (m, 2H), 1.0 (m, 2H), 0.0 (s, 9H); $^{13}$C (CDCL$_3$) 155.03, 127.75, 63.77, 59.15, 56.00, 55.73, 55.25, 53.66 52.38, 51.94, 34.18, 17.83, 1.55 ppm; $^{19}$F (CDCL$_3$) −77.21 ppm.

Example 7

N-TEOC-3S-amino-5-azidomethyl-pyrrolidine

N-TEOC-3S-trifluoroacetamido-5-azidomethyl-pyrrolidine (9.9 mmoles) was dissolved in 25 mL of 10% K$_2$CO$_3$ in 5/2 methanol/water and stirred overnight. The solution was then concentrated to one half the volume and poured into water. The solution was extracted three times with ethyl acetate, the extracts combined, dried over MgSO$_4$ and concentrated to an oil. The oil was chromatographed with 1:1 ethyl acetate/hexane to yield (3.0 mmoles) N-TEOC-3S-amino-5-azidomethyl-pyrrolidine as a clear oil.

Example 8

N-Teoc-4S-bromo-D,L-proline Methyl Ester

N-Teoc-4R-hydroxy-D,L-proline methyl ester (48.2 mmoles) was dissolved in dichloromethane (400 mL), to which triphenylphosphine (25.30 g, 96.4 mmoles) and triethylamine (30 mL, 21.46 mmoles) were added and the solution cooled to 0° C. Dibromotetrachloroethylene (31.40 g, 96.4 mmoles) was added as a solution in dichloromethane (125 mL) to the reaction mixture over 20 minutes. After stirring overnight the reaction was concentrated to a solid and suspended in a minimal volume of 15% ethyl acetate/hexane and filtered through a plug of silica gel. The eluent was concentrated to an oil that was used directly without further purification for azide displacement:

$^1$H (CDCL$_3$) δ4.2 (m, 5H), 3.7 (s, 3H), 2.8 (m, 1H), 2.4 (m, 2H), 1.9 (m, 2H), 0.0 (s, 9H); $^{13}$C (CDCL$_3$) 172.21, 171.53, 63.84, 58.02, 55.81, 55.41, 52.10, 43.76, 41.59, 41.32, 40.91, 40.30, 40.05, 39.90, 17.69, −1.67 ppm.

Example 9

N-Teoc-4R-azido-D,L-proline Methyl Ester

N-Teoc-4S-bromo-D,L-proline methyl ester (6.75 g, 19.2 mmoles) was dissolved in 75 mL DMF and sodium azide (1.62 g, 25 mmoles) added. The reaction was heated to a bath temperature of 85° C. and stirred for 4 hours. TLC (2/8 EtOAc/Hexane) indicated consumption of the starting material. The reaction was concentrated to a suspension and poured into saturated NaHCO₃ and extracted three times with ethyl acetate. The extracts were combined and washed with brine, dried over MgSO₄, filtered and concentrated to a clear oil weighing 5.55 g (92 % crude yield):

$^1$H (CDCL₃) δ4.4 (m, 1H), 4.2 (m, 2H), 3.8 (m, 4H), 3.5 (m, 1H), 2.3 (m, 2H), 1.0 (m, 2H), 0.0 (s, 9 H); $^{13}$C (CDCL₃) 172.38, 63.85, 59.26, 59.13, 58.61, 57.55, 52.13, 51.03, 36.26, 36.18, 35.99, 35.54, 35.21, 17.75, −1.66 ppm.

Example 10

N-TEOC-3R-trifluoroacetamido-5-hydroxymethyl-pyrrolidine

N-Teoc-4R-azido-D,L-proline methyl ester (5.55 g, 17.7 mmoles) was reduced according to the procedure of Example 5. The LiBH₄ (13.2 mL, 26.5 mmoles) and 9-BBN (5.2 mL, 2.6 mmoles) were added and the reaction stirred for 4 hours. The reaction was worked up as described in Example 5, and the resulting amine protected with ethyl trifluoroacetate (6.3 mL, 7.54 g, 53.1 mmoles), and triethylamine (7.00 mL, 5.06 g, 50 mmoles). Workup and chromatography yielded a clear oil weighing 3.80 g (57% yield):

$^1$H (CDCL₃) δ4.2 (m, 4), 3.5 (m, 4H), 2.2 (m, 1H), 1.8 (m, 1H) 1.0 (m, 2H), 0.0 (s, 9H); $^{19}$F (CDCL₃) −77.21 ppm.

Example 11

N-TEOC-3R-trifluoracetamido-5-azidomethyl-pyrrolidine

N-TEOC-3R-trifluoroacetamido-5-hydroxymethyl-pyrrolidine (3.80 g, 11 mmoles) was mesylated according to the procedure of Examples 6 and 53 using methanesulfonyl chloride (1.10 mL, 1.60 g, 14 mmoles). After isolation, the crude mesylate was treated with sodium azide (0.550 g, 8.5 mmoles) in DMF at 85° C. for 4 hours. Work up as described in Examples 6 and 55 yielded 3.00 g of the N-TEOC-3R-trifluoracetamido-5-azidomethyl-pyrrolidine (72% yield):

$^1$H (CDCL₃) δ4.1 (m, 4H), 3.5 (m, 4H), 2.1 (m, 2H), 1.0 (t, 2H), 0.0 (s, 9H); $^{19}$F (CDCL₃) −77.20 ppm.

Example 12

N-TEOC-3R-amino-5-azidomethyl-pyrrolidine

N-TEOC-3R-trifluoracetamido-5-azidomethyl-pyrrolidine (9.9 mmoles) was dissolved in 25 mL of 10% K₂CO₃ in 5/2 methanol/water and stirred overnight. The solution was then concentrated to one half the volume and poured into water. The solution was extracted three times with ethyl acetate, the extracts combined, dried over MgSO₄ and concentrated to an oil. The oil was chromatographed with 1:1 ethyl acetate/hexane to yield N-TEOC-3R-amino-5-azidomethyl-pyrrolidine as a clear oil.

Example 13

H-TEOC-3S-amino-5R-azidomethyl-pyrrolidine, and N-TEOC-3S-amino-5S-azidomethyl-pyrrolidine N-TEOC-3S-amino-5-azidomethyl-pyrrolidine is resolved into its two diasteromeric components via the usual methods of resolution known in the literature. Chromatographic, HPLC or crystallization methods allow separation of the diastereomers to afford N-TEOC-3S-amino-5R-azidomethyl-pyrrolidine, and N-TEOC-3S-amino-5S-azidomethyl-pyrrolidine.

Example 14

N-TEOC-3R-amino-5R-azidomethyl-pyrrolidine, and N-TEOC-3R-amino-5S-azidomethyl-pyrrolidine N-TEOC-3R-amino-5-azidomethyl-pyrrolidine is resolved into its two diasteromeric components via the usual methods of resolution known in the literature. Chromatographic, HPLC or crystallization methods allow separation of the diastereomers to afford N-TEOC-3R-amino-5R-azidomethyl-pyrrolidine, and N-TEOC-3R-amino-5S-azidomethyl-pyrrolidine.

Example 15

Methyl N-p-methoxybenzyl-4R-t-butyldimethylsilyloxy-proline 4R-hydroxy-D,L-proline methyl ester (32.00 g, 189 mmoles) was dissolved in 600 mL dichloromethane. To this solution was added p-methoxybenzyl chloride (30.75 mL, 35.52 g, 229 mmoles) and diisopropyl ethyl amine (72.5 mL, 53.77 g, 416 mmoles). The solution was then heated to reflux overnight. After cooling to room temperature, the reaction was concentrated to a viscous oil and dissolved in 500 mL DMF. Imidazole (32.20 g, 473 mmoles) and t-butyldimethylsilylchloride (34.2 g, 0.227 mmoles) were added and the reaction stirred for 2 hours at room temperature. TLC (1:1 EtOAc:hexane) showed complete consumption of starting material. The solution was concentrated to one third the original volume and poured into 600 mL of 0.1 M citric acid and extracted three times with ethyl acetate. The extracts were combined, dried over MgSO₄, filtered, and concentrated to a viscous oil. This crude product was purified by passage through a pad of silica gel and 57.53 g of methyl N-p-methoxybenzyl-4R-t-butyldimethylsilyloxy-proline was isolated (80% crude yield):

$^1$H (CDCL₃) δ7.2 (d, 2H), 6.8 (d, 2H), 4.3 (m, 1H), 4.0–3.4 (m, 9H), 3.2 (m, 2H), 2.9 (dd 0.5H), 2.7 (dd, 0.5H), 2.3 (m, 1H), 2.0 (m, 2H), 0.8 (d, 9H), 0.0 (d, 6H); $^{13}$C (CDCL₃) 174.24, 173.91, 130.32, 130.10, 113.59, 70.44, 64.19, 63.77, 61.56, 60.73, 60.28, 58.60, 57.03, 55.18, 51.67, 51.48, 40.12, 39.61, 25.79, 17.99, 14.18, −4.83 ppm.

Example 16

N-p-methoxybenzyl-3R-(t-butyldimethylsilyloxy)-5-hydroxymethyl Pyrrolidine

Methyl N-p-methoxybenzyl-4R-t-butyldimethylsilyloxy-proline (55.21 g, 146 mmoles) was dissolved in 500 mL dry THF and cooled to 0° C. A 2M solution of LIBH₄ (88.00 mL, 176 moles) was added via syringe and the reaction warmed to room temperature, then heated to reflux for 2 hours when TLC (2:8 EtOAc/Hexane) indicated complete reduction. The reaction was cooled to 0° C. and then quenched by the slow addition of 1M HCl to pH 4, and then back to pH 8 with saturated NaHCO₃. The reaction was concentrated to one third the original volume and poured into 500 mL of saturated NaHCO₃ and extracted three times with ethyl acetate. The extracts were combined, dried over MgSO₄, filtered, and concentrated to give 49.80 g of N-p-methoxybenzyl-3R-(t-butyldimethylsilyloxy)-5-hydroxymethyl pyrrolidine as an oil (97% yield):

$^1$H (CDCL₃) δ7.3 (m, 2H), 6.9 (m, 2H), 4.3–3.9 (m, 2H), 3.9–3.6 (m, 4H), 3.6–3.1 (m, 2H), 2.9–2.6 (m, 1H), 2.5 (dd, 0.5H), 2.2 (m, 1H), 1.9 (m, 1H) 0.9 (m, 9H), 0.0 (m, 6H).

Example 17

N-p-methoxybenzyl-3-hydroxy-5R-(t-butyldimethylsilyloxy)-piperidine

N-p-methoxybenzyl-3R-(t-butyldimethylsilyloxy)-5-hydroxymethyl pyrrolidine (12.67 g, 53.4 mmoles) was dissolved in dry THF and cooled to −78° C. To this solution was added trifluoroacetic anhydride (7.6 mL, 11.34 g, 54.0 mmoles), dropwise, as a 1:1 solution in THF over 15 minutes. The reaction was stirred for 4 hours while warming to 0° C. Triethylamine (22.6 mL, 16.39 g, 162 mmoles) was added and the reaction heated to reflux for 16 hours. The reaction was then cooled to room temperature and sodium hydroxide (6.48 g, 162 mmoles) as a solution in 30 mL water was added. The solution was neutralized to pH 7 with 0.1 M citric acid and concentrated to a suspension. This was then poured into saturated $NaHCO_3$ and extracted three times with ethyl acetate. The combined extracts were dried and concentrated to a brown oil. This was chromatographed with 20% ethyl acetate/hexane to yield 10.0 g of the product (79% yield) as a reddish oil:

$^1H$ ($CDCl_3$) δ7.2 (d, 2H), 6.8 (d, 2H), 3.9 (m, 1 H), 3.8 (s, 3 H), 3.6–3.3 (m, 3 H), 2.9–2.2 (m, 2 H), 2.2–1.6 (3 H), 1.3 (m, 1 H), 0.9 (d, 9 H), 0.0 (d, 6 H).

Example 18

N-TEOC-3-hydroxy-5R-(t-butyldimethylsilyloxy)-piperidine

N-p-methoxybenzyl-3-hydroxy-5R-(t-butyldimethylsilyloxy)-piperidine (52 g, 142 mmoles) was dissolved in methanol and acetic acid (9.3 mL, 9.77 g, 163 mmoles) and then treated with 10% palladium on carbon (5.0 g). The solution was evacuated under vacuum three times and flushed with $H_2$. The solution was hydrogenated at ambient pressure overnight. The solution was again evacuated under vacuum and flushed with argon three times. The solution was filtered through celite and the filtrate concentrated to an oil. This oil was then protected as the trimethyl silyl ethyl carbamate (Teoc) following the procedures of Examples 2 and 51, using triethylamine (30 mL, 21.55 g, 213 mmoles) and TEOC-NHS (38.0 g, 147 mmoles). After work up the product was isolated as an oil weighing 30.0 g (56 %yield):

$^1H$ ($CDCl_3$) δ4.2 (m, 4 H), 3.5 (m, 4 H), 1.8 (m, 2 H), 1.2 (m, 1 H), 0.9 (m, 11 H), 0.1 (m, 15 H); $^{13}C$ ($CDCl_3$) 156.4, 70.35, 66.63, 65.42, 64.76, 64.61, 63.57, 50.59, 50.29, 50.07, 49.94, 40.93, 25.64, 17.76, −1.59, −4.96 ppm.

Example 19

N-TEOC-3-azido-5R-(t-butyldimethylsilyloxy)-piperidine

N-TEOC-3-hydroxy-5R-(t-butyldimethylsilyloxy)-piperidine (27.0 g, 72 mmoles) was mesylated following the procedure of Examples 3 and 53, using methanesulfonyl chloride (6.94 mL,10.25 g, 89 mmoles). After workup the crude mesylate was displaced with sodium azide (5.80 g, 89 mmoles) following the procedure of Examples 4 and 55. Work up and chromatography yielded the azide 18.00 g, 62% as a clear oil:

$^1H$ ($CDCl_3$) δ4.2 (m, 3 H), 3.9–3.2 (m, 3 H), 2.9 (m, 2 H), 2.5 (m, 1 H), 1.8 (m, 1 H), 1.0 (m, 11 H), 0.0 (m, 15 H).

Example 20

N-TEOC-3-(trifluoroacetamido)-5R-(t-butyldimethylsilyloxy)-piperidine

Palladium on carbon (2.00 g) was added to a solution of the crude N-TEOC-3-azido-5R-(t-butyldimethylsilyloxy)-piperidine (17.00 g, 42.4 mmoles) in ethanol and ethyl trifluoroacetate (25 mL, 30.2 g, 212 mmoles) was added. The solution was evacuated three times and flushed with hydrogen. The azide was reduced with hydrogen at ambient pressure overnight. The reaction was evacuated and flushed with argon as in Example 18. The crude product was treated with trifluoroacetic anhydride for several hours. The reaction mixture was concentrated to half its volume. Filtration through celite and chromatography yielded 10.75 g of product (56% yield) as a clear oil:

$^1H$ ($CDCl_3$) δ4.2 (m, 4 H), 3.9–2.8 (m, 4 H), 1.9 (m, 1 H), 1.0 (m, 11 H). 0.0 (m, 15 H).

Example 21

N-TEOC-3-(trifluoroacetamido)-5S-azido-piperidine

N-TEOC-3-(trifluoroacetamido)-5R-(t-butyldimethylsilyloxy)-piperidine (5.20 g, 11 mmoles) was dissolved in 100 mL of 2% HCl in methanol and stirred overnight. The reaction was concentrated to afford 3.5 g N-TEOC-3-(trifluoroacetamido)-5R-hydroxy-piperidine as an oil (94% yield). This was then mesylated following the procedure of Examples 3 and 53, using methanesulfonyl chloride (0.96 mL, 1.41 g, 12.4 mmoles). Work up and concentration gave the mesylate that was displaced with sodium azide (0.815 g, 12.5 mmoles) as described in Examples 4 and 55.

Example 22

N-TEOC-3-amino-5S-azido-piperidine

N-TEOC-3-(trifluoroacetamido)-5S-azido-piperidine was hydrolyzed following the procedure of Examples 12 and 60, using 10% $K_2CO_3$ in 5/2 methanol/water to afford the N-TEOC-3 -amino-5S-azido-piperidine:

$^1H$ ($CDCl_3$) δ4.2 (m, 2 H), 3.8 (m, 2 H), 3.3 (m, 3 H), 3.0 (m, 4 H), 2.7 (m, 2 H), 1.0 (m, 2 H), 0.0 (s, 9 H).

Example 23

N-Teoc-5S-Bromo-3-(trifluoroacetamido)-piperidine

N-TEOC-3-(trifluoroacetamido)-5R-hydroxy-piperidine (5.45 g, 11.6 mmoles) was dissolved in dichloromethane and triphenylphosphine dibromide was added as a 25 mL slurry and the reaction mixture stirred at room temperature overnight. The solution was concentrated to a solid and then chromatographed to yield 0.70 g of N-Teoc-5S-Bromo-3-(trifluoroacetamido)-piperidine as an oil:

$^1H$ ($CDCl_3$) δ5.9 (m, 1 H), 4.5 (m, 1 H), 4.2–3.6 (m, 5 H), 3.4 (m, 1 H) 2.1 (m, 1 H), 58.1 (m, 3 H) 0.0 (m, 15 H).

Example 24

N-Teoc-5R-Azido-3-(trifluoroacetamido)-piperidine

N-Teoc-5S-Bromo-3-(trifluoroacetamido)-piperidine (19.2 mmoles) was dissolved in 75 mL DMF and sodium azide (1.62 g, 25 mmoles) added. The reaction was heated to a bath temperature of 85° C. and stirred for 4 hours. TLC (2/8 EtOAc/Hexane) indicated consumption of the starting material. The reaction was concentrated to a suspension and poured into saturated $NaHCO_3$ and extracted three times with ethyl acetate. The extracts were combined and washed with brine, dried over $MgSO_4$ filtered and concentrated to afford N-Teoc-5R-Azido-3-(trifluoroacetamido)-piperidine as a clear oil.

Example 25

N-TEOC-3-amino-5R-azido-piperidine

N-TEOC-3-(trifluoroacetamido)-5R-azido-piperidine was hydrolyzed following the procedure of Examples 12 and 60, using 10% $K_2CO_3$ in 5/2 methanol/water to afford the N-TEOC-3-amino-5R-azido-piperidine:

$^1$H (CDCl$_3$) δ4.2 (m, 2 H), 3.8 (m, 2 H), 3.3 (m, 3 H), 3.0 (m, 4 H), 2.7 (m, 2 H), 1.0 (m, 2 H), 0.0 (s, 9 H).

Example 26

N-TEOC-3R-amino-5S-azidomethyl-piperidine, and N-TEOC-3S-amino-5S-azidomethyl-piperidine N-TEOC-3-amino-5S-azidomethyl-piperidine is resolved into its two diasteromeric components via the usual methods of resolution known in the literature. Chromatographic, HPLC or crystallization methods allow separation of the diastereomers to afford N-TEOC-3R-amino-5S-azidomethyl-piperidine, and N-TEOC-3S-amino-5S-azidomethyl-piperidine.

Example 27

N-TEOC-3R-amino-SR-azidomethyl-piperidine, and N-TEOC-3S-amino-5R-azidomethyl-piperidine N-TEOC-3-amino-5R-azidomethyl-piperidine is resolved into its two diasteromeric components via the usual methods of resolution known in the literature. Chromatographic, HPLC or crystallization methods allow separation of the diastereomers to afford N-TEOC-3R-amino-5R-azidomethyl-piperidine, and N-TEOC-3S-amino-5R-azidomethyl-piperidine.

Example 28

N-Teoc-3R-hydroxy-5-pyrrolidine Methanol

N-Teoc-4R-hydroxy-D,L-proline methyl ester (127 mmoles), as prepared in Example 2, was reduced using LiBH$_4$ and 9-BBN according to the procedure of Example 5.

N-Teoc-4R-hydroxy-D,L-proline methyl ester(127 mmoles) was dissolved in dry THF (5mL /mmole) and cooled to 0° C. A 2 M solution of LiBH$_4$ (64 mmoles) was added followed by 25 mL of a 0.5 M solution of 9-BBN. The solution was stirred overnight at room temperature. The reaction was cooled to 0° C. and acidified to pH=4 with 3 M H$_2$SO$_4$ and then back to pH=8 with saturated NaHCO$_3$. The solution was concentrated to one third the volume and poured into saturated NaHCO$_3$ (4 mL/mmole) and extracted three times with ethyl acetate. The combined extracts were dried with MgSO$_{41}$ filtered and concetrated to a clear oil that was used crude for tritylation:

$^1$H NMR (CDCl$_3$) δ4.2 (m, 4H), 3.7 (m, 1H), 3.5 (m, 3H), 2.3–1.5 (m, 4H), 0.9 (m, 2H), 0.0 (s, 9H); MS (unit mass) Expected M+H 262 Observed 262.

Example 29

N-Teoc-3R-hydroxy-5-(dimethoxytrityloxymethyl)-pyrrolidine

N-Teoc-3R-hydroxy-5-pyrrolidine methanol was dimethoxytritylated following the general procedure described in Example 56, using 152 mmoles of dimethoxytrityl chloride.

N-Teoc-4-hydroxy-2-pyrrolidine methanol (127 mmoles) was dissolved in dry pyridine (4 mL /mmole) and dimethoxytrityl chloride (152 mmoles) added, and the reaction stirred at room temperature overnight. The solution was then concentrated to one third the volume and poured into 0.1 M citric acid (4 mL /mmole) and extracted three times with ethyl acetate. The extracts were combined, dried over Na$_2$SO$_4$, filtered and concentrated to an oil. The oil was then filtered through a silica gel pad eluting with hexane, 10% EtOAC/hexane, 20% EtOAC/hexane, 30% EtOAC/hexane, and 50% EtOAC/hexane. Two impure fractions were collected, combined and chromatographed with a gradient of EtOAC/hexane 5% -50%. The most polar spot in 3/7 EtOAC/hexane gave 37.0 g (66 mmoles) 51% for the 2 reactions:

$^1$H NMR (CDCl$_3$) δ7.3 (m, 9H), 6.8 (m, 4H), 4.6–3.9 (m, 5H), 3.8 (s, 6H), 3.6 (m, 2H), 3.0 (m, 1H), 2.2 (m, 2H), 1.9 (s, 1H), 1.0 (m, 2H), 0.1 (s, 9H); HRMS (FAB+) Expected M+Cs 696.1758 Observed 696.1738.

Example 30

N-Teoc-3S-bromo-5-(dimethoxytrityloxymethyl)-pyrrolidine

N-Teoc-3R-hydroxy-5-(dimethoxytrityloxymethyl)-pyrrolidine (28.9 mmoles) was brominated following the procedure described in Examples 8 and 54, using triphenylphosphine (57.8 eq) and triethyl amine (127.2 mmoles) in dichloromethane. Dibromotetrachlorethane (57.8 mmoles) was added as a 100 mL dichloromethane solution dropwise over one hour. After workup and filtration 28.3 mmoles of the N-Teoc-3S-bromo-5-(dimethoxytrityloxymethyl)-pyrrolidine was isolated as an oil (98% yield):

$^1$H (CDCL$_3$) δ7.3 (m, 9H), 6.8 (d, 4H), 4.5 (m, 1H), 4.2 (m, 4H), 63.3 (m, 6H), 3.6–3.2 (m, 2H), 2.5 (m, 2H), 1.0 (m, 2H), 0.0 (s, 9H); $^{13}$C (CDCL$_3$) 158.38, 144.84, 135.96, 129.86, 127.98, 127.64, 126.64, 112.99, 85.96, 63.90, 63.77, 63.34, 56.42, 56.30, 56.07, 55.03, 45.66, 17.71, -1.61 ppm; MS Expected (M+Na) 648.2 Observed 648/650.

Example 31

N-Teoc-3R-azido-5-(dimethoxytrityloxymethyl)-pyrrolidine

N-Teoc-3S-bromo-5-(dimethoxytrityloxymethyl)-pyrrolidine (28.34 mmoles) was dissolved in DMF (5 mL/mmole) and sodium azide (36.8 mmoles) was added. The reaction was heated to 85° C. for four hours and monitored until TLC (30% EtOAc/hexane) showed complete reaction. The reaction mixture was concentrated to one third its volume and poured into saturated NaHCO$_3$. The aqueous solution was extracted three times with ethyl acetate, the extracts combined, dried over Na$_2$SO$_4$, filtered, and concentrated to give the desired product, N-Teoc-3R-azido-5-(dimethoxytrityloxymethyl)-pyrrolidine, as an oily residue. This crude oil was used directily for the next reduction step:

$^1$H (CDCL$_3$) δ7.3 (m, 9H), 6.8 (d, 4H), 4.2 (m, 4H), 3.7 (m, 8H), 3.4 (m, 3H), 2.3 (m, 2H), 1.0 (m, 2H), 0.0 (s, 9H); HRMS (FAB+) Expected (M+Cs) 721.1822, Observed 721.1850.

Example 32

N-Teoc-3R-amino-5-(dimethoxytrityloxymethyl)-pyrrolidine

N-Teoc-3R-azido-5-(dimethoxytrityloxymethyl)-pyrrolidine was reduced using a 2M solution of LIBH$_4$ in THF and a 0.5M solution of 9-BBN, following the procedure of Example 5, to afford the desired N-Teoc-3R-amino-5-(dimethoxytrityloxymethyl)-pyrrolidine.

Example 33

N-Teoc-3S-azido-5-(dimethoxytrityloxymethyl)-pyrrolidine

N-Teoc-3R-hydroxy-5-(dimethoxytrityloxymethyl)-pyrrolidine (28.9 mmoles) was dissolved in 1:1 pyridine:dichloromethane (7 mL/mmole) and cooled to 0° C. Methanesulfonyl chloride (37.6 mmoles) was added and the reaction stirred at room temperature for 2 hrs. Work up as described in Examples 3 and 53, yielded the crude mesylate that was displaced with sodium azide (36.8 mmoles) following the procedure of Examples 4 and 55. After 4 hours the reaction mixture was concentrated to one third its original volume, poured into saturated $NaHCO_3$ (5 mL/mmole) and extracted three times with EtOAc. The combined extracts were dried over $Na_2SO_4$, filtered and concentrated to afford N-Teoc-3S-azido-5-(dimethoxytrityloxymethyl)-pyrrolidine as a yellow oil. This crude oil was used directly in the next step.

$^1$H ($CDCL_3$) δ7.3 (m, 9H), 6.8 (d, 4H), 4.2 (m, 2H), 3.8 (m, 7H), 3.4 (4H), 2.2 (m, 2H), 1.0 (m, 2H), 0.1 (s, 9H); HRMS (FAB+) Expected M+Cs 721.1822, Observed 721.1850.

Example 34

N-Teoc-3S-amino-5-(dimethxytrityloxymethyl)-pyrrolidine

N-Teoc-3S-azido-5-(dimethoxytrityloxymethyl)-pyrrolidine was reduced using a 2M solution of $LIBH_4$ in THF and a 0.5M solution of 9-BBN, following the procedure of Example 5 to afford the desired N-Teoc-3S-amino-5-(dimethoxytrityloxymethyl)-pyrrolidine.

Example 35

N-Teoc-3R-amino-5R-(dimethoxytrityloxymethyl)-pyrrolidine, and N-Teoc-3R-amino-SS-(dimethoxytrityloxymethyl)-pyrrolidine

N-Teoc-3R-amino-5-(dimethoxytrityloxymethyl)-pyrrolidine is resolved into its two diasteromeric components via the usual methods of resolution known in the literature. Chromatographic, HPLC or crystallization methods allow separation of the diastereomers to afford N-TEOC-3R-amino-5R-(dimethoxytrityloxymethyl)-pyrrolidine, and N-TEOC-3R-amino-5S-(dimethoxytrityloxymethyl)-pyrrolidine.

Example 36

N-Teoc-3S-amino-5R-(dimethoxytrityloxymethyl)-pyrrolidine, and N-Teoc-3S-amino-5S-(dimethoxytrityloxymethyl)-pyrrolidine

N-Teoc-3S-amino-5-(dimethoxytrityloxymethyl)-pyrrolidine is resolved into its two diasteromeric components via the usual methods of resolution known in the literature. Chromatographic, HPLC or crystallization methods allow separation of the diastereomers to afford N-TEOC-3S-amino-5R-(dimethoxytrityloxymethyl)-pyrrolidine, and N-TEOC-3S-amino-5S-(dimethoxytrityloxymethyl)-pyrrolidine.

Example 37

N-Teoc-3(R,S)-amino-5(R,S)-(dimethoxytrityloxymethyl)-pyrrolidine

The two azido compounds, N-Teoc-3R-azido-5-(dimethoxytrityloxymethyl)-pyrrolidine and N-Teoc-3S-azido-5-(dimethoxytrityloxymethyl)-pyrrolidine (57.8 mmoles) were combined in a single 5 L round bottomed flask, dissolved in dichloromethane (2 mL /mmole) and cooled to 0° C. The reducing reagent was prepared separately by treating $SnCl_2$ (86.7 mmoles 1.5 eq), with triethylamine (433.5 mmoles 7.5 eq), and thiophenol (346.8 mmoles 6 eq) in dichloromethane (10 mL/mole) in small portions. This suspension was stirred for thirty minutes until it became a clear solution. This reducing reagent solution was added to the azide reaction mixture, via cannula, over a period of 30 minutes. The reaction mixture was stirred for 1 hr, and monitored by TLC (10% methanol/dichloromethane) until complete consumption of starting material was observed. The reaction mixture was washed with cold 1 M NaOH (20 mL/mmole), the organic layer dried over $Na_2SO_4$, and chromatographed on silica gel using 1% dimethyl ethyl amine in dichloromethane. The correct fractions containing product, as determined by tlc, were pooled and concentrated to give N-Teoc-3(R,S)-amino-5(R,S)-(dimethoxytrityloxymethyl)-pyrrolidine (46.8 mmoles) as a sticky glass:

$^1$H ($CDCL_3$) δ7.3 (m, 9H), 6.8 (d, 4H), 4.3 (m, 0.5H), 4.0 (m, 4H), 3.7 (m, 7H), 3.3 (m, 4H), 2.3 (m, 2H), 2.7 (m, 1H), 0.9 (m, 3H), 0.0 (d, 9H); $^{13}$C ($CDCL_3$) 157.98, 157.40, 154.20, 145.05, 135.74, 129.58, 127.67, 127.59, 126.58, 113.09, 85.14, 64.23, 62.65, 54.98, 54.28, 51.77, 50.66, 49.73, 49.07, 48.31, 38.11, 17.23, −1.41, −1.57 ppm; HRMS (FAB+) expected (M+Cs) 695.1917 observed 695.1937.

Example 38

N-TEOC-3-(dimethoxytrityloxy)-5R-(t-butyldimethylsilyloxy)-piperidine

N-TEOC-3-hydroxy-5R-(t-butyldimethylsilyloxy)-piperidine was coevaporated with dry pyridine, and redissolved in dry pyridine (0.1M). This material was then dimethoxytritylated following the general procedure described in Example 56, using 1.2 equivalents of dimethoxytrityl chloride. Dimethoxytrityl chloride was added in portions over 15 minutes, and the solution stirred at RT overnight. Methanol was then added (10 ml), and the solvent removed under reduced pressure. The resulting gum was redissolved in ethyl acetate, washed with 0.1 M citric acid, $NaHCO_3$, brine, dried with $MgSO_4$, and evaporated. The product was purified by silica gel flash column chromatography using 3/7 ethyl acetate/hexane.

Example 39

N-TEOC-3-(dimethoxytrityloxy)-5R-hydroxy-piperidine

N-TEOC-3-(dimethoxytrityloxy)-5R-(t-butyldimethylsilyloxy)-piperidine was dissolved in THF (0.1M), and added to a solution of tetrabutylammonium fluoride (3 eq) and acetic acid (9 eq)in THF. The solution was stirred until the starting material was consumed, as determined by TLC. The reaction was quenched with $NaHCO_3$, and extracted with diethyl ether. The organic solution was washed with $NaHCO_3$, brine, dried with $MgSO_4$ and evaporated. The product was purified by silica gel flash column chromatography.

Example 40

N-TEOC-3S-azido-5-(dimethoxytrityloxy)-piperidine

N-Teoc-3-(dimethoxytrityloxymethyl)-5—R-hydroxy-piperidine (29 mmoles) was dissolved in 1:1 pyridine:dichloromethane (7 mL/mmole) and cooled to 0° C. Methanesulfonyl chloride (38 mmoles) was added and the reaction stirred at room temperature for 2 hrs. Work up as described in Examples 3 and 53, yielded the crude mesylate that was displaced with sodium azide (37 mmoles) following the procedure of Examples 4 and 55. After 4 hours the reaction mixture was concentrated to one third its original volume, poured into saturated $NaHCO_3$ (5 mL/mmole) and extracted three times with EtOAc. The combined extracts were dried over $Na_2SO_4$, filtered and concentrated to afford N-TEOC-3S-azido-5-(dimethoxytrityloxy)-piperidine as a yellow oily residue. This crude product was used directly in the next step.

Example 41

N-TEOC-3S-amino-5-(dimethoxytrityloxy)-piperidine

N-TEOC-3S-azido-5-(dimethoxytrityloxy)-piperidine was reduced using a 2M solution of $LIBH_4$ in THF and a 0.5M solution of 9-BBN, following the procedure of Example 5 to afford the desired N-TEOC-3S-amino-5-(dimethoxytrityloxy)-piperidine.

Example 42

N-TEOC-3-(dimethoxytrityloxy)-5S-bromo-piperidine

N-TEOC-3S-amino-5-(dimethoxytrityloxy)-piperidine (29 mmoles) was brominated following the procedure described in Examples 8 and 54, using triphenylphosphine (58 mmoles) and triethyl amine (127 mmoles) in dichloromethane. Dibromotetrachlorethane (58 mmoles) was added as a 100 mL dichloromethane solution dropwise over one hour. After workup and filtration the N-TEOC-3-(dimethoxytrityloxy)-5S-bromo-piperidine was isolated as an oily product.

Example 43

N-TEOC-3R-azido-5-(dimethoxytrityloxy)-piperidine

N-TEOC-3-(dimethoxytrityloxy)-5S-bromo-piperidine (28 mmoles) was dissolved in DMF (5 mL/mmole) and sodium azide (37 mmoles) was added. The reaction was heated to 85° C. for several hours and monitored until TLC (30% EtOAc/hexane) showed complete reaction. The reaction mixture was concentrated to one third its volume and poured into saturated $NaHCO_3$. The aqueous solution was extracted three times with ethyl acetate, the extracts combined, dried over $Na_2SO_{41}$ filtered, and concentrated to give the desired product, N-Teoc-3R-azido-5-(dimethoxytrityloxymethyl)-piperidine, as an oily residue. This crude product was used directly for the next reduction step.

Example 44

N-TEOC-3R-amino-S-(dimethoxytrityloxy)-piperidine

N-TEOC-3R-azido-5-(dimethoxytrityloxy)-piperidine was reduced using a 2M solution of $LIBH_4$ in THF and a 0.5M solution of 9-BBN, following the procedure of Example 5 to afford the desired N-TEOC-3R-amino-5-(dimethoxytrityloxy)-piperidine.

Example 45

N-TEOC-3S-amino-5R-(dimethoxytrityloxy)-piperidine, and N-TEOC-3S-amino-5S-(dimethoxytrityloxy)-piperidine N-Teoc-3S-amino-5-(dimethoxytrityloxymethyl)-piperidine is resolved into its two diasteromeric components via the usual methods of resolution known in the literature. Chromatographic, HPLC or crystallization methods allow separation of the diastereomers to afford N-TEOC-3S-amino-5R-(dimethoxytrityloxymethyl)-piperidine, and N-TEOC-3S-amino-5S-(dimethoxytrityloxymethyl)-piperidine.

Example 46

N-TEOC-3R-amino-5R-(dimethoxytrityloxy)-piperidine, and N-TEOC-3R-amino-5S-(dimethoxytrityloxy)-piperidine N-Teoc-3R-amino-5-(dimethoxytrityloxymethyl)-piperidine is resolved into its two diasteromeric components via the usual methods of resolution known in the literature. Chromatographic, HPLC or crystallization methods allow separation of the diastereomers to afford N-TEOC-3R-amino-5R-(dimethoxytrityloxymethyl)-piperidine, and N-TEOC-3R-amino-5S-(dimethoxytrityloxymethyl)-piperidine.

Example 47

N-TEOC-3-azido-5R-hydroxy-piperidine

N-TEOC-3-azido-5R-(t-butyldimethylsilyloxy)-piperidine was dissolved in THF (0.1M), and added to a solution of tetrabutylammonium fluoride (3 eq) and acetic acid (9 eq)in THF. The solution was stirred until the starting material was consumed, as determined by TLC. The reaction was quenched with $NaHCO_3$, and extracted with diethyl ether. The organic solution was washed with $NaHCO_3$, brine, dried with $MgSO_4$ and evaporated. The crude product was purified by silica gel flash column chromatography to give the desired N-TEOC-3-azido-5R-hydroxy-piperidine.

Example 48

N-TEOC-3-azido-5R-(dimethoxytrityloxy)-piperidine

N-TEOC-3-azido-5R-hydroxy-piperidine was coevaporated with dry pyridine, and redissolved in dry pyridine (0.1M). This material was then dimethoxytritylated following the general procedure described in Example 56, using 1.2 equivalents of dimethoxytrityl chloride. Dimethoxytrityl chloride was added in portions over 15 minutes, and the solution stirred at RT overnight. Methanol was then added (10 ml), and the solvent removed under reduced pressure. The resulting gum was redissolved in ethyl acetate, washed with 0.1 M citric acid, $NaHCO_3$, brine, dried with $MgSO_4$, and evaporated. The product was purified by silica gel flash column chromatography using 3/7 ethyl acetate/hexane.

Example 49

N-TEOC-3-amino-SR-(dimethoxytrityloxy)-piperidine

N-TEOC-3-azido-5R-(dimethoxytrityloxy)-piperidine was reduced using a 2M solution of $LIBH_4$ in THF and a 0.5M solution of 9-BBN, following the procedure of Example 5 to afford the desired N-TEOC-3-amino-5R-(dimethoxytrityloxy)-piperidine.

Example 50

N-TEOC-3-amino-5S-(dimethoxytrityloxy)-piperidine

Equimolar amounts of N-TEOC-3R-amino-5S-(dimethoxytrityloxy)-piperidine and N-TEOC-3S-amino- 5S-(dimethoxytrityloxy)-piperidine are mixed in a round bottom flask. The mixture is dissolved into a mixture of ethyl acetate and THF and the resulting solution concentrated in vacuo to afford the desired product, N-TEOC-3-amino-5S-(dimethoxytrityloxy)-piperidine.

Example 51

General Procedure for TEOC Protection of Amino Groups

The amine (156 mmoles) is dissolved into 500 mL of 1:1 water/dioxane. To this solution is added triethylamine (231 mmoles, 1.5 eq), followed by TEOC-NHS (156 mmoles, 1 eq) and the reaction mixture stirred overnight at room temperature.

The reaction is then concentrated to approximately one half volume and poured into 500 mL 1M HCl and extracted 3× with dichloromethane. The extracts are combined, dried over $MgSO_4$ and concentrated to afford the Teoc-protected product.

Example 52

General Procedure for Methyl Ester Formation

The acid (763 mmoles) is dissolved into 1 L of methanol. To this solution is added trimethylsilyl chloride (1.53 moles, 2 eq) and the reaction mixture stirred overnight. At the end of this time, the solution is concentrated to one third the volume and slowly poured into 2 L of rapidly stirring ethyl ether. The white precipitate is collected by vacuum filtration, and the solid dried under high vacuum to give the desired methyl ester product.

Example 53

General Procedure for Mesylation

The alcohol (75 mmoles) is dissolved in 400 mL of 1:1 dichloromethane/pyridine and cooled to 0° C. To this solution is added methanesulfonyl chloride (98 mmoles, 1.3 eq) and the reaction mixture stirred for 2 hours while allowing it to warm to room temperature. The reaction is monitored by TLC (3:7 EtOAc/hexane). When the reaction is complete, the solution is then concentrated to one third the original volume and poured into 500 mL of O.1M citric acid and extracted three times with ethyl acetate. The extracts are combined and dried over $MgSO_4$, filtered and concentrated to afford the mesylate product. The crude product is used directly for displacement with azide.

Example 54

General Procedure for Bromination

The crude alcohol (48.2 mmoles) is dissolved in dichloromethane (400 mL), triphenylphosphine (96.4 mmoles) and triethylamine (21.46 mmoles) are added and the solution cooled to 0° C. Dibromotetrachloroethylene (96.4 mmoles) is added as a dichloromethane solution (125 mL) over 20 minutes. After stirring overnight the reaction is concentrated to a solid and suspended in a minimal volume of 15% ethyl acetate/hexane and filtered through a plug of silica gel. The eluent is concentrated to afford the crude bromo product that is purified if necessary.

Example 55

General Procedure for Azide Displacement

The bromide or mesylate is dissolved in 400 mL of DMF and $NaN_3$ (100 mmoles, 1.3 ×) added to the solution. The reaction mixture is heated to 85° C. for several hours. Upon completion of the reaction, as determined by TLC, the reaction mixture is concentrated to one third its original volume and poured into 500 mL of saturated $NaHCO_3$ and extracted three times with ethyl acetate. The combined extracts are dried over $Na_2SO_{41}$ filtered and concentrated to an oil. Filtration through a silica gel pad with 3:7 ethyl acetate/hexane gave a clear oil giving 61% yield.

Example 56

General Procedure for Dimethoxytritylation

The alcohol (127 mmoles) is dissolved in 500 mL pyridine and dimethoxytrityl chloride (152 mmoles) is added in small portions and stirred overnight. The reaction is concentrated to one fourth the original volume and poured into 500 mL of 0.1 M citric acid. This suspension is extracted 3× with ethyl acetate, the extracts combined and dried over $Na_2SO_{41}$ filtered and concentrated to an orange syrup. The syrup is filtered through a silica gel pad using an EtOAc/hexane gradient, starting with hexane and increasing the EtOAc concentration from 10–50%. Typically, the fractions containing the product spot are pooled and concentrated to afford the desired product.

Example 57

General Procedure for Ester Reduction

The ester (127 mmoles) is dissolved in anhydrous 750 mL of anhydrous THF and cooled to 0° C. A 2M solution of lithium borohydride (64 mmoles) is added via syringe followed by a 0.5 M solution of 9-BBN (12.7 mmoles). The reaction is stirred at room temperature overnight. At the end of this time the reaction is cooled to 0° C. and quenched with 3 M $H_2SO_4$ to pH 4. The pH is readjusted to 8 with saturated $NaHCO_3$ and the mixture then concentrated to one third its original volume. The solution is poured into 700 mL of saturated $NaHCO_3$ and extracted 3× with ethyl acetate. The extracts are combined, dried over $MgSO_4$, filtered and concentrated to give the crude alcohol product that may be used directly for subsequent reactions or purified, if necessary.

Example 58

General Procedure for Azide Reduction

The azido compound (58 mmoles) in a 5 L round bottomed flask and dissolved in dichloromethane (2 mL/mmole) and then cooled to 0° C. In a separate flask $SnCl_2$ (87 mmoles, 1.5 eq) and triethylamine (433.5 mmoles, 7.5 eq) are suspended in dichloromethane (10 mL/mmole) and thiophenol (347 mmoles, 6 eq) is added in small portions. The suspension is stirred, for approximately thirty minutes, until it becomes a clear solution. This reducing agent solution is next added to the azide solution via cannula over a period of 30 minutes. The flask in which the reducing agent was prepared is rinsed with an additional portion of dichloromethane and added to the reaction. The solution is stirred for a few hours until TLC (10% methanol/dichloromethane) shows complete consumption of starting material. The dichloromethane solution is washed with cold 1 M NaOH (20 mL/mmole) and the organic layer dried over $Na_2SO_4$, and chromatographed on silica gel using 1% dimethyl ethyl aminel dichloromethane. The correct fractions containing the product are pooled and concentrated to give the desired amine product.

Example 59

General Procedure for Trifluoracetylation

The crude amine (19 mmoles) is dissolved in methanol (5 mL/mmole) and ethyl trifluoroacetate (35 mmoles) added to the reaction, followed by triethylamine (40 mmoles). The reaction mixture is stirred overnight at room temperature. The resulting solution is then concentrated in vacuo to an oil. The oil is chromatographed with 20% ethyl acetate/hexane to yield, upon concentration of the fractions, the desired trifluoroacetylated amine product.

Example 60

General Procedure for Detrifluoroacetylation

The trifluoroacetylated amine (9.9 mmoles) is dissolved in 25 ml of 10% $K_2CO_3$ in 5/2 methanol/water and stirred overnight. The solution is then concentrated to one half the volume and poured into water. The solution is extracted three times with ethyl acetate, the extracts combined, dried over $MgSO_4$ and concentrated to an oil. The oil is chromatographed with 1:1 ethyl acetate/hexane, if necessary, to yield the desired amine.

Example 61

General Procedure for Epimerization of Amino Acids

The amino acid (1.2 moles) and $Ba(OH)_2$ (0.6 moles) are placed in a stainless steel bomb and 300 mL of water added. The bomb is sealed and placed in an oil bath at 200° C. for 14 hours. The bomb is cooled to room temperature and the contents transferred to a large (2 L) beaker and acidified to pH 4 with 3M $H_2SO_4$ so as to precipitate the $BaSO_4$. The precipitate is removed by vacuum filtration through a pad of celite. The filtrate is then concentrated to a brown solid and dried overnight under vacuum to yield the epimerized amino acid.

Example 62

General Procedure for Detritylation

The dimethoxytrityl protected alcohol is dissolved in dichloromethane and 10% v/v trifluoroacetic acid is added. The reaction is stirred at room temperature for one hour. Methanol is added to quench the DMT cation and the reaction is concentrated to an oil and chromatographed on silica gel to yield free alcohol product.

Example 63

General Procedure for Chromium Oxidation

The alcohol (0.9 mmoles) is dissolved in dichloromethane and powdered activated 4 A molecular sieves are suspended in the solution. Acetic anhydride (1.5 mmoles is added followed by pyridine and pyridinium dichromate (2 mmoles). After stirring overnight at room temperature the solution is concentrated to a slurry, suspended in ether and filtered through a silica gel pad. The silica bed is washed with excess ether, and the combined ethereal solution is concentrated to give a quantitative yield of the ketone as an oil.

Example 64

General Procedure for Swern Oxidation

To a solution of the alcohol (4.5 mmoles) in dichloromethane is added DMSO (10.8 mmoles) and the solution cooled to −78° C. Oxalyl chloride (5.4 mmoles) is added dropwise and the solution stirred for 30 minutes. Triethylamine (24.8 mmoles) is added and the solution warmed to room temperature. This is diluted with dichloromethane and washed with saturated $NaHCO_3$. The combined organic solution is concentrated to an oily crude product that is chromatographed, if necessary.

Example 65

General Procedure for Attachment of Scaffolds to Resin

(a) Via Reductive Amination

To the appropriate resin containing a benzaldehyde linker (preferably ArgoGel-MB-CHO resin purchased from Argonaut Technologies) is added a solution of the appropriately protected amino scaffold in 4:1 $MeOH/CH(OMe)_3$ (1.15 mmole scaffold/mmole resin functionality in 5 mL/gram dry resin solvent). The mixture is gently shaken for 15 h, then a solution of $BH_3$-pyridine (2 mmole/mmole resin functionality) and acetic acid (2 mmole/mmole resin functionality) in 4:1 $MeOH/CH(OMe)_3$ (0.5 mL/gram dry resin solvent) is added. The suspension is gently shaken (gas evolution occurs) for 3 h at rt, then filtered, and washed with MeOH (3×), $CH_2Cl_2$ (3×), DMF (3×) and $CH_2Cl_2$ (3×) and dried with a flow of inert gas.

The resin bound scaffold is functionalized at linking amino group as a sulfonamide, urea, or amide with an appropriate electrophile, as described in the general procedures below.

(b) Via Succinate Linkers

The hydroxy scaffold (2.0 mmol), succinic anhydride (300 mg, 3.0 mmol), DMAP (1.0 mmol, 120 mg) and triethylamine (0.4 ml, 3.0 mmol) are dissolved in dichloromethane and stirred overnight. The solution is extracted with dichloromethane, washed with 0.1M citric acid, water, brine, dried with magnesium sulfate and evaporated. The residue is filtered through a short pad of silica and the succinate isolated is used directly for coupling to solid supports via either of two methods:

Method 1

The succinate is dissolved in dry dichloromethane (50 ml). DMAP is added (250 mg, 2 mmol) followed by Toluenediisocyanate (288 ul, 2.0 mmol). The mixture is swirled for 10 min then 10 g LCAA-CPG is added followed by DIEA (2 mmol, 0,34 ml). The suspension is kept in the dark and agitated periodically for 6–16 h. The solid is filtered, washed with dichloromethane and ether, then suspended in 80 ml pyridine +20 ml water. After 1 h, the support is filtered, washed with dry pyridine (5×), dichloromethane (3×), and suspended in 60 ml dichloromethane, to which 10 ml TEA, 10 ml acetic anhydride, 3 ml N-methylimidazole were added. After 1 h, the support is filtered, washed extensively with dichloromethane and ether and dried. The CPG is analyzed for loading by weighing a portion of CPG, treating with 0.1M toluene sulfonic acid and measuring the absorbance at 498 nm.

Method 2

A hydroxy scaffold (36 mmol) is dissolved in 400 ml $CH_2Cl_2$, and triethylamine (45 mmol, 6.25 ml) and succinic anhydride (40 mmol, 4.0 g) added. A catalytic amount of DMAP is added (5 mol %) and the solution stirred at room temperature overnight. TLC showed all the starting material is converted to a more polar spot. To the solution is then added pentafluorophenyl trifluoroacetate (6.9 ml, 40 mmol). The solution is stirred 1 hr, and the polar material is converted to a non-polar spot on TLC. Toluene (150 ml) is added, and the solvents evaporated. The oily residue is loaded on a flash chromatography column, and eluted with ethyl acetate and hexanes to give the product (33 mmol, 93%).

Amino derivatized solid support (50 g, 11 mmol $NH_2$) is swelled in 150 ml $CH_2Cl_2$, then washed with 5% diisopropylethylamine in $CH_2Cl_2$, followed by $CH_2Cl_2$. The resin is sucked dry, and a solution of monomer succinate PFP ester (17 mmol) in 120 ml $CH_2Cl_2$ and triethylamine (3.5 ml, 25 mmol) were added. The solution is agitated on a wrist shaker for 6 hours, filtered and rinsed with $CH_2Cl_2$, and a second portion of PFP ester (16 mmol) and triethylamine (3.5 ml) added. The solid support is shaken overnight, filtered and resuspended in 60 ml $CH_2Cl_2$, 60 ml pyridine and 10 ml acetic anhydride added. After 1 hr, the resin is filtered and washed with $CH_2Cl_2$, pyridine/$CH_2Cl_2$/Methanol (1:8:1), and diethyl ether. The resin is dried under high vacuum.

Method 3

Hydroxy derivatized solid support (such as Argogel-Wang resin) is first treated eight times with 160 mL of a 0.2 M solution of carbonyl diimidazole in acetonitrile, with a 5 minute wait after each addition. The activated support so generated is then washed with 5×300 mL acetonitrile and 1× with DMF.

There are a variety of different reagents that may be used to affect activation of the hydroxy group, in a manner similar to that described for carbonyl diimidazole. These include, but are not limited to, bis-(p-nitrophenyl)carbonate, disuccinimidyl carbonate, carbonyl ditriazole, carbonyl bisbenzotriazole, triphosgene and diphosgene.

The activated solid support is treated six times with 200 mL of a 1 M solution of an amine scaffold, with a 5 min. wait after each addition. The amine scaffold is generally dissolved in DMF (less soluble amine scaffolds may be used as a saturated solution in DMF). Following reaction with the amine scaffold, the support is washed with 5×300 ml DMF, 3×300 mL DCM and 3×300 mL acetonitrile. Upon drying this affords the amine scaffold attached to the solid support via a carbamate linkage. Following derivatization of the scaffold at combinatorial sites and combinatorial chemistry, as described in the general procedures, the product is cleaved from the support via acidic cleavage using trifluoroacetic acid.

Example 66

General Procedure for Sulfonylation of Nitrogen Centers on Resin-bound Scaffold, Using Sulfonyl Halide Building Blocks To the appropriate resin bound scaffold is added a 0.1 M solution (25 mL/mmole scaffold) of the appropriate sulfonyl chloride in 4:1 NMP/$CH_2Cl_2$ containing 0.15 M DIPEA. The suspension is allowed to stand for 3 h at rt, then filtered, and washed with DMF (3×) and $CH_2Cl_2$ (3×) and dried with a flow of inert gas.

Example 67

General Procedure for Urea Formation at Nitrogen Centers, on Resin-bound Scaffolds, using Isocyanate Building Blocks To the appropriate resin bound scaffold is added a 0.15 M solution (25 mL/mmole scaffold) of the appropriate isocyanate building block in NMP. The suspension is allowed to stand for 3 h at rt, then filtered, and washed with DMF (3×) and $CH_2Cl_2$ (3×) and dried with a flow of inert gas.

Example 68

General Procedure for Urea Formation at Nitrogen Centers, on Resin-bound Scaffolds, Using Amine Building Blocks To the appropriate resin bound scaffold is added a 0.06 M solution (5 mL/g of dry resin) of triphosgene in $CH_2Cl_2$, followed by a 0.18 M solution (5 mL/g of dry resin) of DIPEA in $CH_2Cl_2$. The suspension is allowed to stand for 0.25 h, and a 0.2 M solution of an appropriate amine building block (10 mL/g) in NMP is added. The suspension is allowed to stand for 2.5 h at rt, then filtered, and washed with DMF (3×) and $CH_2Cl_2$ (3×) and dried with a flow of inert gas.

Example 69

General Procedure for Thiourea Formation at Nitrogen Centers, on Resin-bound Scaffolds, Using Isothiocyanate Building Blocks To the appropriate resin bound scaffold is added a 0.15 M solution (25 mL/mmole scaffold) of the appropriate isothiocyanate building block in NMP. The suspension is allowed to stand for 3 h at rt, then filtered, and washed with DMF (3×) and $CH_2Cl_2$ (3×) and dried with a flow of inert gas.

Example 70

General Procedure for Thiourea Formation at Nitrogen Centers, on Resin-bound Scaffolds, Using Amine Building Blocks To the appropriate resin bound scaffold is added a 0.18 M solution (5 mL/g of dry resin) of thiophosgene in $CH_2Cl_2$, followed by a 0.18 M solution (5 mL/g of dry resin) of DIPEA in $CH_2Cl_2$. The suspension is allowed to stand for 0.25 h, and 0.2 M solution of an appropriate amine building block (10 mL/g) in NMP is added. The suspension is allowed to stand for 2.5 h at rt, then filtered, and washed with DMF (3×) and $CH_2Cl_2$ (3×) and dried with a flow of inert gas.

Example 71

General Procedure for Acylation at Nitrogen Centers, on Resin-bound Scaffolds, Using Acyl halide Building Blocks To the appropriate resin bound scaffold is added a 0.10 M solution (25 mL/mmole scaffold) of the appropriate acid halide building block in 1:1 pyridine/$CH_2Cl_2$. The suspension is allowed to stand for 3 h at rt, then filtered, and washed with DMF (3×) and $CH_2Cl_2$ (3×) and dried with a flow of inert gas.

Example 72

General Procedure for Acylation at Nitrogen Centers, on Resin-bound Scaffolds, Using Carboxylic Acid Building Blocks To the appropriate resin bound scaffold is added a 0.20 M solution (5 mL/g of dry resin) of the appropriate carboxylic acid building block in 1:1 NMP/$CH_2Cl_2$. A 1.0 M solution of DIPEA in $CH_2Cl_2$ (2 mL/g of dry resin) is added, followed by a 0.33 M solution of O-(7-azabenzotriazol-1-yl)-1,1,3,3-tetramethyluronium hexafluorophosphate (HATU) in NMP (3 mL/g of dry resin). The suspension is allowed to stand for 3 h at rt, then filtered, and washed with $CH_2Cl_2$ (3×), DMF (3×), $CH_2Cl_2$ (3×) and dried with a flow of inert gas.

Example 73

General Procedure for Alkylation at Nitrogen Centers, on Resin-bound Scaffolds, Using Alkyl halide Building Blocks To the appropriate resin bound scaffold is added a 0.10 M solution (25 mL/mmole scaffold) of the appropriate alkyl halide building block in 10:1 NMP/DIPEA. The suspension is allowed to stand for 3 h at rt, then filtered, and washed with DMF (3×) and $CH_2Cl_2$ (3×) and dried with a flow of inert gas.

Example 74

General Procedure for Alkylation at Nitrogen Centers, on Resin-bound Scaffolds, Using Aldehyde or Ketone Building Blocks To the appropriate resin bound scaffold is added a 0.20 M solution (5 mL/g of dry resin) of the appropriate carbonyl compound building block in 4:1 $MeOH/CH(OMe)_3$, followed by a freshly prepared 1.0 M solution (1 mL/g of dry resin) of $BH_3$.pyridine complex in 4:1 $MeOH/CH(OMe)_3$ containing 6% v/v acetic acid. The suspension is allowed to stand for 3 h at rt, then filtered, and washed with $CH_2Cl_2$ (3×), DMF (3×), $CH_2Cl_2$ (3×) and dried with a flow of inert gas.

Example 75

General Procedure for Protection of Nitrogen Centers on Resin-bound Scaffolds

To the appropriate resin bound scaffold bearing a free amino group, is added a 0.2 M solution (25 mL/mmole scaffold) of di-tert-butyldicarbonate in NMP. The suspension is allowed to stand for 3 h at rt, then filtered, and washed with DMF (3×) and $CH_2Cl_2$ (3×) and dried with a flow of inert gas.

Example 76

General Procedure for Solid Phase Removal of Teoc Protecting Group

To the appropriate resin bound scaffold is added a 0.2 M solution (25 mL/mmole scaffold) of TBAF in NMP. The suspension is allowed to stand for 1 h at rt, then filtered, and washed with DMF (3×) and $CH_2Cl_2$ (3×) and dried with a flow of inert gas. This unmasks the second diversity site on the scaffold, in the form of a free amino group.

The resin bound scaffold is functionalized at this second position as a sulfonamide, urea, amide, alkyl amine, or aryl amine with an appropriate electrophile as described above.

Example 77

General Procedure for Solid Phase Reduction of Azide

A solution of $SnCl_2$ (0.2 M), PhSH (0.4 M), and $Et_3N$ (0.4 M) in $CH_2Cl_2$ is added to the appropriate resin bound scaffold (25 mL/mmole scaffold), and the mixture is allowed to stand for 0.5 h at rt (gas evolved). The suspension is filtered, and washed with $CH_2Cl_2$ (3×), DMF (3×), and $CH_2Cl_2$ (3×), then dried with a flow of inert gas. This typically unmasks the third diversity site on the scaffold, in the form of a free amino group.

The resin bound scaffold is functionalized at this third position as a sulfonamide, urea, amide, aryl amine, or alkyl amine with an appropriate electrophile as described in the general procedures, above. If this functionalization is done using an aldehyde or ketone according to the general procedure, the resulting amine product offers a fourth combinatorial position, which can be functionalized as a sulfonamide, urea, amide, aryl amine or alkyl amine with the appropriate electrophile as described in the general procedures above.

Example 78

General Procedure for Cleavage from Support

To the resin-bound functionalized scaffold is added TFA containing 2.5% $Et_3SiH$ (25 mL/mmole scaffold), and the suspension is allowed to stand for 4 h at rt. The mixture is filtered, the resin washed with TFA (3×10 mL/mmole scaffold), and the combined filtrates concentrated under reduced pressure, then dried over KOH at 0.1 mm Hg to provide the appropriate compound or mixture of compounds.

Example 79

General Procedure for the Solid Phase Removal of DMT Protection

To the appropriate resin bound scaffold is added a 3 v/v % solution of dichloroacetic acid in $CH_2Cl_2$ (25 mL/mmole scaffold). The suspension is allowed to stand for 1 min at rt, then filtered, and washed with MeOH (3×) and $CH_2Cl_2$ (3×). This process is repeated four additional times, and the resin washed with DMF (3×) and $CH_2Cl_2$ (3×) and dried with a flow of inert gas.

Example 80

General Procedure for Solid Phase Oxidation of a Hydroxyl Group to an Aldehyde or Ketone A solution of sulfur trioxide pyridine complex (0.8 M) in 1:1 $Et_3N/DMSO$ is added to the appropriate resin bound scaffold (25 mL/mmole scaffold), and the mixture is allowed to stand for 2 h at rt. The suspension is filtered, and washed with DMSO (3×), DMF (3×), and $CH_2Cl_2$ (3×), then dried with a flow of inert gas.

The resulting resin-bound aldehyde or ketone may then be reductively aminated according to the general procedure below.

Example 81

General Procedure for Solid Phase Reductive Alkylation of an Aldehyde or Ketone with an Amine Building Block To the resin bound aldehyde or ketone is added a solution of the appropriate amine building block in 4:1 $MeOH/CH(OMe)_3$ (3 mmole amine/mmole resin functionality in 5 mL/gram dry resin solvent). The mixture is allowed to stand for 0.5 h at rt, then a solution of $BH_3$-pyridine (3 mmole/ mmole resin functionality) and acetic acid (3 mmole/mmole resin functionality) in 4:1 MeOH/CH(OMe)$_3$ (0.5 mL/gram dry resin solvent) is added. The suspension is allowed to stand for 2 h at rt, then filtered, and washed with MeOH (3×), CH$_2$Cl$_2$ (3×), DMF (3×) and CH$_2$Cl$_2$ (3×) and dried with a flow of inert gas.

The resulting amine can then be cleaved from support, or can serve as a fourth combinatorial position, and can be functionalized into a sulfonamide, urea, amide, aryl amine or alkyl amine with the appropriate electrophile as described in the general procedures above. The material so obtained is then cleaved from the support as described in the general procedure.

Example 82

General Procedure for the Solid Phase Removal of FMOC Protection

To the appropriate resin bound scaffold is added a 10 v/v % solution of piperidine in DMF (25 mL/mmole scaffold). The suspension is allowed to stand for 0.2 h at rt, then filtered, and washed with DMF (3×) and CH$_2$Cl$_2$ (3×) and dried with a flow of inert gas.

Example 83

General Procedure for the Solid Phase Synthesis of Bicyclic Scaffolds from Diamine Scaffolds Step 1

The appropriate resin is derivatized with a scaffold containing a protected hydroxyl group suitable for cyclization as described below according to the general procedure. This resin bound scaffold is then functionalized, if desired, at the first diversity site (linking amino group) as a sulfonamide, urea, or amide according to the general procedures described above.

Step 2

The protecting group at the second diversity site is removed according to the general procedure, and this position is then functionalized with a protected amino acid derivative (preferably an FMOC-amino acid) according to the general procedure for functionalization with a carboxylic acid described in Example 72.

Step 3

To this resin bound scaffold is added a 10 v/v % solution of piperidine in DMF (25 mL/mmole scaffold) so as to cleave the Fmoc group. The suspension is allowed to stand for 0.2 h at rt, then filtered, and washed with DMF (3×) and CH$_2$Cl$_2$ (3×) and dried with a flow of inert gas.

Step 4

The resin bound amino acid derivatized scaffold is then treated with a 0.1 M solution (25 mL/mmole scaffold) solution of 2-nitrobenzenesulfonyl chloride in CH$_2$Cl$_2$ containing 0.15 M DIPEA. The suspension is allowed to stand for 1 h at rt, then filtered, and washed with DMF (3×) and CH$_2$Cl$_2$ (3×) and dried with a flow of inert gas.

Step 5

To this resin bound scaffold is next added a 3 v/v % solution of dichloroacetic acid in CH$_2$Cl$_2$ (25 mL/mmole scaffold) so as to cleave the DMT group protecting the hydroxy functionality. The suspension is allowed to stand for 1 min at rt, then filtered, and washed with MeOH (3×) and CH$_2$Cl$_2$ (3×). This process is repeated four additional times, and the resin washed with DMF (3×) and CH$_2$Cl$_2$ (3×) and dried with a flow of inert gas.

Step 6

The resin bound material is then treated with a 0.1 M solution of 5-triphenylphosphonium-1,1-dioxo-3,3-dimethyl-2,5-thiadiazolidine betaine in 19:1 CH$_2$Cl$_2$/DMF (25 mL/mmole scaffold) for 1 h, then washed with DMF (3×) and CH$_2$Cl$_2$ (3×) and dried with a flow of inert gas to afford a bicyclic scaffold attached to the resin.

Step 7

The resin bound bicyclic scaffold is then treated with a 0.5 M solution of 2-mercaptoacetic acid in NMP (25 mL/mmole scaffold) containing 1 M DBU for 1 h, then washed with DMF (3×) and CH$_2$Cl$_2$ (3×) and dried with a flow of inert gas.

Step 8

The resin bound scaffold is next functionalized at the third position as a sulfonamide, urea, amide, aryl amine, or alkyl amine with an appropriate electrophile as described in the general procedures as described above.

Step 9

The product is cleaved from the solid support and isolated as described in the general procedure in Example 78.

Example 84

General Procedure for the Solid Phase Synthesis of Carbamate Linked Oligomers

Step 1

The appropriate resin is derivatized with a diamine scaffold containing a protected hydroxyl group suitable for carbamate formation according to the general procedure, as described in Example 65. This resin bound scaffold is then functionalized at the first position as a sulfonamide, urea, or amide according to the general procedures described above.

Step 2

The protecting group at the second position is removed according to the general procedure as described in Example 76, and this position is then functionalized as a sulfonamide, urea, amide, alkyl amine, or aryl amine with an appropriate electrophile following the general procedures described above.

Step 3

The alcohol protecting group is then removed, and the hydroxyl group activated for carbamate formation by treatment with a 0.06 M solution (5 mL/g of dry resin) of triphosgene in CH$_2$Cl$_2$, followed by a 0.4 M solution (5 mL/g of dry resin) of DIPEA in CH$_2$Cl$_2$. The suspension is allowed to stand for 0.25 h, and 0.1 M solution of an appropriate amine scaffold (10 mL/g) in NMP is added. The suspension is allowed to stand for 2.5 h at rt, then filtered, and washed with DMF (3×) and CH$_2$Cl$_2$ (3×) and dried with a flow of inert gas to afford a product comprising two scaffolds connected to each other via a carbamate linkage and the product is attached to the solid support.

Step 4

The scaffold thus introduced is then appropriately functionalized at its remaining combinatorializable positions as described above in the general procedures.

Step 5

Alternatively the second scaffold is functionalized, then linked to another scaffold as described above and this process repeated thereby allowing the assembly of oligomeric structures. Attachment of additional scaffolds may be via carbamate linkages or via urea, thiourea, guanidino or amino linkages as described in Examples 85, 86, 87 and 88. Bicyclic scaffolds may be introduced or generated, where desired, in these oligomeric structures.

Step 6

After the desired level of functionality has been introduced, the material so obtained is cleaved from support according to the general procedure of Example 78.

Example 85

General Procedure for the Solid Phase Synthesis of Urea and Thiourea Linked Oligomers Step 1

The appropriate resin is derivatized with a triamine scaffold according to the general procedure, as described in Example 65. This resin bound scaffold is then functionalized at the first position as a sulfonamide, urea, or amide according to the general procedures described above.

Step 2

The protecting group at the second position is removed according to the general procedure as described in Example 76, and this position is then functionalized as a sulfonamide, urea, amide, alkyl amine, or aryl amine with an appropriate electrophile following the general procedures described above.

Step 3

The azide is then reduced according to the general procedure described in Example 77, and the resulting amino group activated for urea or thiourea formation by treatment with a either a 0.06 M solution of triphosgene (for urea synthesis) or a 0.18 M solution of thiophosgene (for thiourea synthesis) in $CH_2Cl_2$ (5 mL/g of dry resin), followed by a 0.4 M solution (5 mL/g of dry resin) of DIPEA in $CH_2Cl_2$. The suspension is allowed to stand for 0.25 h, and a 0.1 M solution of an appropriate amine scaffold (10 mL/g) in NMP is added. The suspension is allowed to stand for 2.5 h at rt, then filtered, and washed with DMF (3x) and $CH_2Cl_2$ (3x) and dried with a flow of inert gas to afford a product comprising two scaffolds connected to each other via a urea or thiourea linkage and the product is attached to the solid support.

Step 4

The scaffold thus introduced is then appropriately functionalized at the remaining combinatorializable positions as described above in the general procedures. Alternatively the second scaffold is functionalized, then linked to another scaffold as described above and this process repeated thereby allowing the assembly of oligomeric structures. Attachment of additional scaffolds may be via carbamate, urea, thiourea, guanidino or amino linkages as described in Examples 84, 86, 87 and 88. Also, bicyclic scaffolds may be introduced or generated, where desired, in these oligomeric structures.

Step 5

After the desired level of functionality has been introduced, the material so obtained is cleaved from support according to the general procedure of Example 78.

Example 86

General Procedure for the Solid Phase Synthesis of Guanidine Linked Oligomers

Step 1

The appropriate resin is derivatized with a triamine scaffold according to the general procedure, as described in Example 65. This resin bound scaffold is then functionalized at the first position as a sulfonamide, urea, or amide according to the general procedures described above.

Step 2

The protecting group at the second position is removed according to the general procedure as described in Example 76, and this position is then functionalized as a sulfonamide, urea, amide, alkyl amine, or aryl amine with an appropriate electrophile following the general procedures described above.

Step 3

The scaffold is then linked to another scaffold employing a thiourea linkage as described above in Example 85. The thiourea is alkylated by treatment with a 0.2 M solution (25 mL/mmole scaffold) of iodoacetonitrile in 10:1 NMP/DIPEA. The suspension is allowed to stand for 1 h at rt, then filtered, and washed with NMP. To the corresponding resin bound S-alkyl isothiourea is added a 1.0 M solution of an appropriate amine building block (10 mL/g) in NMP. The suspension is allowed to stand for 3 h at rt, then filtered, and washed with DMF (3x) and $CH_2Cl_2$ (3x) and dried with a flow of inert gas to afford a product comprising two scaffolds connected to each other via a guanidino linkage and the product is attached to the solid support.

Step 4

The scaffold thus introduced is then appropriately functionalized at the remaining combinatorializable positions, as described above in the general procedures. Alternatively the second scaffold is functionalized, then linked to another scaffold as described above and this process repeated thereby allowing the assembly of oligomeric structures. Attachment of additional scaffolds may be via carbamate, urea, thiourea, guanidino or amino linkages as described in Examples 84, 85, 87 and 88. Also, bicyclic scaffolds may be introduced or generated, where desired, in these oligomeric structures.

Step 5

After the desired level of functionality has been introduced, the material so obtained is cleaved from support according to the general procedure of Example 78.

Example 87

General Procedure for the Solid Phase Synthesis of Amine Linked Oligomers

Step 1

The appropriate resin is derivatized with a triamine scaffold according to the general procedure, as described in Example 65. This resin bound scaffold is then functionalized at the first position as a sulfonamide, urea, or amide according to the general procedures described above.

Step 2

The protecting group at the second position is removed according to the general procedure as described in Example 76, and this position is then functionalized as a sulfonamide, urea, amide, alkyl amine, or aryl amine with an appropriate electrophile following the general procedures described above.

Step 3

The primary amine is then unmasked by deprotection or reduction of the azide according to the general procedure. This amine is then reductively alkylated with a ketone scaffold according to the general procedure for alkylation at nitrogen with aldehydes or ketones, as described in Examples 74 and 81.

Step 4

The resulting secondary amine is then functionalized as a sulfonamide, urea, amide, alkyl amine, or aryl amine with an appropriate electrophile following the general procedures described above.

Step 5

The scaffold thus introduced is then appropriately functionalized at the remaining combinatorializable positions, as described above in the general procedures. Alternatively the second scaffold is functionalized, then linked to another scaffold as described above and this process repeated thereby allowing the assembly of oligomeric structures. Attachment of additional scaffolds may be via carbamate, urea, thiourea, guanidino or amino linkages as described in Examples 84, 85, 86 and 88. Also, bicyclic scaffolds may be introduced or generated, where desired, in these oligomeric structures.

Step 6

After the desired level of functionality has been introduced, the material so obtained is cleaved from support according to the general procedure of Example 78.

Example 88

General Procedure for the Solid Phase Synthesis of Amine Linked Oligomers From Diamine Scaffolds Containing a Protected Hydroxyl Group Step 1

The appropriate resin or resin bound scaffold is derivatized with a diamine scaffold containing a protected hydroxyl group suitable for elaboration according to the general procedure, as described in Example 65. This resin bound scaffold is then functionalized at the first position as a sulfonamide, urea, or amide according to the general procedures described above.

Step 2

The protecting group at the second position is removed according to the general procedure as described in Example 76, and this position is then functionalized as a sulfonamide, urea, amide, alkyl amine, or aryl amine with an appropriate electrophile following the general procedures described above.

Step 3

The alcohol protecting group is then removed, and the hydroxyl group oxidized according to the general procedure, as described in Example 80. The resulting carbonyl moiety is then reductively aminated with an amine scaffold according to the general procedure for alkylation at nitrogen with aldehydes or ketones, as described in Examples 74 and 81.

Step 4

The resulting secondary amine is then functionalized as a sulfonamide, urea, amide, alkyl amine, or aryl amine with an appropriate electrophile following the general procedures described above.

Step 5

The scaffold thus introduced is then appropriately functionalized at the remaining combinatorializable positions, as described above in the general procedures. Alternatively the second scaffold is functionalized, then linked to another scaffold as described above and this process repeated thereby allowing the assembly of oligomeric structures. Attachment of additional scaffolds may be via carbamate, urea, thiourea, guanidino or amino linkages as described in Examples 84, 85, 86 and 87. Also, bicyclic scaffolds may be introduced or generated, where desired, in these oligomeric structures.

Step 6

After the desired level of functionality has been introduced, the material so obtained is cleaved from support according to the general procedure of Example 78.

Example 89

N-Fmoc-4R-Hydroxy-L-Proline trans-4-Hydroxy-L-proline (5.00 g, 38.2 mmol) and $NaHCO_3$ (8.00 g, 95.2 mmol) were suspended in 150 ml $H_2O$/Dioxane (1:1). Fluorenylmethyl chloroformate (11.4 g, 44.0 mmol) in 25 ml toluene was added dropwise. The temperature of the reaction was not allowed to rise above 25° C. during the addition. The mixture was stirred vigorously overnight, and then quenched with 50 ml saturated $NaHCO_3$ solution and 50 ml water. The solution was then extracted with 100 ml diethyl ether. The aqueous layer was acidified to pH 1 with concentrated HCl, and extracted twice with ethyl acetate, and the organic extracts washed with brine. The solution was dried with $MgSO_4$, filtered and the solvent removed in vacuo. The pure product crystallized from the concentrated solution. Yield: 13.4 g (100%).

$^1$H NMR: ($CDCl_3$, 200 MHz) δ7.75–7.15 (8H, m, ArH), 4.55–4.05 (5H, m, $ArCHCH_2$, H2, H4), 3.65–3.45 (2H, m, 2 H5), 2.35–2.10 (2H, m, 2 H3).

Example 90

N-Fmoc-3R-hydroxypyrrolidine-5S-methanol

To a solution of N-Fmoc-4R-hydroxy-L-proline (13.4 g, 38.1 mmol) in 250 ml THF was added borane-methyl sulfide (78 mmol, 5.78 g, 7.22 ml) dropwise at room temperature. After the evolution of $H_2$ had ceased, the solution was heated to reflux with mechanical stirring. After 1 hour a white precipitate had formed. Methanol was carefully added, and the resulting solution refluxed for a further 15 minutes. The solution was cooled to room temperature, the solvents evaporated under reduced pressure, and the residual gum coevaporated with 2×100 ml methanol. The resulting crystalline product weighed 12.0 g (35.3 mmol, 93%).

$^1$H NMR: (CDCl3, 200 MHz) δ7.85–7.25 (8H, m, ArH), 4.50–4.10 (5H, m, ArCHCH2, H3, H5), 3.80–3.40 (4H, m, 2 H2, 2 H6), 2.15–1.95 (1H, m, H2a), 1.80–1.60 (1H, m, H2b).

Example 91

N-Fmoc-5S-(dimethoxytrityloxymethyl)-3R-hydroxypyrrolidine

N-Fmoc-3R-hydroxypyrrolidine-5S-methanol (10.59 g, 31.2 mmol) was coevaporated with dry pyridine (2×50 ml), redissolved in 200 ml dry pyridine, and cooled in an ice bath. Dimethoxytrityl chloride (11.0 g, 32.5 mmol) was added in portions over 30 min, and the solution stirred at 0° C. overnight. Methanol was then added (10 ml), and the solvent removed under reduced pressure. The resulting gum was redissolved in toluene (100 ml), filtered to remove the pyridinium hydrochloride and taken to dryness again. The residue was dissolved in CH$_2$Cl$_2$ (300 ml), washed with 150 ml 0.1 M citric acid solution, 150 ml sat NaHCO$_3$, brine, and dried with MgSO$_4$ followed by evaporation. The residue was crystallized from methanol and dried to give (15.4 g, 23.9 mmol, 77%).

Example 92

5S-(dimethoxytrityloxymethyl)-3R-hydroxypyrrolidine

N-Fmoc-5S-(dimethoxytrityloxymethyl)-3R-hydroxypyrrolidine was dissolved in a 20% (v/v) solution of piperidine in DMF. The reaction mixture was stirred at room temperature, and monitored by TLC for complete deprotection of the Fmoc group. The solvent was removed and a fresh portion of piperidine/DMF was added and the mixture stirred for an additional 15 minutes. The reaction mixture was concentrated and the residue partitioned into water and ethyl acetate. The aqueous layer was extracted three times with ethyl acetate. The extracts were pooled and concentrated to afford a crude product that was purified by flash column chromatography on silica gel using a mixture of ethyl acetate and hexane to afford the desired 5S-(dimethoxytrityloxymethyl )-3R-hydroxypyrrolidine.

Example 93

N-Teoc-5S-(dimethoxytrityloxymethyl)-3R-hydroxypyrrolidine 5S-(dimethoxytrityloxymethyl)-3R-hydroxypyrrolidine was protected with the trimethylsilylethoxycarbonyl group (Teoc) using Teoc-NHS following the general procedure of Example 51. 78 mmoles of the amine were dissolved into 250 mL of 1:1 water/dioxane. To this solution was added triethylamine (115 mmoles, 1.5 eq), followed by TEOC-NHS (78 mmoles, 1 eq) and the reaction mixture stirred overnight at room temperature. The reaction was then concentrated to approximately one half its original volume and poured into 250 mL of 1M HCl and extracted 3× with dichloromethane. The extracts are combined, dried over MgSO$_4$ and concentrated to afford the N-Teoc-5S-(dimethoxy-trityloxymethyl)-3R-hydroxypyrrolidine.

Example 94

N-Teoc-5S-(dimethoxytrityloxymethyl)-3R-O-methanesulfonyl-pyrrolidine

N-Teoc-5S-(dimethoxytrityloxymethyl)-3R-hydroxypyrrolidine was mesylated following the general procedure of Example 53. N-Teoc-5S-(dimethoxytrityloxymethyl)-3R-hydroxypyrrolidine (75 mmoles) was dissolved into 400 mL of a 1:1 mixture of dichloromethane/pyridine and cooled to 0° C. To this solution was added methanesulfonyl chloride (98 mmoles, 1.3 eq) and the reaction mixture stirred for 2 hours while allowing it to warm to room temperature. The reaction was monitored for completion by TLC (3:7 EtOAc/hexane). The solution was then concentrated to one third its original volume and poured into 500 mL of 0.1M citric acid and extracted three times with ethyl acetate. The extracts are combined and dried over MgSO$_4$, filtered and concentrated to afford the mesylate. The crude product was used directly, without further purification, for the next step.

Example 95

N-Teoc-5S-(dimethoxytrityloxymethyl)-3S-azido-pyrrolidine

The title compound was prepared from N-Teoc-5S-(dimethoxytrityloxymethyl)-3R-O-methanesulfonyl-pyrrolidine by following the procedure of Example 55. The mesylate was dissolved in 400 mL of DMF and NaN$_3$ (1.3 equivalents) added to the solution. The reaction mixture was heated to 85° C. for several hours and upon completion of the reaction, as determined by TLC, the reaction mixture was concentrated to one third its original volume. This concentrate was poured into 500 mL of saturated NaHCO$_3$ and extracted three times with ethyl acetate. The combined extracts were dried over Na$_2$SO$_4$, filtered and concentrated to give an oily residue. Filtration through a silica gel pad with 3:7 ethyl acetate/hexane afforded N-Teoc-5S-(dimethoxytrityloxymethyl)-3S-azido-pyrrolidine.

Example 96

N-Teoc-5S-(dimethoxytrityloxymothyl)-3S-amino-pyrrolidine

Reduction of the azide synthesized in Example 95 is performed following the procedure of Example 58. N-Teoc-5S-(dimethoxytrityloxymethyl)-3S-azido-pyrrolidine (58 mmoles) is dissolved in dichloromethane (2 mL/mmole) in a 5 L round bottomed flask and then cooled to 0° C. In a separate flask SnCl$_2$ (87 mmoles, 1.5 eq) and triethylamine (433.5 mmoles, 7.5 eq) are suspended in dichloromethane (10 mL/mmole) and thiophenol (347 mmoles, 6 eq) added in small portions. This suspension is stirred, for approximately thirty minutes, until it becomes a clear solution. This reducing agent solution is next added to the azide solution by means of a cannula, over a period of 30 minutes. The flask in which the reducing agent was prepared is rinsed with an additional portion of dichloromethane and added to the reaction. The reaction mixture is stirred for a few hours until TLC (10% methanol/dichloromethane) showed complete consumption of starting material. The dichloromethane solution is washed with cold 1 M NaOH (20 mL/mmole) and the organic layer dried over Na$_2$SO$_4$, and chromatographed on silica gel using 1% dimethyl ethyl amine/dichloromethane. Pooling of the product fractions and concentration afford the product, N-Teoc-5S-(dimethoxytrityloxymethyl)-3S-amino-pyrrolidine.

Example 97

Loading of 4-Hydroxybenzaldehyde onto Solid Supports

A variety of solid supports may be used for anchoring the 4-hydroxybenzaldehyde. Theis includes anchoring onto carboxy supports via an ester linkage, hydroxy and amino supports via a succinate linker or alternatively, the 4-hydroxybenzaldehyde may be attached onto a hydroxy resin support via and ether linkage that is generated by Mitsunobu chemistry. The use of standard Mitsunobu conditions to effect coupling of hydroxybenzaldehydes to hydroxy supports (Hamper et al., *Tetrahedron Lett.,* 1996, 37, 3671) afforded the desired ether linkage and attachment of hydroxybenzaldehyde onto the support, but the product was contaminated with other adducts. An alternate coupling method was developed.

1 g of Argogel-OH support (Argonaut Technologies, Inc., San Carlos, Calif.) was washed with 5% DMF in dichloromethane and then treated with an excess of 4-hydroxybenzaldehyde and a 0.1 M solution of 5-triphenylphosphonium-1,1-dioxo-3,3-dimethyl-2,5-thiadiazolidine betaine in 19:1 $CH_2Cl_2$/DMF (25 mL/mmole scaffold) for several hours. The reagents were removed by vacuum filtration and the resin washed with DMF (3×) and $CH_2Cl_2$ (3×) and dried with a flow of inert gas to afford resin bearing 4-oxybenzaldehyde groups attached to the resin via an ether linkage.

Example 98

Attachment of N-Teoc-5S-(dimethoxytrityloxymethyl)-3S-amino-pyrrolidine Scaffold onto the Argogel Solid Support The 4-hydroxybenzaldehyde derivatized Argogel-OH support (from Example 97) was loaded with the N-Teoc-5S-(dimethoxytrityloxymethyl)-3R-amino-pyrrolidine scaffold via reductive alkylation, following the general procedure of Example 81.

To the Argogel resin-bound aldehyde, from the previous example, was added a solution of the N-Teoc-5S-(dimethoxytrityloxymethyl)-3S-amino-pyrrolidine scaffold in 4:1 MeOH/CH(OMe)$_3$ (3 mmole scaffold/mmole resin functionality in 5 mL solvent /gram of dry resin). The mixture was allowed to stand for 0.5 h at rt, then a solution of $BH_3$-pyridine (3 mmole/mmole resin functionality) and acetic acid (3 mmole/mmole resin functionality) in 4:1 MeOH/CH(OMe)$_3$ (0.5 mL/gram dry resin solvent) was added. The suspension was allowed to stand for 2 h at rt, then filtered, and washed with MeOH (3×), $CH_2Cl_2$ (3×), DMF (3×) and $CH_2Cl_2$ (3×) and dried with a flow of inert gas.

Loading of the resin could be determined via cleavage and spectroscopic quantitation of the dimethoxytrityl group using a dilute solution of dichloroacetic acid in dichloromethane. A loading of 0.35 mmole/g was observed, indicating a quantitative yield of the loading reaction.

Example 99

5S-hydroxymethyl-3S-((N-(4-methylphenyl) Amino) Carbonyl) Amino-pyrrolidinium Trifluoroacetate Step 1

To the Argogel bound N-Teoc-5S-(dimethoxytrityloxymethyl)-3S-amino-pyrrolidine scaffold from Example 98 was added a 0.15 M solution (25 mL/mmole scaffold) p-tolylisocyanate in NMP. The suspension was allowed to stand for 3 h at rt, then filtered, and washed with DMF (3×) and $CH_2Cl_2$ (3×) and dried with a flow of inert gas.

Step 2

The resin bound functionalized scaffold was treated with a 3 v/v % solution of dichloroacetic acid in $CH_2Cl_2$ (25 mL/mmole scaffold). The suspension was allowed to stand for 1 min at rt, then filtered, and washed with MeOH (3×) and $CH_2Cl_2$ (3×). This process was repeated four additional times, to ensure complete cleavage of the dimethoxytrityl group and the resin washed with DMF (3×) and $CH_2Cl_2$ (3×) and dried with a flow of inert gas.

Step 3

Next, the resin-bound, detritylated scaffold was treated with trifluoroacetic acid containing 2.5% $Et_3SiH$ (25 mL/mmole scaffold), and the suspension was allowed to stand for 4 h at rt. The mixture was filtered, the resin washed with TFA (3×10 mL/mmole scaffold), and the combined filtrates concentrated under reduced pressure, then dried over KOH at 0.1 mm Hg to provide 5S-hydroxymethyl-3R-(N-(4-methylphenyl)aminocarbonyl)-3R-amino-pyrrolidine as its trifluoroacetate salt. Cleavage of product from the resin was determined to be quantitative and HPLC of a sample of the product revealed purity to be >90%.

Example 100

3-Methyl-8S-((N-(4-methylphenyl)amino)carbonyl) amino-1,4-diazabicyclo[4.3.0]nonan-2-one trifluoroacetate salt Step 1

Resin bound 5S-hydroxymethyl-3R-((N-(4-methylphenyl)amino)-carbonyl)aminopyrrolidine, from Example 99, was treated with a 0.2 M solution (25 mL/mmole scaffold) of TBAF in NMP. The suspension was allowed to stand for 1 h at rt, then filtered, and washed with DMF (3×) and $CH_2Cl_2$ (3×) and dried with a flow of inert gas.

Step 2

The free amino group so formed was derivatized with a 0.20 M solution (5 mL/g of dry resin) of N-Fmoc-Ala-OH in 1:1 NMP/$CH_2Cl_2$. A 1.0 M solution of DIPEA in $CH_2Cl_2$ (2 mL/g of dry resin) was added, followed by a 0.33 M solution of O-(7-azabenzotriazol-1-yl)-1,1,3,3-tetramethyluronium hexafluorophosphate (HATU) in NMP (3 mL/g of dry resin). The suspension is allowed to stand for 3 h at rt to allow acylation to proceed to completion, then filtered, and washed with $CH_2Cl_2$ (3×), DMF (3×), $CH_2Cl_2$ (3×) and dried with a flow of inert gas.

Step 3

To this resin bound amino acid derivatized scaffold was added a 10 v/v % solution of piperidine in DMF (25 mL/mmole scaffold) so as to cleave the Fmoc group. The suspension was allowed to stand for 0.2 h at rt, then filtered, and washed with DMF (3×) and $CH_2Cl_2$ (3×) and dried with a flow of inert gas.

Step 4

The free amino group of the pendant amino acid was next treated with a 0.1 M solution (25 mL/mmole scaffold) solution of 2-nitrobenzenesulfonyl chloride in $CH_2Cl_2$ containing 0.15 M DIPEA. The suspension was allowed to stand for 1 h at rt, then filtered, and washed with DMF (3×) and $CH_2Cl_2$ (3×) and dried with a flow of inert gas.

Step 5

To the resin was next added a 3 v/v % solution of dichloroacetic acid in $CH_2Cl_2$ (25 mL/mmole scaffold) so as to cleave the DMT group protecting the hydroxy functionality. The suspension was allowed to stand for 1 min at rt, then filtered, and washed with MeOH (3×) and $CH_2Cl_2$ (3×). This process was repeated four additional times, and the resin washed with DMF (3×) and $CH_2Cl_2$ (3×) and dried with a flow of inert gas.

Step 6

The resin bound material was then treated with a 0.1 M solution of 5-triphenylphosphonium-1,1-dioxo-3,3-dimethyl-2,5-thiadiazolidine betaine in 19:1 $CH_2Cl_2$/DMF (25 mL/mmole scaffold) for 1 h, then washed with DMF (3×) and $CH_2Cl_2$ (3×) and dried with a flow of inert gas. This step leads to the formation of the substituted bicyclic scaffold, 1,4-diazabicyclo[4.3.0]nonan-2-one, attached to the resin.

Step 7

The resin bound bicyclic scaffold was then treated with a 0.5 M solution of 2-mercaptoacetic acid in NMP (25 mL/mmole scaffold) containing 1 M DBU for 1 h, so as to cleave the nitrophenylsulfonyl group. The resin was washed with DMF (3×) and $CH_2Cl_2$ (3×) and dried with a flow of inert gas.

Step 8

At this point of the synthesis, the 4-position nitrogen atom of the 1,4-diazabicyclo[4.3.0]nonan-2-one scaffold may be further functionalized, if desired, via reaction with a variety of building blocks.

Step 9

Finally, the resin-bound functionalized scaffold was treated with TFA containing 2.5% $Et_3SiH$ (25 mL/mmole scaffold), and the suspension allowed to stand for 4 h at rt. The mixture was filtered, the resin washed with TFA (3×10 mL/mmole scaffold), and the combined filtrates concentrated under reduced pressure, then dried over KOH at 0.1 mm Hg to provide the desired compound, 3-Methyl-8S-((N-(4-methylphenyl)amino)carbonyl)amino-1,4-diazabicyclo[4.3.0]nonan-2-one as its trifluoroacetate salt.

Example 101

3-Methyl-4-(2-(1-thyminyl)-acetyl)-8S-((N-(4-methylphenyl)amino)carbonyl)amino-1,4-diazabicyclo[4.3.0]nonan-2-one Step 1

The solid support bound 3-Methyl-8S-((N-(4-methylphenyl)amino)carbonyl)amino-1,4-diazabicyclo[4.3.0]nonan-2-one prepared in Example 100 was further functionalized at the 4-position nitrogen center.

Step 2

The 4-position amino group was derivatized with a 0.20 M solution (5 mL/g of dry resin) of 2-(1-thyminyl)-acetic acid in 1:1 NMP/$CH_2Cl_2$. A 1.0 M solution of DIPEA in $CH_2Cl_2$ (2 mL/g of dry resin) was added, followed by a 0.33 M solution of O-(7-azabenzotriazol-1-yl)-1,1,3,3-tetramethyluronium hexafluorophosphate (HATU) in NMP (3 mL/g of dry resin). The suspension was allowed to stand for 3 h at rt to allow acylation to proceed to completion, then filtered, and washed with $CH_2Cl_2$ (3×), DMF (3×), $CH_2Cl_2$ (3×) and dried with a flow of inert gas.

Step 3

The fully functionalized product was finally cleaved from the solid support. The resin was treated with TFA containing 2.5% $Et_3SiH$ (25 mL/mmole scaffold), and the suspension allowed to stand for 4 h at rt. The mixture was filtered, the resin washed with TFA (3×10 mL/mmole scaffold), and the combined filtrates concentrated under reduced pressure, then dried over KOH at 0.1 mm Hg to provide the desired compound, 3-Methyl-4-(2-(1-thyminyl)-acetyl)-8S-((N-(4-methylphenyl)amino)carbonyl)amino-1,4-diazabicyclo[4.3.0]nonan-2-one.

Example 102

Synthesis of a Library of Di- and Tri-substituted 8S-amino-1,4-diazabicyclo[4.3.0]nonan-2-ones Step 1

The 4-hydroxybenzaldehyde derivatized Argogel-OH support (from Example 97) is added a solution of the N-Teoc-5S-(dimethoxytrityloxymethyl)-3S-amino-pyrrolidine scaffold in 4:1 MeOH/$CH(OMe)_3$ (3 mmole scaffold/mmole resin functionality in 5 mL solvent /gram of dry resin). The mixture is allowed to stand for 0.5 h at rt, then a solution of $BH_3$-pyridine (3 mmole/mmole resin functionality) and acetic acid (3 mmole/mmole resin functionality) in 4:1 MeOH/$CH(OMe)_3$ (0.5 mL/gram dry resin solvent) is added. The suspension is allowed to stand for 2 h at rt, then filtered, and washed with MeOH (3×), $CH_2Cl_2$ (3×), DMF (3×) and $CH_2Cl_2$ (3×) and dried with a flow of inert gas.

Loading of the resin is determined via cleavage and spectroscopic quantitation of the dimethoxytrityl group using a dilute solution of dichloroacetic acid in dichloromethane.

Step 2

This resin bound scaffold is then functionalized, if desired, at the first diversity site (linking amino group) as a sulfonamide, urea, or amide, using a variety of building blocks, according to the general procedures described in Examples 66, 67, 68, 69, 70, 71 and 72, above.

Step 3

This material is next treated with a 0.2 M solution (25 mL/mmole scaffold) of TBAF in NMP, so as to cleave the Teoc group. The suspension is allowed to stand for 1 h at rt, then filtered, and washed with DMF (3×) and $CH_2Cl_2$ (3×) and dried with a flow of inert gas.

Step 4

The free amino group so formed is derivatized with a 0.20 M solution (5 mL/g of dry resin) of any N-Fmoc-amino acid in 1:1 NMP/$CH_2Cl_2$. A 1.0 M solution of DIPEA in $CH_2Cl_2$ (2 mL/g of dry resin) is added, followed by a 0.33 M solution of O-(7-azabenzotriazol-1-yl)-1,1,3,3-tetramethyluronium hexafluorophosphate (HATU) in NMP (3 mL/g of dry resin). The suspension is allowed to stand for 3 h at rt to allow acylation to proceed to completion, then filtered, and washed with $CH_2Cl_2$ (3×), DMF (3×), $CH_2Cl_2$ (3×) and dried with a flow of inert gas.

Step 5

To this resin bound amino acid derivatized scaffold is added a 10 v/v % solution of piperidine in DMF (25 mL/mmole scaffold) so as to cleave the Fmoc group. The suspension is allowed to stand for 0.2 h at rt, then filtered, and washed with DMF (3×) and $CH_2Cl_2$ (3×) and dried with a flow of inert gas.

Step 6

The free amino group of the pendant amino acid is next treated with a 0.1 M solution (25 mL/mmole scaffold) solution of 2-nitrobenzenesulfonyl chloride in $CH_2Cl_2$ containing 0.15 M DIPEA. The suspension is allowed to stand for 1 h at rt, then filtered, and washed with DMF (3×) and $CH_2Cl_2$ (3×) and dried with a flow of inert gas.

Step 7

To the resin is next added a 3 v/v % solution of dichloroacetic acid in $CH_2Cl_2$ (25 mL/mmole scaffold) so as to cleave the DMT group protecting the hydroxy functionality. The suspension is allowed to stand for 1 min at rt, then filtered, and washed with MeOH (3×) and $CH_2Cl_2$ (3×). This process is repeated four additional times, and the resin washed with DMF (3×) and $CH_2Cl_2$ (3×) and dried with a flow of inert gas.

Step 8

The resin bound material is then treated with a 0.1 M solution of 5-triphenylphosphonium-1,1-dioxo-3,3-dimethyl-2,5-thiadiazolidine betaine in 19:1 $CH_2Cl_2$/DMF (25 mL/mmole scaffold) for 1 h, then washed with DMF (3×) and $CH_2Cl_2$ (3×) and dried with a flow of inert gas. This step leads to the formation of the substituted bicyclic scaffold, 1,4-diazabicyclo[4.3.0]nonan-2-one, attached to the resin.

Step 9

The resin bound bicyclic scaffold is then treated with a 0.5 M solution of 2-mercaptoacetic acid in NMP (25 mL/mmole scaffold) containing 1 M DBU for 1 h, so as to cleave the nitrophenylsulfonyl group. The resin is washed with DMF (3×) and $CH_2Cl_2$ (3×) and dried with a flow of inert gas.

Step 10

At this point of the synthesis, the 4-position nitrogen atom of the 1,4-diazabicyclo[4.4.0]decan-2-one scaffold may be further functionalized as a sulfonamide, urea, amide, aryl amine, or alkyl amine, if desired, via reaction with a variety of building blocks as described in Examples 66, 67, 68, 69, 70, 71, 72, 73 and 74.

Step 11

Finally, the resin-bound functionalized scaffold is treated with TFA containing 2.5% $Et_3SiH$ (25 mL/mmole scaffold), and the suspension allowed to stand for 4 h at rt. The mixture is filtered, the resin washed with TFA (3×10 mL/mmole scaffold), and the combined filtrates concentrated under reduced pressure, then dried over KOH at 0.1 mm Hg to provide the desired compound.

The use of a variety of building blocks at the various sites of diversity generated and derivatized in this procedure allows the synthesis of a library of a wide variety of di- and tri- functionalized, 1,4-diazabicyclo[4.3.0]nonan-2-ones to be synthesized.

Example 103

N-TEOC-5-(dimethoxytrityloxymethyl)-pyrrolidin-3-one

N-Teoc-4-hydroxy-2-(dimethoxytrityloxymethyl)-pyrrolidine (5 mmoles) is dissolved in dichloromethane and 4 Å molecular sieves are added followed by acetic anhydride (10 mmoles). To this mixture is added pyridine (10%) followed by slow addition of pyridinium dichromate (10 mmoles), in small portions, and the reaction is stirred overnight. The solution is then concentrated to a slurry and filtered through a silica gel pad eluting with ether. The eluent is concentrated in vacuo to afford N-TEOC-5-(dimethoxytrityloxymethyl)-pyrrolidin-3-one as an oil:

$^1$H NMR (CDCl$_3$) δ7.3 (m, 9 H), 6.8 (d, 2 H), 4.5 (m, 1H), 4.1 (m, 2 H), 3.9 (s, 2 H), 3.8 (s, 3 H), 3.6 (m, 3 H), 3.1 (d, 1 H), 2.7 (m, 1 H), 2.5 (d, 1H), 1.0 (m, 2 H), 0.0 (s, 9 H).

Example 104

N-TEOC-5-(azidomethyl)-pyrrolidin-3-one

N-TEOC-5-(dimethoxytrityloxymethyl)-pyrrolidin-3-one is dissolved in 3% dichloroacetic acid in dichloromethane. The reaction is stirred for 1 hour, and then quenched with methanol until clear. This solution is concentrated to an oil and chromatographed with a mixture of ethyl acetate/hexane to give an oil. This oil is dissolved in 1:1 dichloromethane/pyridine and 1.2 eq methane sulfonyl chloride added and the reaction stirred for 4 hours at room temperature. Work up following the general procedure of Example 53 yields an oily crude product which is used directly for azide displacement, following the procedure of Example 55, to give the desired product, N-TEOC-5-(azidomethyl)-pyrrolidin-3-one, as a cream colored, waxy solid:

$^1$H NMR (CDCl$_3$) δ4.5 (d, 1 H), 4.2 (t, 2H), 3.9 (m, 2H), 3.4 (dd, 1 H), 2.8 (m, 1H), 2.5 (dd, 1H), 1.0 (t, 2H), 0.1 (s, 9 H).

Example 105

N-TEOC-3-Azido-piperidin-5-one

N-TEOC-3-azido-5R-(tert-butyldimethylsilyloxy)-piperidine is desilylated with 2% concentrated HCl in THF, following the procedure of Example 21 to give the 5-hydroxy-piperidine intermediate. This is oxidized using pyridinium dichromate according to the procedure described in Example 104, to provide the N-TEOC-3-Azido-piperidin-5-one as a colorless oil.

Example 106

N-Teoc-3,5-dihydroxy-2-[(dimethoxytrityloxy)methyl]-piperidine.

Either 1,3-Dideoxynojirimycin or its enantiomer (both of which can be prepared by asymmetric synthesis; see: C. R. Johnson et. al. *Tetrahedron Letters* 1994, 35, 1833–1834.) is protected with the Teoc group via reaction with Teoc-NHS, according to the general procedure described in Example 51, to provide a quantitative yield of N-TEOC-1,3-dideoxynojirimycin. This material is then dimethoxytritylated according to the general procedure of Example 56 to provide the desired compound that is selectively protected on the primary hydroxyl group.

Example 107

N-Teoc-3(5)-hydroxy-5(3)-mesyloxy-2-[(dimethoxytrityloxy)-methyl]piperidine

A solution of N-Teoc-3,5-dihydroxy-2-[(dimethoxytriphenyl-methoxy)methyl]piperidine is reacted with 1.0 eq of methanesulfonyl chloride according to the general procedure of Example 53 to provide a mixture of the 3- and 5-mesyl derivatives. This mixture is used without further purification for azide displacement.

Example 108

N-Teoc-3(5)-bromo-5(3)-hydroxy-2-[(dimethoxytrityloxy)methyl]-piperidine

A solution of N-Teoc-3,5-dihydroxy-2-[(dimethoxytrityloxy)methyl]piperidine is reacted with 1.0 eq of triphenylphosphine and 1.0 eq of dibromotetrachloroethylene according to the general procedure described in Example 54, to provide a mixture of the corresponding 3- and 5- bromo derivatives.

Example 109

N-Teoc-3(5)-azido-5(3)-hydroxy-2-[(dimethoxytrityloxzy)methyl]-piperidine

An equimolar mixture of N-Teoc-3(5)-hydroxy-5(3)-mesyloxy-2-[(dimethoxytrityloxy)methyl]piperidine and N-Teoc-3(5)-bromo-5(3)-hydroxy-2-[(dimethoxytrityloxy)methyl]piperidine are combined, and reacted according to the general procedure for azide displacement, as described in Example 55. The resulting prodcut mixture containing 3- and 5-monoazides having both cis (from mesylation and azide displacement) and trans (from bromination and azide displacement) relationships relative to the hydroxymethyl group is purified by silica gel chromatography (EtOAc/hexane gradient) to provide a mixture of 4 diastereomeric compounds. If the mesylate and bromide are not combined for this step, then the cis (mesylation/displacement) and trans (bromination/displacement) azides are obtained as separate mixtures of regioisomers comprising two diasteromers each

Example 110

N-Teoc -5(3)-hydroxy-3(5)-trifluoroacetylamino-2-[(dimethoxy-trityloxy)methyl]piperidine N-Teoc-3(5)-azido-5(3)-hydroxy-2-[(dimethoxytrityloxy)-methyl]piperidine, either as a mixture of cis and trans stereoisomers, or as pure species is reduced with $SnCl_2$/PhSH, and then trifluoroacetylated according to the general procedure described in Examples 58 ad 59. At this step the 3- and 5-trifluoroacetyl regioisomers are separated by silica gel chromatography if pure scaffolds are desired.

Example 111

N-Teoc-5(3)-amino-3(5)-azido-2-[(dimethoxytrityloxy)methyl]-piperidine

Either a mixture of all four possible isomers of N-Teoc -5(3)-hydroxy-3(5)-trifluoroacetylamino-2-[(dimethoxytrityloxy)-methyl]piperidine or each of the pure isomers, if enantiomerically pure compounds are desired, are either mesylated (following the procedure of Example 53) or brominated (according to the procedure of Example 54).

If pure isomers are desired, each of the reaction products is reacted separately with sodium azide (following the procedure of Example 55), and subsequently detrifluoroacetylated according to the general procedure described in Example 60. If an isomeric mixture of scaffolds is desired, an equimolar mixture of the mesylated and brominated intermediates above are similarly converted to the azides, and then detrifluoroacetylated according to the general procedure to provide a mixture of all eight possible stereoisomers of N-Teoc -5(3)-amino-3(5)- azido-2-[(dimethoxytrityloxy)methyl]piperidine suitable for library synthesis.

Example 112

Library Synthesis with N-Teoc-5(3)-amino-3(5)-azido-2-[(dimethoxytrityloxy)methyl]piperidine scaffold

Step 1

The 4-hydroxybenzaldehyde derivatized Argogel-OH support (from Example 97) is loaded with the N-Teoc -5(3)-amino-3(5)-azido-2-[(dimethoxytrityloxy)methyl] piperidine scaffold via reductive alkylation, following the general procedure of Example 81.

To the Argogel resin-bound aldehyde, from the previous example, is added a solution of the N-Teoc -5(3)-amino-3 (5)-azido-2-[(dimethoxytrityloxy)methyl]piperidine scaffold in 4:1 MeOH/CH(OMe)$_3$ (3 mmole scaffold/mmole resin functionality in 5 mL solvent/gram of dry resin). The mixture is allowed to stand for 0.5 h at rt, then a solution of BH$_3$-pyridine (3 mmole/mmole resin functionality) and acetic acid (3 mmole/mmole resin functionality) in 4:1 MeOH/CH(OMe)$_3$ (0.5 mL/gram dry resin solvent) is added. The suspension is allowed to stand for 2 h at rt, then filtered, and washed with MeOH (3×), CH$_2$Cl$_2$ (3×), DMF (3×) and CH$_2$Cl$_2$ (3×) and dried with a flow of inert gas.

Step 2

Loading of the resin is determined via cleavage and spectroscopic quantitation of the dimethoxytrityl group using a dilute solution of dichloroacetic acid in dichloromethane.

Step 3

This resin bound scaffold is then functionalized, if desired, at the first diversity site (linking amino group) as a sulfonamide, urea, or amide according to the general procedures described in Examples 66, 67, 68, 69, 70, 71 and 72, above.

Step 4

This material is next treated with a 0.2 M solution (25 mL/mmole scaffold) of TBAF in NMP, so as to cleave the Teoc group. The suspension is allowed to stand for 1 h at rt, then filtered, and washed with DMF (3×) and CH$_2$Cl$_2$ (3×) and dried with a flow of inert gas.

Step 5

The free amino group so formed is derivatized with a 0.20 M solution (5 mL/g of dry resin) of any N-Fmoc-amino acid in 1:1 NMP/CH$_2$Cl$_2$. A 1.0 M solution of DIPEA in CH$_2$Cl$_2$ (2 mL/g of dry resin) is added, followed by a 0.33 M solution of O-(7-azabenzotriazol-1-yl)-1,1,3,3-tetramethyluronium hexafluorophosphate (HATU) in NMP (3 mL/g of dry resin). The suspension is allowed to stand for 3 h at rt to allow acylation to proceed to completion, then filtered, and washed with CH$_2$Cl$_2$ (3×), DMF (3×), CH$_2$Cl$_2$ (3×) and dried with a flow of inert gas.

Step 6

To this resin bound amino acid derivatized scaffold is added a 10 v/v % solution of piperidine in DMF (25 mL/mmole scaffold) so as to cleave the Fmoc group. The suspension is allowed to stand for 0.2 h at rt, then filtered, and washed with DMF (3×) and $CH_2Cl_2$ (3×) and dried with a flow of inert gas.

Step 7

The free amino group of the pendant amino acid is next treated with a 0.1 M solution (25 mL/mmole scaffold) of 2-nitrobenzenesulfonyl chloride in $CH_2Cl_2$ containing 0.15 M DIPEA. The suspension is allowed to stand for 1 h at rt, then filtered, and washed with DMF (3×) and $CH_2Cl_2$ (3×) and dried with a flow of inert gas.

Step 8

To the resin is next added a 3 v/v % solution of dichloroacetic acid in $CH_2Cl_2$ (25 mL/mmole scaffold) so as to cleave the DMT group protecting the hydroxy functionality. The suspension is allowed to stand for 1 min at rt, then filtered, and washed with MeOH (3×) and $CH_2Cl_2$ (3×). This process is repeated four additional times, and the resin washed with DMF (3×) and $CH_2Cl_2$ (3×) and dried with a flow of inert gas.

Step 9

The resin bound material is then treated with a 0.1 M solution of 5-triphenylphosphonium-1,1-dioxo-3,3-dimethyl-2,5-thiadiazolidine betaine in 19:1 $CH_2Cl_2$/DMF (25 mL/mmole scaffold) for 1 h, then washed with DMF (3×) and $CH_2Cl_2$ (3×) and dried with a flow of inert gas. This step leads to the formation of the substituted bicyclic scaffold, 1,4-diazabicyclo[4.4.0]decan-2-one, attached to the resin.

Step 10

The resin bound bicyclic scaffold is then treated with a 0.5 M solution of 2-mercaptoacetic acid in NMP (25 mL/mmole scaffold) containing 1 M DBU for 1 h, so as to cleave the nitrophenylsulfonyl group. The resin is washed with DMF (3×) and $CH_2Cl_2$ (3×) and dried with a flow of inert gas.

Step 11

At this point of the synthesis, the 4-position nitrogen atom of the 1,4-diazabicyclo[4.4.0]decan-2-one scaffold may be further functionalized as a sulfonamide, urea, amide, aryl amine, or alkyl amine, if desired, via reaction with a variety of building blocks as described in Examples 66, 67, 68, 69, 70, 71, 72, 73 and 74.

Step 12

This 3,4,9-substituted 7-azido-1,4-diazabicyclo[4.4.0] decan-2-one attached to the solid support is next reduced according to the general procedure of Example 77 to generate a 7-amino group. The amino group may be derivatized with an appropriate electrophile, so as to now provide functionalization at a fourth position on the bicyclic scaffold, as a sulfonamide, urea, amide, aryl amine, or alkyl amine, as described in the general procedures, above. If this functionalization is done via reductive alkylation, using an aldehyde or ketone, according to the general procedure of Example 74, the product is a secondary amine. This makes available a fifth combinatorial position on the bicyclic scaffold, and can be further functionalized as a sulfonamide, urea, amide, aryl amine or alkyl amine with the appropriate electrophile as described in the general procedures, above.

Step 13

Finally, the resin-bound functionalized scaffold is treated with TFA containing 2.5% $Et_3SiH$ (25 mL/mmole scaffold), and the suspension allowed to stand for 4 h at rt. The mixture is filtered, the resin washed with TFA (3×10 mL/mmole scaffold), and the combined filtrates concentrated under reduced pressure, then dried over KOH at 0.1 mm Hg to provide the desired compound.

The use of a variety of building blocks at the various sites of diversity generated and derivatized in this procedure allows the synthesis of a library of a wide variety of highly functionalized, 1,4-diazabicyclo[4.4.0]decan-2-ones to be synthesized.

Example 113

FMOC-Ser-Ser-OMe

To a suspension of either D, L, or DL serine methyl ester hydrochloride (1.0 eq.) and FMOC-D, L or DL serine (1 eq.) in DMF (0.2 M) is added collidine (3 eq.), followed by HATU (1.1 eq). The resulting solution is stirred at rt overnight, and then diluted with EtOAc and washed with 5% $NaHCO_3$, dried over $MgSO_4$, concentrated in vacuo, and chromatographed on silica gel (EtOAc/hexane) to provide a nearly quantitative yield of FMOC-Ser-Ser-OMe. This material can be prepared as either the DD, DL, LD, or LL stereoisomers, or a mixture of any of the above by varying the chirality of the starting serine derivatives.

Example 114

Methyl 6-(FMOC-amino)-1-TEOC-1,4-diazepin-2-carboxylate

FMOC-Ser-Ser-OMe, either pure or as an equimolar mixture of stereoisomers, is reduced by refluxing with $BH_3$ (3 eq.) in THF according to the procedure of Jung and Rohloff (J. Org. Chem. , 1985, Vol. 50, pg. 4909). This material is then protected on the nitrogen using TEOC-NHS (1.2 eq.) according to the general procedure described in Example 51, and the product purified by silica gel chromatography (EtOAc/hexane). The resulting diol is oxidized to the corresponding dialdehyde by treatment with 2.2 eq. of Dess-Martin Periodinane in $CH_2Cl_2$ (0.2M) at rt for 3 h. The reaction mixture is diluted with ether, then washed with $Na_2S_2O_3$ (25 g/100 mL saturated aqueous $NaHCO_3$ solution), saturated $NaHCO_3$, water, and then dried with $MgSO_4$, and concentrated to provide the crude dialdehyde. This material is immediately dissolved in methanol, and treated with ammonium acetate (10 eq.), followed by sodium cyanoborohydride (2.0 eq). After stirring overnight at rt, the mixture is adjusted to pH 1 with 1N HCl, allowed to stir for 15 min, and then adjusted to pH 10 with iN NaOH. The mixture is extracted with ether, and the organic layer dried with $Na_2SO_4$, then concentrated, and the residue purified by flash column chromatography to provide methyl 6-(FMOC-amino)-1-TEOC-1,4-diazepin-2-carboxylate.

Example 115

[6-(FMOC-amino)-4-(2-nitrobenzenesulfonyl)-1-TEOC-1,4-diazepin-2-yl]methanol

Methyl 6-(FMOC-amino)-1-TEOC-1,4-diazepin-2-carboxylate is treated with 2-nitrobenzenesulfonyl chloride (1.2 eq) in $CH_2Cl_2$ containing DIEA (1.5 eq.) overnight, and the product isolated by extraction with 5% $NaHCO_3$, fol-

Example 116

6-amino-2-(dimethoxytrityloxymethyl)-4-(2-nitrobenzenesulfonyl)-1-TEOC-1,4-diazepine

[6-(FMOC-amino)-4-(2-nitrobenzensulfonyl)-1-TEOC-1,4-diazepin-2-yl]methanol is protected at the free hydroxy by dimethoxytritylation according to the general procedure described in Example 56. Subsequently, the FMOC protecting group is removed by treatment with 10% piperidine in DMF (0.5 M) for 15 minutes. The mixture is diluted with water, and the product extracted into ether, dried over $MgSO_4$, concentrated under reduced pressure, and purified by column chromatography on silica gel to provide the desired 1,4-diazepine scaffold which is suitable for library synthesis.

Example 117

Library Synthesis with 6-amino-2-(dimethoxytrityloxymethyl)-4-(2-nitrobenzenesulfonyl)-1-TEOC-1,4-diazepine scaffold.

Step 1

The 4-hydroxybenzaldehyde derivatized Argogel-OH support (from Example 97) is loaded with the 6-amino-2-(dimethoxytrityloxymethyl)-4-(2-nitrobenzenesulfonyl)-1-TEOC-1,4-diazepine scaffold via reductive alkylation, following the general procedure of Example 81.

Step 2

To the Argogel resin-bound aldehyde, is added a solution of the 6-amino-2-(dimethoxytrityloxymethyl)-4-(2-nitrobenzenesulfonyl)-1-TEOC-1,4-diazepine scaffold in 4:1 MeOH/CH(OMe)$_3$ (3 mmole scaffold/mmole resin functionality in 5 mL solvent/gram of dry resin). The mixture is allowed to stand for 0.5 h at rt, then a solution of BH$_3$-pyridine (3 mmole/mmole resin functionality) and acetic acid (3 mmole/mmole resin functionality) in 4:1 MeOH/CH(OMe)$_3$ (0.5 mL/gram dry resin solvent) is added. The suspension is allowed to stand for 2 h at rt, then filtered, and washed with MeOH (3×), CH$_2$Cl$_2$ (3×), DMF (3×) and CH$_2$Cl$_2$ (3×) and dried with a flow of inert gas.

Loading of the resin is determined via cleavage and spectroscopic quantitation of the dimethoxytrityl group using a dilute solution of dichloroacetic acid in dichloromethane.

Step 3

This resin bound scaffold is then functionalized, if desired, at the first diversity site (linking amino group) as a sulfonamide, urea, or amide according to the general procedures described in Examples 66, 67, 68, 69, 70, 71 and 72, above.

Step 4

The resin bound scaffold is then treated with a 0.5 M solution of 2-mercaptoacetic acid in NMP (25 mL/mmole scaffold) containing 1 M DBU for 1 h, so as to cleave the 4-nitrobenzene-sulfonyl group. The resin is washed with DMF (3×) and CH$_2$Cl$_2$ (3×) and dried with a flow of inert gas.

Step 5

The resin bound scaffold is then functionalized, if desired, at this second diversity site (4-position nitrogen) as a sulfonamide, urea, amide, aryl amine or alkyl amine according to the general procedures described in Examples 66, 67, 68, 69, 70, 71, 72, 73 and 74, above.

Step 6

This material is next treated with a 0.2 M solution (25 mL/mmole scaffold) of TBAF in NMP, so as to cleave the Teoc group. The suspension is allowed to stand for 1 h at rt, then filtered, and washed with DMF (3×) and CH$_2$Cl$_2$ (3×) and dried with a flow of inert gas.

Step 7

The free amino group so formed is derivatized with a 0.20 M solution (5 mL/g of dry resin) of any N-Fmoc-amino acid in 1:1 NMP/CH$_2$Cl$_2$. A 1.0 M solution of DIPEA in CH$_2$Cl$_2$ (2 mL/g of dry resin) is added, followed by a 0.33 M solution of O-(7-azabenzotriazol-1-yl)-1,1,3,3-tetramethyluronium hexafluorophosphate (HATU) in NMP (3 mL/g of dry resin). The suspension is allowed to stand for 3 h at rt to allow acylation to proceed to completion, then filtered, and washed with CH$_2$Cl$_2$ (3×), DMF (3×), CH$_2$Cl$_2$ (3×) and dried with a flow of inert gas.

Step 8

To this resin bound amino acid derivatized scaffold is added a 10 v/v % solution of piperidine in DMF (25 mL/mmole scaffold) so as to cleave the Fmoc group. The suspension is allowed to stand for 0.2 h at rt, then filtered, and washed with DMF (3×) and CH$_2$Cl$_2$ (3×) and dried with a flow of inert gas.

Step 9

The free amino group of the pendant amino acid is next treated with a 0.1 M solution (25 mL/mmole scaffold) of 2-nitrobenzenesulfonyl chloride in CH$_2$Cl$_2$ containing 0.15 M DIPEA. The suspension is allowed to stand for 1 h at rt, then filtered, and washed with DMF (3×) and CH$_2$Cl$_2$ (3×) and dried with a flow of inert gas.

Step 10

To the resin is next added a 3 v/v % solution of dichloroacetic acid in CH$_2$Cl$_2$ (25 mL/mmole scaffold) so as to cleave the DMT group protecting the hydroxy functionality. The suspension is allowed to stand for 1 min at rt, then filtered, and washed with MeOH (3×) and CH$_2$Cl$_2$ (3×). This process is repeated four additional times, and the resin washed with DMF (3×) and CH$_2$Cl$_2$ (3×) and dried with a flow of inert gas.

Step 11

The resin bound material is then treated with a 0.1 M solution of 5-triphenylphosphonium-1,1-dioxo-3,3-dimethyl-2,5-thiadiazolidine betaine in 19:1 CH$_2$Cl$_2$/DMF (25 mL/mmole scaffold) for 1 h, then washed with DMF (3×) and CH$_2$Cl$_2$ (3×) and dried with a flow of inert gas. This step leads to the formation of the substituted bicyclic scaffold, 1,4,8-triazabicyclo[5.4.0]undecan-2-one, attached to the resin.

Step 12

The resin bound bicyclic scaffold is then treated with a 0.5 M solution of 2-mercaptoacetic acid in NMP (25 mL/mmole scaffold) containing 1 M DBU for 1 h, so as to cleave the nitrophenylsulfonyl group. The resin is washed with DMF (3×) and CH$_2$Cl$_2$ (3×) and dried with a flow of inert gas.

At this point of the synthesis, the 4-position nitrogen atom of the 1,4,8-triazabicyclo[5.4.0]undecan-2-one scaffold may be further functionalized as a sulfonamide, urea, amide, aryl amine, or alkyl amine, if desired, via reaction with a variety of building blocks as described in Examples 66, 67, 68, 69, 70, 71, 72, 73 and 74.

Step 13

Finally, the resin-bound functionalized scaffold is treated with TFA containing 2.5% Et$_3$SiH (25 mL/mmole scaffold), and the suspension allowed to stand for 4 h at rt. The mixture is filtered, the resin washed with TFA (3×10 mL/mmole scaffold), and the combined filtrates concentrated under reduced pressure, then dried over KOH at 0.1 mm Hg to provide the desired compound.

The use of a variety of building blocks at the various sites of diversity generated and derivatized in this procedure allows the synthesis of a library of a wide variety of highly functionalized, 1,4,8-triazabicyclo[5.4.0]undecan-2-ones to be synthesized.

Example 118

[3S,5S]-1-(2-nitrobenzenesulfonyl-L-alanyl)-3-(t-butyldiphenylsilyl)oxy-5-(hydroxymethyl) pyrrolidine A solution of 1-Fmoc-5-(dimethoxytrityloxymethyl)-3-hydroxypyrrolidine (1.3 g) was silylated by treatment with 1.25 eq. Tert-butyldiphenylsilyl chloride and 3.5 eq. imidazole in DMF overnight, to yield upon work up the 1-Fmoc-5-(dimethoxytrityloxymethyl)-3-(tert-butyldiphenylsilyloxy)-pyrrolidine. This material was treated with 10% piperidine in DMF for 0.5 h to remove the Fmoc protection. The product was extracted into EtOAc from water, then purified by silica gel chromatography (EtOAc/hexane) to give a 66% yield of 5-(dimethoxytrityloxymethyl)-3-(tert-butyldiphenylsilyloxy)-pyrrolidine.

This material was coupled with 1.2 eq FMOC-Ala-OH using 2.5 eq. DIEA and 1.2 eq. HATU as an activator in CH$_2$Cl$_2$, and the product purified by silica gel chromatography. The resulting foam was dwassolved in DMF containing 10% piperidine, and stirred for 0.5 h, then concentrated, azeotroped with dry pyridine (3×), and dwassolved in CH$_2$Cl$_2$. This product was treated with 0.36 g, 2.6 mmol, of 2-nitrobenzensulfonyl chloride and DIEA (0.50 mL) for 1 h at room temperature. A solution of NaHCO$_3$ was added, and the organic layer separated and dried with MgSO$_4$, then concentrated and chromatographed on silica gel (EtOAc/hexane) to provide 1.01 g (83%) of the [3S,5S]-1-(2-nitrobenzenesulfonyl-L-alanyl)-3-(t-butyldiphenylsilyl)oxy-5-(dimethoxytrityloxymethyl)-pyrrolidine.

This product was dissolved in 10% MeOH/CH$_2$Cl$_2$, then treated with acetyl chloride (0.1 mL), and allowed to stir at rt 2 h. 10% aqueous NaHCO$_3$ was added, and the organic layer dried with MgSO$_4$, concentrated, and chromatographed on silica gel (80% EtOAc/hexane) to provide 0.34 g of [3S,5S]-1-(2-nitrobenzenesulfonyl-L-alanyl)-3-(t-butyldiphenylsilyl)oxy-5-(hydroxymethyl)pyrrolidine: R$_f$ (0.53) 70% EtOAc/hexane. Anal. Calcd for C$_{30}$H$_{37}$N$_3$O$_7$SiS: C, 58.90; H, 6.10; N, 6.87. Found: C, 58.55; H, 6.02; N, 6.69.

Example 119

[3S,6S,8S]-8-(t-Butyldiphenylsilyl)oxy-3-methyl-4-(2-nitrobenzenesulfonyl)-1,4-diazabicyclo[3.4.0]nonan-2-one To a solution of [3S,5S]-1-(2-nitrobenzenesulfonyl-L-alanyl)-3-(t-butyldiphenylsilyl)oxy-5-(hydroxymethyl) pyrrolidine (250 mg, 0.41 mmol) and triphenylphosphine (160 mg, 0.61 mmol) in dry THF was added DEAD (0.10 mL, 0.61 mmol) dropwise with stirring. The mixture was allowed to stir overnight, then concentrated, and chromatographed with 1% acetone/CH$_2$Cl$_2$ to provide 240 mg (99%) of [3S,6S,8S]-8-(t-Butyldiphenylsilyl)oxy-3-methyl-4-(2-nitrobenzenesulfonyl)-1,4-diazabicyclo[3.4.0]nonan-2-one: R$_f$ (0.45) 1% acetone/CH$_2$Cl$_2$; HRMS (FAB$^+$, CsI/NBA) calcd for C$_{30}$H$_{35}$N$_3$O$_6$SSi+H 594.2094, found 594.2084.

Example 120

[3S,6S,8S]-8-Hydroxy-3-methyl-4-(2-nitrobenzenesulfonyl)-1,4-diazabicyclo[3.4.0]nonan-2-one To 54 mg (0.10 mmol) of [3S,6S,8S]-8-(t-Butyldiphenylsilyl)oxy-3-methyl-4-(2-nitrobenzenesulfonyl)-1,4-diazabicyclo[3.4.0]nonan-2-one in THF (1 mL) was added Et$_3$N.3HF (0.16 mL, 1 mmol) and Et$_3$N (0.07 mL, 0.50 mmol) at rt, and the solution stirred overnight. EtOAc and NaHCO$_3$ (aqueous, 10% w/w) is added, the organic layer dried (MgSO$_4$) and the residue chromatographed (0–7% MeOH/CH$_2$Cl$_2$) to provide 31 mg (86%) of [3S,6S,8S]-8-Hydroxy-3-methyl-4-(2-nitrobenzenesulfonyl)-1,4-diazabicyclo[3.4.0]nonan-2-one: R$_f$ 0.24 (5% MeOH/CH$_2$Cl$_2$);

$^1$H NMR (CDCl$_3$) δ8.10 (d, 1H), 7.74 (m, 3H), 4.50 (m, 2H), 4.27 (dd, 1H), 4.03 (m, lH), 3.83 (dd, 1H), 3.37 (d, 1H), 3.02 (dd, 1H), 2.60 (s, 1H), 2.10 (dd, 1H), 1.57 (ddd, 1H), 1.39 (d, 3H); $^{13}$C NMR (CDCl$_3$) d 166.59, 147.65, 134.02, 133.78, 132.24, 130.95, 124.61, 68.10, 56.07, 54.83, 53.45, 44.65, 39.26,17.81 ppm; HRMS (FAB$^+$, CsI/NBA) calcd for C$_{14}$H$_{17}$N$_3$O$_6$S 355.0838, found 356.0910.

Example 121

[3S, 6S, 8S]-8-(t-Butyldiphenylsilyl)oxy-3-methyl-1,4-diazabicyclo[3.4.0]nonan-2-one A solution of [3S,6S,8S]-8-(t-Butyldiphenylsilyl)oxy-3-methyl-4-(2-nitrobenzenesulfonyl)-1,4-diazabicyclo[3.4.0]nonan-2-one (214 mg, 0.36 mmol), PhSH (0.10 mL, 1 mmol) and Et$_3$N (0.20 mL, 1.5 mmol) in degassed DMF (5 mL) were stirred at rt for 4 days. EtOAc and H$_2$O were added, and the organic layers washed with NaHCO$_3$ (aqueous 5% w/w), dried (MgSO$_4$), concentrated, and chromatographed (1:1 EtOAc/hexane to 10% MeOH in 1:1 EtOAc/hexane) to provide 92 mg (63%) of [3S,6S,8S]-8-(t-Butyldiphenylsilyl)oxy-3-methyl-1,4-diazabicyclo[3.4.0]nonan-2-one: R$_f$ 0.26 (10% MeOH in 1:1 EtOAc/hexane);

$^1$H NMR (CDCl$_3$) δ7.67–7.33 (m, 10H), 4.44 (t, 1H), 4.03 (m, 1H), 3.77–3.58 (m, 2H), 3.45 (d, 1H), 3.18 (dd, 1H), 2.61 (dd, 1H), 1.93 (dd, 1H), 1.38–1.26 (m, 1H), 1.36 (d, 3H), 1.07 (s, 9H).

Example 122

[3S,6S,8S]-8-Hydroxy-3-methyl-4-(3-nitrophenylmethyl)-1,4-diazabicyclo[3.4.0]nonan-2-one A solution of [3S,6S,8S]-8-(t-Butyldiphenylsilyl)oxy-3-methyl-4-(2-nitrobenzenesulfonyl)-1,4-diazabicyclo[3.4.0]nonan-2-one (85 mg, 0.21 mmol), Et$_3$N (70 mL, 0.50 mmol) and 3-nitrobenzylbromide (68 mg, 0.31 mmol) in 1:1 THF/DMF (5 mL) were stirred at rt for 9 h, at which point the reaction is complete by TLC (10% MeOH/1:1 EtOAc/hexane). A solution of sodium 2-mercaptoethane sulfonate (164 mg, 1 mmol) and $K_2CO_3$ (138 mg, mmol) in water (2 mL) was added, and the mixture stirred for 0.5 h, then partitioned between water and EtOAc. The organic layer contained no unreacted alkylating agent by TLC, and was washed with water, brine, and dried ($MgSO_4$), then concentrated. The residue is dissolved in THF (5 mL), and TBAF (1 M in THF, 0.30 mL, 0.30 mmol) is added. After stirring for 1 h at rt, silica (600 mg) was added, the solvent removed, and the residue loaded onto a column and chromatographed (10% MeOH/1:1 EtOAc/hexane) to provide 42 mg (66%) of [3S,6S,8S]-8-Hydroxy-3-methyl-4-(3-nitrophenylmethyl)-1,4-diazabicyclo[3.4.03nonan-2-one: $R_f$ 0.25(10% MeOH/1:1 EtOAc/hexane); HRMS (FAB$^+$, CsI/NBA) calcd for $C_{15}H_{19}N_3O_4$ 305.1375, found 306.1464.

Example 123

N-CBZ-cis-4-Amino-2-cyclopenten-1-ol

The product is prepared by the method of A. R. Ritter, M. J. Miller, Tetrahedron Lett. 1994, 35, 9379.

Example 124

N-CBZ-cis-4-Amino-cyclopentan-1-ol-2,3-epoxide

N-CBZ-cis-4-amino-2-cyclopenten-1-ol is dissolved in dichloromethane and meta-chloroperbenzoic acid is added. The solution is stirred until the starting material disappears. The reaction is quenched by the addition of a 5% solution of sodium bisulfite, extracted with dichloromethane, washed with $NaHCO_3$, brine and dried. The title compound is purified by silica gel flash column chromatography.

Example 125

N-CBZ-cis-4-Aminocyclopentan-1,2-diol

The epoxide of Example 124 is dissolved in THF, and treated with 2 eq $LiBH_4$ in the presence of a catalytic amount of $Ti(OiPr)_4$. Stirring is continued until the reaction is complete. The reaction is diluted with ethyl acetate, washed with 0.1 M citric acid, $NaHCO_3$, brine, dried with $MgSO_4$ and evaporated. The title compound is purified by silica gel flash column chromatography.

Example 126

N-CBZ-cis-4-Amino-2-dimethoxytrityloxy-cyclopentan-1-ol

N-CBZ-cis-4-Aminocyclopentan-1,2-diol is coevaporated with dry pyridine, and redissolved in dry pyridine (0.1 M). Dimethoxytrityl chloride (1.0 eq) is added in portions over 15 minutes and the solution stirred at RT overnight. Methanol is then added (10 ml), and the solvent removed under reduced pressure. The resulting gum is redissolved in ethyl acetate, washed with 0.1 M citric acid, $NaHCO_3$, brine, dried with $MgSO_4$, and evaporated. The title compound is purified by silica gel flash column chromatography.

Example 127

Cis-4-(N-Teoc-amino)-2-dimethoxytrityloxy-cyclopentan-1-ol

N-CBZ-cis-4-Amino-2-dimethoxytrityloxy-cyclopentan-1-ol is dissolved in ethanol and 10% Pd/C is added. The mixture is shaken under 1 ATM $H_2$ until all the material is consumed. The deprotected amine is isolated via extraction of the product and concentration.

The amine (15.6 mmoles) is dissolved into 500 mL of 1:1 water/dioxane. To this solution is added triethylamine (23.1 mmoles, 1.5 eq), followed by TEOC-NHS (15.6 mmoles, 1 eq) and the reaction mixture stirred overnight at room temperature. The reaction is then concentrated to approximately one half volume and poured into 500 mL 1M HCl and extracted 3× with dichloromethane. The extracts are combined, washed with brine, dried with $MgSO_4$, filtered and the solvent removed in vacuo. The title compound is purified by silica gel flash column chromatography.

Example 128

1-(Azido)-2-(Dimethoxytrityloxy)-4-(N-Teoc-amino)-cyclopentane

Cis-4-(N-Teoc-amino)-2-dimethoxytrityloxy-cyclopentan-1-ol (3 mmoles) is dissolved in 1:1 pyridine:dichloromethane (7 mL/mmole) and cooled to 0° C. Methanesulfonyl chloride (4 mmoles) is added and the reaction stirred at room temperature for 2 hrs. Work up as described in Examples 3 and 53, yields the crude mesylate that is displaced with sodium azide (4 mmoles) following the procedure of Examples 4 and 55. After several hours the reaction mixture is concentrated to one third its original volume, poured into saturated $NaHCO_3$ (5 mL/mmole) and extracted three times with EtOAc. Drying over $Na_2SO_4$, followed by filtration and concentration afford the title compound that is used directly in the next step.

Example 129

1-(Trifluoroacetylamido)-2-(Dimethoxytrityloxy)-4-(N-Teoc-amino)-cyclopentane 1-(Azido)-2-(Dimethoxytrityloxy)-4-(N-Teoc-amino)-cyclopentane is reduced using a 2M solution of $LIBH_4$ in THF and a 0.5M solution of 9-BBN, following the procedure of Example 5. The reaction was worked up as described, and the resulting amine protected with ethyl trifluoroacetate and triethylamine. Workup and chromatography yielded the desired 1-(trifluoroacetylamido)-2-(Dimethoxytrityloxy)-4-(N-Teoc-amino)-cyclopentane.

Example 130

1-Amino-2-(Dimethoxytrityloxy)-4-(N-Teoc-amino)-cyclopentane 1-(Trifluoroacetylamido)-2-(Dimethoxytrityloxy)-4-(N-Teoc-amino)-cyclopentane is hydrolyzed following the procedure of Examples 12 and 60, using 10% $K_2CO_3$ in 5/2 methanol/water to afford the 1-amino-2-(Dimethoxytrityloxy)-4-(N-Teoc-amino)-cyclopentane.

Example 131

=b 1-Azido-2-(Trifluoroacetylamido)-4-(N-Teoc-amino)-cyclopentane 1-(Trifluoroacetylamido)-2-(Dimethoxytrityloxy)-4-(N-Teoc-amino)-cyclopentane is detritylated following the general procedure as described in Example 62. The resulting 2-hydroxy compound is converted to its mesylate according to the procedure described in Example 53 and subsequently reacted with sodium azide as described in Example 55 to afford the title compound.

Example 132

3-Benzyl-9-(methoxybenzenesulfonamido)-7-((thien-3-yl) methyl)-amino-4-m-toluoyl-1,4-diazabicyclo[4.4.0]decan-2-one Step 1

The 4-hydroxybenzaldehyde derivatized Argogel-OH support (from Example 97) is loaded with the N-Teoc -5(3)-amino-3(5)-azido-2-[(dimethoxytrityloxy)methyl] piperidine scaffold via reductive alkylation, following the general procedure of Example 81.

To the Argogel resin-bound aldehyde, from the previous example, is added a solution of the N-Teoc -5(3)-amino-3 (5)-azido-2-[(dimethoxytrityloxy)methyl]piperidine scaffold in 4:1 MeOH/CH(OMe)$_3$ (3 mmole scaffold/mmole resin functionality in 5 mL solvent/gram of dry resin). The mixture is allowed to stand for 0.5 h at rt, then a solution of BH$_3$-pyridine (3 mmole/mmole resin functionality) and acetic acid (3 mmole/mmole resin functionality) in 4:1 MeOH/CH(OMe)$_3$ (0.5 mL/gram dry resin solvent) is added. The suspension is allowed to stand for 2 h at rt, then filtered, and washed with MeOH (3×), CH$_2$Cl$_2$ (3×), DMF (3×) and CH$_2$Cl$_2$ (3×) and dried with a flow of inert gas.

Step 2

Loading of the resin is determined via cleavage and spectroscopic quantitation of the dimethoxytrityl group using a dilute solution of dichloroacetic acid in dichloromethane.

Step 3

This resin bound scaffold is then functionalized at the first diversity site (linking amino group) as a sulfonamide, by reaction with methoxybenzene sulfonyl chloride following the general procedure described in Example 66, above.

Step 4

This material is next treated with a 0.2 M solution (25 mL/mmole scaffold) of TBAF in NMP, so as to cleave the Teoc group. The suspension is allowed to stand for 1 h at rt, then filtered, and washed with DMF (3×) and CH$_2$Cl$_2$ (3×) and dried with a flow of inert gas.

Step 5

The free amino group so formed is derivatized with a 0.20 M solution (5 mL/g of dry resin) of N-Fmoc-phenylalanine in 1:1 NMP/CH$_2$Cl$_2$. A 1.0 M solution of DIPEA in CH$_2$Cl$_2$ (2 mL/g of dry resin) is added, followed by a 0.33 M solution of O-(7-azabenzotriazol-1-yl)-1,1,3,3-tetramethyluronium hexafluorophosphate (HATU) in NMP (3 mL/g of dry resin). The suspension is allowed to stand for 3 h at rt to allow acylation to proceed to completion, then filtered, and washed with CH$_2$Cl$_2$ (3×), DMF (3×), CH$_2$Cl$_2$ (3×) and dried with a flow of inert gas.

Step 6

To this resin bound amino acid derivatized scaffold is added a 10 v/v % solution of piperidine in DMF (25 mL/mmole scaffold) so as to cleave the Fmoc group. The suspension is allowed to stand for 0.2 h at rt, then filtered, and washed with DMF (3×) and CH$_2$Cl$_2$ (3×) and dried with a flow of inert gas.

Step 7

The free amino group is next treated with a 0.1 M solution (25 mL/mmole scaffold) of 2-nitrobenzenesulfonyl chloride in CH$_2$Cl$_2$ containing 0.15 M DIPEA. The suspension is allowed to stand for 1h at rt, then filtered, and washed with DMF (3×) and CH$_2$Cl$_2$ (3×) and dried with a flow of inert gas.

Step 8

To the resin is next added a 3 v/v % solution of dichloroacetic acid in CH$_2$Cl$_2$ (25 mL/mmole scaffold) so as to cleave the DMT group protecting the hydroxy functionality. The suspension is allowed to stand for 1 min at rt, then filtered, and washed with MeOH (3×) and CH$_2$Cl$_2$ (3×). This process is repeated four additional times, and the resin washed with DMF (3×) and CH$_2$Cl$_2$ (3×) and dried with a flow of inert gas.

Step 9

The resin bound material is then treated with a 0.1 M solution of 5-triphenylphosphonium-1,1,-dioxo-3,3-dimethyl-2,5-thiadiazolidine betaine in 19:1 CH$_2$Cl$_2$/DMF (25 mL/mmole scaffold) for 1 h, then washed with DMF (3×) and CH$_2$Cl$_2$ (3×) and dried with a flow of inert gas. This step leads to the formation of the substituted bicyclic scaffold, 1,4-diazabicyclo[4.4.0]decan-2-one, attached to the resin.

Step 10

The resin bound bicyclic scaffold is then treated with a 0.5 M solution of 2-mercaptoacetic acid in NMP (25 mL/mmole scaffold) containing 1 M DBU for 1 h, so as to cleave the nitrophenylsulfonyl group. The resin is washed with DMF (3×) and CH$_2$Cl$_2$ (3×) and dried with a flow of inert gas.

Step 11

At this point of the synthesis, the 4-position nitrogen atom of the 1,4-diazabicyclo[4.4.0]decan-2-one scaffold is further functionalized as an amide, via reaction with m-toluic acid as described in Example 72.

Step 12

This 3,4,9-substituted 7-azido-1,4-diazabicyclo[4.4.0] decan-2-one attached to the solid support is next reduced according to the general procedure of Example 77 to generate a 7-amino group. The amino group is derivatized via reductive alkylation with thiophene-3-carboxaldehyde, as described in Example 74, above.

Step 13

Finally, the resin-bound functionalized scaffold is treated with TFA containing 2.5% Et$_3$SiH (25 mL/mmole scaffold), and the suspension allowed to stand for 4 h at rt. The mixture is filtered, the resin washed with TFA (3×10 mL/mmole scaffold), and the combined filtrates concentrated under reduced pressure, then dried over KOH at 0.1 mm Hg to provide the title compound.

Example 133

10-Benzylcarbamoylamino-3-methyl-4,8-di(2-nitrobenzenesulfonyl)-1,4,8-triazabicyclo[5.4.0]undecan-2-one Step 1

The 4-hydroxybenzaldehyde derivatized Argogel-OH support (from Example 97) is loaded with the 6-amino-2-(dimethoxytrityloxymethyl)-4-(2-nitrobenzenesulfonyl)-1-TEOC-1,4-diazepine scaffold via reductive alkylation, following the general procedure of Example 81.

Step 2

To the Argogel resin-bound aldehyde, is added a solution of the 6-amino-2-(dimethoxytrityloxymethyl)-4-(2-nitrobenzenesulfonyl)-1-TEOC-1,4-diazepine scaffold in 4:1 MeOH/CH(OMe)$_3$ (3 mmole scaffold/mmole resin functionality in 5 mL solvent/gram of dry resin). The mixture is allowed to stand for 0.5 h at rt, then a solution of BH$_3$-pyridine (3 -mmole/mmole resin functionality) and acetic acid (3 mmole/mmole resin functionality) in 4:1 MeOH/CH (OMe)$_3$ (0.5 mL/gram dry resin solvent) is added. The suspension is allowed to stand for 2 h at rt, then filtered, and washed with MeOH (3×), CH$_2$Cl$_2$ (3×), DMF (3×) and CH$_2$Cl$_2$ (3×) and dried with a flow of inert gas.

Loading of the resin is determined via cleavage and spectroscopic quantitation of the dimethoxytrityl group using a dilute solution of dichloroacetic acid in dichloromethane.

Step 3

This resin bound scaffold is then functionalized, at the first diversity site (linking amino group) as an urea, by reacting with benzyl isocyanate, according to the general procedure described in Example 67 above.

Step 4

This material is next treated with a 0.2 M solution (25 mL/mmole scaffold) of TBAF in NMP, so as to cleave the Teoc group. The suspension is allowed to stand for 1 h at rt, then filtered, and washed with DMF (3×) and CH$_2$Cl$_2$ (3×) and dried with a flow of inert gas.

Step 5

The free amino group so formed is derivatized with a 0.20 M solution (5 mL/g of dry resin) of N-Fmoc-alanine in 1:1 NMP/CH$_2$Cl$_2$. A 1.0 M solution of DIPEA in CH$_2$Cl$_2$ (2 mL/g of dry resin) is added, followed by a 0.33 M solution of O-(7-azabenzotriazol-1-yl)-1,1,3,3-tetramethyluronium hexafluorophosphate (HATU) in NMP (3 mL/g of dry resin). The suspension is allowed to stand for 3 h at rt to allow acylation to proceed to completion, then filtered, and washed with CH$_2$Cl$_2$ (3×), DMF (3×), CH$_2$Cl$_2$ (3×) and dried with a flow of inert gas.

Step 6

To this resin bound amino acid derivatized scaffold is added a 10 v/v % solution of piperidine in DMF (25 mL/mmole scaffold) so as to cleave the Fmoc group. The suspension is allowed to stand for 0.2 h at rt, then filtered, and washed with DMF (3×) and CH$_2$Cl$_2$ (3×) and dried with a flow of inert gas.

Step 7

The free amino group of the pendant amino acid is next treated with a 0.1 M solution (25 mL/mmole scaffold) of 2-nitrobenzenesulfonyl chloride in CH$_2$Cl$_2$ containing 0.15 M DIPEA. The suspension is allowed to stand for 1 h at rt, then filtered, and washed with DMF (3×) and CH$_2$Cl$_2$ (3×) and dried with a flow of inert gas.

Step 8

To the resin is next added a 3 v/v % solution of dichloroacetic acid in CH$_2$Cl$_2$ (25 mL/mmole scaffold) so as to cleave the DMT group protecting the hydroxy functionality. The suspension is allowed to stand for 1 min at rt, then filtered, and washed with MeOH (3×) and CH$_2$Cl$_2$ (3×). This process is repeated four additional times, and the resin washed with DMF (3×) and CH$_2$Cl$_2$ (3×) and dried with a flow of inert gas.

Step 9

The resin bound material is then treated with a 0.1 M solution of 5-triphenylphosphonium-1,1-dioxo-3,3-dimethyl-2,5-thiadiazolidine betaine in 19:1 CH$_2$Cl$_2$/DMF (25 mL/mmole scaffold) for 1 h, then washed with DMF (3×) and CH$_2$Cl$_2$ (3×) and dried with a flow of inert gas. This step leads to the formation of the substituted bicyclic 1,4,8-triazabicyclo[5.4.0]undecan-2-one, attached to the resin.

Step 10

Finally, the resin-bound functionalized scaffold is treated with TFA containing 2.5% Et$_3$SiH (25 mL/mmole scaffold), and the suspension allowed to stand for 4 h at rt. The mixture is filtered, the resin washed with TFA (3×10 mL/mmole scaffold), and the combined filtrates concentrated under reduced pressure, then dried over KOH at 0.1 mm Hg to provide the 10-Benzylcarbamoylamino-3-methyl-4,8-di(2-nitrobenzenesulfonyl)-1,4,8-triazabicyclo[5.4.0]undecan-2-one Example 134

4-(Methoxybenzenesulfonyl)-7-(nicotinamido)-1,4-diazabicyclo[3.3.1]nonan-2-one

Step 1

The 4-hydroxybenzaldehyde derivatized Argogel-OH support (from Example 97) is loaded with the N-Teoc -3-amino-5S-(dimethoxytrityloxy)-piperidine scaffold (from Example 50) via reductive alkylation, following the general procedure of Example 81.

To the Argogel resin-bound aldehyde, from the previous example, is added a solution of the N-Teoc -3-amino-5S-(dimethoxytrityloxy)-piperidine scaffold in 4:1 MeOH/CH (OMe)$_3$ (3 mmole scaffold/mmole resin functionality in 5 mL solvent/gram of dry resin). The mixture is allowed to stand for 0.5 h at rt, then a solution of BH$_3$-pyridine (3 mmole/mmole resin functionality) and acetic acid (3 mmole/mmole resin functionality) in 4:1 MeOH/CH(OMe)$_3$ (0.5 mL/gram dry resin solvent) is added. The suspension is allowed to stand for 2 h at rt, then filtered, and washed with MeOH (3×), CH$_2$Cl$_2$ (3×), DMF (3×) and CH$_2$Cl$_2$ (3×) and dried with a flow of inert gas.

Step 2

Loading of the resin is determined via cleavage and spectroscopic quantitation of the dimethoxytrityl group using a dilute solution of dichloroacetic acid in dichloromethane.

Step 3

This resin bound scaffold is then functionalized at the first diversity site (linking amino group) as an amide, by reaction with nicotinoyl chloride following the general procedure described in Example 71, above.

Step 4

This material is next treated with a 0.2 M solution (25 mL/mmole scaffold) of TBAF in NMP, so as to cleave the Teoc group. The suspension is allowed to stand for 1 h at rt, then filtered, and washed with DMF (3×) and CH$_2$Cl$_2$ (3×) and dried with a flow of inert gas.

Step 5

The free amino group so formed is derivatized with a 0.20 M solution (5 mL/g of dry resin) of N-Fmoc-glycine in 1:1

NMP/CH$_2$Cl$_2$. A 1.0 M solution of DIPEA in CH$_2$Cl$_2$ (2 mL/g of dry resin) is added, followed by a 0.33 M solution of O-(7-azabenzotriazol-1-yl)-1,1,3,3-tetramethyluronium hexafluorophosphate (HATU) in NMP (3 mL/g of dry resin). The suspension is allowed to stand for 3 h at rt to allow acylation to proceed to completion, then filtered, and washed with CH$_2$Cl$_2$ (3×), DMF (3×), CH$_2$Cl$_2$ (3×) and dried with a flow of inert gas.

Step 6

To this resin bound amino acid derivatized scaffold is added a 10 v/v % solution of piperidine in DMF (25 mL/mmole scaffold) so as to cleave the Fmoc group. The suspension is allowed to stand for 0.2 h at rt, then filtered, and washed with DMF (3×) and CH$_2$Cl$_2$ (3×) and dried with a flow of inert gas.

Step 7

The free amino group is next treated with a 0.1 M solution (25 mL/mmole scaffold) of 2-nitrobenzenesulfonyl chloride in CH$_2$Cl$_2$ containing 0.15 M DIPEA. The suspension is allowed to stand for 1 h at rt, then filtered, and washed with DMF (3×) and CH$_2$Cl$_2$ (3×) and dried with a flow of inert gas.

Step 8

To the resin is next added a 3 v/v % solution of dichloroacetic acid in CH$_2$Cl$_2$ (25 mL/mmole scaffold) so as to cleave the DMT group protecting the hydroxy functionality. The suspension is allowed to stand for 1 min at rt, then filtered, and washed with MeOH (3×) and CH$_2$Cl$_2$ (3×). This process is repeated four additional times, and the resin washed with DMF (3×) and CH$_2$Cl$_2$ (3×) and dried with a flow of inert gas.

Step 9

The resin bound material is then treated with a 0.1 M solution of 5-triphenylphosphonium-1,1-dioxo-3,3-dimethyl-2,5-thiadiazolidine betaine in 19:1 CH$_2$Cl$_2$/DMF (25 mL/mmole scaffold) for 1 h, then washed with DMF (3×) and CH$_2$Cl$_2$ (3×) and dried with a flow of inert gas. This step leads to the formation of the substituted bicyclic scaffold, 1,4-diazabicyclo[3.3.1]nonan-2-one, attached to the resin.

Step 10

The resin bound bicyclic scaffold is then treated with a 0.5 M solution of 2-mercaptoacetic acid in NMP (25 mL/mmole scaffold) containing 1 M DBU for 1 h, so as to cleave the nitrophenylsulfonyl group. The resin is washed with DMF (3×) and CH$_2$Cl$_2$ (3×) and dried with a flow of inert gas.

Step 11

The 4-position nitrogen atom of the 1,4-diazabicyclo [3.3.1]nonan-2-one scaffold is further functionalized as a sulfonamide, via reaction with methoxybenzene sulfonyl chloride as described in Example 66.

Step 12

Finally, the resin-bound functionalized scaffold is treated with TFA containing 2.5% Et$_3$SiH (25 mL/mmole scaffold), and the suspension allowed to stand for 4 h at rt. The mixture is filtered, the resin washed with TFA (3×10 mL/mmole scaffold), and the combined filtrates concentrated under reduced pressure, then dried over KOH at 0.1 mm Hg to provide the title compound.

Example 135

3R-(Benzylcarbamoyl)-5-((N-benzyl-N-methyl) aminomethyl)-N-(thymidin-1-yl-acetyl)-pyrrolidine Step 1

The 4-hydroxybenzaldehyde derivatized Argogel-OH support (from Example 97) is loaded with the N-Teoc -3R-amino-5-azidomethyl-pyrrolidine scaffold (from Example 12) via reductive alkylation, following the general procedure of Example 81.

To the Argogel resin-bound aldehyde, from the previous example, is added a solution of the N-Teoc -3R-amino-5-azidomethyl-pyrrolidine scaffold in 4:1 MeOH/CH(OMe)$_3$ (3 mmole scaffold/mmole resin functionality in 5 mL solvent/gram of dry resin). The mixture is allowed to stand for 0.5 h at rt, then a solution of BH3-pyridine (3 mmole/mmole resin functionality) and acetic acid (3 mmole/mmole resin functionality) in 4:1 MeOH/CH(OMe)$_3$ (0.5 mL/gram dry resin solvent) is added. The suspension is allowed to stand for 2 h at rt, then filtered, and washed with MeOH (3×), CH$_2$Cl$_2$ (3×), DMF (3×) and CH$_2$Cl$_2$ (3×) and dried with a flow of inert gas.

Step 2

Loading of the resin is determined via cleavage and spectroscopic quantitation of the dimethoxytrityl group using a dilute solution of dichloroacetic acid in dichloromethane.

Step 3

This resin bound scaffold is then functionalized at the first diversity site (linking amino group) as an urea, by reaction with benzylisocyanate following the general procedure described in Example 67, above.

Step 4

This material is next treated with a 0.2 M solution (25 mL/mmole scaffold) of TBAF in NMP, so as to cleave the Teoc group. The suspension is allowed to stand for 1 h at rt, then filtered, and washed with DMF (3×) and CH$_2$Cl$_2$ (3×) and dried with a flow of inert gas.

Step 5

The free amino group so formed is derivatized with a solution of thymidin-1-yl-acetic acid, following the procedure of Example 72, then filtered, and washed with CH$_2$Cl$_2$ (3×), DMF (3×), CH$_2$Cl$_2$ (3×) and dried with a flow of inert gas.

Step 6

To this resin bound azide is reduced according to the procedure of Example 77 so as to afford a reactive aminomethyl functionality.

Step 7

This amino group is reacted further with via reductive alkylation, following the procedure of Example 74 using benzaldehyde.

Step 8

The secondary amine generated in the above step is further reacted with methyl iodide, following the procedure of Example 73 and the resin washed with $CH_2Cl_2$ (3×), DMF (3×), $CH_2Cl_2$ (3×) and dried with a flow of inert gas.

Step 9

Finally, the resin-bound functionalized scaffold is treated with TFA containing 2.5% $Et_3SiH$ (25 mL/mmole scaffold), and the suspension allowed to stand for 4 h at rt. The mixture is filtered, the resin washed with TFA (3×10 mL/mmole scaffold), and the combined filtrates concentrated under reduced pressure, then dried over KOH at 0.1 mm Hg to provide the title compound.

Example 136

5S-(N-acetyl-N-isopropyl)amino)-3-(2-nitrobenzenesulfonamido)-N-(phenylthiocarbamoyl)-piperidine Step 1

The 4-hydroxybenzaldehyde derivatized Argogel-OH support (from Example 97) is loaded with the N-Teoc-3-amino-5S-azido-piperidine scaffold (from Example 22) via reductive alkylation, following the general procedure of Example 81.

To the Argogel resin-bound aldehyde, from the previous example, is added a solution of the N-Teoc-3-amino-5S-azido-piperidine scaffold in 4:1 $MeOH/CH(OMe)_3$ (3 mmole scaffold/mmole resin functionality in 5 mL solvent/gram of dry resin). The mixture is allowed to stand for 0.5 h at rt, then a solution of $BH_3$-pyridine (3 mmole/mmole resin functionality) and acetic acid (3 mmole/mmole resin functionality) in 4:1 $MeOH/CH(OMe)_3$ (0.5 mL/gram dry resin solvent) is added. The suspension is allowed to stand for 2 h at rt, then filtered, and washed with MeOH (3×), $CH_2Cl_2$ (3×), DMF (3×) and $CH_2Cl_2$ (3×) and dried with a flow of inert gas.

Step 2

Loading of the resin is determined via cleavage and spectroscopic quantitation of the dimethoxytrityl group using a dilute solution of dichloroacetic acid in dichloromethane.

Step 3

This resin bound scaffold is then functionalized at the first diversity site (linking amino group) as a sulfonamide, by reaction with 2-nitrobenzenesulfonyl chloride following the general procedure described in Example 66, above.

Step 4

This material is next treated with a 0.2 M solution (25 mL/mmole scaffold) of TBAF in NMP, so as to cleave the Teoc group. The suspension is allowed to stand for 1 h at rt, then filtered, and washed with DMF (3×) and $CH_2Cl_2$ (3×) and dried with a flow of inert gas.

Step 5

The free amino group so formed is derivatized with a solution of phenylisothiocyanate, following the procedure of Example 69, then filtered, and washed with $CH_2Cl_2$ (3×), DMF (3×), $CH_2Cl_2$ (3×) and dried with a flow of inert gas.

Step 6

To this resin bound azide is reduced according to the procedure of Example 77 so as to afford a reactive aminomethyl functionality.

Step 7

This amino group is reacted further via reductive alkylation, following the procedure of Example 74 using acetone.

Step 8

The secondary amine generated in the above step is further reacted with acetyl chloride, following the procedure of Example 71 and the resin washed with $CH_2Cl_2$ (3×), DMF (3×), $CH_2Cl_2$ (3×) and dried with a flow of inert gas.

Step 12

Finally, the resin-bound functionalized scaffold is treated with TFA containing 2.5% $Et_3SiH$ (25 mL/mmole scaffold), and the suspension allowed to stand for 4 h at rt. The mixture is filtered, the resin washed with TFA (3×10 mL/mmole scaffold), and the combined filtrates concentrated under reduced pressure, then dried over KOH at 0.1 mm Hg to provide the title compound.

Example 137

Derivatization of Scaffolds on Solid Support

General Procedure for Coupling of Carboxylic acid Building Blocks to Amino Combinatorial Sites Method 1

An solid support-bound scaffold is placed in a shaker flask and purged with argon for 15 minutes. The support is pre-swelled in $CH_2Cl_2$ (60 min.) then washed with DMF(6 ml).

The Teoc protecting group, if present, is removed following the procedure of Example 76. The support was washed with DMF (6 ml×5). A solution of a carboxylic acid (0.4 M, ~5 eq.) and DIEA (0.8 M, ~10 eq.) in DMF was added, followed by a solution of activator, BOP or HATU in DMF (0.4 M, 5 eq). The reaction mixture was agitated (30 min.) and then washed with DMF (6 ml×3) and $CH_2Cl_2$ (6 ml×3). Several other activating agents can also be used. These include carbodiimides such as dicyclohexyl carbodiimide (DCC), diisopropyl carbodiimide (DIC), dimethylaminopropyl ethyl carbodiimide hydrochloride (EDC), EEDQ and IIDQ, carbonyl diimidazole, with or without the addition of additives such as dimethylaminopyridine, N-hydroxybenzotriazole, N-hydroxy-7-azabenzotriazole, and others known to those skilled in the art. Other useful coupling agents include substituted uronium salts and phosphonium salts such as HBTU, TBTU, BOP, PyBROP and other analogous reagents, and reagents for producing acyl fluorides, such as cyanuric fluoride. Representative examples of each of these reagents can be found in Bodanszky, M. Principles of Peptide Synthesis, 2nd Ed. Springer-Verlag, Berlin, 1993.

Representative carboxylic acids that can be used to derivatize an amino group of scaffold of the invention include:

2-oxovaleric acid
2-oxo-octanoic acid
2-oxo-2-(2-furyl)acetic acid
indole-3-pyruvic acid
2-nitrophenylpyruvic acid
2-furylthiopyruvic acid
methacrylic acid 2-methylpropionic acid (isobutyric acid)
cyanoacetic acid
methoxyacetic acid
3-methylthiopropionic acid
4-methylpentanoic acid
3-trimethylsilylpropionic acid sodium salt
N-BOC-5-aminovaleric acid]
3-(N,N-diethylamino)propionic acid hydrochloride
monomethyl glutarate
7-oxo-octanoic acid
neodecanoic acid
1,2,3-thiadiazole-4-carboxylic acid
3-amino-1,2,4-triazole-5-carboxylic acid
3-furoic acid
2-furoic acid
4-(S)-butyrolactone-4-carboxylic acid
1-methylpyrrole-2-carboxylic acid
4-methyl-2-phenyl-1,2,3-triazole-5-carboxylic acid
1-(3'-aminophenyl)-3-carboxy-5-pyrazolone
4-phenyl-5-trifluoromethyl-thiophene-2-carboxylic acid
3-(4-chlorophenylthio)thiophene-4-carboxylic acid
5-(2-pyridylthiomethyl)-2-furancarboxylic acid
indole-2-carboxylic acid
1-methylindole-2-carboxylic acid
7-benzyloxyindole-2-carboxylic acid
4-oxo-4,5,6,7-tetrahydrobenzo[b]furan-3-carboxylic acid
1-methylindene-2-carboxylic acid
4-chloro-3-sulfamoylbenzoic acid
2-hydroxybenzoic acid (salicylic acid)
a-mercapto-p-toluic acid
BOC 4-(aminomethyl)benzoic acid
BOC 4-(methylamino)benzoic acid
N-acetyl-4-aminobenzoic acid
4-isopropoxybenzoic acid
4-(2-[methylsulfonamido]ethoxy) benzoic acid
4-(1H-pyrrol-1-yl)benzoic acid
4-(3-methyl-5-oxo-2-pyrazolin-1-yl)benzoic acid
4'-(trifluoromethyl)-2-biphenylcarboxylic acid
2-(4-nitrophenylthio)benzoic acid
2-phenoxybenzoic acid
2-(4-chlorobenzoyl)benzoic acid
2-benzoylbenzoic acid
a-phenyl-o-toluic acid
a-(4-methoxy-1-naphthyl)-o-toluic acid
2-(1,2,3,4-tetrahydro-6-naphthylmethyl)benzoic acid
2-(2-pyridylcarbonyl)benzoic acid
4-(3-fluorobenzamido)benzoic acid
3'-carboxy-3-methylbenzanilide
2'-methoxyphthalanilic acid
3-benzyloxy-4-methoxybenzoic acid
N-(3-methyl-2-pyridyl)phthalamic acid
1-(4-carboxyphenyl)-3-(o-tolyl)urea
benzotriazole-5-carboxylic acid
5-benzimidazolecarboxylic acid
piperonylic acid
2,2,5,7-tetramethylindan-1-one-4-carboxylic acid
2-naphthoic acid
2-pyrazinecarboxylic acid
picolinic acid
nicotinic acid
isonicotinic acid
6-hydroxynicotinic acid
tetrahydropyran-4-carboxylic acid
N-BOC 4-piperidinecarboxylic acid (isonipecotic acid)
1,3-dimethyl-6-uracilcarboxylic acid
2-pyrrolopyridine-5-carboxylic acid
2-phenoxynicotinic acid
2-(4-methylphenoxy)pyridine-3-carboxylic acid
2-phenylimidazo(1,2-A)pyridine-6-carboxylic acid
3-isoquinolinecarboxylic acid
4-quinolinecarboxylic acid
4-hydroxy-7-trifluoromethyl-3-quinolinecarboxylic acid
2-p-tolylcinchoninic acid
nalidixic acid
thiophene-2-acetic acid
5-(1-pyrrolidine)2-tetrazoleacetic acid
N-phthaloylglycine
indole-3-acetic acid
cyclopentylacetic acid
2-indanylacetic acid
pentafluorophenylacetic acid
2-(2-fluorophenyl)acetic acid
(S)-(+)-mandelic acid
(a,a,a-trifluoro-m-tolyl)acetic acid
R-(−)-a-methoxyphenylacetic acid
2-(4-chlorophenyl)-2,2-dimethylacetic acid
(R)-(−)-2-phenylbutyric acid
(3,4-dimethoxyphenyl)acetic acid]
4-(dimethylamino)phenylacetic acid
4-biphenylacetic acid
2-benzyloxyphenylacetic acid
1-(4-methylphenyl)-1-cyclopropanecarboxylic acid
benzilic acid
orotic acid
4-pyridylacetic acid hydrochloride
phenylacetic acid
2-(2-phenyl-1-cyclohexenyl)acetic acid
trans-3-furanacrylic acid
2-methyl-4-nitro-1-imidazolepropionic acid
5-phenyl-2-pyrrolepropionic acid
2-(4-chlorophenoxy)acetic acid
phenoxyacetic acid
N-phenylglycine
2,5-difluorocinnamic acid
3-(4-iodophenyl)propionic acid
N-(2,4-dinitrophenyl)-L-alanine
3-(3-hydroxyphenyl)propionic acid
p-toluenesulfonylacetic acid
BOC-3-(p-aminophenyl)propionic acid
4-cyanocinnamic acid
4-methoxycinnamic acid
2-(p-chlorophenoxy)-2-methylpropionic acid p-(p-nitrobenzyloxy)cinnamic acid
2-naphthoxyacetic acid
3,3-diphenylpropionic acid
3,5,6-trichloro-2-pyridoxyacetic acid
4-pyridylthioacetic acid
5-trifluoromethyl-2-pyridylthioacetic acid
1-piperidinepropionic acid
4-oxo-4-(1-pyrrolidine)butyric acid
3-(4-fluorobenzoyl)propionic acid
3-benzoylpropionic acid
N-methylhippuric acid
4-oxo-4-(2-trifluoromethylphenyl)butyric acid
3-(4-methoxybenzoyl)propionic acid
3-(4-methylsulfonylbenzoyl)propionic acid
4-(4-acetylphenyl)butyric acid
4-oxo-4-(2-naphthyl)butyric acid
dansyl glycine
3-(4-methoxy-1-naphthoyl)propionic acid
(−)-O,O'-dibenzoyl-L-tartaric acid mono(dimethylamide)
1-(3-carboxy-1-oxopropyl)-1,2,3,4-tetrahydroquinoline
1,2-dihydro-2-methyl-1-oxo-3-isoquinolinebutyric acid
2-(2-carboxyethylthio)-3,5,6-trimethyl-1,4-benzoquinone
(+)-biotin
4-(2-mercaptobenzothiazolyl)butyric acid
Z-styrenesulfonylacetic acid
4-(p-chlorophenoxy)butyric acid
3-(benzylthio)propionic acid
N-(2-pyridyl)succinamic acid
Cbz-glycine
2-[(2-phenoxyethyl)thio]acetic acid
2-(benzenesulfonyl)ethylthioacetic acid
2'-carbamoylglutaranilic acid.

Example 138

Coupling of Acyl Groups to Scaffold Amino Combinatorial Site—General Procedure

To the free scaffold amine on solid support are added simultaneously a solution of a activated acylating agent (0.1 mmol/ml) and diisopropylethylamine (0.25 mmol/ml) in Pyridine/$CH_3CN$. A tenfold excess of reagents are added at the 10 umol scale level. The reaction is allowed to proceed for 30 minutes, the solid support is washed with Pyridine/$CH_3CN$ until all the reagents are removed. Building blocks useful for acylating the free amine combinatorial site include acid halides, acid fluorides, acid imidazolides, acid anhydrides, sulfonyl chlorides, chloroformates, isocyanates, and isothiocyanates.

Example 139

Acylation of Scaffolds with Acyl Chlorides, Anhydrides, and Activated Carboxylic Acid Derivatives.

General Procedure

A cyclic amine, cycloalkyl amine or bicyclic amine scaffold loaded solid support (0.5 g Tentagel, 0.15 mmol/g) was placed in a shaker flask and purged with argon (15 min.). The support was pre-swelled in $CH_2Cl_2$ (60 min.) then washed with DMF(6 ml). The Teoc protecting group is removed following the procedure of Example 76. The support was washed with DMF (6 ml×5). A solution of py/DMF (10%, 3 mL, ~50 eq.), acid chloride/DMF (0.12 M, 3 mL, ~5 eq.) was added, and the reaction mixture agitated for 30 minutes. A solution of acid anhydride or other activated derivative in DMF could be used instead of acid chloride. The support was then washed with DMF (6 ml×3) and $CH_2Cl_2$ (6 ml×3). Examples of reagents which can be substituted for acid chlorides are: acid anhydrides and mixed anhydrides, imidazolides, or active esters such as N-hydroxy succinimide esters and other O-acyl hydroxylamine derivatives, acyl azides, 4-nitrophenol esters, pentachlorophenyl or pentafluorophenyl esters and other active aryl and vinyl esters. Representative examples of each of these reagents can be found in Bodanszky, M. Principles of Peptide Synthesis, 2nd Ed. Springer-Verlag, Berlin, 1993.

One or more of the following acid halides listed here are representative of the types of acylating building blocks that may be used in the generation of compounds of the present invention:

Using this procedure, libraries of cyclic amine, cycloalkylamine and bicyclic amine compounds that are derivatized with one or more of the following acid halides available from Aldrich Chemical Company, Inc., Milwaukee, Wis., may be prepared. The Aldrich catalog number is given in the left hand column and the compound name right hand is given in the column:

10663-1 p-Toluoyl chloride
30253-8 3-Cyanobenzoyl chloride
13096-6 (+/−)-2-Cloro-2-phenylacetyl chloride
26366-4 3-(Chloromethyl)benzoyl chloride
27078-4 4-(Chloromethyl)benzoyl chloride
24947-5 4-(Trifluoromethyl)benzoyl chloride
19394-1 4-(Chlorophenoxyacetyl) chloride
24948-3 2-(Trifluoromethyl)benzoyl chloride
19394-1 4-Chlorophenoxyacetyl chloride
24948-3 2-(Trifluoromethyl)benzoyl chloride
10663-1 p-Toluoyl chloride
25027-9 3-(Trifluoromethyl)benzoyl chloride
S67828-7 2-(2,4,5-Trichlorophenoxy)acetyl chloride
12201-7 o-Toluoyl chloride
40248-6 4-(Trifluoromethoxy)benzoyl chloride
37502-0 3-(Dichloromethyl)benzoyl chloride
12225-4 m-Toluoyl chloride
12482-6 4-Cyanobenzoyl chloride
P1675-3 Phenylacetyl chloride
S88415-4 2-(Phenylthio)propionyl chloride
15862-3 Phenoxyacetyl chloride
36475-4 trans-4-Nitrocinnamoyl chloride
28882-9 4-Ethoxybenzoyl chloride
23024-3 m-Anisoyl chloride
S67595-4 2,3-Dibromo-3-phenylpropionyl chloride
30101-9 Benzyloxyacetyl chloride
25470-3 o-Anisoyl chloride
$C_{8110}$-1 Cinnamoyl chloride
31693-8 3-Methoxyphenylacetyl chloride
A8847-6 p-Anisoyl chloride
16519-0 Acetylsalicyloyl chloride
36569-6 4-Methoxyphenylacetyl chloride
24944-0 Hydrocinnamoyl chloride
26528-4 3,5-Bis(trifluoromethyl)benzoyl chloride 28350-94 Ethylbenzoyl chloride
S40503-5 2-Phenoxypropionyl chloride
33304-2 2,5-Bis(trifluoromethyl)benzoyl chloride
S62043-2 p-Tolylacetyl chloride
16171-3 3,5-Dimethoxybenzoyl chloride
42339-4 (R)-(−)-A-Methoxy-A-(trifluoromethyl)-phenylacetyl chloride
25804-0 3,4-Dimethoxybenzoyl chloride
$T_{6980}$-9 3,4,5-Trimethoxybenzoyl chloride
26242-0 2,6-Dimethoxybenzoyl chloride
13430-9 trans-2-Phenyl-1-cyclopropanecarbonyl chloride
S62264-8 5-(Dimethylsulfamoyl)-2-methoxybenzoyl chloride
37383-4 2,4-Dimethoxybenzoyl chloride
A1740-4 o-Acetylmandelic chloride
24945-9 4-Phenyl-1,2,3,4-tetrachloro-1,3-butadiene-1-carbonyl cloride
36848-2 trans-3-(trifluoromethyl)cinnamoyl chloride
15712-0 4-tert-butylbenzoyl chloride
S42860-4 2-Phenylbutyryl chloride
22203-8 4-Butylbenzoyl chloride
23747-7 3,4-Dimethoxyphenylacetyl chloride
22204-6 4-Butoxybenzoyl chloride
S65659-3 2-(4-Chlorobenzoyl)benzoyl chloride
22214-3 4-Pentylbenzoyl chloride
$C_{3928}$-8 2-Chloro-2,2-diphenylacetyl chloride
S43639-9 4(4-Nitrophenylazo)benzoyl chloride
33158-9 Diphenylacetyl chloride
S80926-8 4-(Phenylazo)benzoyl chloride
S61661-3 2-Diphenylacetyl chloride
16114-4 4-Biphenylcarbonyl chloride
22209-7 4-Hexylbenzoyl chloride
22205-4 4-Heptyloxybenzoyl chloride
22211-9 4-Hexyloxybenzoyl chloride
22206-2 4-Heptyloxybenzoyl chloride Example 140

General Procedure for Coupling of Acid Halide and Sulfonyl Halide Building Blocks to Scaffold Amino Combinatorial Sites Deprotected amino combinatorial sites on cyclic amine, cycloalkyl amine or bicyclic amine scaffolds attached to solid supports are treated with 2×100 µL of a 0.2 M solution of the acid halide building block or the sulfonyl halide building block in pyridine, with a 15 min. wait after each addition. The support was washed 3× with DMF followed by 3× with DCM and dried.

Representative acid halides and sulfonyl halides that may be used include:
2-thiopheneacetyl chloride
methylsuccinyl chloride
4-nitrobenzoyl chloride
2(methylthio)nicotinoyl chloride
nicotinoyl chloride hydrochloride
isobutyryl chloride
1-methylimidazole-4-sulfonyl chloride
2-thiophenesulfonyl chloride
3,5-dimethylisoxazole-4-sulfonyl chloride
benzofurazan-4-sulfonyl chloride
methyl 2-(chlorosulfonyl)benzoate
2-(methoxycarbonyl)thiophene-s-sulfonyl chloride
3-methylbenzo[b]thiophene-2-sulfonyl chloride
2-acetamido-4-methyl5-thiazolesulfonyl chloride
3-methoxy-4-(methoxycarbonyl_thiophene-2-sulfonyl chloride
trans-β-styrenesulfonyl chloride
3,4-dimethoxybenzenesulfonyl chloride
8-quinolinesulfonyl chloride
p-bromobenzenesulfonyl chloride Example 141

General Procedure for the Reaction of Amine Building Blocks with Solid Support Bound Scaffolds at the Amino Combinatorial Site The monocyclic amine scaffold or bicyclic amine scaffold bound to a solid support is treated first with an activating reagent such as an alkyl haloformate or triphosgene and subsequently reacted with amine building block to afford a urea product.

The resin bound amine is first treated with 3×(50 µL of a 0.033 M solution of triphosgene in DCM, and without any gas flush, directly followed by 50 µL of 1 M DIPEA in DCM) with no wait between additons and a 5 min. wait after the final addition. The support is flushed with inert gas, and then treated with 2×(100 µL of a 0.2 M solution of the amine building block in either DCM or pyridine) with a 5 min. wait after each addition. The support is washed with 3×DCM, 3×DMF and finally 3×DCM, and dried to afford solid support bound urea derivatives.

Representative amine building blocks that may be used in this reaction include:
allylamine
3,3-Dimethylaminopropylamine
1-Phenyl-1,3,8-Triazaspiro[4.5]decan-4-one
Azetidine
Benzylamine
Butylamine
L-(−)-2-Aminocaprolactam
Heptamethyleneimine
cyclopropylamine
Diethylamine
Dimethoxyethylamine
2,5-Dimethyl-N-phenylpiperazine
Methylaminomethyl-1,3-dioxolane
N-Acetyl Ethylenediamine
3-Aminopropyl Imidazole
Methoxyethylamine
Morpholine
3-Aminopropyl Morpholine
Isonipecotamide
Piperonylamine
2-Aminomethylpyridine
Piperidine
Piperidone ethylene ketal
2-Aminoethyl-1-methylpyrrolidine
N(2-Pyridyl)piperazine
Piperonylpiperazine 3-Isopropoxypropylamine
Piperazine
Thienylethylamine
3-Trifluoromethoxybenzylamine
Tryptamine
Tetrahydrofurylamine Example 142

General Procedure for the Reaction of Aldehyde Building Blocks with Solid Support Bound Amino Scaffolds The cyclic amine, cycloalkyl amine or bicyclic amine scaffold bound to a solid support is treated with 2×(100 pL of a 1.0 M solution of the aldehyde building block in 30:10:1 methanol:trimethylorthoformate: acetic acid, followed directly by 100 μL of 1.0 M pyridine borane complex in 3:1 methanol:trimethylorthoformate) with no wait or flush. between additons. This cycle of steps is repeated one time, with a 15 min. wait after the last addition in each cycle. The support is washed with 3×DMF and 3×DCM, and dried to afford solid support bound alkylated amines.

Using this procedure cyclic amine, cycloalkyl amine or bicyclic amine scaffolds bound to a solid support may be derivatized with one or more of the following aldehydes available from Aldrich Chemical Company, Inc., Milwaukee, Wis. The Aldrich catalog number is given in the left hand column and the compound name is given in the right hand column:

Aromatic Aldehydes 10793-5 Phenylacetaldehyde
D20425 Diphenylacetaldehyde
24582-8 Hydrocinnamaldehyde
24136-9 Phenylpropionaldehyde
28902-7 (+/−)-3-Phenylbutyraldehyde
28899-3 Alpha-amylcinnamaldehyde
16116-0 Alpha-bromocinnamaldehyde
26813-5 4-Stilbenecarboxaldehyde
B133-4 Benzaldehyde
11755-2 o-Tolualdehyde
25069-4 Alpha.alpha.alpha-trifluoro-o-tolualdehyde
F480-7 2-Fluorobenzaldehyde
12497-4 2-Chlorobenzaldehyde
B5700-1 2-Bromobenzaldehyde
10962-2 o-Anisaldehyde
15372-9 2-Ethoxybenzaldehyde
N1080-2 2-Nitrobenzaldehyde
$T_{3550}$-5 m-Tolualdehyde
19687-8 Alpha.alpha.alpha-trifluoro-m-tolualdehyde
F500-5 3-Fluorobenzaldehyde
$C_{2340}$-3 3-Chlorobenzaldehyde
B5720-6 3-Chlorobenzaldehyde
12965-8 m-Anisaldehyde
34648-9 3-(Trifluoromethoxy)-benzaldehyde
34199-1 3-(1,1,2,2-Tetrafluoroethoxy)-benzaldehyde
H1980-8 3-Hydroxybenzaldehyde
N1084-5 3-Nitrobenzaldehyde
11528-2 Isophthaldehyde
$T_{3560}$-2 p-Tolualdehyde
23363-3 4-Ethylbenzaldehyde
13517-8 4-Isopropylbenzaldehyde
22494-4 Alpha.alpha.alpha-trifluoro-p-tolualdehyde
12837-6 4-Fluorobenzaldehyde
11221-6 4-Chlorobenzaldehyde
B5740-0 4-Bromobenzaldehyde
A8810-7 p-Anisaldehyde
17360-6 4-Ethoxybenzaldehyde
33363-8 4-Propoxybenzaldehyde
23808-2 4-Butoxybenzaldehyde
37060-6 4-(Trifluoromethoxy)-benzaldehyde
27486-0 Terephthaldehyde mono-(diethyl acetal)
14408-8 4-Hydroxybenzaldehyde
22277-1 4-(Methylthio)benzaldehyde
10976-2 4-(Dimethylamino)benzaldehyde
D8625-6 4-(Dimethylamino)benzaldehyde
33851-6 4-(Dibutylamino)benzaldehyde
29355-5 4-(3-Dimethylaminopropoxy)benzaldehyde
13017-6 4-Nitrobenzaldehyde
$T_{220}$-7 Terephthaldicarboxaldehyde
34252-1 3-Fluoro-2-methylbenzaldehyde
34649-7 2-Fluoro-3-(trifluoromethyl)-benzaldehyde
26514-4 2,3-Difluorobenzaldehyde
26515-2 2,6-Difluorobenzaldehyde
14124-0 2-Chloro-6-fluorobenzaldehyde
D5650-0 2,6-Dichlorobenzaldehyde
25483-5 2,3-Dichlorobenzaldehyde
D13020-6 2,3-Dimethoxybenzaldehyde
29250-8 2,6-Dimethoxybenzaldehyde
31980-5 3-Fluorosalicylaldehyde
12080-4 o-Vanillin
18983-9 2,3-Dihydroxybenzaldehyde
10604-6 2-Chloro-6-nitrobenzaldehyde
16382-1 3-methoxy-2-nitrobenzaldehyde
11750-1 2,6-Dinitrobenzaldehyde
15104-1 2,4-Dimethylbenzaldehyde
15106-8 2,5-Dimethylbenzaldehyde
37682-5 2-Chloro-5-(trifluoromethyl)benzaldehyde
26516-0 3,4-Difluorobenzaldehyde
26517-9 2,4-Difluorobenzaldehyde
26518-7 2,5-Difluorobenzaldehyde
30600-2 3-Chloro-4-fluorobenzaldehyde
34807-4 2-Chloro-4-fluorobenzaldehyde
33954-7 3-Bromo-3-fluorobenzaldehyde
D5660-8 3,4-Dichlorobenzaldehyde
14675-7 2,4-Dichlorobenzaldehyde
15212-9 3-Methyl-p-anisaldehyde
15558-6 3-Fluoro-p-anisaldehyde
15429-6 5-Bromo-o-anisaldehyde
D13040-0 2,4-Dimethoxybenzaldehyde
D13060-5 2,5-Dimethoxybenzaldehyde
14375-8 3,4-Dimethoxybenzaldehyde
25275-1 3-Ethoxy-4-methoxybenzaldehyde
P4910-4 Piperonal
26459-8 1,4-Benzodioxan-6-carboxaldehyde
31691-1 4-Hydroxy-3-methylbenzaldehyde 34606-3 2-Chloro-4-hydroxybenzaldehyde
25975-6 5-Chlorosalicylaldehyde
13728-6 5-Bromosalicylaldehyde
14686-2 2-Hydroxy-5-methoxybenzaldehyde
16069-5 2-Hydroxy-4-methoxybenzaldehyde
14368-5 3-Hydroxy-4-methoxybenzaldehyde
V110-4 Vanillin
12809-0 3-Ethoxy-4-hydroxybenzaldehyde
34215-7 5-(Trifluoromethoxy)salicylaldehyde
D10840-5 3,4-Dihydroxybenzaldehyde
D10820-0 2,5-Dihydroxybenzaldehyde
16863-7 2,4-Dihydroxybenzaldehyde
22568-1 4-(Diethylamino)salicylaldehyde
$C_{5880}$-0 5-Chloro-2-nitrobenzaldehyde
13903-3 2-Chloro-5-nitrobenzaldehyde
$C_{5870}$-3 4-Chloro-3-nitrobenzaldehyde
14432-0 4-Hydroxy-3-nitrobenzaldehyde
15616-7 3-Hydroxy-4-nitrobenzaldehyde
27535-2 2-Hydroxy-5-nitrobenzaldehyde
H4810-7 5-Hydroxy-2-nitrobenzaldehyde
D19360-7 2,4-Nitrobenzaldehyde
29013-0 3,5-Bis(trifluoromethyl)benzaldehyde
29017-3 3,5-Difluorobenzaldehyde
13940-8 3,5-Dichlorobenzaldehyde
36811-3 3,5-Dihydroxybenzaldehyde
12269-2 3,5-Dimethoxybenzaldehyde
36810-5 3,5-Dibenzyloxybenzaldehyde
M680-8 Mesitaldehyde
29233-8 2,3,5-Trichlorobenzaldehyde
13061-3 5-Bromoveratraldehyde
13871-1 2,4,6-Trimethoxybenzaldehyde
$T_{6840}$-3 3,4,5-Trimethoxybenzaldehyde
14039-2 3,5-Dimethyl-4-hydroxybenzaldehyde
35768-5 2,6-Dimethyl-4-hydroxybenzaldehyde
14040-6 3,5-Di-tert-butyl-4-hydroxybenzaldehyde hemihydrate
26181-5 3,5-Dichlorosalicylaldehyde
12213-0 3,5-Dibromosalicylaldehyde
28344-4 3,5-Diiodosalicylaldehyde
13060-5 5-Bromovanillin
12948-8 5-Iodovanillin
13879-7 4,6-Dimethoxysalicylaldehyde
25871-7 5-Nitrovanillin
S760-2 3,5-Dinitrosalicylaldehyde
25959-4 2,5-Dimethyl-p-anisaldehyde
$T_{6540}$-4 5-Bromo-2,4-dimethoxybenzaldehyde
N2800-0 4-Nitrovanillin
27680-4 3,5-Dinitrosalicylaldehyde
15205-6 2,5-Dimethyl-p-anisaldehyde
29251-6 5-Bromo-2,4-dimethoxybenzaldehyde
15557-8 6-Bromoveratraldehyde
13215-2 2,4,5-Trimethoxybenzaldehyde
27960-9 6-Nitroveratraldehyde
13765-0 6-Nitropiperonal
27679-0 2,5-Dichloroterephthaldehyde
33066-3 2,3,4-Trifluorobenzaldehyde
29231-1 2,3,6-Trichlorobenzaldehyde
15201-3 2,3-Dimethyl-p-anisaldehyde
29627-9 2,4-Dimethoxy-3-methylbenzaldehyde
15209-9 2,3,4-Trimethoxybenzaldehyde
26084-3 2,3,4-Trihydroxybenzaldehyde
32893-6 Tetrafluorobenzaldehyde
10374-8 Pentafluorobenzaldehyde
B3468-0 4-Biphenylcarboxaldehyde
19175-2 3-Phenoxybenzaldehyde
B2700-5 3-Benzloxybenzaldehyde
19540-5 3-(4-Methylphenoxy)benzaldehyde
19592-8 3-(4-tert-Butylphenoxy)benzaldehyde
19539-1 3-[3-(Trifluoromethyl)phenoxy]benzaldehyde
19530-8 3-(4-Chlorophenoxy)benzaldehyde
19590-1 3-(3,4-Dichlorophenoxy)benzaldehyde
19774-2 3-(3,5-Dichlorophenoxy)benzaldehyde
19589-8 3-(4-Methoxyphonoxy)benzaldehyde
21126-5 4-Phenoxybenzaldehyde
12371-4 4-Benzyloxybenzaldehyde
16361-9 4-Benzyloxy-3-methoxybenzaldehyde
16395-3 3-Benzyloxy-4-methoxybenzaldehyde
34603-9 3-Methoxy-4-(4-nitrobenzyloxy)benzaldehyde
D3600-3 3,4-Dibenzyloxybenzaldehyde
N10-9 1-Naphthaldehyde
N20-6 2-Naphthaldehyde
15134-3 2-Methoxy-1-naphthaldehyde
10324-1 4-Methoxy-1-naphthaldehyde
H4535-3 2-Hydroxy-1-naphthaldehyde
27208-6 4-Dimethylamino-1-naphthaldehyde
38201-9 2,3-Naphthalendicarboxaldehyde
15014-2 2-Fluorenecarboxaldehyde
27868-8 9-Anthraldehyde
M2965-7 10-Methylanthracene-9-carboxaldehyde
15211-0 10-Chloro-9-anthraldehyde
P1160-3 Phenanthrene-9-carboxaldehyde
14403-7 1-Pyrenecarboxaldehyde Aliphatic Aldehydes 25254-9 Formaldehylde
11007-8 Acetaldehyde
P5145-1 Propionaldehyde
24078-8 Isobutyraldehyde
$T_{7150}$-1 Trimethylacetaldehyde
B10328-4 Butyraldehyde
M3347-6 2-Methylbutyraldehyde
11009-4 2-Ethylbutyraldehyde
14645-5 Isovaleraldehyde
35990-4 3,3-Dimethylbutyraldehyde
11013-2 Valeraldehyde
25856-3 2-Methylvaleraldehyde
D19050-0 2,4-Dimethylvaleraldehyde
11560-6 Hexanal
E2910-9 2-Ethylhexanal
30355-0 3,5,5-Trimethylhexanal
H212-0 Heptaldehyde
0560-8 Octyl aldehyde
N3080-3 Nonyl aldehyde
12577-6 Decyl aldehyde U220-2 Undecylic aldehyde
M8675-8 2-Methylundecanal
D22200-3 Dodecyl aldehyde
26923-9 Tridecanal
$T_{1000}$-6 Tetradecy aldehyde
11022-1 Acrolein
13303-5 Methacrolein
25614-5 2-Ethylacrolein
25613-7 2-Butylacrolein
13298-5 Crotonaldehyde
19261-9 trans-2-Methyl-2-butenal
29468-3 2-Ethyl-trans-2-butenal
30407-7 3-Methyl-2-butenal
26925-5 trans-2-pentenal
29466-7 2-Methyl-2-pentenal
29097-1 2,2-Dimethyl-4-pentenal
13265-9 trans-2-Hexenal
25176-3 trans-2-Heptenal
30796-3 2,6-Dimethyl-5-heptenal
26995-6 trans-2-Octenal
34364-1 (R)-(+)-Citronellal
37375-3 (S)-(−)-Citronellal
37562-4 cis-4-Decenal
36733-8 trans-4-Decenal
13227-6 Undecylenic aldehyde
24911-4 dis-9-hexadecenal
27221-3 Cyclopropanecarboxaldehyde
10846-4 Cyclohexanecarboxaldehyde
10933-9 Cyclooctanecarboxaldehyde
30441-7 3–Cyclohexylpropionaldehyde
$T_{1220}$-3 Tetrahydrobenzaldehyde
21829-4 (S)-(−)-Perillaldehyde
26467-9 2,6,6-Trimethyl-1-cyclohexene-1-acetaldehyde
10937-1 5-Norbornen-2-carboxaldehyde
21824-3 (1R)-(−)-Myrtenal
37531-4 Glyoxal-1,1-dimethyl acetal
21877-4 7-Methoxy-3,7-dimethyloctanal
23254-8 3-Ethoxymethacrolein
27525-5 2,5-Dimethoxy-3-tetrahydrofurancarboxaldehyde
26918-2 2,2-Dimethyl-3-hydroxypropionaldehyde
G480-2 DL-Glyceraldehyde
G478-0 D-Glyceraldehyde
21665-8 L-Glyceraldehyde
34140-1 3-(Methylthio)propionaldehyde
30583-9 3-(Dimethylamino)acrolein
36549-9 3-(Dimethylamino)-2-methyl-2-propenal
17733-4 Pyruvic aldehyde
27706-1 (S)-(−)-2-(Methoxymethyl)-1-pyrrolidinecarboxaldehyde
29211-7 2-Methoxy-1-pyrrolidinecarboxaldehyde
29210-9 2-Methoxy-1-piperidinecarboxaldehyde Example 143

Quality Control of Synthesized Cyclic Amine, Cycloalkyl amine, Bicyclic Amines and Oligomeric Compounds Discrete cyclic amine, cycloalkyl amine, bicyclic amines and mixtures thereof synthesized according to the methods of the present invention are analyzed by several techniques to determine the quality and the identity of the compounds.

Both single compounds and mixtures of compounds were analyzed by reversed-phase high performance liquid chromatography (RP-HPLC) using either ultraviolet detection (UV) or evaporative light scattering detection (ELSD). Area under the curve obtained by integration of the HPLC chromatograms gives an indication of the quality of the products. Purity is more easily interpreted for HPLC chromatograms of discrete cyclic amine, cycloalkyl amine and bicyclic amines than for mixtures of these compounds.

Both discrete compounds and mixtures of compounds were also analyzed by mass spectrometry (MS) to establish identity of the synthesized products. MS was performed using either electrospray (ESMS) or chemical ionization (CIMS) techniques. MS is useful for verifying the identity of the cyclic amine, cycloalkyl amine and bicyclic amine compounds of the present invention and is useful for both single compounds and mixtures of compounds. MS is less precise for determining purity, and such estimates are generally ±20%.

Example 144

General Procedure for the Manual Synthesis of Discrete Cyclic Amine Libraries

A solid support is derivatized with a cyclic amine scaffold, such as N-TEOC-3R-amino-5R-azidomethyl-pyrrolidine, following the procedure of Example 65. The support is now divided into sixteen equal portions and each portion transferred into a separate reaction vessel.

The reactive amino combinatorial site may now be reacted with an appropriate building block, such as an isocyanate following the procedure described in Example 67. As an example, four isocyanates may be used: benzylisocyanate, isopropylisocyanate, phenylisocyanate, and tolylisocyanate. Four reaction vessels are charged with the first isocyanate, another four with the second isocyanate, yet another four with the third isocyanate building block and the last four reaction vessels are charged with the fourth isocyanate building block. Following carbamoylation in all 16 reaction vessels, the sixteen supports are separately washed and subjected to reducing conditions, as in Example 77, to convert the 5-azidomethyl group to a 5-aminomethyl group.

The support bound scaffolds in each reaction vessel are then reacted with a new building block selected from a group of aldehydes: benzaldehyde, m-tolualdehyde, m-anisaldehyde, and 3,4,5-trimethoxybenzaldehyde, following the reductive alkylation procedure of Example 74.

Of the four vessels from the reaction with the first isocyanate, one is charged with the first aldehyde, another is charged with the second aldehyde, yet another is charged with the third aldehyde and the last of that set charged with the fourth aldehyde. This distribution of aldehydes is repeated for the remaining three sets of reaction vessels derived from the other three isocyanates used earlier. The sixteen solid support bound substituted pyrrolidines so synthesized in sixteen different reaction vessels are next cleaved separately, using trifluoroacetic acid, as in Example 78. Concentration of the cleaved product solutions affords 16 discrete trisubstituted pyrrolidines which may be analyzed by HPLC and MS as described in Example 143.

The 16 individual disubstituted pyrrolidines are unique from each other. They all possess the same 3R-amino-5R-aminomethyl-pyrrolidine scaffold structure. However, each product bears a unique combination of the two building blocks used in the synthesis of the library. The products represent the complete combinations of four isocyanates attached to the first amino combinatorial site of the scaffold via a urea linkage and four aldehyde building blocks attached to the second site of the scaffold.

While this method does not involve functionalization of the pyrrolidine ring nitrogen, a more complex library may be generated via removal of the N-Teoc group, following reactions with isocyanates, as described in Example 76, followed by reaction with different building blocks. Cleavage would then afford trisubstituted pyrrolidines.

Example 145

General Procedure for the Manual Synthesis of Mixtures of Cyclic Amine Libraries Method 1. Split-Mix Strategy A solid support is derivatized with cyclic amine scaffold, such as N-Teoc-3-amino-5S-azido-piperidine, as in Example 65. The available amino combinatorial site may now be reacted with an appropriate building block, such as an isocyanate following the procedure described in Example 67. As an example, four isocyanates may be used: benzylisocyanate, isopropylisocyanate, phenylisocyanate, and tolylisocyanate. The solid support is divided into 4 equal portions and each portion is reacted with one of benzylisocyanate, isopropylisocyanate, phenylisocyanate, and tolylisocyanate to effect coupling to the resulting free amino as per the method of Example 67, and the portions of solid support recombined.

The combined solid support is treated with a solution of 3TBAF in NMP to cleave the N-Teoc group from the solid support bound scaffold, as described in Example 76. The solid support is once again divided into four equal portions and each portion of support reacted with a new building block selected from a group of aldehydes: benzaldehyde, m-tolualdehyde, m-anisaldehyde, and 3,4,5-trimethoxybenzaldehyde, following the reductive alkylation procedure of Example 74, and the method of Look, G. C., et al., (*Tetrahedron Lett.,* 1995, 36, 2937–2940).

All four solid supports are once again mixed well and the combined solid support subjected to reducing conditions so as to convert the azido group to a reactive amino group, following the procedure of Example 77. The solid support is yet again divided into four equal portions and each portion of support reacted with a new building block selected from a group of sulfonyl chlorides: benzenesulfonyl chloride, p-tolylsulfonyl chloride, methoxybenzenesulfonyl chloride and 2-nitrobenzenesulfonyl chloride, following the procedure of Example 66.

All four solid supports are once again mixed well and the combined solid support cleaved using TFA as in Example 78. Concentration of the cleaved product solution affords a mixture of 64 trisubstituted pyrrolidines which may be analyzed by HPLC and MS as described in Example 143.

All 64 products are comprised of the same pyrrolidine scaffold. The products represent the complete combinations of four isocyanates, four aldehyde buiding blocks and four sulfonyl chlorides attached to the three amino combinatorial sites on the pyrrolidine scaffold.

Method 2

A solid support is derivatized with cyclic amine scaffold, such as N-Teoc-3-amino-5S-azido-piperidine, as in Example 65. The available amino combinatorial site may now be reacted with an appropriate building block, such as an isocyanate following the procedure described in Example 67 As an example, four isocyanates may be used: benzylisocyanate, isopropylisocyanate, phenylisocyanate, and tolylisocyanate. Instead of dividing the solid support into four portions, as in method 1 above, the support is reacted concurrently, in one reaction vessel, with a mixture of all four isocyanates. This affords directly, a solid support bound scaffold with four different carbamoyl substituents at the amino combinatorial site.

The support is next treated with a solution of 3TBAF in NMP to cleave the N-Teoc group from the solid support bound scaffold, as described in Example 76. The reactive amino group of the scaffold is subjected to the next round of combinatorialization. Reaction is performed with a mixture of benzaldehyde, m-tolualdehyde, m-anisaldehyde, and 3,4,5-trimethoxybenzaldehyde, following the reductive alkylation procedure of Example 74.

The solid support is then subjected to reducing conditions so as to convert the azido group to a reactive amino group, following the procedure of Example 77. Reaction with a mixture of benzenesulfonyl chloride, p-tolylsulfonyl chloride, methoxybenzenesulfonyl chloride and 2-nitrobenzenesulfonyl chloride, following the procedure of Example 66, leads to sulfonylation of the amino group.

Finally, the solid support is cleaved using TFA as in Example 78. Concentration of the cleaved product solution affords a mixture of 128 trisubstituted pyrrolidines which may be analyzed by HPLC and MS as described in Example 143.

All 128 products are comprised of the same pyrrolidine scaffold. Twice the number of compounds are obtained because of the deliberate choice of N-Teoc-3-amino-5S-azido-piperidine as scaffold. Combinatorial reactions with three sets of building blocks comprising four reagents each affords 64 distinct substitution patterns. However, since the scaffold used is a mixture of two diastereomers, the 3R,5S and 3S,5S piperidines, this library synthesized has twice the number of distinct compounds present in the mixture isolated.

The 128 products represent the complete combinations of four isocyanates, four aldehyde buiding blocks and four sulfonyl chlorides attached to the three amino combinatorial sites on the two diastereomeric pyrrolidine scaffolds used.

Example 146

General Procedures for Solid Phase Synthesis

All solid phase reactions, as described in the above examples, are performed in a vessel suitable for solid-phase synthesis. Reaction vessels typically have an open top that can be pressurized and sealed if desired, with a frit at the bottom to contain solid-phase synthesis support but allow liquid reagents and solvents to pass through and a mechanism for containing the liquid within the vessel during the reaction steps. Reactions are performed under an inert atmosphere of dry argon or nitrogen, and the pressure of the source can be modulated to allow liquid reagents and solvents to remain within the vessel or to be flushed through the frit and out the bottom, as desired.

Unless, otherwise specified, each reagent treatment and solvent wash of the solid support is followed by "flushing" the vessel of its liquid contents, by the application of an increased positive pressure of inert gas. During "wait" steps the reagents and solvents are left within the vessel and flushed out at the end of the wait period.

Example 147

General Procedure for the Automated Synthesis of Cyclic and Bicyclic Amine Libraries

Part 1. General Notes

In the general solid phase synthesis procedures described above, the reaction vessels typically have a nominal volume of 0.75 mL, and the synthesis scale was adjusted to accomodate the vessel size. Larger-scale reactions may be performed in any suitable vessel by simply scaling the reagents accordingly.

Substituted cyclic and bicyclic amines are synthesized using a 96-well microtiter-format automated synthesizer, in which the synthesis vessels are individual wells of a modified 96 well plate. Each well has an open top and a capillary at the bottom, with a polyethylene frit above the capillary to retain solid phase synthesis support. The capillary allows liquid to be retained under ambient gas pressure, and flushed under increased pressure from the top of the wells.

The automated synthesizer is controlled by a computer, which in turn follows commands represented in a "command file" and delivers different reagents to different reaction wells as dictated by a "sequence file." Both command file and sequence file refer to a "reagent table" for instructions on identity and concentration of reagents. For example, when a general command file is "run" it executes the following general protocol for the synthesis of libraries of cyclic and bicyclic amines in wells within which scaffold bound to solid support is placed:

Part 2. General Automated Synthesizer Protocol

1. Wash with DMF (5×300 µL);
2. Wash with DCM (6×300 µL);
3. Add building block (isocyanate in NMP);
4. Wait for 3 hours;
5. Repeat steps 3 and 4
6. Wash with DMF (10×300 µL);
7. Add TBAF (350 µL in NMP);
8. Wait for 1 hour;
9. Repeat Steps 7 and 8;
10. Wash with DMF (10×300 µL);
11. Add building block (amino acid and HATU in NMP);
12. Wait for 3 hours;
13. Repeat Steps 11 and 12;
14. Wash with DMF (6×300 µL);
15. Add piperidine (10% in DMF);
16. Wait for 15 minutes;
17. Repeat Steps 15 and 16;
18. Wash with DMF (5×300 µL);
19. Add 2-nitrobenzenesulfonyl chloride (300 µL);
20. Wait for 3 hours;
21. Repeat Steps 19 and 20;
22. Wash with DCM (8×300 µL);
23. Wash with DMF (5×300 µL);
24. Wash with DCM (5×300 µL);
25. Add TCA in DCM (300 µL);
26. Wait for 1 minute;
27. Repeat Steps 25 and 26, ten times;
28. Wash with DCM (5×300 µL);
29. Wash with acetonitrile (5×300 µL);
30. Wash with DCM (7×300 µL);
31. Add Mitsunobu cyclization reagent (300 µL);
32. Wait for 1 hour;
33. Repeat Steps 31 and 32 five times;
34. Wash with DCM (6×300 µL);
35. Wash with DMF (5×300 µL);
36. Add mercaptoacetic acid in NMP (300 µL);
37. Wait for 1 hour;
38. Repeat Steps 37 and 38;
39. Wash with DMF (8×300 µL);
40. Wash with acetonitrile (5×300 uL);
41. Wash with DCM (6×300 µL);
42. Add building block (acid chloride in 1:1 pyridine/DCM);
43. Wait for 3 hours;
44. Repeat Steps 43 and 44 five times;
45. Wash with DCM (8×300 µL);
46. Wash with acetonitrile (8×300 µL);
47. Add TFA containing 2.5% triethylsilane;
48. Wait for 4 hours;
49. Wash with TFA (2×200 µL);
50. Collect eluant;
51. Evaporate eluant to dryness and analyze.

Some examples of the discrete bicyclic amines synthesized, using the protocol described above, are shown below.

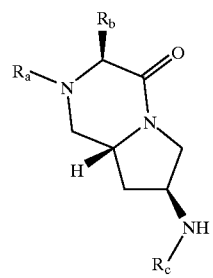

147-2

2,3,8-Trisubstituted 1,4-Diazabicyclo[4.3.0]nonan-2-ones

| Compd. | $R_a$ | $R_b$ | $R_c$ | HPLC purity | Mass Expected/ Found |
|---|---|---|---|---|---|
| 1 | tolyl | Me | H | 80 | 302 |
| 2 | isopropyl | Me | H | 80 | 254 |
| 3 | Benzyl | Me | H | 85 | 302 |
| 4 | tolyl | Benzyl | H | 80 | 378 |
| 5 | isopropyl | Benzyl | H | 85 | 330 |
| 6 | Benzyl | Benzyl | H | 75 | 378 |
| 7 | tolyl | Me | tolylcarbamoyl | 95 | 451 |
| 8 | tolyl | Me | L-alanyl | 88 | 373 |

Part 3. Automated Synthesis of Libraries of Mixtures of Cyclic Amines, Bicyclic Amines, and Oligomeric Compounds In order to synthesize more than one compound per well during automated synthesis of cyclic amines, bicyclic amines, and oligomeric compounds, several different strategies are available and may be used.

The mixture of solid supports bearing different cyclic or bicyclic amine scaffolds, say five scaffolds for example, prior to placing support in the reaction wells, followed by automated synthesis as describe above in Part 2, will lead to the synthesis of five related compounds per reaction well and the isolation of one "product" that is a mixture of five compounds. All five cyclic amine compounds generated in one well will display the same substituents derived from the specific building blocks added to that reaction well during synthesis. However, each of the five compounds posesses a different cyclic or bicyclic amine scaffold that originates from the five different support bound scaffolds mixed into the well prior to commencement of automated synthesis.

Another strategy to generating libraries of mixtures involves the use of multiple building blocks during synthesis. Thus, if library synthesis commences, as in Part 2 above, with one support bound scaffold per well but proceeds via the use of two building blocks at each combinatorial site of the scaffold then during the first round of combinatorialization at the amino site of the scaffold two products are formed. In the second round of combinatorialzciation, the use of a mixture of two isocyanates in one reaction well will lead to 2×2=4 compounds being synthesized per well. Upon completion of such an automated synthesis, the library so generated will be comprised of mixtures of 4 compounds/ reaction well. All four compounds from a given reaction well, will have originated from the same cyclic or bicyclic amine scaffold and share this similarity in all their structures.

Another strategy, may involve the use of a mixture of scaffolds and a mixture of building blocks in each reaction well so as to yield even higher levels of structural diversity in the mixture of compounds generated. However, such an approach when applied to the synthesis protocol of Part 2, also leads to a more complex mixture of cyclic, bicyclic and oligomeric amine compounds present in the "product" from each well.

Yet another strategy for the generation of mixtures of cyclic, bicyclic and oligomeric amines involves the use of diastereomeric scaffold mixtures during library generation. Thus, if a mixture of two or four diastereomers of the same scaffold is used for loading onto the solid support, then upon library synthesis using single reagents in each reaction vessel will still afford a product that is a mixture of two or four diastereomeric products that are identical in terms of their scaffold and substituents present but differ in the relative stereochemical configurations of these substitutents The following library of a mixture of bicyclic amine compounds was synthesized using the protocols described above. The general structure of these 3,8-Disubstituted 1,4-Diazabicyclo[4.3.0]nonan-2-ones and the substituents are shown below:

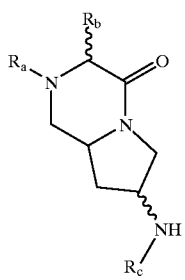

147-3

| Cpd. | $R_a$ | $R_b$ | $R_c$ | Mass Expected/ Found |
|---|---|---|---|---|
| 9 | m-toluoyl | H | 2- | 458 |
| 10 | tolylcarbamoyl | H | 2- | 473 |
| 11 | methoxybenzenesulfony | H | 2- | 510 |
| 12 | tolylcarbamoyl | H | m-toluoyl | 406 |

-continued

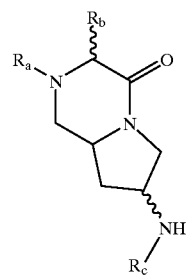

147-3

| Cpd. | $R_a$ | $R_b$ | $R_c$ | Mass Expected/ Found |
|---|---|---|---|---|
| 13 | methoxybenzenesulfony | H | tolylcarbamoyl | 458 |
| 14 | m-toluoyl | H | methoxybenzenesulfony | 443 |
| 15 | thymidi-1-yl-acetyl | H | thymidi-1-yl-acetyl | 439 |
| 16 | thymidi-1-yl-acetyl | H | m-toluoyl | 487 |
| 17 | tolylcarbamoyl | H | thymidi-1-yl-acetyl | 454 |
| 18 | methoxybenzenesulfony | H | m-toluoyl | 443 |
| 20 | tolylcarbamoyl | H | m-toluoyl | 406 |
| 21 | methoxybenzenesulfony | H | thymidi-1-yl-acetyl | 491 |
|  | nicotinoyl | H | thymidi-1-yl-acetyl | 426 |

Example 148

N-(N-beanzoyl-5S-(2-nitrobenzeneulfonamido)-piperidin-3-yl)-1-(N-ethyl-3R-(N-(m-toluoyl)-amino)-pyrroldin-5-yl)-methyl carbamate Step 1

The appropriate resin is derivatized with N-Teoc-3R-amino-5-(dimethoxytrityloxymethyl)-pyrrolidine according to the general procedure, as described in Example 65.

Step 2

This resin bound scaffold is then functionalized at the available amino combinatorial site as an amide, using m-toluoyl chloride according to the general procedure described in Example 71.

Step 3

The Teoc protecting group is removed, using TBAF, according to the general procedure as described in Example 76, and this amino group is then functionalized via reductive alkylation, using acetaldehyde, and following the general procedure as described in Example 74, above.

Step 4

The alcohol protecting group is then removed following the procedure of Example 79, and the hydroxyl group activated for carbamate formation by treatment with a 0.06 M solution (5 mL/g of dry resin) of triphosgene in $CH_2Cl_2$, followed by a 0.4 M solution (5 mL/g of dry resin) of DIPEA in $CH_2Cl_2$. The suspension is allowed to stand for 0.25 h, and 0.1 M solution of N-Teoc-3-amino-5S-azido-piperidine (10 mL/g) in NMP is added. The suspension is allowed to stand for 2.5 h at rt, then filtered, and washed with DMF (3×) and $CH_2Cl_2$ (3×) and dried with a flow of inert gas to afford a product comprising the two scaffolds connected to each other via a carbamate linkage and the product is attached to the solid support.

Step 5

The Teoc protecting group is removed, using TBAF, according to the general procedure as described in Example 76, and this amino group is then acylated, using benzoyl chloride, following the general procedure as described in Example 71, above.

Step 6

The azido group is next reduced, according to the general procedure as described in Example 77, and this amino group is then sulfonylated, using 2-nitrobenzenesulfonyl chloride, and following the general procedure as described in Example 66, above. Alternatively the second scaffold may be linked to yet another scaffold as described above.

Step 7

Cleavage from the support is accomplished using TFA, according to the general procedure of Example 78. Upon concentration, the title compound is isolated.

Example 149

N-(3S-Methyl-4-(2-nitrobenzenesulfonyl)-2-oxo-1, 4-diazabicyclo[4.3.0]nonan-8S-yl)-1-(N-ethyl-3R-(N-(m-toluoyl)-amino)-pyrrolidin-5-yl)-methyl carbamate

Step 1

The appropriate resin is derivatized with N-Teoc-3R-amino-5-(dimethoxytrityloxymethyl)-pyrrolidine according to the general procedure, as described in Example 65.

Step 2

This resin bound scaffold is then functionalized at the available amino combinatorial site as an amide, using m-toluoyl chloride according to the general procedure described in Example 71.

Step 3

The Teoc protecting group is removed, using TBAF, according to the general procedure as described in Example 76, and this amino group is then functionalized via reductive alkylation, using acetaldehyde, and following the general procedure as described in Example 74, above.

Step 4

The alcohol protecting group is then removed following the procedure of Example 79, and the hydroxyl group activated for carbamate formation by treatment with a 0.06 M solution (5 mL/g of dry resin) of triphosgene in $CH_2Cl_2$, followed by a 0.4 M solution (5 mL/g of dry resin) of DIPEA in $CH_2Cl_2$. The suspension is allowed to stand for 0.25 h, and 0.1 M solution of N-Teoc-3S-amino-5-(dimethyltrityloxymethyl)-pyrrolidine (10 mL/g) in NMP is added. The suspension is allowed to stand for 2.5 h at rt, then filtered, and washed with DMF (3×) and $CH_2Cl_2$ (3×) and dried with a flow of inert gas to afford a product comprising the two scaffolds connected to each other via a carbamate linkage and the product is attached to the solid support.

Step 5

The Teoc group is removed with a 0.2 M solution (25 mL/mmole scaffold) of TBAF in NMP, following the procedure of Example 76. The amino group is next reacted with a mixture of N-Fmoc-Ala-OH, DIPEA and HATU acording to the procedure of Example 72.

Step 6

The Fmoc group is cleaved using piperidine in DMF, as in Example 82, and the exposed amino group reacted with 2-nitrobenzenesulfonyl chloride, following the procedure of Example 66.

Step 7

Treatment with dichloroacetic acid in $CH_2Cl_2$ (25 mL/mmole scaffold), as described in Example 79, cleaves the DMT group protecting the hydroxy functionality.

Step 8

The resin bound material is then treated with a 0.1 M solution of 5-triphenylphosphonium-1,1-dioxo-3,3-dimethyl-2,5-thiadiazolidine betaine, following the procedure of Example 83, leads to the formation of the substituted, bicyclic, 1,4-diazabicyclo[4.3.0]nonan-2-one, attached via a carbamate linkage to the resin-bound aminopyrrolidine scaffold.

Step 9

Finally, this resin-bound material was treated with TFA containing 2.5% $Et_3SiH$ (25 mL/mmole scaffold), according to the procedure of Example 78, to provide the desired product. This product is a mixture of four diastereomers.

Example 150

N-(N-benzyl-5R-acetamido-piperidin-3-yl)-N'-(1-(N-(p-toluenesufonyl)-3S-butyramido-pyrrolidin-5-yl)-methyl) thiourea

Step 1

The appropriate resin is derivatized with N-Teoc-3S-amino-5-azidomethyl-pyrrolidine according to the general procedure, as described in Example 65.

Step 2

This resin bound scaffold is then functionalized at the available amino combinatorial site via acylation, using butanoyl chloride, according to the general procedure described in Example 71.

Step 3

The Teoc protecting group is removed, using TBAF, according to the general procedure as described in Example 76, and this amino group is then sulfonylated, using p-toluensulfonyl chloride, and following the general procedure as described in Example 66, above.

Step 4

The azide is then reduced according to the general procedure described in Example 77, and the resulting amino group activated for urea formation by treatment with a 0.18 M solution of thiophosgene in $CH_2Cl_2$ (5 mL/g of dry resin), followed by a 0.4 M solution (5 mL/g of dry resin) of DIPEA in $CH_2Cl_2$. The suspension is allowed to stand for 0.25 h, and a 0.1 M solution of N-Teoc-3-amino-5R-azidopiperidine (10 mL/g) in NMP is added. The suspension is allowed to stand for 2.5 h at rt, then filtered, and washed with DMF (3×) and $CH_2Cl_2$ (3×) and dried with a flow of inert gas to afford a product comprising the pyrrolidine and piperidine scaffolds connected to each other via a thiourea linkage and the product is attached to the solid support.

Step 5

The Teoc protecting group is removed, using TBAF, according to the general procedure as described in Example 76, and this amino group is then alkylated, using benzaldehyde, following the general procedure as described in Example 74, above.

Step 6

The azido group is next reduced, according to the general procedure as described in Example 77, and this amino group is then acylated, using acetyl chloride, and following the general procedure as described in Example 71, above. Alternatively the second scaffold may be linked to yet another scaffold as described above.

Step 7

Finally, this resin-bound material was treated with TFA containing 2.5% Et₃SiH (25 mL/mmole scaffold), according to the procedure of Example 78, to provide the desired product. This product is a mixture of four diastereomers.

Example 151

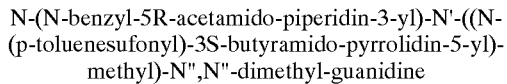

N-(N-benzyl-5R-acetamido-piperidin-3-yl)-N'-((N-(p-toluenesufonyl)-3S-butyramido-pyrrolidin-5-yl)-methyl)-N'',N''-dimethyl-guanidine

Step 1

The appropriate resin is derivatized with N-Teoc-3S-amino-5-azidomethyl-pyrrolidine according to the general procedure, as described in Example 65.

Step 2

This resin bound scaffold is then functionalized at the available amino combinatorial site via acylation, using butyric acid, according to the general procedure described in Example 72.

Step 3

The Teoc protecting group is removed, using TBAF, according to the general procedure as described in Example 76, and this amino group is then sulfonylated, using p-toluenesulfonyl chloride, and following the general procedure as described in Example 66, above.

Step 4

The azide is then reduced according to the general procedure described in Example 77, and the resulting amino group activated for urea formation by treatment with a 0.18 M solution of thiophosgene in CH₂Cl₂ (5 mL/g of dry resin), followed by a 0.4 M solution (5 mL/g of dry resin) of DIPEA in CH₂Cl₂. The suspension is allowed to stand for 0.25 h, and a 0.1 M solution of N-Teoc-3-amino-5R-azido-piperidine (10 mL/g) in NMP is added. The suspension is allowed to stand for 2.5 h at rt, then filtered, and washed with DMF (3×) and CH₂Cl₂ (3×) and dried with a flow of inert gas to afford a product comprising the pyrrolidine and piperidine scaffolds connected to each other via a thiourea linkage and the product is attached to the solid support.

Step 5

The thiourea is alkylated by treatment with a 0.2 M solution (25 mL/mmole scaffold) of iodoacetonitrile in 10:1 NMP/DIPEA. The suspension is allowed to stand for 1 h at rt, then filtered, and washed with NMP. To the corresponding resin bound S-alkyl isothiourea is added a 1.0 M solution of dimethylamine (10 mL/g) in NMP. The suspension is allowed to stand for 3 h at rt, then filtered, and washed with DMF (3×) and CH₂Cl₂ (3×) and dried with a flow of inert gas to afford a product comprising two scaffolds connected to each other via a guanidino linkage and the product is attached to the solid support.

Step 6

The Teoc protecting group is removed, using TBAF, according to the general procedure as described in Example 76, and this amino group is then alkylated, using benzaldehyde, following the general procedure as described in Example 74, above.

Step 7

The azido group is next reduced, according to the general procedure as described in Example 77, and this amino group is then acylated, using acetyl chloride, and following the general procedure as described in Example 71, above. Alternatively the second scaffold may be linked to yet another scaffold as described above.

Step 8

Finally, this resin-bound material was treated with TFA containing 2.5% Et₃SiH (25 mL/mmole scaffold), according to the procedure of Example 78, to provide the desired product. This product is a mixture of four diastereomers.

Example 152

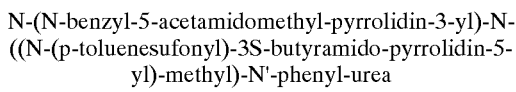

N-(N-benzyl-5-acetamidomethyl-pyrrolidin-3-yl)-N-((N-(p-toluenesufonyl)-3S-butyramido-pyrrolidin-5-yl)-methyl)-N'-phenyl-urea

Step 1

The appropriate resin is derivatized with N-Teoc-3S-amino-5-azidomethyl-pyrrolidine according to the general procedure, as described in Example 65.

Step 2

This resin bound scaffold is then functionalized at the available amino combinatorial site via acylated, using butanoyl chloride, according to the general procedure described in Example 71.

Step 3

The Teoc protecting group is removed, using TBAF, according to the general procedure as described in Example 76, and this amino group is then sulfonylated, using p-toluenesulfonyl chloride, and following the general procedure as described in Example 66, above.

Step 4

The azide is then reduced according to the general procedure described in Example 77, and the resulting amino group is then reductively alkylated with N-Teoc-5-azidomethyl-pyrrolidin-3-one according to the general procedure for alkylation at nitrogen with aldehydes or ketones, as described in Examples 74 and 81.

Step 4

The resulting secondary amine is then functionalized as a urea, using phenyl isocyanate, and following the general procedure of Example 67.

Step 6

The Teoc protecting group is removed, using TBAF, according to the general procedure as described in Example 76, and this amino group is then alkylated, using benzaldehyde, following the general procedure as described in Example 74, above.

Step 7

The azido group is next reduced, according to the general procedure as described in Example 77, and this amino group is then acylated, using acetyl chloride, and following the general procedure as described in Example 71, above. Alternatively the second scaffold may be linked to yet another scaffold as described above.

Step 8

Finally, this resin-bound material was treated with TFA containing 2.5% Et$_3$SiH (25 mL/mmole scaffold), according to the procedure of Example 78, to provide the desired product. This product is a mixture of six diastereomers.

BIOLOGICAL ASSAYS

PROCEDURE 1

Antimicrobial Assay (*Staphylococcus aureus*)

*Staphylococcus aureus* is known to cause localized skin infections as a result of poor hygiene, minor trauma, psoriasis or eczema. It also causes respiratory infections, pneumonia, toxic shock syndrome and septicemia. It is a common cause of acute food poisoning. It exhibits rapid emergence of drug resistance to penicillin, cephalosporin, vancomycin and nafcillin.

In this assay, the strain S. aureus ATCC 25923 (American Type Culture Collection) is used. To initiate the exponential phase of bacterial growth prior to the assay, a sample of bacteria grown overnight at 37° C. in typtocase soy broth (BBL). This bacteria is then used to reinoculate sample wells of 96-well microtiter plates. The assays are carried out in the 96-well microtiter plates in 150 μL volume with approximately 1×10$^6$ cells per well.

Bacteria in typtocase soy broth (75 μL) is added to the compound mixtures in solution in 75 μL water/4% DMSO in the individual well of the microtiter plate. Final concentrations of the compound mixtures are 25 μM, 10 μM and 1 μM. Each concentration of the compound mixtures are assayed in triplicate. The plates are incubated at 37° C. and growth monitored over a 24 hour period by measuring the optical density at 595 nm using a BioRad model 3550 UV microplate reader. The percentage of growth relative to a well containing no compound is determined. Ampicillin and tetracycline antibiotic positive controls are concurrently tested in each screening assay.

PROCEDURE 2

Antimicrobial Assays

A. Streptococcus Pyogenes

In this assay, the strain *S. aureus* ATCC 14289 (American Type Culture Collection) is used. To initiate the exponential phase of bacterial growth prior to the assay, a sample of bacteria is grown overnight at 37° C. in 1×Todd-Hewitt broth. This bacteria is then used to reinoculate sample wells of 96-well microtiter plates. The assays are carried out in the 96-well microtiter plates in 150 μL volume with approximately 1×10$^6$ cells per well.

Bacteria in 1×Todd-Hewitt broth (75 μL) is added to the compound mixtures in solution in 75 μL water in the individual well of the microtiter plate. Final concentrations of the compound mixtures are 25 μM, 10 μM and 1 μM. Each concentration of the compound mixtures are assayed in triplicate. The plates are incubated at 37° C. and growth monitored over a 24 hour period by measuring the optical density at 595 nm using a BioRad model 3550 UV microplate reader. The percentage of growth relative to a well containing no compound is determined. Ampicillin and tetracycline antibiotic positive controls are concurrently tested in each screening assay.

A series of compounds prepared according to Example 147 were assayed for their ability to inhibit growth of Streptococcus Pyogenes as described above. The following single compounds and mixtures of compounds were found to completely inhibit growth at the indicated concentration.

| R1 | R2 | R3 | Inhibitory |
|---|---|---|---|
| Formula 147-2 | | | |
| tolylcarbamoyl | CH$_2$Ph | H | 275 μM |
| Formula 147-3 | | | |
| tolylcarbamoyl | H | thymine-1-acetyl | 275 μM |
| t-butylcarbamoyl | H | thymine-1-acetyl | 275 μM |
| methoxybenzenesulfo | H | thymine-1-acetyl | 275 μM |
| 8-quinolinesulfonyl | H | thymine-1-acetyl | 275 μM |
| isopropylsulfonyl | H | thymine-1-acetyl | 275 μM |
| nicotinoyl | H | thymine-1-acetyl | 275 μM |
| 3-toluoyl | H | thymine-1-acetyl | 275 μM |
| tolylcarbamoyl | H | 3-toluoyl | 275 μM |
| B. E. coli imp- | | | |

In this assay, the strain *E. coli* imp- obtained from Spenser Bensen (Sampson, B. A., Misra, R. & Benson, S. A. (1989), *Genetics*, 122, 491–501, Identification and characterization of a new gene of *Escherichia coli* K-12 involved in outer membrane permeability) is used. To initiate the exponential phase of bacterial growth prior to the assay, a sample of bacteria is grown overnight at 37° C. in Luria broth. This bacteria is then used to reinoculate sample wells of 96-well microtiter plates. The assays are carried out in the 96-well microtiter plates in 150 μL volume with approximately 1×10$^6$ cells per well.

Bacteria in Luria broth (75 μL) is added to the compound mixtures in solution in 75 μL water in the individual well of the microtiter plate. Final concentrations of the compound mixtures are 25 μM, 10 μM and 1 μM. Each concentration of the compound mixtures are assayed in triplicate. The plates are incubated at 37° C. and growth monitored over a 24 hour period by measuring the optical density at 595 nm using a BioRad model 3550 UV microplate reader. The percentage of growth relative to a well containing no compound is determined. Ampicillin and tetracycline antibiotic positive controls are concurrently tested in each screening assay.

Combinatorial libraries in accordance with the present invention have been tested for antibacterial activity utilizing assays that determine the minimum inhibitory concentration (MIC). The antibacterial assays utilize streptococcus pyogenes and escherichia coli imp-.

PROCEDURE 3

*Antfungal Assay

C. albicans

In this assay, the strain C. albicans ATCC 10231 (American Type Culture Collection) is used. To initiate the exponential phase of yeast growth prior to the assay, a sample of yeast is grown overnight at 37° C. in YM media. This yeast is then used to reinoculate sample wells of 96-Well microtiter plates. The assays are carried out in the 96-well microtiter plates in 150 μL volume with approximately 1×10$^6$ cells per well.

Yeast in YM media (75 μL) is added to the compound mixtures in solution in 75 μL water in the individual well of the microtiter plate. Final concentrations of the compound mixtures are 25 μM, 10 μM and 1 μM. Each concentration of the compound mixtures are assayed in triplicate. The plates are incubated at 37° C. and growth monitored over a 24 hour period by measuring the optical density at 595 nm using a BioRad model 3550 UV microplate reader. The percentage of growth relative to a well containing no compound is determined. Amphotericin B positive control is concurrently tested in each screening assay.

PROCEDURE 4

RNA Binding Assay

The Effect of Libraries and Individual Compounds on Tat/TAR Interactions

The effects of combinatorial libraries, and individual members thereof, on tat/TAR, RNA/protein interactions are examined using a rapid and reproducible binding assay. The assay consists of a biotinylated truncated version of the HIV-1 TAR stem-loop, which is anchored to the wells of a 96 well ELISA plate which has been coated with streptavidin. The TAR RNA is recognized by the HIV-1 protein tat and the amount of tat bound is quantitated using an antibody raised against tat and a secondary antibody conjugated to an alkaline phosphatase or HRP enzyme to produce a calorimetric reaction.

Materials

A 39 residue tat peptide (aa 49–85 of HIV tat protein). This is the C terminal basic binding domain of the tat protein. This peptide was synthesized by a contract lab.

A 30 base RNA oligonucleotide consisting of the bulge and stem/loop structure of HIV TAR which has also been Biotin conjugated. This RNA oligonucleotide was synthesized in house.

A biotinylated HIV RRE RNA oligonucleotide synthesized in house.

Binding buffer: 40 mM Tris-HCl (pH 8.0), 0.01% NP-40, 20% glycerol, 1.5 mM MgCl, 0.01% NaN3, 50 mM KCl.

Streptavidin coated 96 well microtitre plates (Elkay Labsystems).

Protein A/G alkaline phosphatase (Pierce).

Anti tat antiserum (BioDesign).

PNPP substrate (Pierce).

Methods

To each well of a Streptavidin coated 96 well ELISA plate is added 200 μl of a solution of the 30 base TAR sequence (20 nM) in binding buffer. The plate is incubated at 4° C. for 1 hour. The biotintylated HIV RRE RNA oligonucleotide is bound to selected wells as a negative control RNA. The plate is washed with binding buffer three times and 100 μl of a 100 nM solution of the 39 residue tat peptide in binding buffer is added to each well. Combinatorial libraries as mixtures, or discrete members thereof, are added to selected wells of the plate at initial concentrations of 100 μM. The plate is incubated for 1 hour at room temperature.

The plate is washed with binding buffer three times and blocked with binding buffer +5% FCS. 100 μl of tat antiserum diluted 1:700 in binding buffer is added to the wells of the plate and the plate is incubated for 1.5 hours at 4° C. The plate is washed three times with binding buffer and 150 μL of a solution of protein A/G alkaline phosphatase diluted 1:5000 in binding buffer is added to each well. The plate is incubated for 1.5 hours at 4° C. followed by washing three times with binding buffer. 150 μL of PNPP substrate is added to each well and the plate is incubated for 1 hour at 37° C. The absorbance of each well is read in a multiwell plate reader.

PROCEDURE 5

Antimicrobial Mechanistic Assay

Bacterial DNA Gyrase

DNA gyrase is a bacterial enzyme which can introduce negative supercoils into DNA utilizing the energy derived from ATP hydrolysis. This activity is critical during DNA replication and is a well characterized target for antibiotic inhibition of bacterial growth. In this assay, libraries of compounds are screened for inhibition of DNA gyrase. The assay measures the supercoiling of a relaxed plasmid by DNA gyrase as an electrophoretic shift on an agarose gel. Initially all libraries are screened for inhibitory activity at 30 μM and then a dose response analysis is effected with active compounds. Novobiocin, an antibiotic that binds to the β subunit of DNA gyrase is used as a positive control in the assay. The sensitivity of the DNA gyrase assay was determined by titrating the concentration of the know DNA gyrase inhibitor, Novobiocin, in the supercoiling assay. The $IC_{50}$ was determined to be 8 nM, sufficient to identify the activity of a single active species of comparable activity in a library having 30 μM concentration.

PROCEDURE 6

Use of a Combinatorial Library for Identifying Metal Chelators and Imaging Agents This procedure is used to identify compounds of the invention from libraries of compounds constructed to include a ring that contains an ultraviolet chromophore. Further the chemical functional groups attached to the compounds of the invention are selected from metal binders, coordinating groups such as amine, hydroxyl and carbonyl groups, and other groups having lone pairs of electrons, such that the compounds of the invention can form coordination complexes with heavy metals and imaging agents. The procedure is used to identify compounds of the invention useful for chelating and removing heavy metals from industrial broths, waste stream eluents, heavy metal poisoning of farm animals and other sources of contaminating heavy metals, and for use in identifying imaging agent carriers, such as carriers for technetium 99.

An aliquot of a test solution having the desired ion or imaging agent at a known concentration is added to an aliquot of standard solution of the library under assay. The UV spectrum of this aliquot is measured and is compared to the UV spectrum of a further aliquot of the same solution lacking the test ion or imaging agent. A shift in the extinction coefficient is indicative of binding of the metal ion or imaging ion to a compound in the library being assayed.

PROCEDURE 7

Assay of Combinatorially Derived Compounds and Libraries for $PLA_2$ Inhibitors

A preferred target for assay of a combinatorially generated library of compounds is the phospholipase $A_2$ family.

Phospholipases $A_2$ ($PLA_2$) are a family of enzymes that hydrolyze the sn-2 ester linkage of membrane phospholipids resulting in release of a free fatty acid and a lysophospholipid (Dennis, E. A., The Enzymes, Vol. 16, pp. 307–353, Boyer, P.D., ed., Academic Press, New York, 1983). Elevated levels of type II $PLA_2$ are correlated with a number of human inflammatory diseases. The $PLA_2$-catalyzed reaction is the rate-limiting step in the release of a number of pro-inflammatory mediators. Arachidonic acid, a fatty acid commonly linked at the sn-2 position, serves as a precursor to leukotrienes, prostaglandins, lipoxins and thromboxanes. The lysophospholipid can be a precursor to platelet-activating factor. $PLA_2$ is regulated by pro-inflammatory cytokines and, thus, occupies a central position in the inflammatory cascade (Dennis, ibid.; Glaser et al., TiPs Reviews 1992, 14, 92; and Pruzanski et al., Inflammation 1992, 16, 451). All mammalian tissues evaluated thus far have exhibited $PLA_2$ activity. At least three different types of $PLA_2$ are found in humans: pancreatic (type I), synovial fluid (type II) and cytosolic. Studies suggest that additional isoenzymes exist. Type I and type II, the secreted forms of $PLA_2$, share strong similarity with phospholipases isolated from the venom of snakes. The $PLA_2$ enzymes are important for normal functions including digestion, cellular membrane remodeling and repair, and in mediation of the inflammatory response. Both cytosolic and type II enzymes are of interest as therapeutic targets. Increased levels of the type II $PLA_2$ are correlated with a variety of inflammatory disorders including rheumatoid arthritis, osteoarthritis, inflammatory bowel disease and septic shock, suggesting that inhibitors of this enzyme would have therapeutic utility. Additional support for a role of $PLA_2$ in promoting the pathophysiology observed in certain chronic inflammatory disorders was the observation that injection of type II $PLA_2$ into the footpad of rats (Vishwanath et al., Inflammation 1988, 12, 549) or into the articular space of rabbits (Bomalaski et al., J. Immunol. 1991, 146, 3904) produced an inflammatory response. When the protein was denatured before injection, no inflammatory response was produced.

The type II $PLA_2$ enzyme from synovial fluid is a relatively small molecule (about 14 kD) and can be distinguished from type I enzymes (e.g. pancreatic) by the sequence and pattern of its disulfide bonds. Both types of enzymes require calcium for activity. The crystal structures of secreted $PLA_2$ enzymes from venom and pancreatic $PLA_2$, with and without inhibitors, have been reported (Scott et al., Science 1990, 250, 1541). Recently, the crystal structure of $PLA_2$ from human synovial fluid has been determined (Wery et al., Nature 1991, 352, 79). The structure clarifies the role of calcium and amino acid residues in catalysis. Calcium acts as a Lewis acid to activate the scissile ester carbonyl bond of 1,2-diacylglycerophospholipids and binds to the lipid, and a His-Asp side chain diad acts as a general base catalyst to activate a water molecule nucleophile. This is consistent with the absence of any acyl enzyme intermediates, and is also comparable to the catalytic mechanism of serine proteases. The catalytic residues and the calcium ion are at the end of a deep cleft (ca. 14 Å) in the enzyme. The walls of this cleft contact the hydrocarbon portion of the phospholipid and are composed of hydrophobic and aromatic residues. The positively-charged amino-terminal helix is situated above the opening of the hydrophobic cleft. Several lines of evidence suggest that the N-terminal portion is the interfacial binding site (Achari et al., Cold Spring Harbor Symp. Quant. Biol. 1987, 52, 441; Cho et al., J. Biol. Chem. 1988, 263, 11237; Yang et al., Biochem. J. 1989, 262, 855; and Noel et al., J. Am. Chem. Soc. 1990, 112, 3704).

Much work has been reported in recent years on the study of the mechanism and properties of $PLA_2$-catalyzed hydrolysis of phospholipids. In in vitro assays, $PLA_2$ displays a lag phase during which the enzyme adsorbs to the substrate bilayer and a process called interfacial activation occurs. This activation may involve desolvation of the enzyme/lipid interface or a change in the physical state of the lipid around the cleft opening. Evidence favoring this hypothesis comes from studies revealing that rapid changes in $PLA_2$ activity occur concurrently with changes in the fluorescence of a membrane probe (Burack et al., Biochemistry 1993, 32, 583). This suggests that lipid rearrangement is occurring during the interfacial activation process. $PLA_2$ activity is maximal around the melting temperature of the lipid, where regions of gel and liquid-crystalline lipid coexist. This is also consistent with the sensitivity of $PLA_2$ activity to temperature and to the composition of the substrate, both of which can lead to structurally distinct lipid arrangements separated by a boundary region. Fluorescence microscopy was used to simultaneously identify the physical state of the lipid and the position of the enzyme during catalysis (Grainger et al., FEBS Lett. 1989, 252, 73). These studies clearly show that $PLA_2$ binds exclusively at the boundary region between liquid and solid phase lipid. While the hydrolysis of the secondary ester bond of 1,2-diacylglycerophospholipids catalyzed by the enzyme is relatively simple, the mechanistic and kinetic picture is clouded by the complexity of the enzyme-substrate interaction. A remarkable characteristic of $PLA_2$ is that maximal catalytic activity is observed on substrate that is aggregated (i.e. phospholipid above its critical micelle concentration), while low levels of activity are observed on monomeric substrate. As a result, competitive inhibitors of $PLA_2$ either have a high affinity for the active site of the enzyme before it binds to the substrate bilayer or partition into the membrane and compete for the active site with the phospholipid substrate. Although a number of inhibitors appear to show promising inhibition of $PLA_2$ in biochemical assays (Yuan et al., J. Am. Chem. Soc. 1987, 109, 8071; Lombardo et al., J. Biol. Chem. 1985, 260, 7234; Washburn et al., J. Biol. Chem. 1991, 266, 5042; Campbell et al., J. Chem. Soc., Chem. Commun. 1988, 1560; and Davidson et al., Biochem. Biophys. Res. Commun. 1986, 137, 587), reports describing in vivo activity are limited (Miyake et al., J. Pharmacol. Exp. Ther. 1992, 263, 1302).

In one preferred embodiment, compounds of the invention are selected for their potential to interact with, and preferably inhibit, the enzyme $PLA_2$. Thus, compounds of the invention can be used for topical and/or systemic treatment of inflammatory diseases including atopic dermatitis and inflammatory bowel disease. In selecting the functional groups, advantage can be taken of $PLA_2$'s preference for anionic vesicles over zwitterionic vesicles. Preferred compounds of the invention for assay for $PLA_2$ include those having aromatic diversity groups to facilitate binding to the cleft of the $PLA_2$ enzyme (Oinuma et al., J. Med. Chem. 1991, 34, 2260; Marki et al., Agents Actions 1993, 38, 202; and Tanaka et al., J. Antibiotics 1992, 45, 1071). Benzyl and 4-hexylbenzyl groups are preferred aromatic diversity groups. $PLA_2$-directed compounds of the invention can further include hydrophobic functional groups such as tetraethylene glycol groups. Since the $PLA_2$ enzyme has a hydrophobic channel, hydrophobicity is believed to be an important property of inhibitors of the enzyme.

The libraries additionally can be screened in other in vitro assays to determine further mechanisms of inhibition. The libraries are screened for inhibition of $PLA_2$ in the assay using *E. coli* labeled with $^3$H-oleic acid (Franson et al., *J. Lipid Res.* 1974, 15, 380; and Davidson et al., *J. Biol. Chem.* 1987, 262, 1698) as the substrate. Type II PLA$_2$ (originally isolated from synovial fluid), expressed in a baculovirus system and partially purified, serves as a source of the enzyme. A series of dilutions of each of the libraries is performed: 10 μl of each library of compounds is incubated for 5 minutes at room temperature with a mixture of 10 μl PLA$_2$, 20 μl 5X PLA$_2$ Buffer (500 mM Tris 7.0–7.5, 5 mM CaCl$_2$), and 50 μl water. Samples of each library are run in duplicate. At this point, 10 μl of $^3$H *E. coli* cells is added. This mixture is incubated at 37° C. for 15 minutes. The enzymatic reaction is stopped with the addition of 50 μL 2M HCl and 50 μL fatty-acid-free BSA (20 mg/mL PBS), vortexed for 5 seconds, and centrifuged at high speed for 5 minutes. 165 μL of each supernate is then put into a scintillation vial containing 6 ml of scintillant (ScintiVerse) and cpms are measured in a Beckman Liquid Scintillation Counter. As a control, a reaction without the combinatorial pool (or library of compounds) is run alongside the other reactions as well as a baseline reaction containing no compounds of the invention as well as no PLA$_2$ enzyme. CPMs are corrected for by subtracting the baseline from each reaction data point.

Confirmation of the "winners" is made to confirm that a compound of the invention binds to enzyme rather than substrate and that the inhibition by a compound of the invention that is selected is specific for type II PLA$_2$. An assay using $^{14}$C-phosphatidyl ethanolamine ($^{14}$C-PE) as substrate, rather than *E. coli* membrane, is used to insure enzyme rather than substrate specificity. Micelles of $^{14}$C-PE and deoxycholate are incubated with the enzyme and a compound of the invention. $^{14}$C-labeled arachidonic acid released as a result of PLA$_2$-catalyzed hydrolysis is separated from substrate by thin layer chromatography and the radioactive product is quantitated. The "winner" is compared to phosphatidyl ethanolamine, the preferred substrate of human type II PLA$_2$, to confirm its activity. PLA$_2$ from other sources (snake venom, pancreatic, bee venom) and phospholipase C, phospholipase D and lysophospholipase can be used to further confirm that the inhibition is specific for human type II PLA$_2$.

PROCEDURE 8

Leukotriene B$_4$ Assay

Leukotriene B$_4$ (LTB$_4$) has been implicated in a variety of human inflammatory diseases, and its pharmacological effects are mediated via its interaction with specific surface cell receptors. Library products, either as discrete compounds or as small mixtures of compounds, are screened for competitive inhibition of radiolabeled LTB$_4$ binding to a receptor preparation.

A Nenquest™ Drug Discovery System Kit (NEN Research Products, Boston, Mass.) is used to select an inhibitor of the interaction of Leukotriene B$_4$ (LTB$_4$) with receptors on a preparation of guinea pig spleen membrane. [$^3$H]Leukotriene B$_4$ reagent is prepared by adding 5 mL of ligand diluent (phosphate buffer containing NaCl, MgCl$_2$, EDTA and Bacitracin, pH 7.2) to 0.25 mL of the radioligand. The receptor preparation is made by thawing the concentrate, adding 35 mL of ligand diluent and swirling gently in order to re-suspend the receptor homogeneously. Reagents are kept on ice during the course of the experiment, and the remaining portions are stored at −20° C.

Library products prepared as per the general procedures of examples above are diluted to 5 μM, 50 μM and 500 μM in phosphate buffer (1x PBS, 0.1% azide and 0.1% BSA, pH 7.2), yielding final test concentrations of 0.5 μM, 5 μM and 50 μM, respectively. Samples are assayed in duplicate. [$^3$H]LTB$_4$ (25 μL) is added to 25 μL of either appropriately diluted standard (unlabeled LTB$_4$) or library product. The receptor suspension (0.2 mL) is added to each tube. Samples are incubated at 4 C. for 2 hours. Controls include [$^3$H]LTB$_4$ without receptor suspension (total count vials), and sample of ligand and receptor without library molecules (standard).

After the incubation period, the samples are filtered through GF/B paper that had been previously rinsed with cold saline. The contents of each tube are aspirated onto the filter paper to remove unbound ligand from the membrane preparation, and the tubes washed (2x4 mL) with cold saline. The filter paper is removed from the filtration unit and the filter disks are placed in appropriate vials for scintillation counting. Fluor is added, and the vials shaken and allowed to stand at room temperature for 2 to 3 hours prior to counting. The counts/minute (cpm) obtained for each sample are subtracted from those obtained from the total counts to determine the net cpm for each sample. The degree of inhibition of binding for each library product is determined relative to the standard (sample of ligand and receptor without library product).

TABLE 1

| Compd. | Target | Test Dose | % Inhibition |
|---|---|---|---|
| 36 | *E. coli* | 20.00 | 98.3 |
| 36 | *E. coli* | 100.00 | 99.4 |
| 36 | *K. pneumoniae* | 20.00 | 95.4 |
| 36 | *K. pneumoniae* | 100.00 | 96 |
| 36 | *P. vulgaris* | 20.00 | 96.9 |
| 36 | *P. vulgaris* | 100.00 | 99.7 |
| 36 | *S. pyogenes* | 20.00 | 99.5 |
| 36 | *S. pyogenes* | 20.00 | 97.5 |
| 36 | *S. pyogenes* | 100.00 | 99.7 |
| 42 | *E. coli* | 20.00 | −38.6 |
| 42 | *E. coli* | 100.00 | 96.4 |
| 42 | *K. pneumoniae* | 20.00 | −15.7 |
| 42 | *K. pneumoniae* | 100.00 | 83.7 |
| 42 | *P. vulgaris* | 20.00 | −0.2 |
| 42 | *P. vulgaris* | 100.00 | 98 |
| 42 | *S. pyogenes* | 20.00 | 81.6 |
| 42 | *S. pyogenes* | 20.00 | 99.2 |
| 42 | *S. pyogenes* | 100.00 | 95.6 |
| 23 | *E. coli* | 20.23 | 99.5 |
| 23 | *S. pyogenes* | 20.23 | 79.6 |
| 24 | *E. coli* | 23.80 | 98.6 |
| 24 | *S. pyogenes* | 23.80 | 90.1 |
| 25 | *E. coli* | 21.41 | 99 |
| 25 | *S. pyogenes* | 21.41 | 90.6 |
| 26 | *E. coli* | 23.83 | 96 |
| 26 | *S. pyogenes* | 23.83 | 78.1 |
| 27 | *E. coli* | 21.41 | 100.5 |
| 27 | *S. pyogenes* | 21.41 | 99.8 |
| 28 | *E. coli* | 19.46 | 99.2 |
| 28 | *S. pyogenes* | 19.46 | 100.3 |
| 29 | *E. coli* | 21.44 | 98.5 |
| 29 | *S. pyogenes* | 21.44 | 99.7 |
| 30 | *E. coli* | 23.83 | 96 |
| 30 | *s. pyogenes* | 23.83 | 83.7 |
| 31 | *E. coli* | 23.87 | 70.5 |
| 32 | *E. coli* | 23.80 | 97.6 |
| 32 | *S. pyogenes* | 23.80 | 70.7 |
| 33 | *E. coli* | 21.41 | 99.5 |
| 33 | *S. pyogenes* | 21.41 | 99.7 |
| 34 | *E. coli* | 23.83 | 75.7 |
| 35 | *E. coli* | 21.41 | 98.5 |
| 35 | *S. pyogenes* | 21.41 | 99.8 |
| 36 | *E. coli* | 19.46 | 98.3 |
| 36 | *S. pyogenes* | 19.46 | 95.5 |
| 37 | *E. coli* | 21.44 | 98 |
| 37 | *S. pyogenes* | 21.44 | 99.9 |

TABLE 1-continued

| Compd. | Target | Test Dose | % Inhibition |
|---|---|---|---|
| 38 | E. coli | 23.83 | 80.9 |
| 39 | E. coli | 23.80 | 96 |
| 40 | E. coli | 21.41 | 98.5 |
| 40 | S. pyogenes | 21.41 | 99.7 |
| 41 | E. coli | 21.41 | 97.5 |
| 41 | S. pyogenes | 21.41 | 99.5 |
| 42 | E. coli | 19.46 | 97.9 |
| 42 | S. pyogenes | 19.46 | 100.4 |
| 43 | E. coli | 21.44 | 100 |
| 43 | S. pyogenes | 21.44 | 99.9 |
| 44 | E. coli | 23.80 | 97 |
| 45 | E. coli | 21.41 | 97.5 |
| 45 | S. pyogenes | 21.41 | 99.5 |
| 46 | E. coli | 21.41 | 100.5 |
| 46 | S. pyogenes | 21.41 | 99.8 |
| 47 | E. coli | 19.46 | 97.4 |
| 47 | S. pyogenes | 19.46 | 100 |
| 48 | E. coli | 21.44 | 99 |
| 48 | S. pyogenes | 21.44 | 99.6 |
| 49 | E. coli | 23.87 | 99.5 |
| 49 | S. pyogenes | 23.87 | 95 |

Those skilled in the art will appreciate that numerous changes and modifications may be made to the preferred embodiments of the invention and that such changes and modifications may be made without departing from the spirit of the invention. It is, therefore, intended that the appended claims cover all such equivalent variations as fall within the true spirit and scope of the invention.

What is claimed is:

1. A compound having the formula:

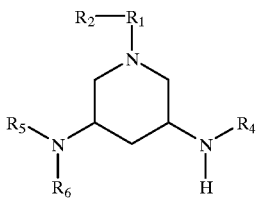

wherein:

$R_1$ and $R_{1'}$ are, individually $CH_2$, $CH(R_2)$, C=O, C=S, $S(=O)_2$, C(=O)NH, C(=S)NH or C(=O)O;

$R_2$ is H, substituted or unsubstituted $C_1$–$C_{10}$ alkyl, substituted or unsubstituted $C_2$–$C_{10}$ alkenyl, substituted or unsubstituted $C_2$–$C_{20}$ alkynyl, substituted or unsubstituted $C_6$–$C_{14}$ aryl, substituted or unsubstituted $C_6$–$C_{14}$ aralkyl, substituted or unsubstituted $C_3$–$C_{14}$ cycloalkyl, substituted or unsubstituted $C_5$–$C_{14}$ fused cycloalkyl, substituted or unsubstituted $C_4$–$C_{14}$ heterocyclyl, substituted or unsubstituted $C_4$–$C_{14}$ heterocyclylalkyl, substituted or unsubstituted $C_4$–$C_{14}$ heteroaryl; substituted or unsubstituted $C_4$–$C_{14}$ heteroaralkyl, $CH(R_7)$—NH—$R_{7'}$ or $CH(R_7)$—NH—$R_{1'}$—$R_3$; wherein the substituent groups are selected from the group consisting of acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone sulfonate, sulfonamide, thiol, and thioalkoxy; or $R_1$ and $R_2$, together, are H, or an amino protecting group;

$R_3$ is H;

$R_4$ is H, $R_1$–$R_2$ or $R_{11}$–$R_{12}$;

$R_5$ is, H, substituted or unsubstituted $C_1$–$C_1$ alkyl, substituted or unsubstituted $C_2$–$C_{10}$ alkenyl, substituted or unsubstituted $C_2$–$C_{20}$ alkynyl, substituted or unsubstituted $C_6$–$C_{14}$ aryl, substituted or unsubstituted $C_6$–$C_{14}$ aralkyl, substituted or unsubstituted $C_3$–$C_{14}$ cycloalkyl, substituted or unsubstituted $C_5$–$C_{14}$ fused cycloalkyl, substituted or unsubstituted $C_4$–$C_{14}$ heterocyclyl, substituted or unsubstituted $C_4$–$C_{14}$ heterocyclylalkyl, substituted or unsubstituted $C_4$–$C_{14}$ heteroaryl; substituted or unsubstituted $C_4$–$C_{14}$ heteroaralkyl, —$R_1$-$R_2$, or $N(R_8)(R_9)$—C(=O); wherein the substituent groups are selected from the group consisting of acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy;

$R_6$ is, H, substituted or unsubstituted $C_1$–$C_{10}$ alkyl, substituted or unsubstituted $C_2$–$C_{10}$ alkenyl, substituted or unsubstituted $C_2$–$C_{20}$ alkynyl, substituted or unsubstituted $C_6$–$C_{14}$ aryl, substituted or unsubstituted $C_6$–$C_{14}$ aralkyl, substituted or unsubstituted $C_3$–$C_{14}$ cycloalkyl, substituted or unsubstituted $C_5$–$C_{14}$ fused cycloalkyl, substituted or unsubstituted $C_4$–$C_{14}$ heterocyclyl, substituted or unsubstituted $C_4$–$C_{14}$ heterocyclylalkyl, substituted or unsubstituted $C_4$–$C_{14}$ heteroaryl; substituted or unsubstituted $C_4$–$C_{14}$ heteroaralkyl, —$R_1$-$R_2$, or —C(=O)O—$R_3$; wherein the substituent groups are selected from the group consisting of acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy; or $R_5$ and $R_6$, together, are $(CH_2)_{nd}$, $(CH_2)_{nd}$—O—$(CH_2)_{ne}$, $(CH_2)_{nd}$—N($R_{10}$)—$(CH_2)_{ne}$, or $(CH_2)_{nd}$—S—$(CH_2)_{ne}$;

$R_7$ is H, substituted or unsubstituted $C_1$–$C_{10}$ alkyl, substituted or unsubstituted $C_2$–$C_{10}$ alkenyl, substituted or unsubstituted $C_2$–$C_{20}$ alkynyl, substituted or unsubstituted $C_6$–$C_{14}$ aryl, substituted or unsubstituted $C_6$–$C_{14}$ aralkyl, substituted or unsubstituted $C_3$–$C_{14}$ cycloalkyl, substituted or unsubstituted $C_5$–$C_{14}$ fused cycloalkyl, substituted or unsubstituted $C_4$–$C_{14}$ heterocyclyl, substituted or unsubstituted $C_4$–$C_{14}$ heterocyclylalkyl, substituted or unsubstituted $C_6$–$C_{14}$ heteroaryl; substituted or unsubstituted $C_6$–$C_{14}$ heteroaralkyl, or a group selected from the group consisting of groups attached to the α-position of amino acids, wherein the substituent groups are selected from the group consisting of acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy;

$R_{7'}$ is H or an amino protecting group;

$R_8$ and $R_9$ are each, independently, H, substituted or unsubstituted $C_1$–$C_{10}$ alkyl, substituted or unsubstituted $C_2$–$C_{10}$ alkenyl, substituted or unsubstituted $C_2$–$C_{20}$ alkynyl, substituted or unsubstituted $C_6$–$C_{14}$ aryl, substituted or unsubstituted $C_6$–$C_{14}$ aralkyl, substituted or unsubstituted $C_3$–$C_{14}$ cycloalkyl, substituted or unsubstituted $C_5$–$C_{14}$ fused cycloalkyl, substituted or unsubstituted $C_4$–$C_{14}$ heterocyclyl, substituted or unsubstituted $C_4$–$C_{14}$ heterocyclylalkyl, substituted or unsubstituted $C_4$–$C_{14}$ heteroaryl; substituted or unsubstituted $C_4$–$C_{14}$ heteroaralkyl, wherein the substituent groups are selected from the group consisting of acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy; or $R_8$ and $R_9$, together, are $(CH_2)_{nd}$, $(CH_2)_{nd}$—O—$(CH_2)_{ne}$, $(CH_2)_{nd}$—N $(R_{10})$—$(CH_2)_{ne}$, or $(CH_2)_{nd}$—S—$(CH_2)_{ne}$;

$R_{10}$ is substituted or unsubstituted $C_1$–$C_{10}$ alkyl, substituted or unsubstituted $C_6$–$C_{14}$ aryl, or substituted or unsubstituted $C_6$–$C_{14}$ aralkyl, substituted or unsubstituted $C_4$–$C_{14}$ heteroaryl; substituted or unsubstituted $C_4$–$C_{14}$ heteroaralkyl, wherein the substituent groups are selected from the group consisting of acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy;

$R_{11}$ is a linker moiety;

$R_{12}$ is a solid support; and nd and ne are each, independently, 1 to 4;

provided that said compound is not:

N-[1-[1,1'-biphenyl]-4-ylsulfonyl)-5-[[[4-[(2,4-dioxo-5-thiazolidinylidene)methyl]bezoy]amino] methyl]-3-pyrrolidinyl]-4-[(3-oxo-2(3H)-isothizolyl)methyl]-, [3S-[3.alpha.,5.alpha.(E)]]-benzamide; or N-[(4-amino-2-pyrrolidinyl) methyl]-3-methyl-L-valyl-L-1,2,3,4-tetrahydro-3-isoquinolinecarbonyl-, (2S-trans)-, tris (trifluoroacetate)-L-glutamine; or N-[[1-[(1,1-dimethylethoxy) carbonyl]-4-[[(1,1-dimethyletyhoxy) carbonyl]amino]-2-pyrrolidinyl]methyl]-3 -methyl-L-1,2,3,4-tetrahydor-3-isoquinolinecarbonyl-, (2S-trans)-, tris (trifluoroacetate)- L-glutamine; or N-[(4-amino-2-pyrrolidinyl) methyl]-3-methyl-L-valyl-L-1,2,3,4-tetrahydro-3-isoquinolinecarbonyl-, (2S-trans)-trifluoroacetate L-glutamine; or N-[(4-amino-2-pyrrolidinyl) methyl]-3-methyl-L-valyl-L-1,2,3,4-tetrahydro-3-isoquinolinecarbonyl-, (2S-trans)- L-glutamine; or 3-[[[1-[(4-chlorophenyl) sulfonyl]-4-[[(4-chlorophenyl) sulfonyl]amino]-2-pyrrolidinyl] methyl]amino]-,(2S-trans)-benzoic acid; or 4-azido-2-(azidomethyl)-1-(p-tolylsulfonyl)-, (−)-pyrrolidine.

2. The compound of claim 1 wherein the individual stereochemical configurations at positions 3 and 5 of the piperidine rind are specifically R, specifically S, or a mixture of R and S.

* * * * *